(12) United States Patent
Gray et al.

(10) Patent No.: US 9,879,003 B2
(45) Date of Patent: Jan. 30, 2018

(54) HOST TARGETED INHIBITORS OF DENGUE VIRUS AND OTHER VIRUSES

(71) Applicants: President and Fellows of Harvard College, Cambridge, MA (US); Dana-Farber Cancer Institute, Inc., Boston, MA (US)

(72) Inventors: Nathanael Gray, Boston, MA (US); Priscilla Yang, Boston, MA (US); Qingsong Liu, Brookline, MA (US); Mélissanne de Wispelaere, Paris (FR)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/391,638

(22) PCT Filed: Mar. 15, 2013

(86) PCT No.: PCT/US2013/032488
§ 371 (c)(1),
(2) Date: Oct. 9, 2014

(87) PCT Pub. No.: WO2013/154778
PCT Pub. Date: Oct. 17, 2013

(65) Prior Publication Data
US 2015/0166532 A1    Jun. 18, 2015

Related U.S. Application Data

(60) Provisional application No. 61/622,828, filed on Apr. 11, 2012.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC . C07D 487/02; C07D 487/04; A61K 31/4162
USPC ............................................. 546/80; 514/290
See application file for complete search history.

(56) References Cited

U.S. PATENT DOCUMENTS

| | | | |
|---|---|---|---|
| 5,756,466 | A | 5/1998 | Bemis et al. |
| 6,992,089 | B2 | 1/2006 | LaVoie et al. |
| 7,319,105 | B2 | 1/2008 | LaVoie et al. |
| 8,088,781 | B2 | 1/2012 | Honigberg et al. |
| 8,394,818 | B2 * | 3/2013 | Gray et al. ............. 514/292 |
| 8,889,706 | B2 * | 11/2014 | Gray et al. ............. 514/292 |
| 2004/0102443 | A1 | 5/2004 | LaVoie et al. |
| 2006/0199804 | A1 | 9/2006 | Hummersone et al. |
| 2008/0045538 | A1 | 2/2008 | LaVoie et al. |
| 2011/0212053 | A1 | 9/2011 | Qian et al. |
| 2011/0230476 | A1 | 9/2011 | Niu et al. |
| 2011/0288091 | A1 | 11/2011 | Gray et al. |
| 2012/0190676 | A1 | 7/2012 | Moorman et al. |
| 2015/0246913 | A1 | 9/2015 | Gray et al. |

FOREIGN PATENT DOCUMENTS

| | | |
|---|---|---|
| CN | 101128440 A | 2/2008 |
| WO | WO 03/041660 A2 | 5/2003 |
| WO | WO 2004/014906 A2 | 2/2004 |
| WO | WO 2004/014918 A1 | 2/2004 |
| WO | WO 2006/065448 A2 | 6/2006 |
| WO | WO 2006/122806 A2 | 11/2006 |
| WO | WO 2007/002931 A2 | 1/2007 |
| WO | WO 2007/087395 A2 | 8/2007 |
| WO | WO 2007/106503 A2 | 9/2007 |
| WO | 2010044885 * | 4/2010 |
| WO | WO 2010/044885 A2 | 4/2010 |
| WO | WO 2013/154778 A1 | 10/2013 |
| WO | WO 2014/063054 A1 | 4/2014 |

OTHER PUBLICATIONS

Qingsong Liu et al , Feb. 2011, Discovery of 9-(6-Aminopyridin-3-yl)-1-(3-(trifluoromethyl)-phenyl)benzo[h][1,6]naphthyridin-2(1H)-one (Torin2) as a Potent, Selective, and Orally Available Mammalian Target of Rapamycin (mTOR) Inhibitor for Treatment of Cancer.*
The Bruton tyrosine kinase inhibitor PCI-32765 blocks B-cell activation and is efficacious in models of autoimmune disease and B-cell malignancy . . . Lee A. Honigberg et al. 2010.*
International Search Report and Written Opinion for PCT/US2013/032488, dated Jun. 5, 2013.
International Preliminary Report on Patentability for PCT/US2013/032488, dated Oct. 23, 2014.
Bain et al., The selectivity of protein kinase inhibitors: a further update. Biochem J. Dec. 15, 2007;408(3):297-315.
Berge et al., Pharmaceutical salts. J Pharm Sci. Jan. 1977;66(1):1-19.
Carter et al., Inhibition of drug-resistant mutants of ABL, KIT, and EGF receptor kinases. Proc Natl Acad Sci U S A. Aug. 2, 2005;102(31):11011-6. Epub Jul. 26, 2005.
Chu et al., c-Src protein kinase inhibitors block assembly and maturation of dengue virus. Proc Natl Acad Sci U S A. Feb. 27, 2007;104(9):3520-5. Epub Feb. 21, 2007.
Cohen et al., Structural bioinformatics-based design of selective, irreversible kinase inhibitors. Science. May 27, 2005;308(5726):1318-21.

(Continued)

*Primary Examiner* — Rita Desai
(74) *Attorney, Agent, or Firm* — Wolf, Greenfield & Sacks, P.C.

(57) ABSTRACT

Novel antiviral compounds of Formulae (I)-(III) are provided: (I) (II) (III) The inventive compounds, pharmaceutical compositions thereof, and kits including the inventive compounds are useful for the prevention and treatment of infectious diseases caused by viruses, for example, by Flaviviridae virus (e.g., Dengue virus (DENY)), Kunjin virus, Japanese encephalitis virus, vesicular stomatitis virus (VSV), herpes simplex virus 1 (HSV-1), human cytomegalovirus (HCMV), poliovirus, Junin virus, Ebola virus, Marburg virus (MARV), Lassa fever virus (LASV), Venezuelan equine encephalitis virus (VEEV), or Rift Valley Fever virus (RVFV).

25 Claims, 50 Drawing Sheets

(56) References Cited

OTHER PUBLICATIONS

Davis et al., Comprehensive analysis of kinase inhibitor selectivity. Nat Biotechnol. Oct. 30, 2011;29(11):1046-51. doi: 10.1038/nbt.1990.

Fabian et al., A small molecule-kinase interaction map for clinical kinase inhibitors. Nat Biotechnol. Mar. 2005;23(3):329-36. Epub Feb. 13, 2005.

Feng et al., Synthesis of N-substituted 5-[2-(N alkylamino)ethyl]dibenzo[c,h][1,6]naphthyridines as novel topoisomerase I-targeting antitumor agents. Bioorg Med Chem. Oct. 15, 2008;16(20):9295-301. Epub Sep. 5, 2008.

Galkin et al., Identification of NVP-TAE684, a potent, selective, and efficacious inhibitor of NPM-ALK. Proc Natl Acad Sci U S A. Jan. 2, 2007;104(1):270-5. Epub Dec. 21, 2006. Erratum in: Proc Natl Acad Sci U S A. Feb. 6, 2007;104(6):2025.

Goldstein et al., High-throughput kinase profiling as a platform for drug discovery. Nat Rev Drug Discov. May 2008;7(5):391-7. doi:10.1038/nrd2541.

Henise et al., Irreversible Nek2 kinase inhibitors with cellular activity. J Med Chem. Jun. 23, 2011;54(12):4133-46. doi: 10.1021/jm200222m. Epub May 31, 2011.

Honigberg et al., The Bruton tyrosine kinase inhibitor PCI-32765 blocks B-cell activation and is efficacious in models of autoimmune disease and B-cell malignancy. Proc Natl Acad Sci U S A. Jul. 20, 2010;107(29):13075-80. doi: 10.1073/pnas.1004594107. Epub Jul. 6, 2010.

Huang et al., Finding new components of the target of rapamycin (TOR) signaling network through chemical genetics and proteome chips. Proc Natl Acad Sci U S A. Nov. 23, 2004;101(47):16594-9. Epub Nov. 11, 2004.

Johnson et al., Strategies for discovering and derisking covalent, irreversible enzyme inhibitors. Future Med Chem. Jun. 2010;2(6):949-64.

Karaman et al., A quantitative analysis of kinase inhibitor selectivity. Nat Biotechnol. Jan. 2008;26(1):127-32. doi: 10.1038/nbt1358.

Kontopidis et al., Differential binding of inhibitors to active and inactive CDK2 provides insights for drug design. Chem Biol. Feb. 2006;13(2):201-11.

Kwak et al., Irreversible inhibitors of the EGF receptor may circumvent acquired resistance to gefitinib. Proc Natl Acad Sci U S A. May 24, 2005;102(21):7665-70. Epub May 16, 2005.

Kwiatkowski et al., Small-molecule kinase inhibitors provide insight into Mps1 cell cycle function. Nat Chem Biol. May 2001;6(5):359-68. doi: 10.1038/nchembio.345. Epub Apr. 11, 2010.

Leproult et al., Cysteine mapping in conformationally distinct kinase nucleotide binding sites: application to the design of selective covalent inhibitors. J Med Chem. Mar. 10, 2011;54(5):1347-55. doi: 10.1021/jm101396q. Epub Feb. 15, 2011.

Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.

Liu et al., Discovery of 9-(6-aminopyridin-3-yl)-1-(3-(trifluoromethyl)phenyl)benzo[h][1,6]naphthyridin-2(1H)-one (Torin2) as a potent, selective, and orally available mammalian target of rapamycin (mTOR) inhibitor for treatment of cancer. J Med Chem. Mar. 10, 2011;54(5):1473-80. doi: 10.1021/jm101520v.

Liu et al., Rational design of inhibitors that bind to inactive kinase conformations. Nat Chem Biol. Jul. 2006;2(7):358-64.

Miduturu et al., High-throughput kinase profiling: a more efficient approach toward the discovery of new kinase inhibitors. Chem Biol. Jul. 29, 2011;18(7):868-79. doi: 10.1016/j.chembiol.2011.05.010.

Panchal et al., Identification of an antioxidant small-molecule with broad-spectrum antiviral activity. Antiviral Res. Jan. 2012;93(1):23-9.doi:10.1016/j.antiviral.2011.10.011.Epub Oct. 18, 2011.

Pelech, Hitting the right kinase targets: protein kinase selection for drug discovery. Bioforum Eur. Jun. 2008;12(6):36-8.

Ranson, ZD1839 (Iressa): for more than just non-small cell lung cancer. Oncologist. Aug. 2002;7 Suppl 4:16-24.

Reid et al., Dual inhibition of ErbB1 (EGFR/HER1) and ErbB2 (HER2/neu). Eur J Cancer. Feb. 2007;43(3):481-9. Epub Jan. 8, 2007.

Rewcastle et al., Tyrosine kinase inhibitors. 5. Synthesis and structure-activity relationships for 4-[(phenylmethyl)amino]- and 4-(phenylamino)quinazolines as potent adenosine 5'-triphosphate binding site inhibitors of the tyrosine kinase domain of the epidermal growth factor receptor. J Med Chem. Sep. 1, 1995;38(18):3482-7.

Savage et al., Imatinib mesylate—a new oral targeted therapy. N Engl J Med. Feb. 28, 2002;346(9):683-63.

Schirmer et al., Targeted covalent inactivation of protein kinases by resorcylic acid lactone polyketides. Proc Natl Acad Sci U S A. Mar. 14, 2006;103(11):4234-9. Epub Mar. 6, 2006.

Singh et al., The resurgence of covalent drugs. Nat Rev Drug Discov. Apr. 2011;10(4):307-17. doi: 10.1038/nrd3410.

Smaill et al., Tyrosine kinase inhibitors. 17. Irreversible inhibitors of the epidermal growth factor receptor: 4-(phenylamino)quinazoline- and 4-(phenylamino)pyrido[3,2-d]pyrimidine-6-acrylamides bearing additional solubilizing functions. J Med Chem. Apr. 6, 2000;43(7):1380-97.

Stauffer et al., Blocking the PI3K/PKB pathway in tumor cells. Curr Med Chem Anticancer Agents. Sep. 2005;5(5):449-62.

Thoreen et al., An ATP-competitive mammalian target of rapamycin inhibitor reveals rapamycin-resistant functions of mTORC1. J Biol Chem. Mar. 20, 2009;284(12):8023-32. doi: 10.1074/jbc.M900301200. Epub Jan. 15, 2009.

Tsou et al., Optimization of 6,7-disubstituted-4-(arylamino)quinoline-3-carbonitriles as orally active, irreversible inhibitors of human epidermal growth factor receptor-2 kinase activity. J Med Chem. Feb 24, 2005;48(4):1107-31.

Verheijen et al., Phosphatidylinositol 3-kinase (PI3K) inhibitors as anticancer drugs. Drugs Fut. Jun. 2007;32(6):537-47.

Wang et al., 2-Anilino-4-(thiazol-5-yl)pyrimidine CDK inhibitors: synthesis, SAR analysis, X-ray crystallography, and biological activity. J Med Chem. Mar. 25, 2004;47(7):1662-75.

Weerapana et al., Disparate proteome reactivity profiles of carbon electrophiles. Nat Chem Biol. Jul. 2008;4(7):405-7. doi:10.1038/nchembio.91. Epub May 18, 2008. Erratum in: Nat Chem Biol. Jul. 2008;4(7):following 407.

Weerapana et al., Quantitative reactivity profiling predicts functional cysteines in proteomes. Nature. Dec. 9, 2010;468(7325):790-5. doi: 10.1038/nature09472. Epub Nov. 17, 2010.

Wu et al., Discovery of a potent, covalent BTK inhibitor for B-cell lymphoma. ADS Chem Biol. May 16, 2014;9(5):1086-91. doi: 10.1021/cb4008524. Epub Mar. 17, 2014.

Yang et al., Pharmacological inhibition of BMK1 suppresses tumor growth through promyelocytic leukemia protein. Cancer Cell. Sep. 14, 2010;18(3):258-67. doi:10.1016/j.ccr.2010.08.008. Erratum in: Cancer Cell. Oct. 19, 2010;18(4):396.

Zhang et al., Discovery of Potent and Selective Covalent Inhibitors of JNK, Chemistry & Biology, Jan. 2012, 19(1):140-154.

Zhou et al., A structure-guided approach to creating covalent FGFR inhibitors. Chem Biol. Mar. 26, 2010;17(3):285-95. doi: 10.1016/j.chembiol.2010.02.007.

Zhou et al., Novel mutant-selective EGFR kinase inhibitors against EGFR T790M. Nature. Dec. 24, 2009;462(7276):1070-4. doi: 10.1038/nature08622.

International Search Report and Written Opinion for PCT/US2013/065689, dated Mar. 4, 2014.

International Preliminary Report on Patentability for PCT/US2013/065689, dated Apr. 30, 2015.

Chen et al., Tyrosine kinase BMX phosphorylates phosphotyrosine-primed motif mediating the activation of multiple receptor tyrosine kinases. Sci Signal. May 28, 2013;6(277):ra40.

Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.

Liu et al., Discovery and optimization of potent and selective benzonaphthyridinone analogs as small molecule mTOR inhibitors

(56) References Cited

OTHER PUBLICATIONS with improved mouse microsome stability. Bioorg Med Chem Lett. Jul. 1, 2011;21(13):4036-40. doi: 10.1016/j.bmcl.2011.04.129. Epub May 7, 2011.

Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.

* cited by examiner

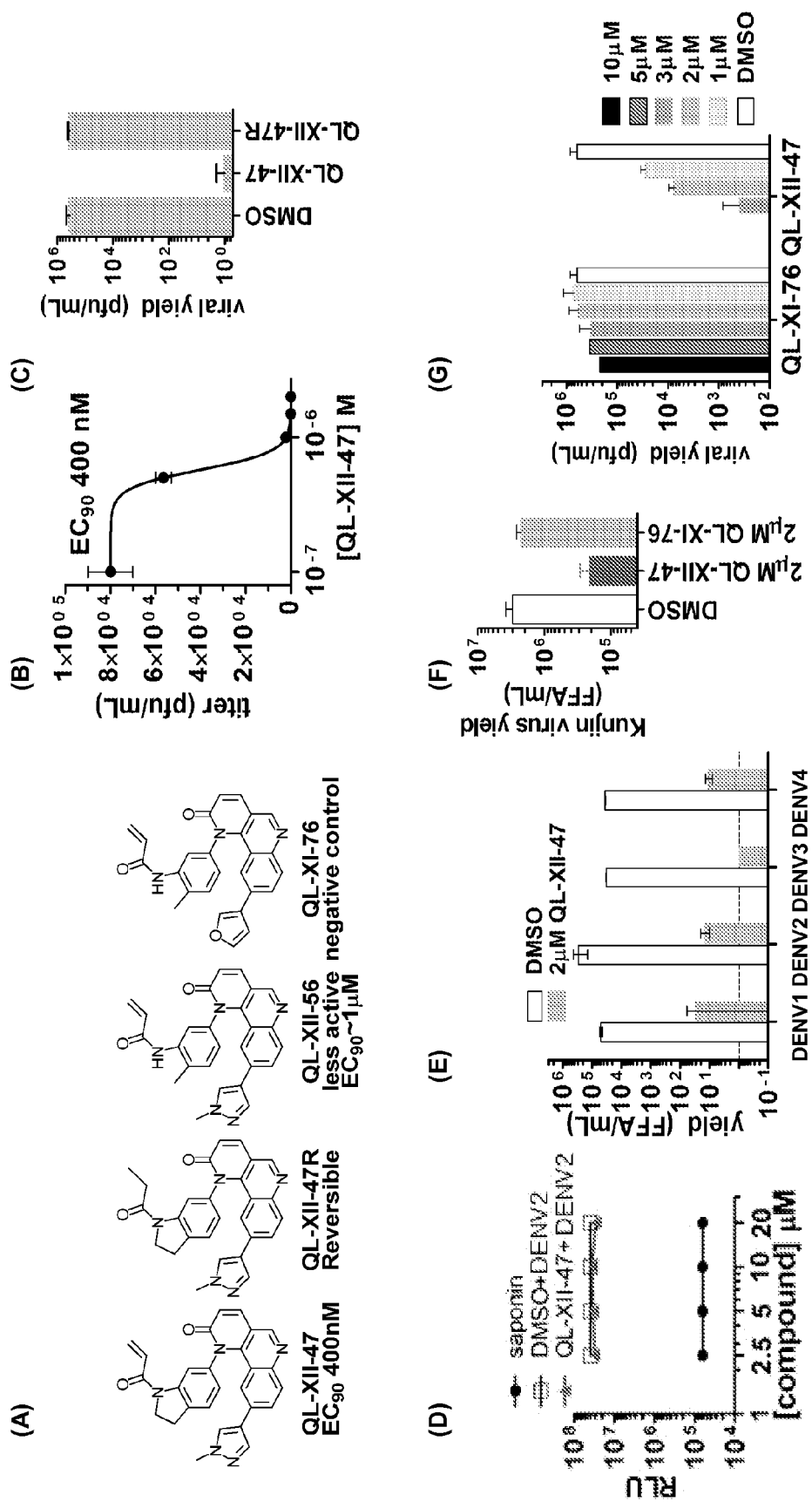
Figure 2A-G

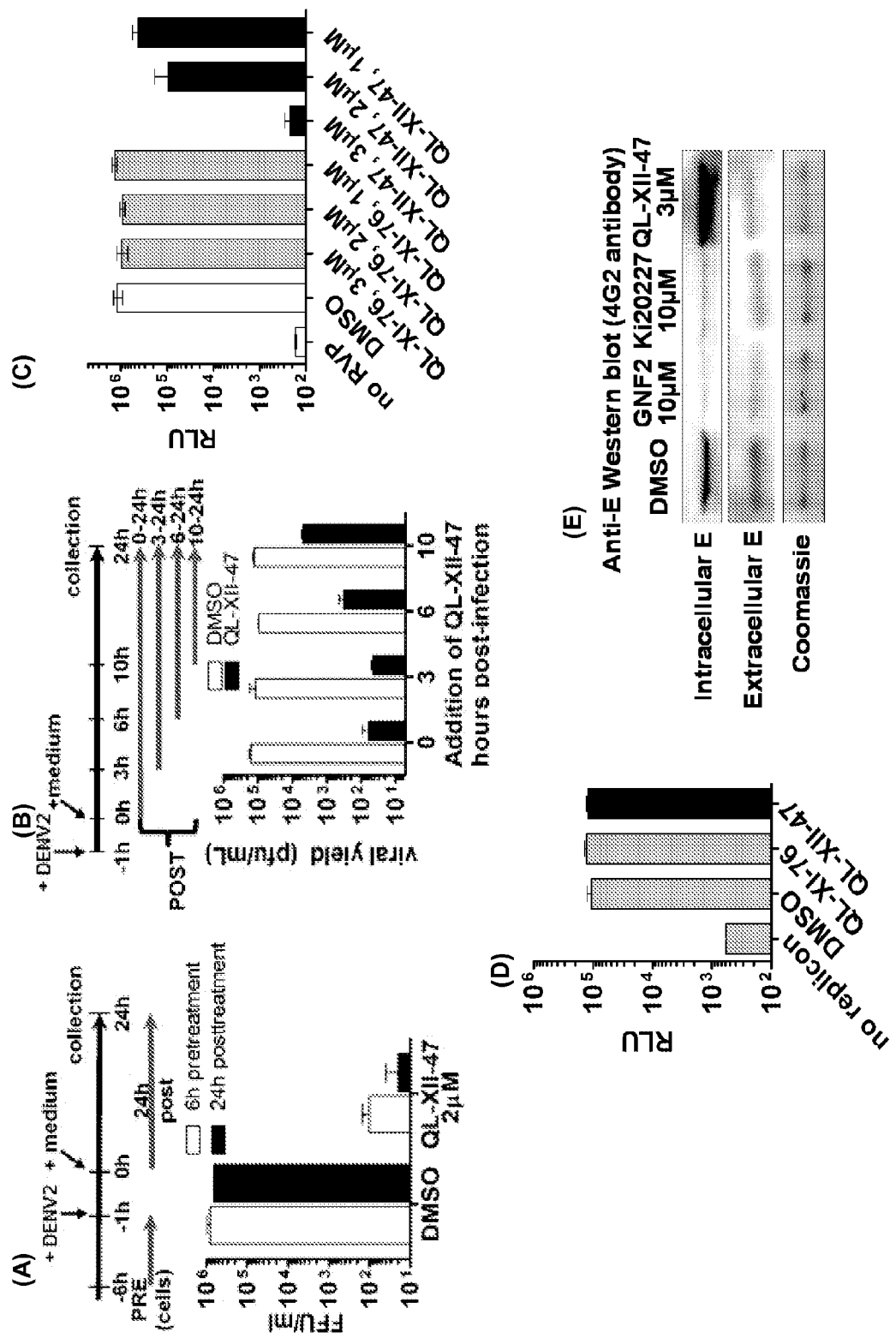
Figure 3A-E

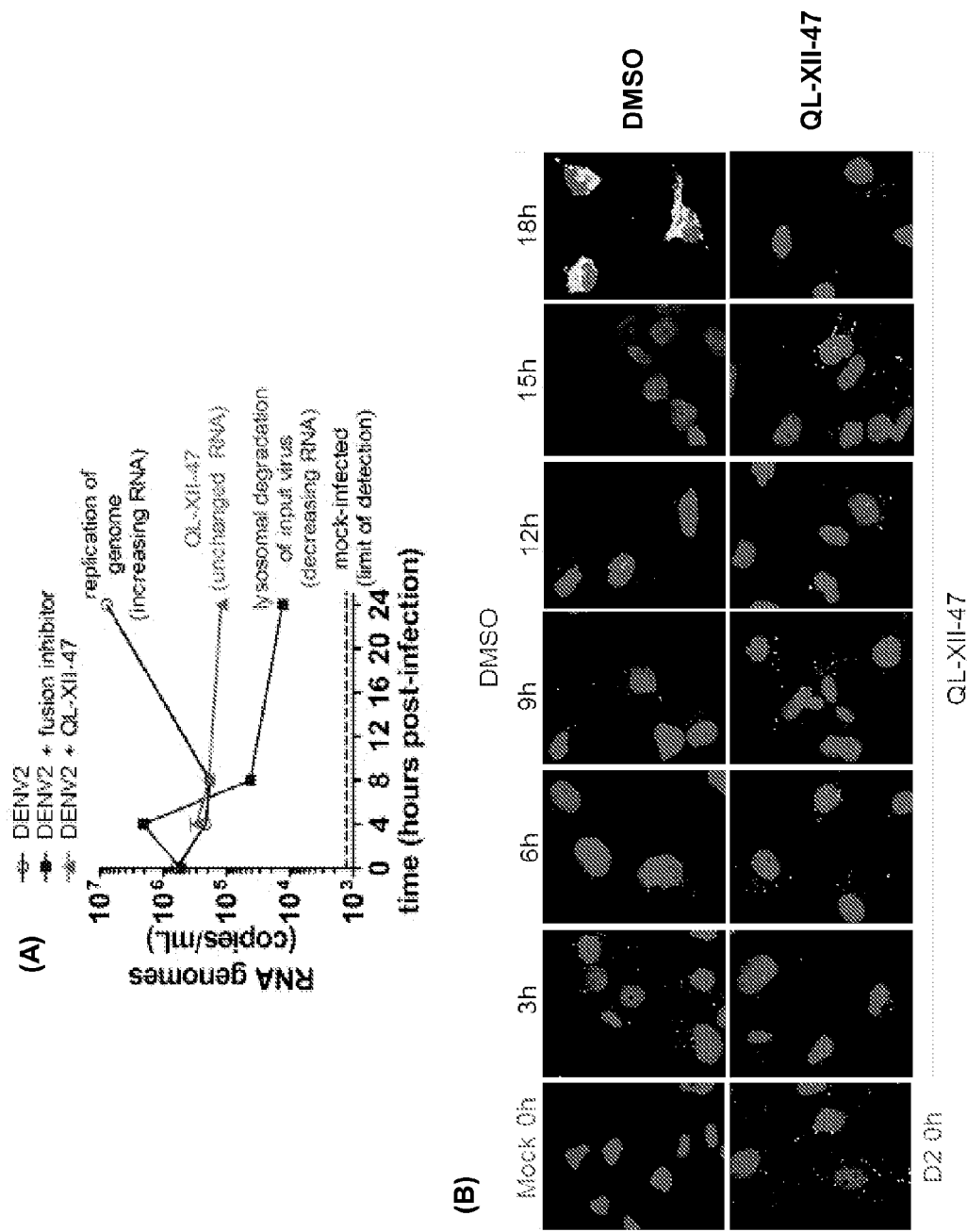
Figure 4A-B

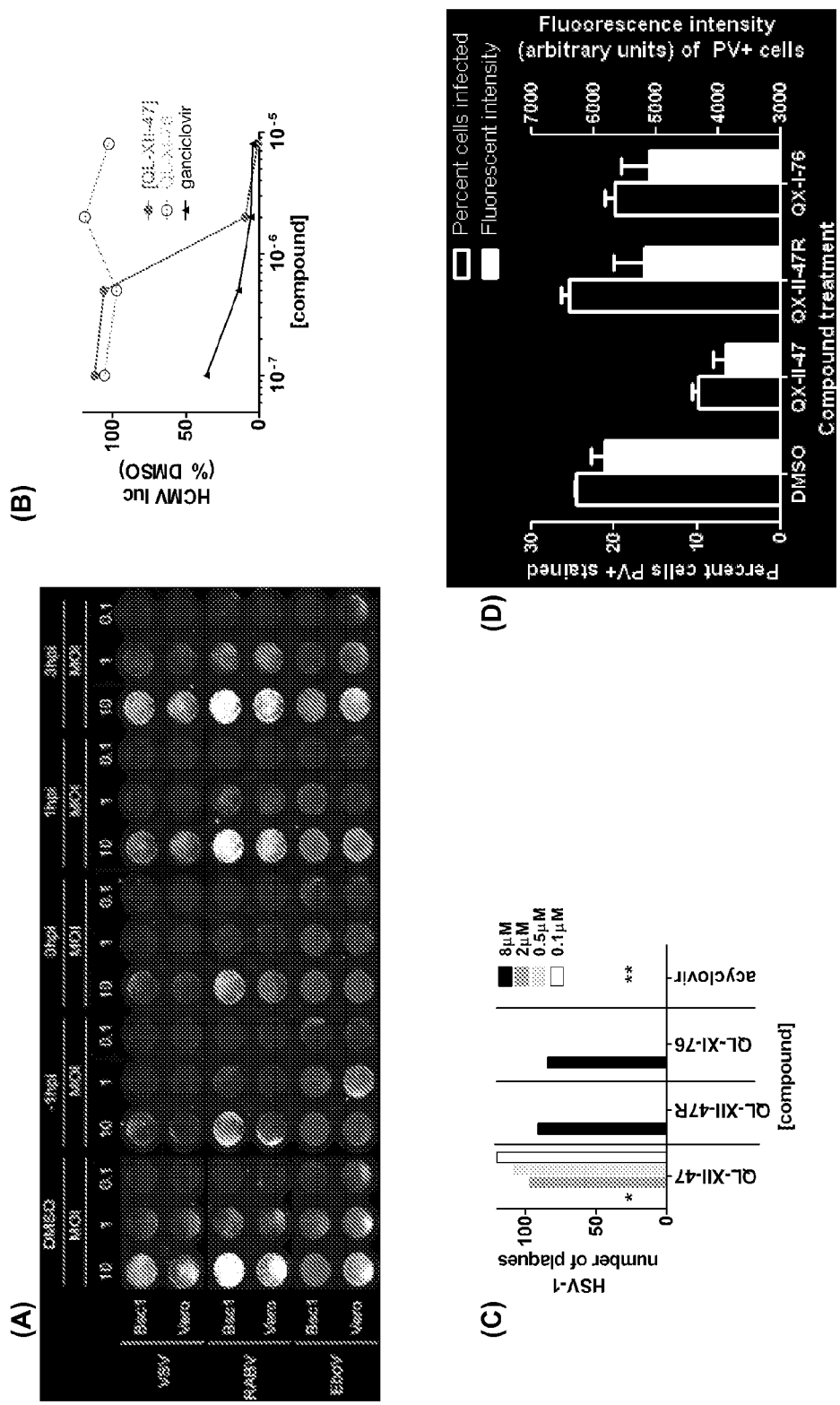
Figure 5A-D

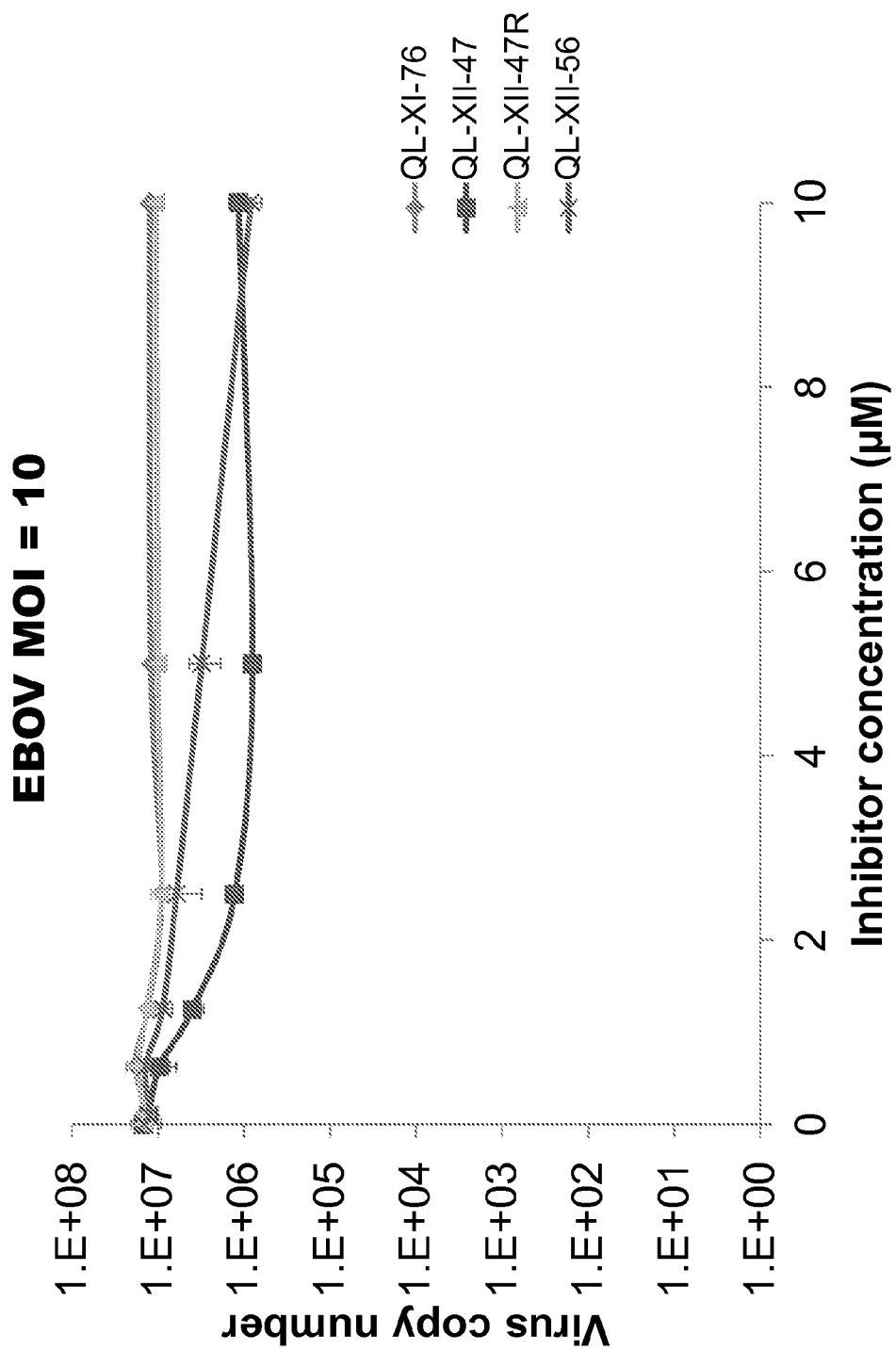
Figure 5G2

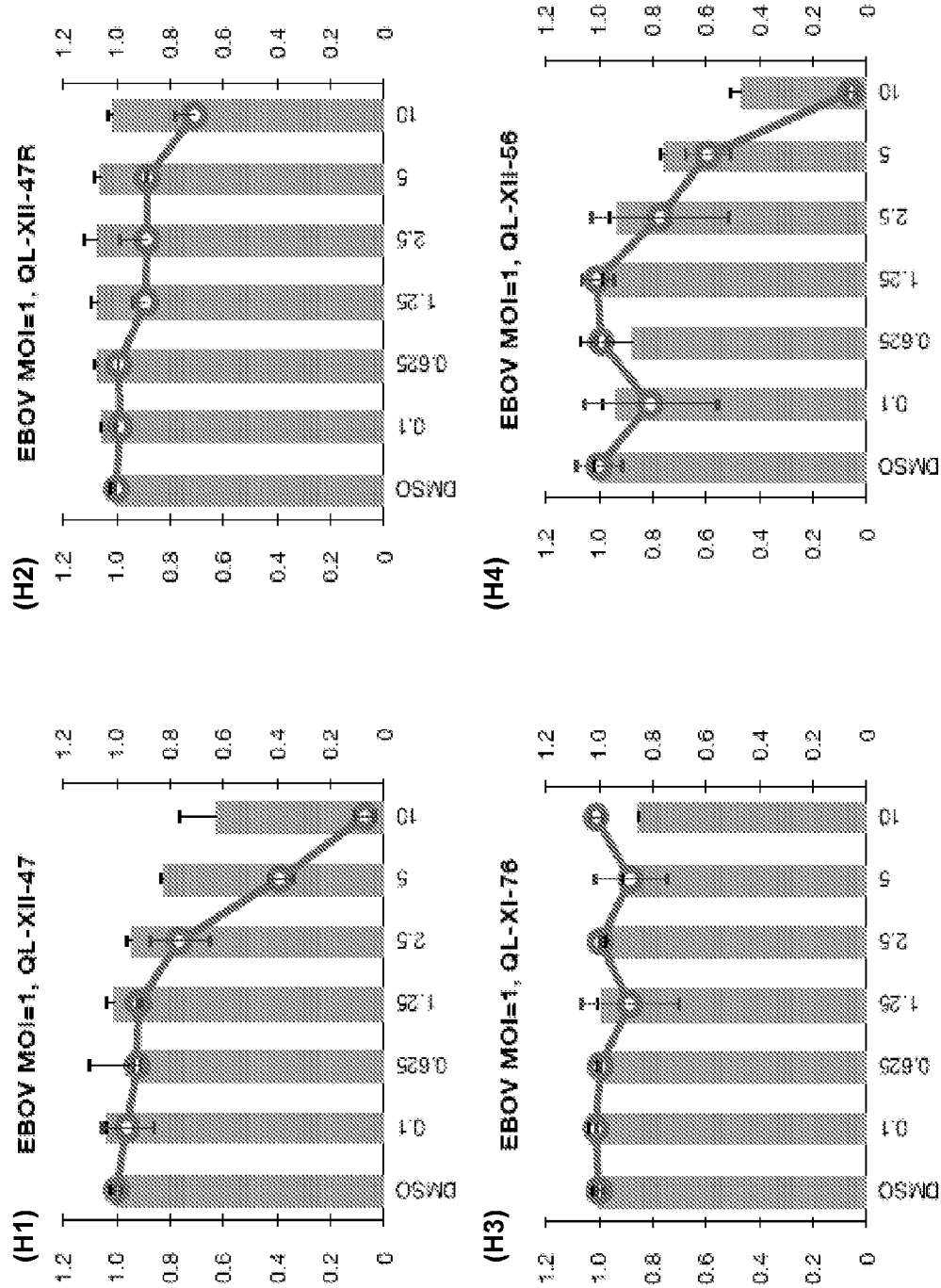
Figure 5H1-H4

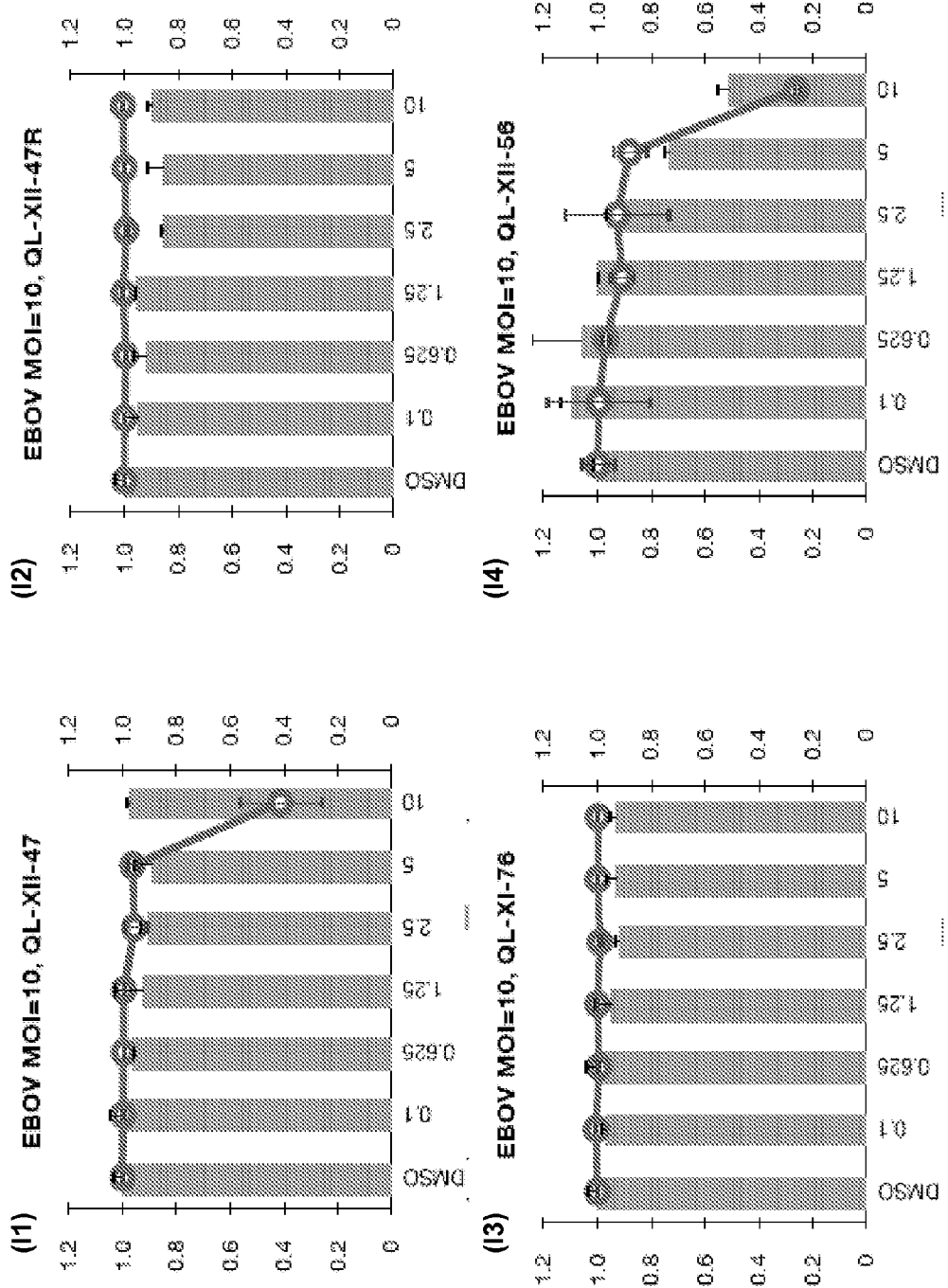
Figure 5I1-I4

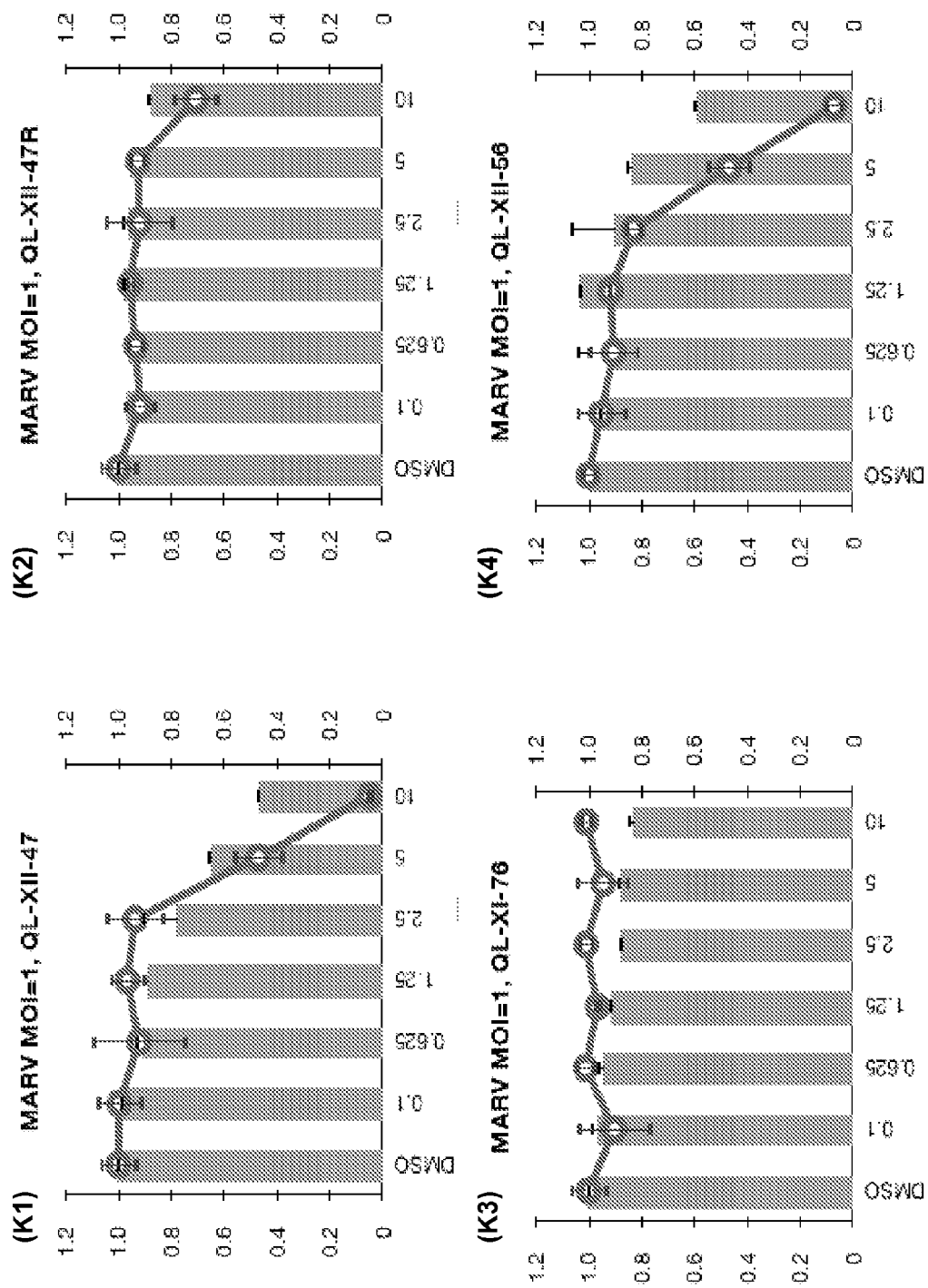
Figure 5K1-K4

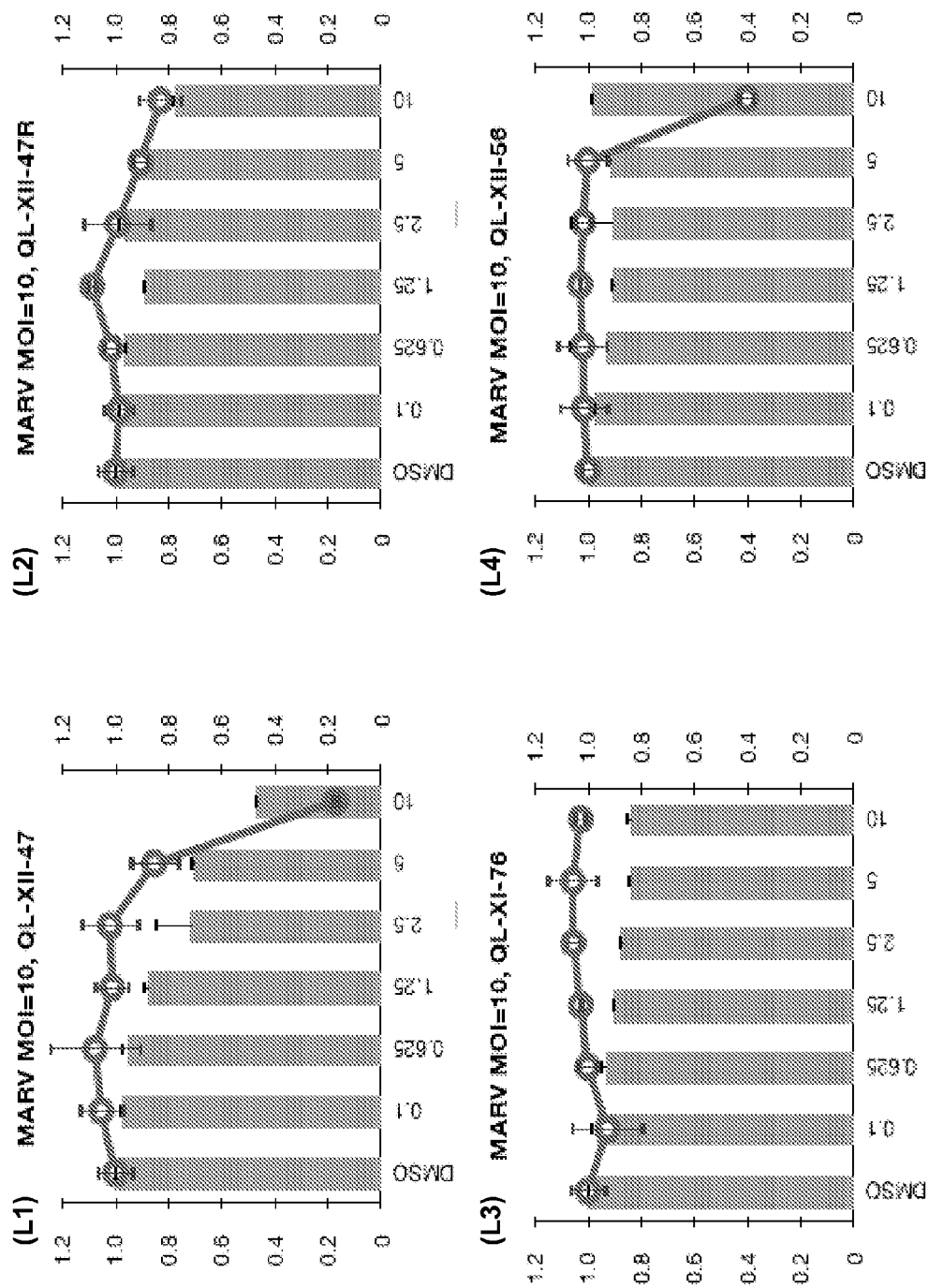
Figure 5L1-L4

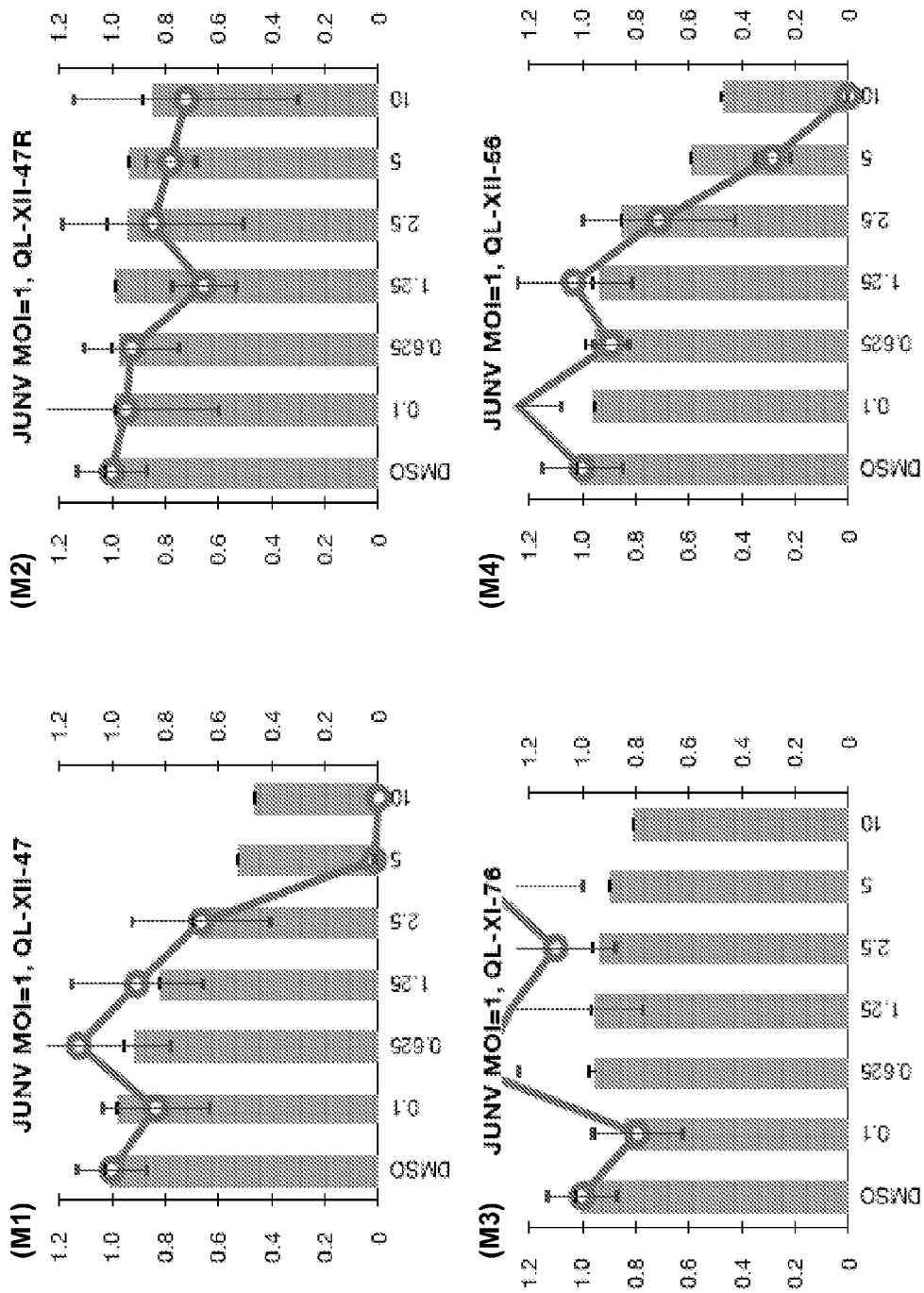
Figure 5M1-M4

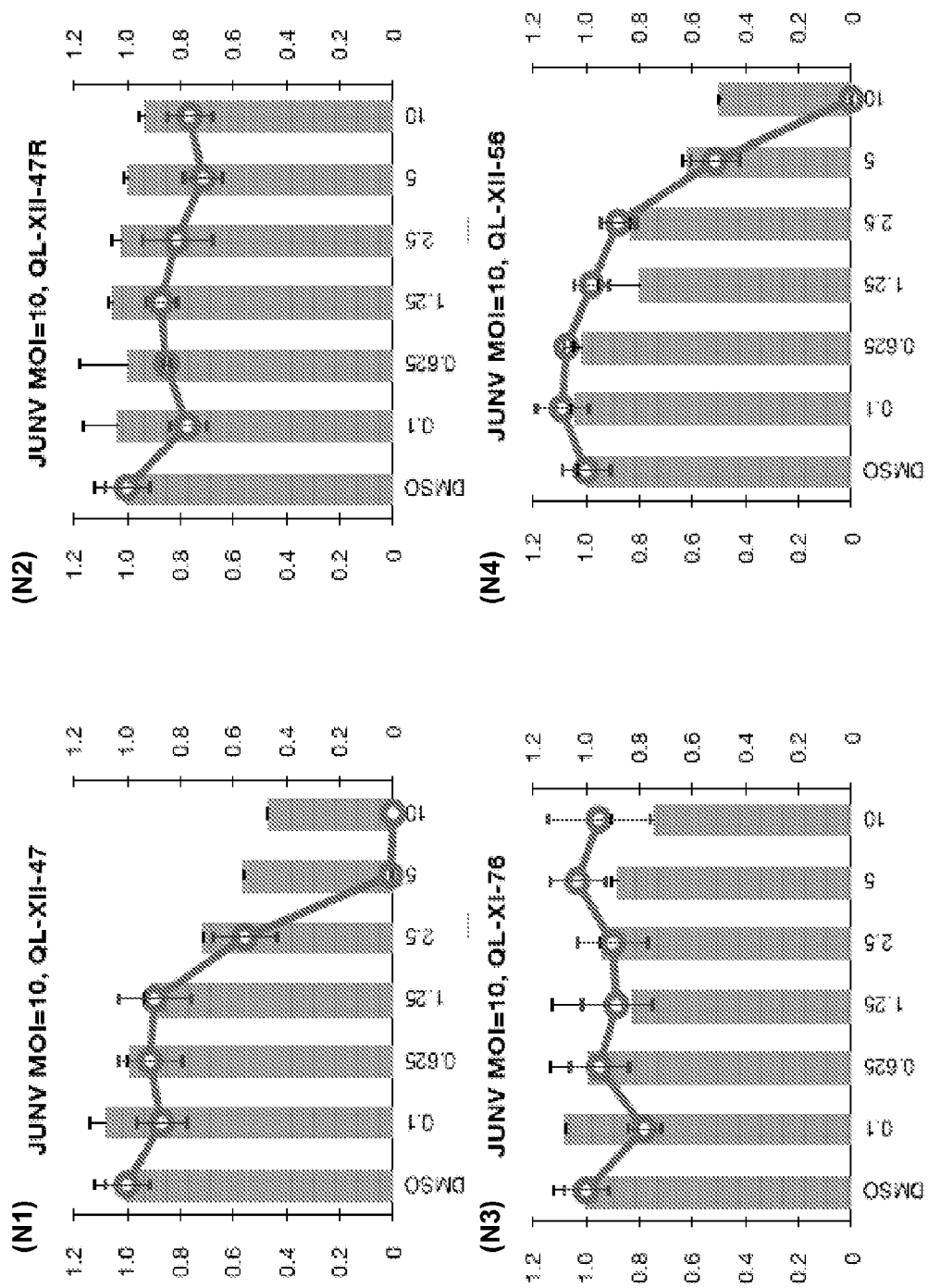
Figure 5N1-N4

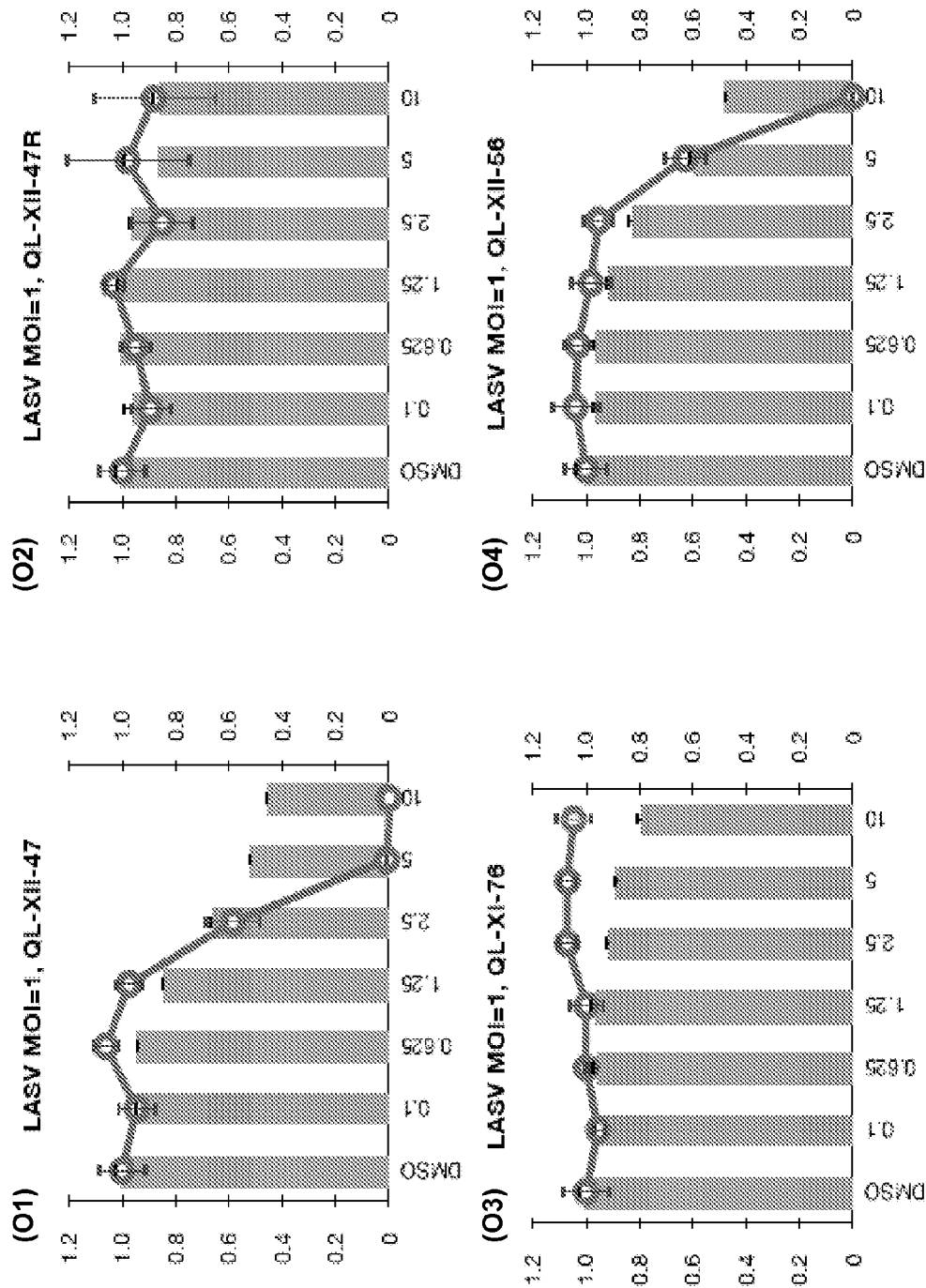
Figure 5O1-O4

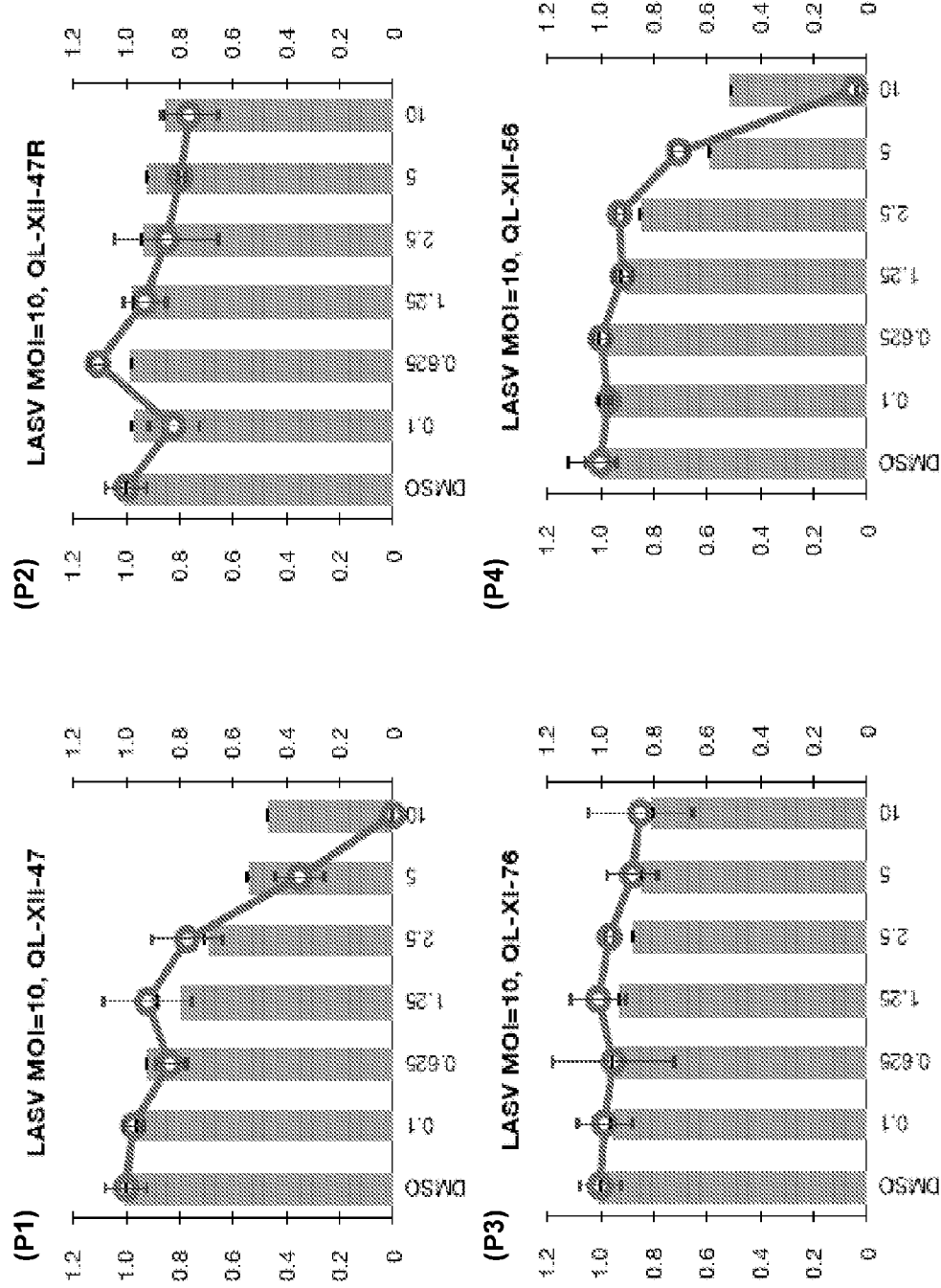
Figure 5P1-P4

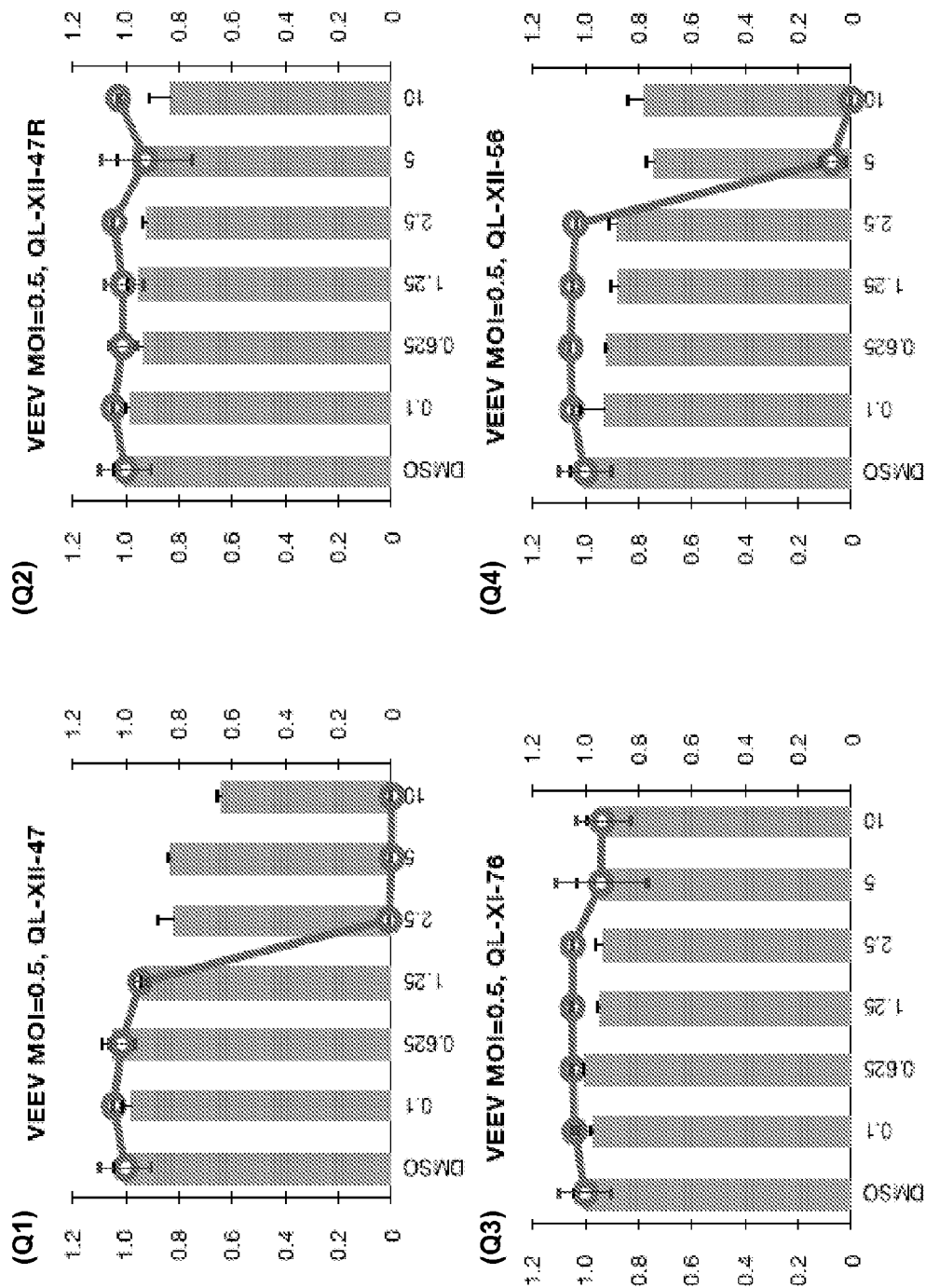
Figure 5Q1-Q4

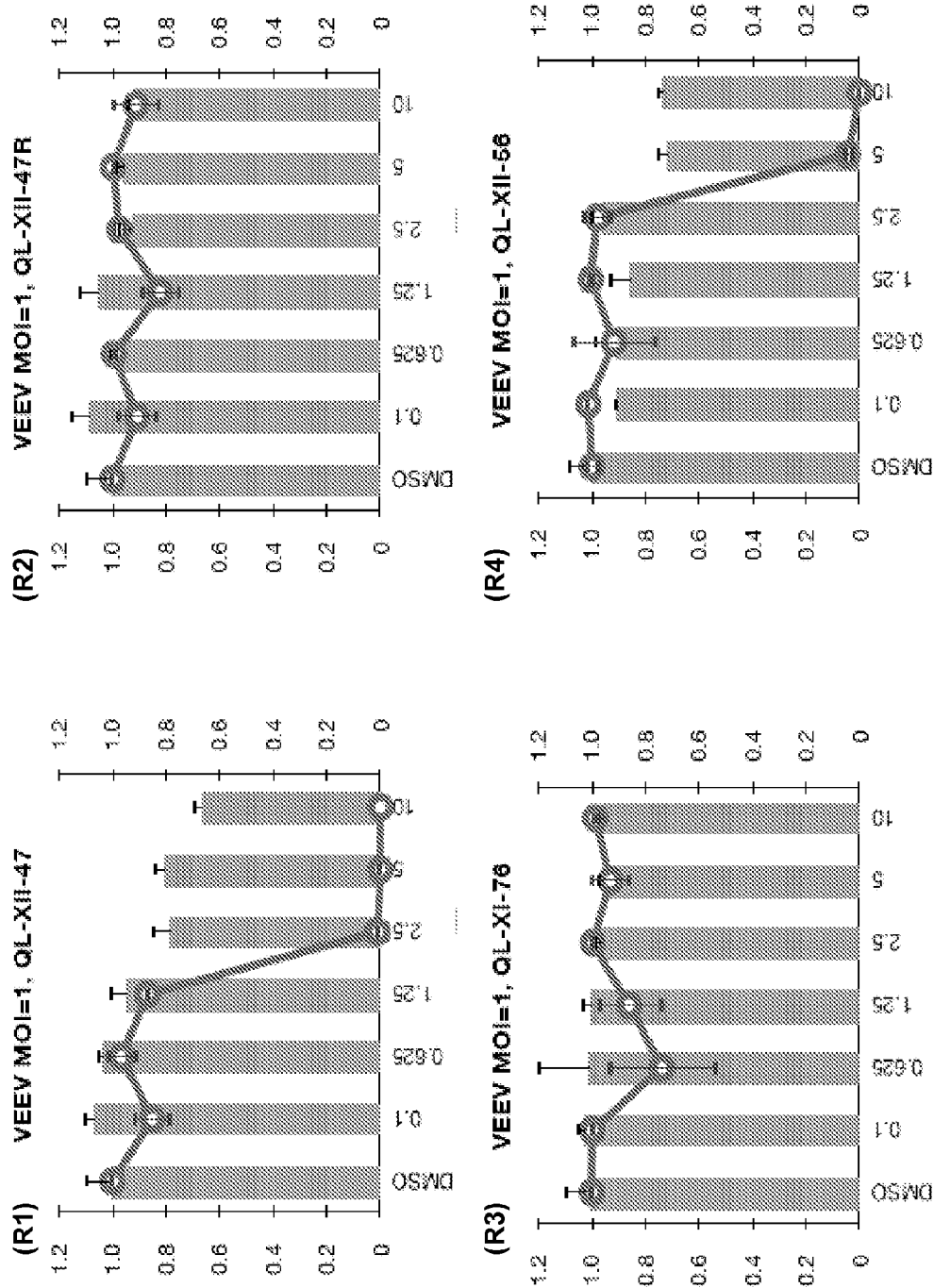
Figure 5R1-R4

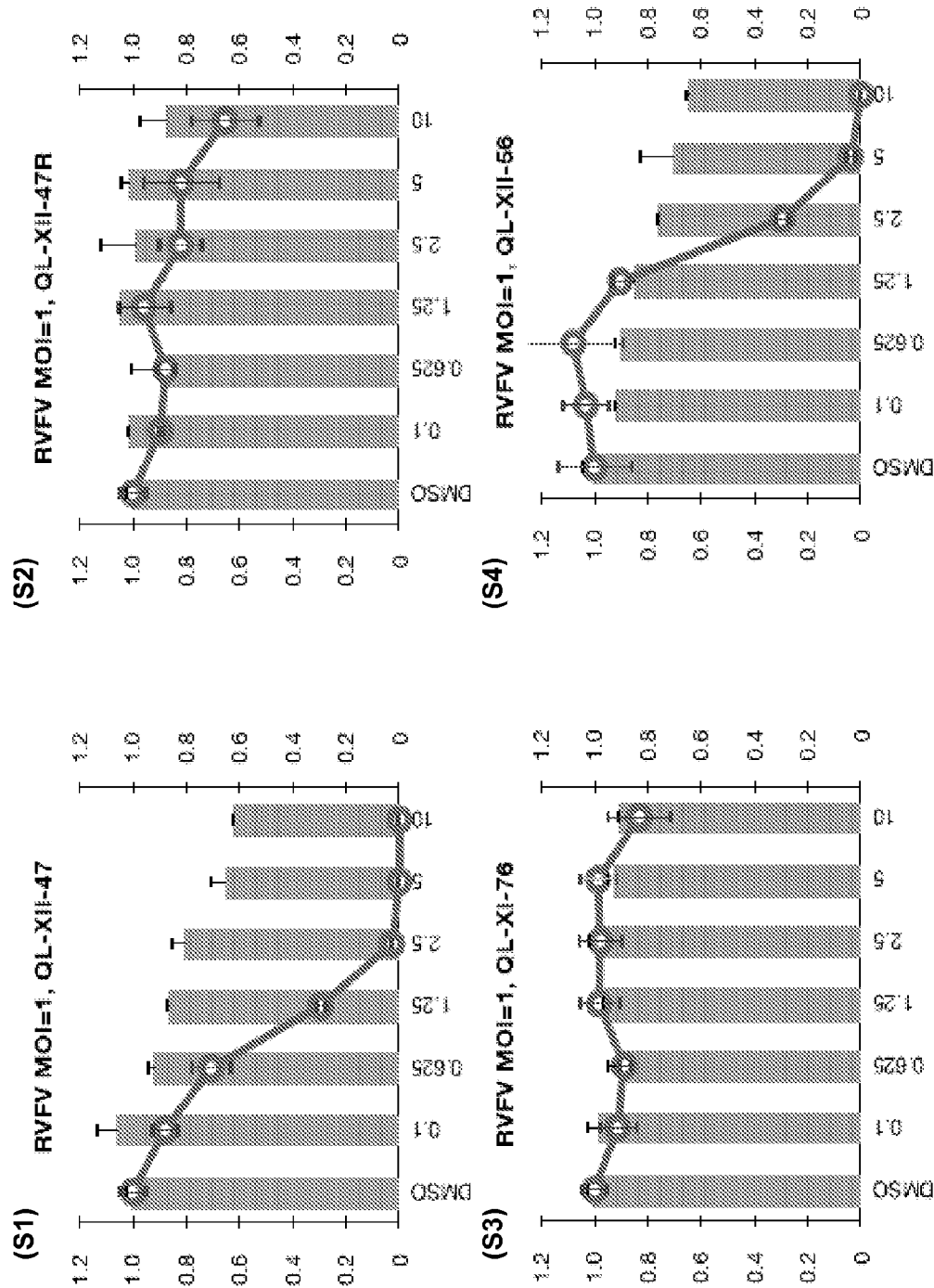
Figure 5S1-S4

Figure 5T1-T4

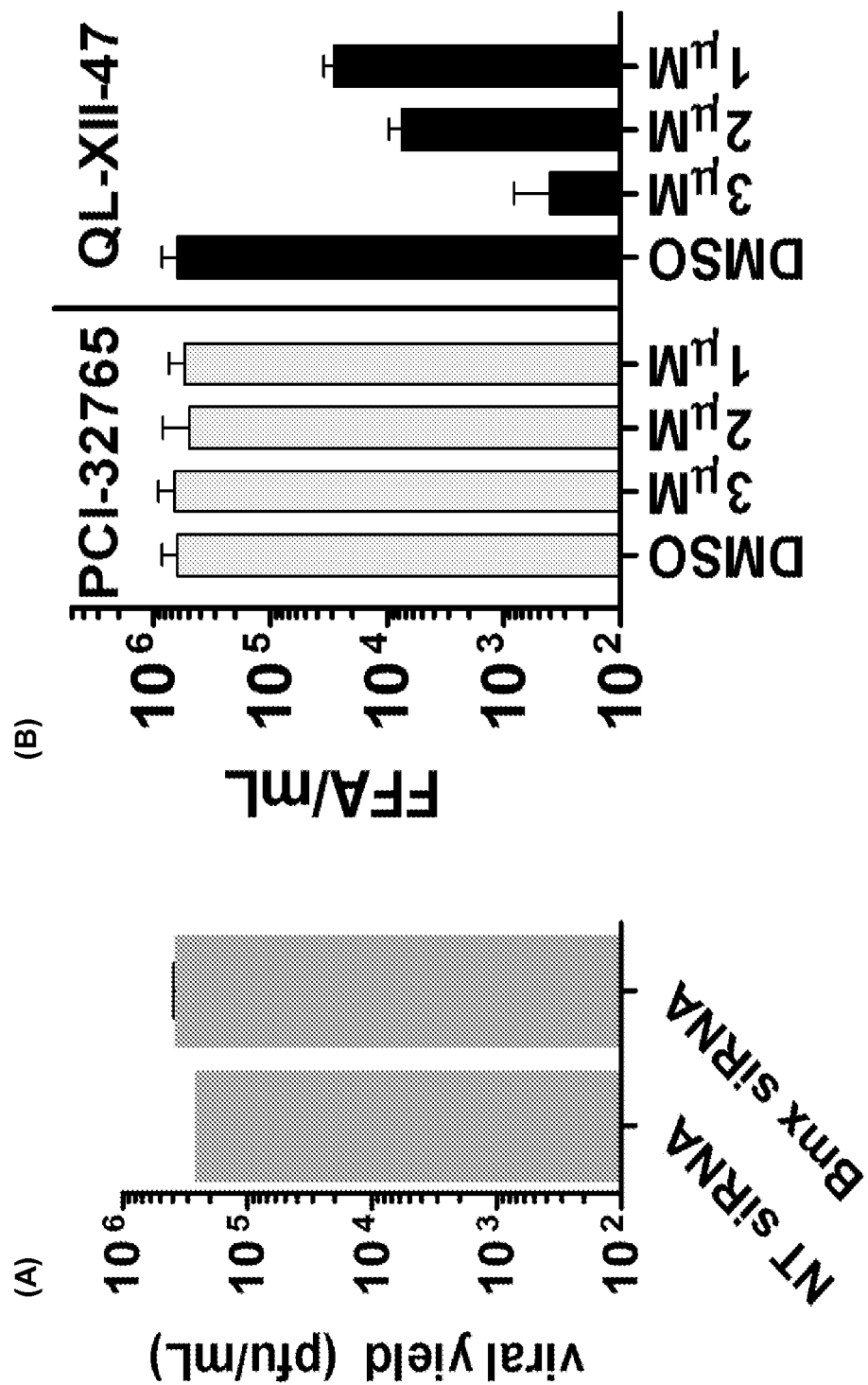
Figure 6A-B

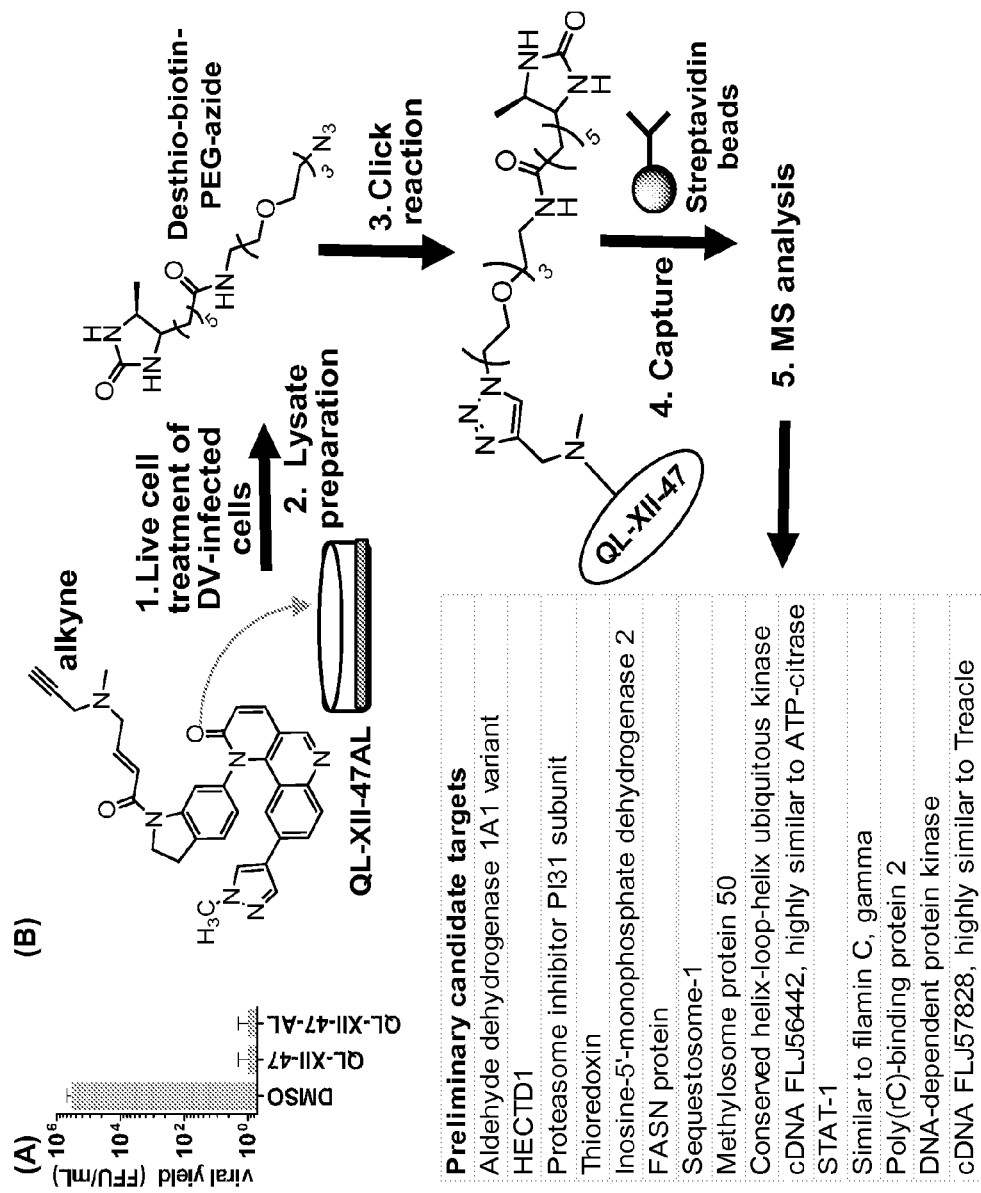
Figure 8A-B

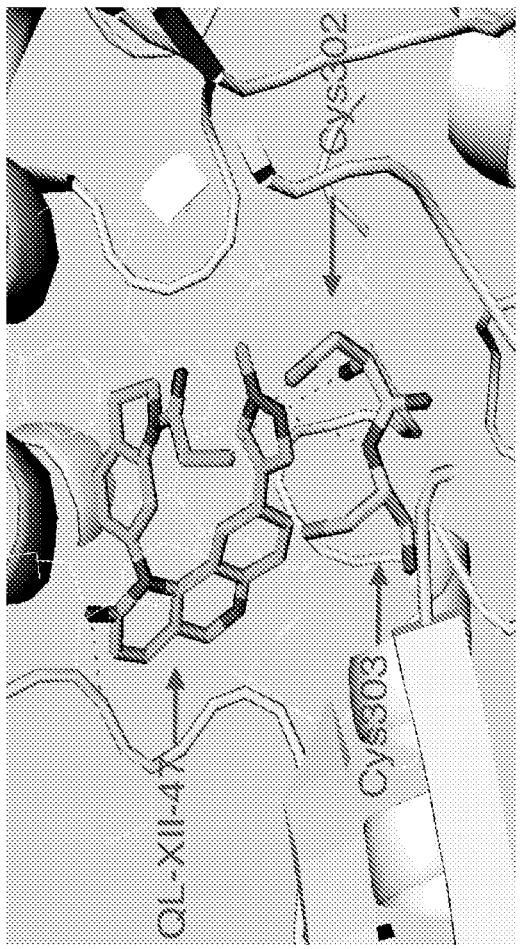
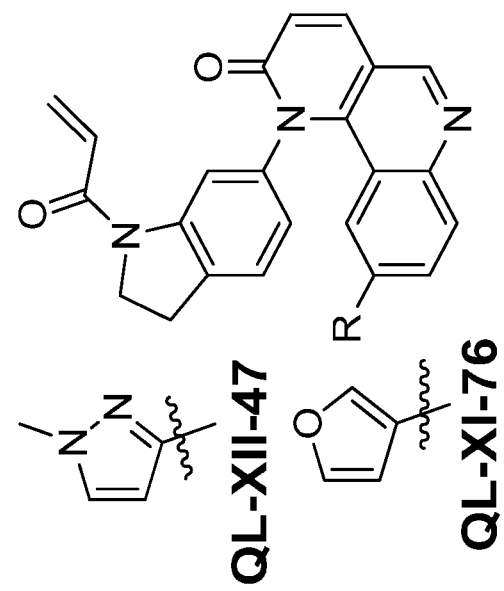
Figure 9A-B

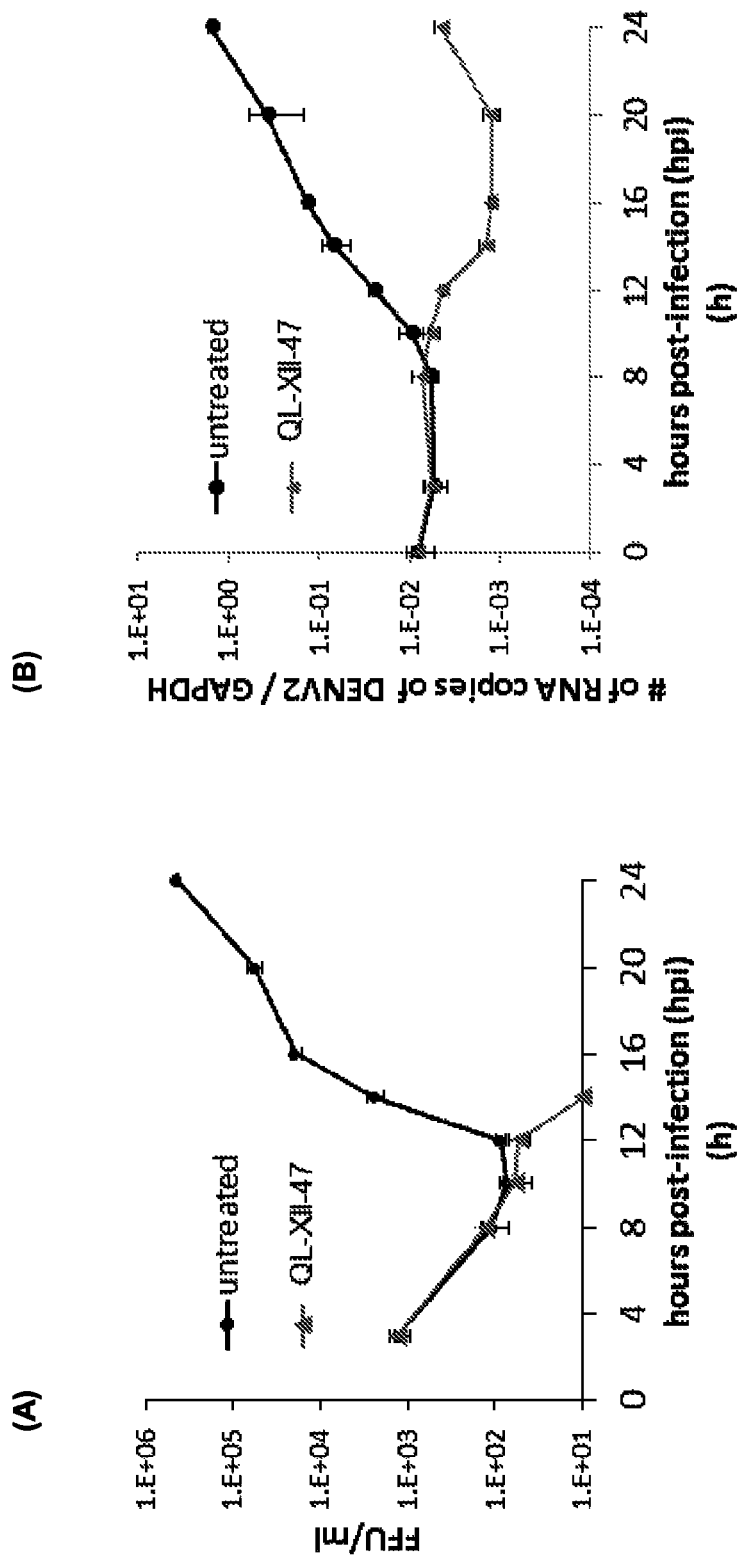
Figure 10A-B

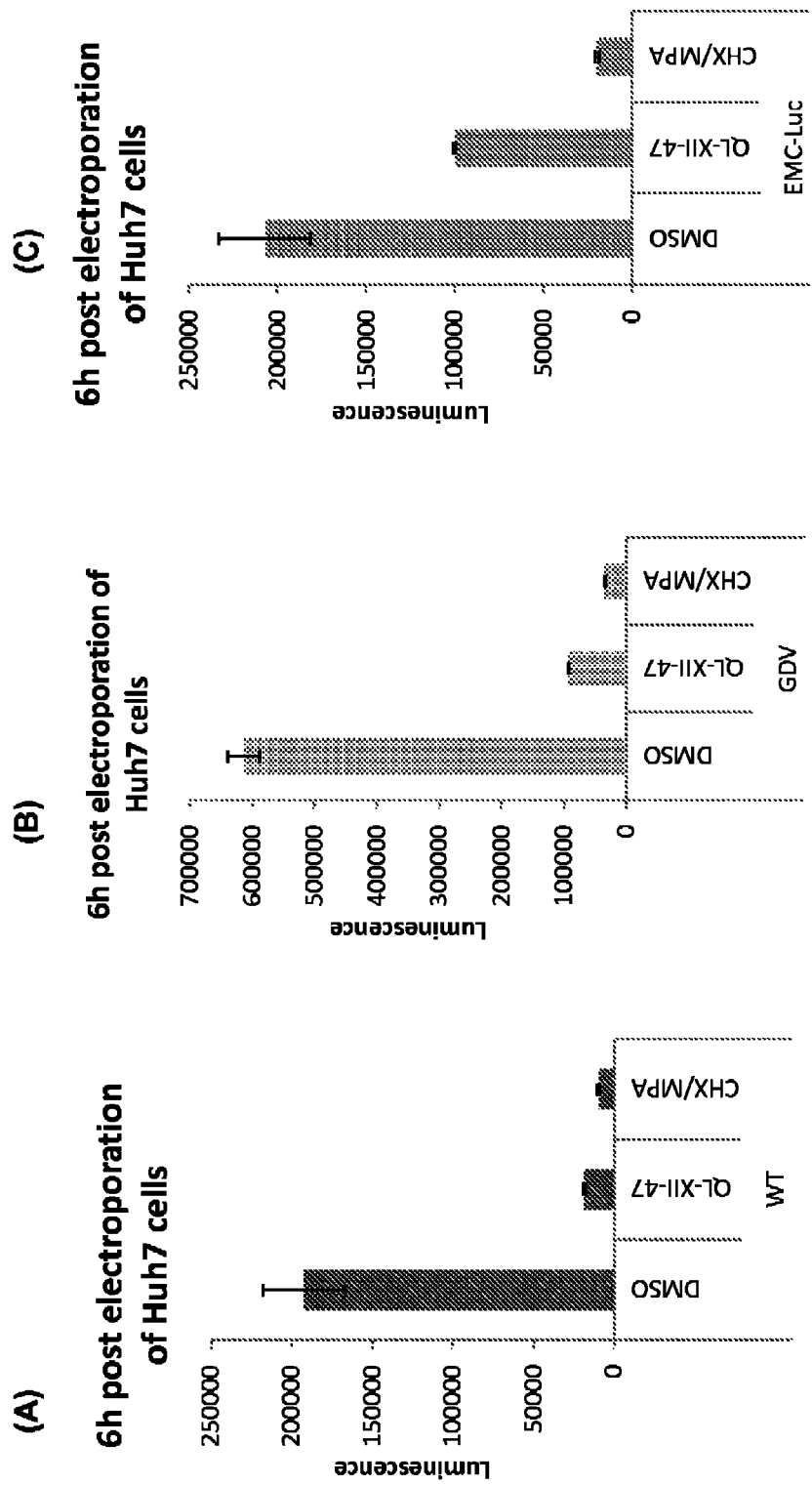
Figure 13A-C

Figure 15A-B

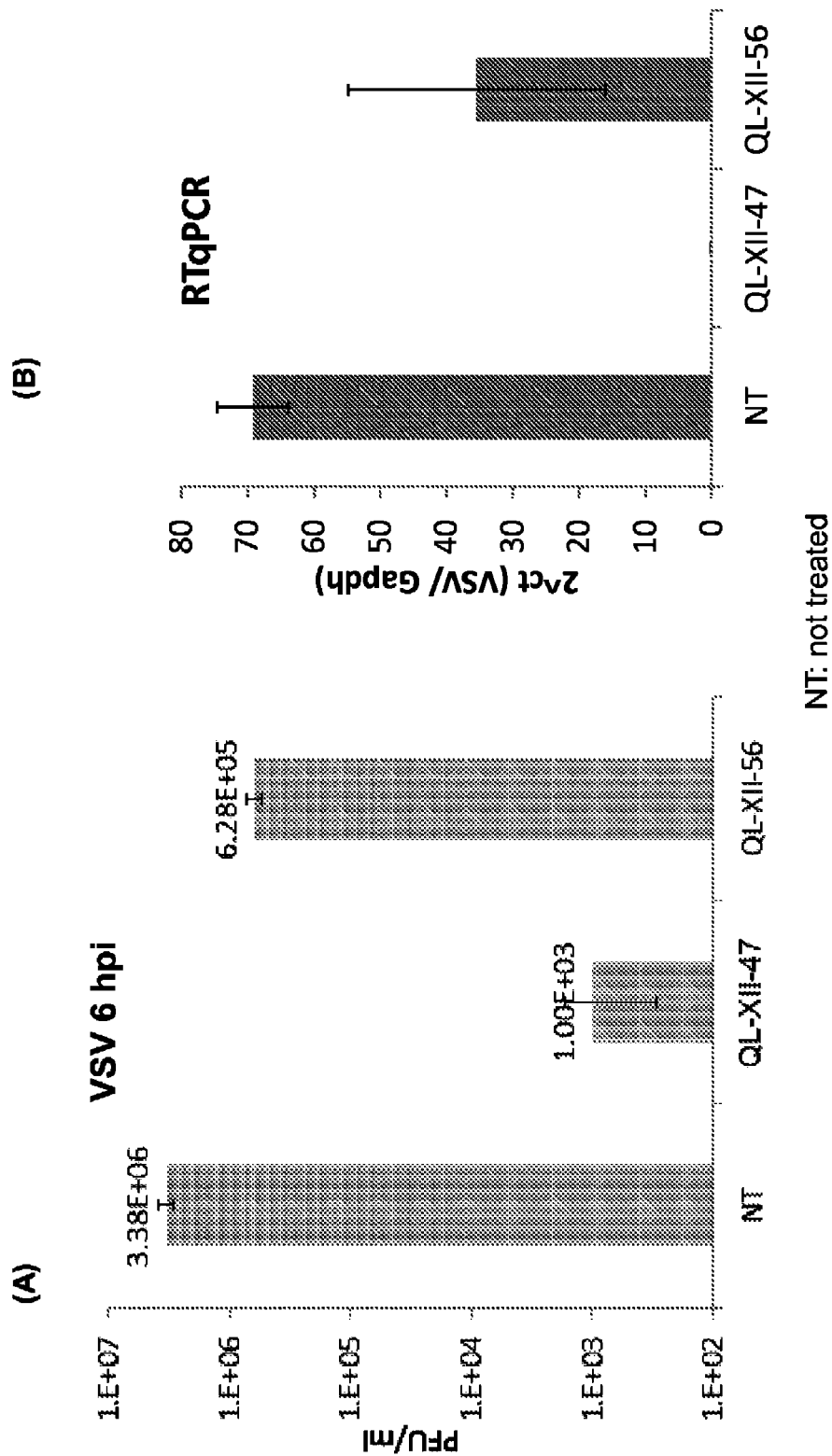
Figure 18A-B

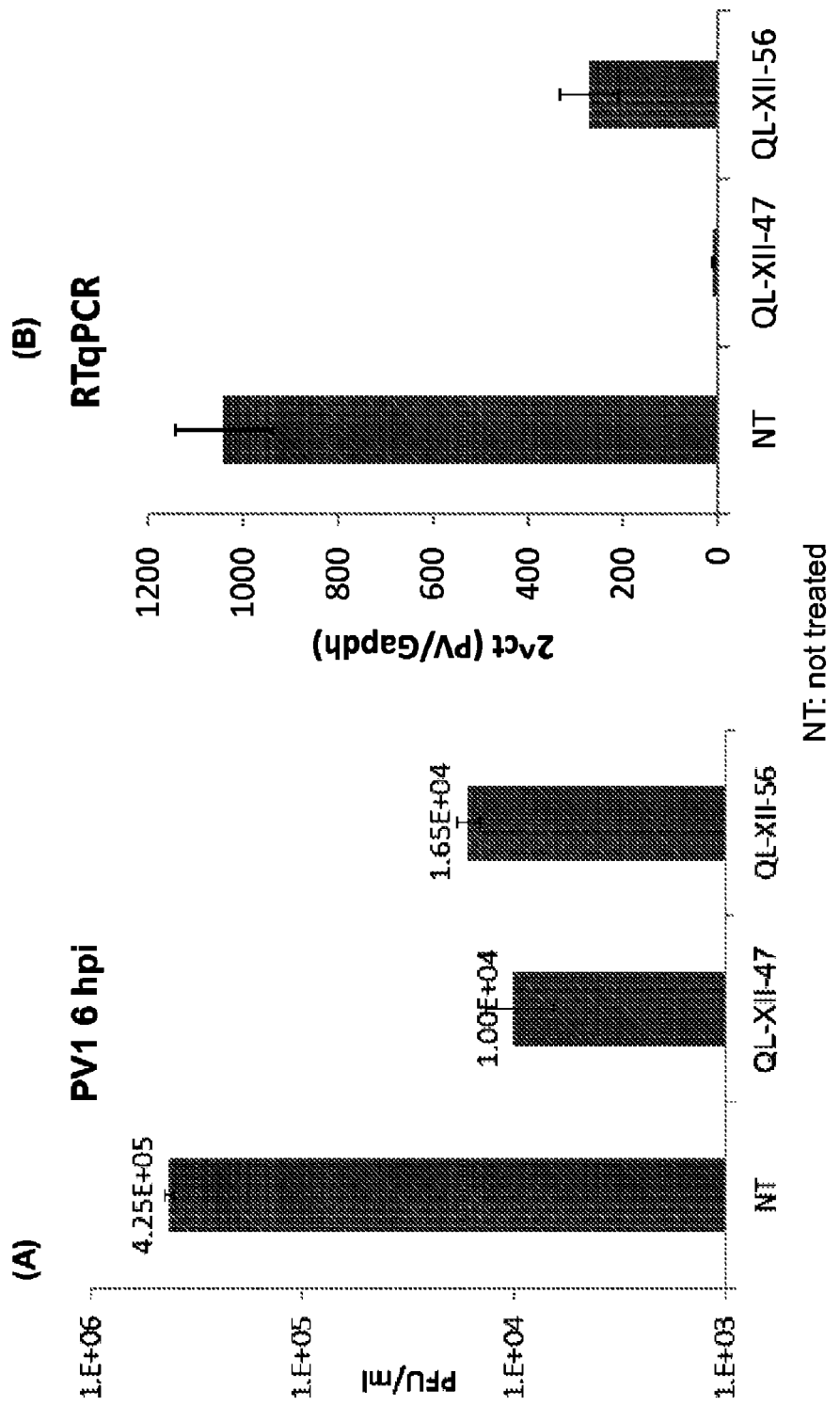
Figure 19A-B

| Compound No. | 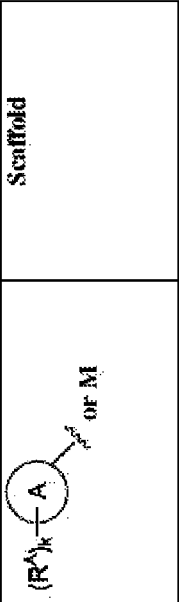 | 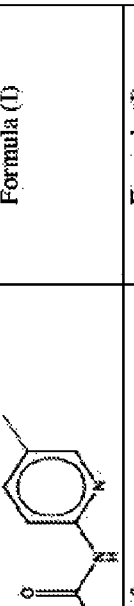 | Scaffold |
|---|---|---|---|
| QL-XI-57 | | | Formula (I) |
| QL-XI-55 | | | Formula (I) |
| QL-VI-50 | | | Formula (I) |
| QL-XI-65 | | | Formula (II) |
| QL-V-85 | | | Formula (I) |
Figure 20B

| Compound No. | | Scaffold |
|---|---|---|
| QL-IX-97 | | Formula (I) |
| QL-X-39 | | Formula (I) |
| QL-X-132 | | Formula (I) |
| QL-XI-99 | | Formula (III) |
| QL-XI-100 | | Formula (III) |

Figure 20C

| Compound No. | ![RD-L-C-(RC)m structure] | ![(RA)k-A or M structure] | Scaffold |
|---|---|---|---|
| QL-XI-75 | phenyl with acrylamide | thiophene | Formula (I) |
| QL-XII-01 | phenyl with acrylamide | furan-2-carboxamide | Formula (I) |
| QL-XII-03 | phenyl with acrylamide | pyridine | Formula (I) |
| QL-XII-37 | phenyl with acrylamide | phenyl-acetamide | Formula (I) |
| QL-XII-40 | phenyl with acrylamide | Cl | Formula (a) |
| QL-XII-58 | phenyl with acrylamide | substituted phenyl | Formula (I) |
| QL-XII-61 | phenyl with acrylamide | sulfonyl phenyl | Formula (I) |

| Compound No. | m-C) | (RA)k-A or M | Scaffold |
|---|---|---|---|
| QL-XII-56 | | | Formula (I) |
| QL-XII-115 | | | Formula (I) |
| QL-XII-54 | | | Formula (I) |
| QL-XII-38 | | Br | Formula (a) |
| QL-XII-45 | | | Formula (I) |
| QL-XII-46 | | | Formula (I) |

Figure 20F

| Compound No. | 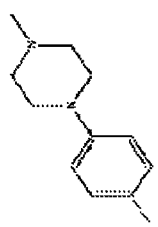 | 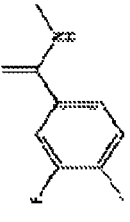 | Scaffold |
|---|---|---|---|
| QL-XII-91 | 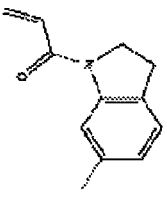 |  | Formula (I) |
| QL-XII-48 | 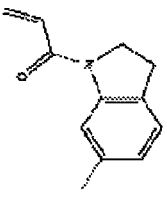 |  | Formula (I) |
| QL-XII-50 | 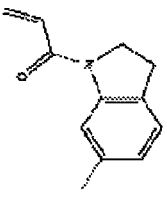 |  | Formula (I) |
| QL-XII-51 | 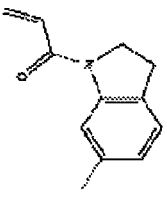 | | Formula (I) |
| QL-XII-47 |  | | Formula (I) |
Figure 20G

| Compound No. | | | Scaffold |
|---|---|---|---|
| QL-XII-44 | | | Formula (I) |

Figure 20H

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 1
aatatgctga aacgcgagag a                                                 21

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
gggattgtta ggaaacgaag g                                                 21

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
gagtcaacgg atttggtcgt                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
ttgattttgg agggatctcg                                                   20
```

HOST TARGETED INHIBITORS OF DENGUE VIRUS AND OTHER VIRUSES

RELATED APPLICATIONS

The present invention is a national stage filing under 35 U.S.C. §371 of international PCT application, PCT/US2013/032488, filed Mar. 15, 2013, which claims priority under 35 U.S.C. §119(e) to U.S. provisional patent application, U.S. Ser. No. 61/622,828, filed Apr. 11, 2012, each of which is incorporated herein by reference.

GOVERNMENT SUPPORT

This invention was made with Government support under grant numbers HG006097, R01AI076442, U54 CA156732-01, and U54AI057159 awarded by The National Institutes of Health. The government has certain rights in the invention.

BACKGROUND OF THE INVENTION

Dengue virus (DENV) is one of the most significant mosquito-borne viral infections affecting humans today and is an NIAID (National Institute of Allergy and Infectious Diseases) Category A Biodefense pathogen. DENV is a plus-stranded RNA virus and a member of the Flaviviridae family. The four Dengue virus serotypes (DENV1, DENV2, DENV3, and DENV4) are defined by the viral envelope protein (E) and share 60% sequence homology at the amino acid level. Due to the large number of people at risk for infection, DENV is the most widespread mosquito-borne virus affecting humans today. An estimated 2.5 billion people live in areas at risk for epidemic transmission, and an estimated 100 million people are infected with DENV annually. Infection with DENV is responsible for diseases ranging from Dengue fever to the much more severe and life-threatening Dengue hemorrhagic fever (DHF) and Dengue shock syndrome (DSS) that are characterized by vascular leakage. An estimated 500,000 cases of DHF and DSS occur annually and are associated with 2.5% fatality although fatality rates for DHF and DSS can exceed 20% if untreated (Dengue and Dengue haemorrhagic fever. Vol. 2010 (WHO Media Centre, 2010)).

The determinants of disease severity for DENV infection and the pathogenesis mechanisms underlying DHF and DSS are poorly understood. Vascular leakage, which is the hallmark of DHF, is largely believed to be caused by a host-mounted "cytokine storm" but is correlated with high levels of viremia, particularly early in infection (Halstead, *Science* (1988) 239:476-481; Gubler, *Dengue and Dengue Hemorrhagic Fever*; Guple et al., Ed.; CAB International: New York, 1997; Vol. 1; pp. 1-22; Vaughn et al., *J. Infect. Dis.* (2000) 181:2-9; Libraty et al., *J. Infect. Dis.* (2002) 185: 1213-1221; Wang et al., *Virology* (2003) 305:330-338; and Endy et al., *J. Infect. Dis.* (2004) 189:990-1000). In vivo data have suggested that therapies that lower Dengue viral burden can ameliorate the inflammatory "cytokine storm" associated with DHF or DSS.

The strong correlation between viral load and disease severity suggests that antivirals that inhibit DENV and reduce viral burden might reduce the severity of DENV-associated disease. Peak virus titers on the order of $10^7$ to $10^8$ $MID_{50}$/mL (median infectious dose/mL plasma) were found in patients with Dengue fever; patients with DHF or DSS exhibited titers 100-fold and 1000-fold higher, respectively (Vaughn et al., *J. Infect. Dis.* (2000) 181:2-9; and Libraty et al., *J. Infect. Dis.* (2002) 185:1213-1221). Additional studies of viremia and estimated infected cell mass confirm this (Libraty et al., *J. Infect. Dis.* (2002) 185:1213-1221; Wang et al., *Virology* (2003) 305:330-338; Libraty et al., *J. Infect. Dis.* (2002) 186:1165-1168; Wang et al., *Clin. Infect. Dis.* (2006) 43:1023-1030; and Halstead, Dengue. *Lancet* (2007) 370:1644-1652). Recent experimental support for the potential efficacy of anti-DENV therapeutics includes the demonstration that reduction of virus titers by 70-93% was associated with a reduction in serum levels of inflammatory cytokines (i.e., IL6, TNFα, IL12p70, and MCP-1) in a mouse model of Dengue fever (Schul et al., *J. Infect. Dis.* (2007) 195:665-674). These effects were observed with 7-DMA, a compound with modest activity against the DENV RNA-dependent polymerase ($EC_{50}$ 15 μM) (Wu et al., *J. Virology* (2002) 76:3596-3604).

Despite the spread of the four DENV serotypes worldwide and the increasing incidence of DHF and DSS over the past fifty years, there currently are no specific therapeutics to combat DENV infection or a vaccine that protects against all four DENV serotypes. It remains an open question whether immunization directed towards a limited set of epitopes conserved across all DENV serotypes can elicit tetravalent protective immunity or if a successful vaccine will require four distinct type-specific responses. Further complicating DENV vaccine development is the potential for non-neutralizing antibody responses to enhance the infection of immune cells and to exacerbate the disease due to the interaction of the antibody Fc region with activating Fcγ receptors (FcγR) on immune cells, a phenomenon known as antibody-dependent enhancement of infection (ADE). Currently, the only treatment for DHF or DSS is supportive care primarily maintaining the patient's circulating fluid volume. Thus, while continuing efforts to develop a protective tetravalent vaccine are imperative, alternative strategies to prevent and control DENV infection are also urgently needed.

SUMMARY OF THE INVENTION

Antiviral agents that act via a host target may have higher barriers to resistance and broader inhibitory activity against multiple viral pathogens, compared with antivirals that act via a viral target. Novel compounds are provided that show efficacy against Flaviviridae viruses (e.g., all four Dengue serotypes (DENV1, DENV2, DENV3, and DENV4)), Kunjin virus, Japanese encephalitis virus, vesicular stomatitis virus, Junin virus, Ebola virus, Marburg virus (MARV), Lassa fever virus (LASV), Venezuelan equine encephalitis virus (VEEV), Rift Valley Fever virus (RVFV), and other viruses. Without wishing to be bound by a particular theory, these compounds are thought to covalently modify cysteine residues of a host target. These compounds suggest a new paradigm for developing broad-based antiviral agents.

The present invention provides compounds of Formula (I), and pharmaceutically acceptable salts, solvates, hydrates, polymorphs, co-crystals, tautomers, stereoisomers, isotopically labeled derivatives, prodrugs, and compositions thereof. The present invention further provides methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of viruses, to treat or prevent infectious diseases caused by viruses, to reduce viral load in a subject, and to screen a compound library to identify compounds that prevent or inhibit entry of viruses into host cells. Also provided are kits, containing one or more inventive compounds, or compositions thereof, for treating or preventing infectious diseases.

In one aspect, the present invention provides compounds of Formula (I):

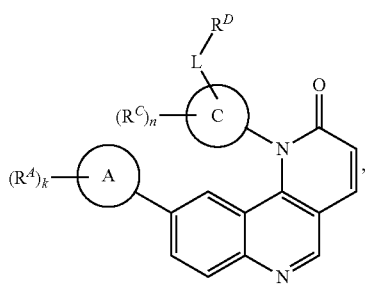

(I)

or a pharmaceutically acceptable salt, solvate, hydrate, polymorph, co-crystal, tautomer, stereoisomer, isotopically labeled derivative, or prodrug thereof;
wherein Ring A, Ring C, $R^A$, $R^C$, $R^D$, L, k, and n are as defined herein.

In one aspect, the present invention provides compounds of Formula (II):

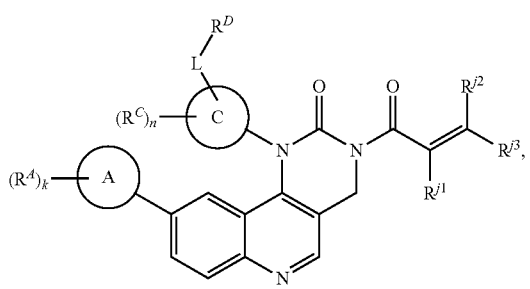

(II)

or a pharmaceutically acceptable salt, solvate, hydrate, polymorph, co-crystal, tautomer, stereoisomer, isotopically labeled derivative, or prodrug thereof;
wherein Ring A, Ring C, $R^A$, $R^C$, $R^D$, $R^{j1}$, $R^{j2}$, $R^{j3}$, L, k, and n are as defined herein.

In one aspect, the present invention provides compounds of Formula (III):

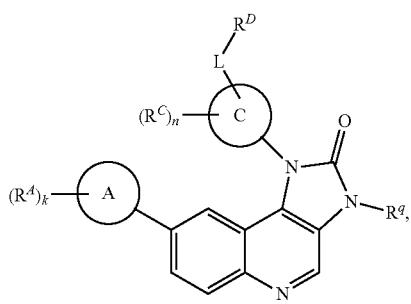

(III)

or a pharmaceutically acceptable salt, solvate, hydrate, polymorph, co-crystal, tautomer, stereoisomer, isotopically labeled derivative, or prodrug thereof;

wherein Ring A, Ring C, $R^A$, $R^C$, $R^D$, $R^q$, L, k, and n are as defined herein.

Exemplary compounds of Formula (I) include, but are not limited to:

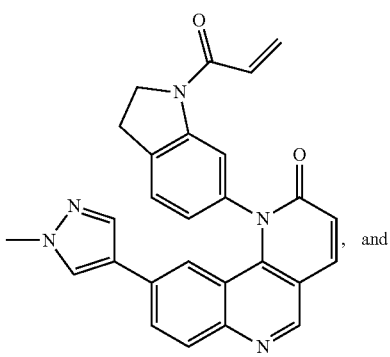

(QL-XII-47)

and

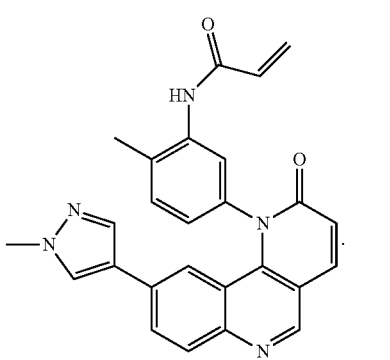

(QL-XII-56)

In another aspect, the present invention provides pharmaceutical compositions including a compound of Formula (I), (II), or (III), or a pharmaceutically acceptable salt, solvate, hydrate, polymorph, co-crystal, tautomer, stereoisomer, isotopically labeled derivative, or prodrug thereof, and optionally a pharmaceutically acceptable excipient.

In still another aspect, the invention provides methods for the treatment of infectious diseases in a subject caused by viruses, methods for reducing viral load in a subject, and methods of preventing viral infections in a subject who was or may be exposed to viruses. The viruses, the infection of which may be treated or prevented by the inventive methods, include Flaviviridae viruses (e.g., Dengue virus (DENY), including Dengue virus 1 (DENV1), Dengue virus 2 (DENV2), Dengue virus 3 (DENV3), and Dengue virus 4 (DENV4); West Nile virus; tick-borne encephalitis virus; yellow fever virus; hepatitis C virus; hepatitis G virus; bovine viral diarrhea; classical swine fever virus; and hog cholera virus), Kunjin virus, Japanese encephalitis virus, vesicular stomatitis virus (VSV), vesicular stomatitis virus (VSV) pseudotyped with rabies glycoprotein, vesicular stomatitis virus (VSV) pseudotyped with Ebola glycoprotein, herpes simplex virus 1 (HSV-1), human cytomegalovirus (HCMV), poliovirus, Junin virus, Ebola virus, Marburg virus (MARV), Lassa fever virus (LASV), Venezuelan equine encephalitis virus (VEEV), and Rift Valley Fever virus (RVFV). The infectious diseases being treated or prevented by the inventive methods include, but are not limited to, dengue fever, dengue hemorrhagic fever, and dengue shock syndrome (DSS). The methods of the invention include administering to the subject a therapeutically or prophylactically effective amount of a compound of the invention, or a pharmaceutically acceptable salt, solvate, hydrate, polymorph, co-crystal, tautomer, stereoisomer, isotopically labeled derivative, or prodrug thereof.

In yet another aspect, the present invention provides methods of screening a library of compounds to identify one or more compounds that prevent or inhibit entry of a virus into a host cell. The methods of screening a library include providing at least two different compounds of the invention, or pharmaceutically acceptable salts, solvates, hydrates, polymorphs, co-crystals, tautomers, stereoisomers, isotopically labeled derivatives, or prodrugs thereof; and performing at least one assay using the different compounds of the invention, or pharmaceutically acceptable salts, solvates, hydrates, polymorphs, co-crystals, tautomers, stereoisomers, isotopically labeled derivatives, or prodrugs thereof, to detect entry of the virus into the host cell.

Another aspect of the present invention relates to uses of the inventive compounds, and pharmaceutically acceptable salts, solvates, hydrates, polymorphs, co-crystals, tautomers, stereoisomers, isotopically labeled derivatives, prodrugs, and pharmaceutical compositions thereof, for treating or preventing an infectious disease in a subject suffering therefrom.

In another aspect, the invention provides kits for treating or preventing an infectious disease (e.g., a viral disease). The inventive kits include a first container containing a therapeutically effective amount of a compound of the invention, or a pharmaceutically acceptable salt, solvate, hydrate, polymorph, co-crystal, tautomer, stereoisomer, isotopically labeled derivative, or prodrug thereof; and instructions for administering the compound to a subject to treat or prevent the infectious disease. A kit may include multiple unit dosages, for example, for multiple days of treatment.

The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., Inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers," and those that are non-superimposable mirror images of each other are termed "enantiomers". When a compound has an asymmetric center, for example, a carbon atom of the compound is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates plane polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1 ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

As used herein, a "hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^A H(C^B H_2 C^C H_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

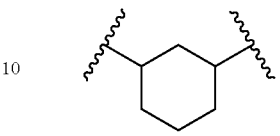

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C≡C and/or C═C bonds anywhere in the hydrocarbon chain. For instance, —CH═CH—$(CH_2)_2$—, —$CH_2$—C≡C—$CH_2$—, and —C≡C—CH═CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2H_5)$— and $CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

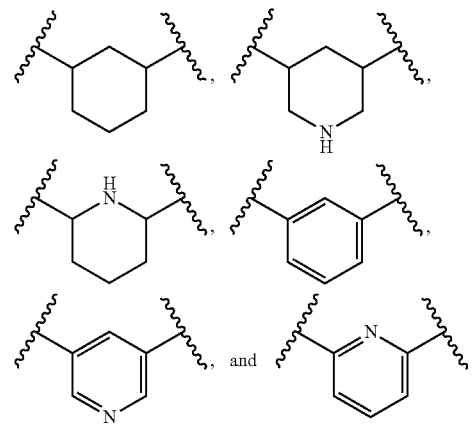

are all examples of a hydrocarbon chain. In contrast, in certain embodiments,

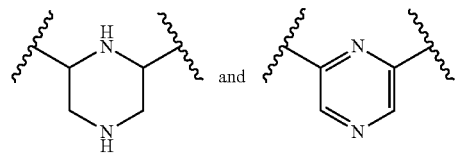 [SMILES: *C1CNCC(*)N1 ; *c1cncc(*)n1]

are not within the scope of the hydrocarbon chains described herein. In certain embodiments, the hydrocarbon chains is alkylene. In certain embodiments, the hydrocarbon chains is alkenylene. In certain embodiments, the hydrocarbon chains is alkynylene.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6 heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (arylheteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix —ene, e.g., alkylene, alkenylene, alkynylene, carbocyclylene, heterocyclylene, arylene, and heteroarylene.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)

($C_{1-6}$ alkyl), —$CO_2H$, —$CO_2(C_{1-6}$ alkyl), —$OC(=O)(C_{1-6}$ alkyl), —$OCO_2(C_{1-6}$ alkyl), —$C(=O)NH_2$, —$C(=O)N(C_{1-6}$ alkyl)$_2$, —$OC(=O)NH(C_{1-6}$ alkyl), —$NHC(=O)(C_{1-6}$ alkyl), —$N(C_{1-6}$ alkyl)$C(=O)(C_{1-6}$ alkyl), —$NHCO_2(C_{1-6}$ alkyl), —$NHC(=O)N(C_{1-6}$ alkyl)$_2$, —$NHC(=O)NH(C_{1-6}$ alkyl), —$NHC(=O)NH_2$, —$C(=NH)O(C_{1-6}$ alkyl), —$OC(=NH)(C_{1-6}$ alkyl), —$OC(=NH)OC_{1-6}$ alkyl, —$C(=NH)N(C_{1-6}$ alkyl)$_2$, —$C(=NH)NH(C_{1-6}$ alkyl), —$C(=NH)NH_2$, —$OC(=NH)N(C_{1-6}$ alkyl)$_2$, —$OC(NH)NH(C_{1-6}$ alkyl), —$OC(NH)NH_2$, —$NHC(NH)N(C_{1-6}$ alkyl)$_2$, —$NHC(=NH)NH_2$, —$NHSO_2(C_{1-6}$ alkyl), —$SO_2N(C_{1-6}$ alkyl)$_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl)$_3$, —$OSi(C_{1-6}$ alkyl)$_3$-$C(=S)N(C_{1-6}$ alkyl)$_2$, $C(=S)NH(C_{1-6}$ alkyl), $C(=S)NH_2$, —$C(=O)S(C_{1-6}$ alkyl), —$C(=S)SC_{1-6}$ alkyl, —$SC(=S)SC_{1-6}$ alkyl, —$P(=O)_2(C_{1-6}$ alkyl), —$P(=O)(C_{1-6}$ alkyl)$_2$, —$OP(=O)(C_{1-6}$ alkyl), —$OP(=O)(OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —$C(=O)R^{aa}$, —CHO, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$C(=O)NR^{bb}SO_2R^{aa}$, —$C(=S)N(R^{bb})_2$, —$C(=O)SR^{aa}$, or —$C(=S)SR^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{aa}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —$C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (t-butoxycarbonyl, BOC, or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-diethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, t-butoxycarbonyl (BOC or Boc), (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3$, $—P(=O)_2R^{aa}$, $—P(=O)(R^{aa})_2$, $—P(=O)(OR^{cc})_2$, $—P(=O)_2N(R^{bb})_2$, and $—P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "leaving group" is a molecular fragment that departs with a pair of electrons in heterolytic bond cleavage. As used herein, the term "leaving group" is given its ordinary meaning in the art of synthetic organic chemistry and refers to an atom or a group capable of being displaced by a nucleophile. Usually a leaving group is a substituent that is present on a chemical compound that is capable of being displaced by another group. Leaving groups can be anions or neutral molecules. Examples of suitable leaving groups include, but are not limited to, halides (such as fluoride, chloride, bromide, and iodide), esters, thioesters, phosphates, sulfates, sulfinates, sulfonates, alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as para-toluenesulfonate ("tosylate," —OTs), methanesulfonate ("mesylate," —OMs), p-bromobenzenesulfonyloxy (brosylate, —OBs), or trifluoromethanesulfonate ("triflate," —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, copper moieties, and boron moieties (such as boronic acids and trihaloborate salts such as trifluoroborate salts).

These and other exemplary substituents are described in more detail in the Detailed Description, Figures, Examples, and claims. The invention is not intended to be limited in any manner by the above exemplary listing of substituents.

Other Definitions

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "polymorphs" means crystal structures in which a compound (or a salt, hydrate, or solvate thereof) can crystallize in different crystal packing arrangements, all of which have the same elemental composition. Different crystal forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Crystalline polymorphs of a compound can be prepared by crystallization under different conditions.

The term "co-crystal" refers to a crystalline structure composed of at least two components, where the components may be atoms, ions, or molecules. Typically, the components interact with one another to form the crystalline structure through ionic or, more commonly, non-ionic interactions. For a specific co-crystal form, all its components can be found within a single crystal lattice (unit cell) and are usually in a definite stoichiometric ratio. A component of a co-crystal may be a solid or liquid when the component is in its pure form. Crystalline salts, crystalline hydrates, and crystalline solvates are also within the meaning of co-crystals.

"Solvate" refers to forms of the compound that are associated with a solvent or water (also referred to as a "hydrate"), usually by a solvolysis reaction. This physical association includes hydrogen bonding. Conventional solvents include water, methanol, ethanol, acetic acid, DMSO, THF, diethyl ether, and the like. The compounds of the invention may be prepared, e.g., in crystalline form, and may be solvated or hydrated. Suitable solvates include pharmaceutically acceptable solvates, such as hydrates, and further include both stoichiometric solvates and non-stoichiometric solvates. In certain instances, the solvate will be capable of isolation, for example, when one or more solvent molecules are incorporated in the crystal lattice of the crystalline solid. "Solvate" encompasses both solution-phase and isolable solvates. Representative solvates include hydrates, ethanolates, and methanolates.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein, "isotopically labeled derivatives" of a compound refer to derivatives of the compound wherein at least one atom of the compound is enriched for an isotope that is higher or lower in molecular weight than the most abundant isotope of the atom found in nature.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

A "subject" to which administration is contemplated includes, but is not limited to, humans (i.e., a male or female of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs), fish, and birds (e.g., commercially relevant birds such as chickens, ducks, geese, and/or turkeys). In certain embodiments, the animal is a mammal. The animal may be a male or female and at any stage of development. A non-human animal may be a transgenic animal, such as a transgenic mouse or transgenic pig.

"Treat," "treating," and "treatment" contemplate an action that occurs while a subject is suffering from a condition, e.g., an infectious disease caused by a virus, and that reduces the severity of the condition or retards or slows the progression of the condition ("therapeutic treatment"), and also contemplates an action that occurs before a subject begins to suffer from the condition and that inhibits or reduces the severity of the condition ("prophylactic treatment").

As used herein, "condition," "disease," and "disorder" are used interchangeably.

An "effective amount" of a compound of the present invention refers to an amount sufficient to elicit the desired biological response, i.e., treating the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound of the present invention is an amount sufficient to provide a therapeutic benefit in the treatment of a condition, e.g., an infectious disease caused by a virus, or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of the present invention is an amount sufficient to prevent a condition, e.g., an infectious disease caused by a virus, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "host factor," as used herein, refers to a biomolecule of a host wherein the biomolecule contributes to a viral infection in the host. An example of the host factor is a membrane receptor.

BRIEF DESCRIPTION OF THE DRAWINGS

FIG. 2 shows the structures and anti-DENV activity of QL-XII-47 and analogs used in the study. All infections were performed in Huh7 cells at an MOI (multiplicity of infection) of 1. Illustrated in FIG. 2A are the chemical structures of exemplary compounds. FIG. 2B includes a dose response curve of QL-XII-47 in a viral yield reduction assay measured against DENV2 NGC (strain New Guinea C), in Huh7 cells. Shown in FIG. 2C is the inhibitory effect of the compounds in yield reduction assays. Compounds were present at 3 µM at 0-24 hours post-infection with DENV2 NGC. Viral yield at 24 hours was quantified by plaque formation assay. QL-XII-47's anti-DENV activity is not due to host cell toxicity since no cytotoxicity is observed at 20 µM, the highest concentration tested in a highly sensitive luminescent assay of cell viability (FIG. 2D). QL-XII-47 exhibits potent activity against strains DENV1 WP74, DENV2 NGC, DENV3 THD3, and DENV4 TVP360 (FIG. 2E). 2 µM QL-XII-47 causes a greater than 10-fold reduction in Kunjin virus yield (FIG. 2F). Negative control compound QL-XI-76 exhibits minimal anti-DENV activity at concentrations up to 10 µM, the highest concentration tested (FIG. 2G).

FIG. 3 demonstrates that QL-XII-47 inhibits a step early in the DENV life cycle via a host target. All infections were with DENV2 NGC in Huh7 cells at an MOI of 1. (A) Preincubation of cells with QL-XII-47 for 6 hours prior to infection with DENV results in inhibition comparable to that observed when infected cells are treated with QL-XII-47 at 0-24 hours post-infection. (B) QL-XII-47 exhibits maximal anti-DENV activity when added 0-3 hours post-infection and begins to lose anti-DENV activity when added at later time points. (C) QL-XII-47 inhibits DENV in a single-cycle reporter virus assay (Ansarah-Sobrinho et al., *Virology* (2008) 381:67-74) that measures successful entry and translation of the viral RNA. Negative control QL-XI-76 does not inhibit DENV in this system. (D) QL-XII-47 does not inhibit gene expression or replication of a reporter replicon RNA5 electroporated into Huh7 cells. (E) QL-XII-47 does not inhibit expression or secretion of DENV virus-like particles (VLPs).

FIG. 4 demonstrates that QL-XII-47 blocks a late step in DENV entry. Huh7 cells were infected with DENV2 NGC at an MOI of 1 for 1 h and then washed exhaustively to remove extracellular virus (FIG. 4A). Cells were lysed at various time points post-infection; intracellular genomic DENV RNA and GAPDH mRNA were quantified by qRT-PCR assay. A DENV2-derived stem peptide was used as a control to block viral fusion during entry. At 24 h post-infection, DENV genomic RNA is increasing due to replication (shown in black), and the DENV RNA in the fusion-inhibited sample is decreasing due to degradation since the virus cannot escape the endosome (shown in blue). DENV genomic RNA in the QL-XII-47-treated sample is relatively unchanged (shown in red), suggesting that the nucleocapsid escapes the endosome but the viral RNA is protected from cytoplasmic nucleases. Huh7 cells were infected at an MOI of 10 and then stained at various times post-transfection by in situ hybridization using a ViewRNA probe (Panomics) specific for a sequence in the 3'UTR of the DENV genome (FIG. 4B). The probe has been validated to detect single copy RNA. In the presence of QL-XII-47, DENV RNA persists in a punctate localization pattern suggesting that it is protected from cytoplasmic nucleases and that the viral entry process is blocked.

FIG. 5 illustrates that QL-XII-47 and QL-XII-56 inhibit viruses outside the Flaviviridae family. 2 µM QL-XII-47 inhibits infection of Bsc1 and Vero cells with VSV and VSV pseudotyped with rabies virus glycoprotein (RABV) and Ebola glycoprotein (EboV), as evidenced by immunostaining for viral proteins (FIG. 5A). Inhibition is maximal when QL-XII-47 is present before (−1 hpi) or at the time of infection (0 hpi). Inhibition is lost when addition of QL-XII-47 is delayed to 1 (1 hpi) or 3 hours post-infection (3 hpi). QL-XII-47 but not QL-XI-76 inhibits: infection of human foreskin fibroblasts by a reporter HCMV that expresses luciferase under the control of the UL97 promoter (FIG. 5B); infection and plaque formation of HSV-1 in Vero cells (FIG. 5C); and poliovirus infection and viral gene expression in Vero cells (FIG. 5D). QL-XII-47 also inhibits the cytopathic effects of Japanese Encephalitis Virus (JEV) (FIG. 5E) and Junin virus (FIG. 5F). * indicates that no plaques were detected at 8 µM of QL-XII-47. ** indicates that no plaques were detected at 8 µM of acyclovir and that lower concentrations were not tested. Data in FIG. 5 were generated in generous collaboration with S. Piccinotti and S. Whelan (VSV pseudotypes); H. Chen and D. Coen (HCMV and HSV-1); E. Sun and X. Zhuang (polio); and IBT Biosciences (JEV and Junin). FIGS. 5G1-5G2, 5H1-5H4, and 5I1-5I4 show the inhibitory activities of QL-XII-47 and QL-XII-56 against Ebola glycoprotein (EBOV) at an MOI of 1 or 10. FIGS. 5J1-5J2, 5K1-5K4, and 5L1-5L4 show the inhibitory activities of QL-XII-47 and QL-XII-56 against Marburg virus (MARV) at an MOI of 1 or 10. FIGS. 5M1-5M4 and 5N-5N4 show the inhibitory activities of QL-XII-47 and QL-XII-56 against Junin virus (JUNV) at an MOI of 1 or 10. FIGS. 5O1-5O4 and 5P1-5P4 show the inhibitory activities of QL-XII-47 and QL-XII-56 against Lassa fever virus (LASV) at an MOI of 1 or 10. FIGS. 5Q1-5Q4 and 5R1-5R4 show the inhibitory activities of QL-XII-47 and QL-XII-56 against Venezuelan equine encephalitis virus (VEEV) at an MOI of 0.5 or 1. FIGS. 5S1-5S4 and 5T1-5T4 show the inhibitory activities of QL-XII-47 and QL-XII-56 against Rift Valley fever virus (RVFV) at an MOI of 1 or 5.

FIG. 6 shows that Bmx is not the target mediating QL-XII-47's anti-DENV activity. RNAi-mediated depletion of Bmx kinase with a MISSION siRNA pool (Sigma) has no effect on DENV yield (FIG. 6A). PCI-32765 also has no effect on DENV yield (FIG. 6B). Compounds were added 1 hour post-infection with DENV2 NGC at an MOI of 1. Viral yield was quantified by FFA at 24 h post-infection.

FIG. 8 illustrates the identification of candidate targets by "click-chemistry." FIG. 8A shows that QL-XII-47AL retains potent anti-DENV activity. Huh7 cells were infected with DENV2 NGC at an MOI of 1; compounds were added at a final concentration of 3 µM at 1 h post-infection. Viral yields were quantified by FFA at 24 h post-infection. FIG. 8B illustrates the treatment of DENV-infected cells with QL-XII-47AL followed by labeling of covalently modified targets with biotinylated azide, capture, and identification by mass spectrometry.

FIG. 9 shows the result of modeling the inventive compounds with ALH1. FIG. 9A shows the chemical structures of the compounds used in the modeling. FIG. 9B depicts a molecular modeling of QL-XII-47 with ALDH1. The result shows that the acrylamide moiety of QL-XII-47 is positioned towards Cys302.

FIG. 10 shows that QL-XII-47 inhibited DENV2 viral production. Huh7 cells were infected with DENV virus. Values of FFU (focus forming units)/ml were decreased for the infected cells treated with QL-XII-47 after about 12 hours of infection compared to the infected cells not treated with a compound of the invention (FIG. 10A). Viral count was also decreased for the infected cells treated with QL-XII-47 after about 12 hours of infection compared to the infected cells not treated with a compound of the invention (FIG. 10B).

FIG. 12 shows luciferase measurements taken in the experiment described in FIG. 11.

FIGS. 13A to 13C show that QL-XII-47 inhibited EMCV-IRES dependant translation in Huh7 cells. Huh7 cells were elecroporated with an in vitro transcribed RNA encoding luciferase under the control of the EMCV IRES. Following electroporation, cell were treated with QL-XII-47 2 µM, cycloheximide 30 µg/ml, MPA 5 µM as indicated on the plot. Cells were lysed and luciferase activity measured at the indicated time points post-electroporation.

FIG. 17 shows the effects of RNAi-mediated depletion of Prdx-1 on dengue virus. Cells were treated with individual (si1-si4) and pooled siRNAs against Prdx-1 for 48 hours and then infected with DV2 at moi 1. Cells were lysed, and culture supernatants were harvested at 24 hours post-infection.

FIGS. 18A-18B show that QL-XII-47 and QL-XII-56 inhibited vesicular stomatitis virus (VSV).

FIGS. 19A-19B show that QL-XII-47 and QL-XII-56 inhibited poliovirus Type 1 (PV1).

FIGS. 20A-20H show the exemplary compounds prepared according to formulae (I)-(III) and (a)-(c). The blue bonds in the structures of the second column and the red bonds in the structures of the third column indicate the point of attachment to the scaffold formulae.

DETAILED DESCRIPTION OF CERTAIN EMBODIMENTS OF THE INVENTION

Figure 1:
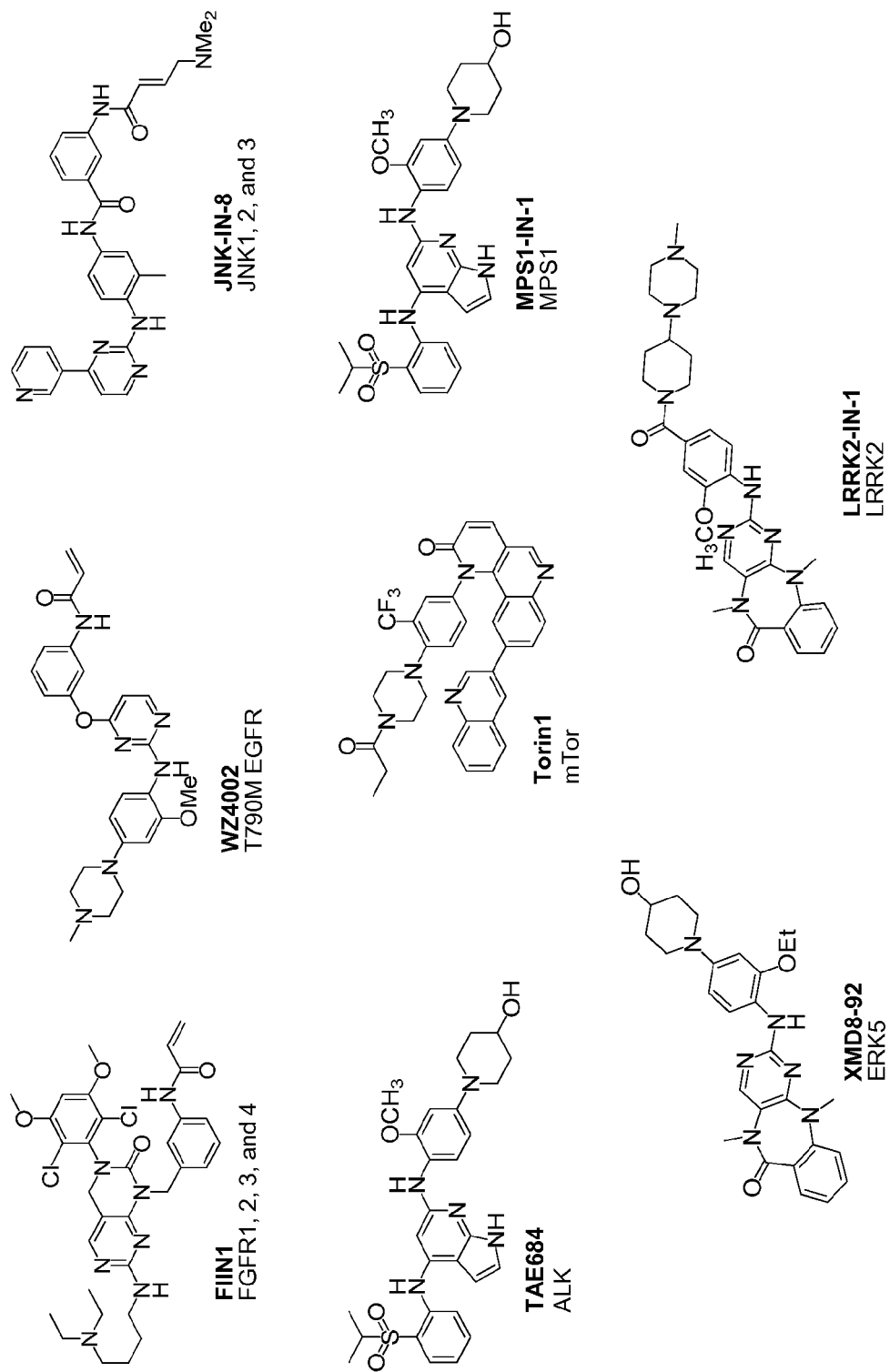
FIG. 1 illustrates the chemical structures of certain selective kinase inhibitors.

The present invention provides compounds, and pharmaceutical compositions thereof, for the prevention and treatment of infectious diseases in a subject. The infectious disease may be caused by a virus, for example, Flaviviridae virus (e.g., Dengue virus (DENV), including Dengue virus 1 (DENV1), Dengue virus 2 (DENV2), Dengue virus 3 (DENV3), and Dengue virus 4 (DENV4); West Nile virus; tick-borne encephalitis virus; yellow fever virus; hepatitis C virus; hepatitis G virus; bovine viral diarrhea; classical swine fever virus; and hog cholera virus), Kunjin virus, Japanese encephalitis virus, vesicular stomatitis virus (VSV), vesicular stomatitis virus (VSV) pseudotyped with rabies glycoprotein, vesicular stomatitis virus (VSV) pseudotyped with Ebola glycoprotein, herpes simplex virus 1 (HSV-1), human cytomegalovirus (HCMV), poliovirus, Junin virus, Ebola virus, Marburg virus (MARV), Lassa fever virus (LASV), Venezuelan equine encephalitis virus (VEEV), Rift Valley Fever virus (RVFV), hepatitis B virus, cytomegalovirus, papillomavirus, coronavirus, Epstein-Barr virus (EBV), human immunodeficiency virus (HIV), orthomyxovirus, paramyxovirus, arenavirus, bunyavirus, adenovirus, poxvirus, retrovirus, rhabdovirus, picornavirus, or herpesvirus. In certain embodiments, the compound inhibits the activity of the virus. In certain embodiments, the compound inhibits the activity of the virus by covalently modifying one or more cysteine residues of a host factor. In certain embodiments, the compound prevents or inhibits entry of the virus into a host cell. The present invention further provides methods of using the compounds described herein, e.g., as biological probes to study the inhibition of the activity of a virus, to study viral entry, and to screen a library of compounds to identify antiviral compounds, and as therapeutics, e.g., in the prevention and treatment of infectious diseases caused by a virus. The infectious diseases include, but are not limited to, Dengue fever, Dengue hemorrhagic fever (DHF), Dengue shock syndrome (DSS), hepatitis B, hepatitis C, fulminant viral hepatitis, severe acute respiratory syndrome (SARS), viral myocarditis, influenza A virus infection, influenza B virus infection, parainfluenza virus infection, RS virus (RSV) infections (e.g., RSV bronchiolitis, RSV pneumonia, especially infant and childhood RSV infections and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes simplex virus 1 infection, poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, encephalitis, Saint Louise encephalitis, Kyasanur Forest disease, Murray Valley encephalitis, tick-borne encephalitis, West Nile encephalitis, yellow fever, and viral infections in subjects with immune disorders.

Novel compounds have been identified and optimized that target essential host factors to further the understanding of host-virus interactions and to validate host targets and lead compounds for further development as a potential new class of antiviral agents. Importantly, because the novel compounds act via a host target, they have the potential to have activity against multiple pathogens that utilize the same host factor or pathway and to circumvent the rapid selection for resistance observed with agents that act via a viral target.

Successful antiviral drug development efforts have traditionally focused on inhibition of viral enzymes that are responsible for catalyzing viral genome replication and polyprotein processing during viral assembly. Lessons from HIV drug development efforts teach that, due to the high mutation rates of RNA viruses and the associated rapid development of resistance to monotherapies, combination therapies targeting multiple stages of the viral life cycle are necessary for effective treatment without the rapid development of resistance. As demonstrated by CCR5 antagonists such as the anti-HIV drug maraviroc, host-targeted antivirals can also contribute to combination antiviral therapies and, in some cases, may prove superior over the long term because the host-targeted antivirals have the potential to be effective against multiple viral pathogens and because their barriers to resistance are higher than those of drugs that act via viral targets.

A large number of cellular proteins have a reactive cysteine that is important as a catalytic residue or as a site of post-translational modification and that can be selectively targeted by a compound that binds and places a reactive group in close proximity to the targeted cysteine. Chemical proteomic studies have identified a large number of proteins that contain reactive cysteines (the reactive "cysteinome") and have established that reactivity in most cases corresponds to residues of significant biological function (Weerapana et al., *Nature Chem. Biol.* (2008) 4:405-407; and Weerapana et al., *Nature* (2010) 468:790-795). The strategy of the present invention is to target essential host factors by developing selective, covalent cysteine-directed inhibitors. Covalent inhibition has several potential benefits, including (1) irreversible inactivation of the target protein that mitigates the need to extensively optimize for potency; (2) full modification of the target with transient exposure of the drug in vivo, which can reduce the need to achieve high and sustained drug exposure and therefore mitigate toxicology concerns; and (3) facilitation of target identification by affinity approaches. The success of covalent inhibitors is well-illustrated by the thirty-nine FDA-approved drugs that are highly effective in humans, including aspirin (Warner et al., *Proc. Nat. Acad. Sci. USA* (2002) 99:13371-13373) (Cox-1, Cox-2, and Cox-3) and the large penicillin-class of antibiotics (bacterial DD-transpeptidase inhibitors) (Waxman et al., *Ann. Rev. Biochem.* (1983) 52:825-869), amongst many others (Johnson et al., *Future Med. Chem.* (2010) 2:949-964; and Singh et al., *Nat. Rev. Drug Discov.* (2011) 10:307-317).

Small molecule inhibitors have been developed that form a covalent bond to a free cysteine of a target protein. While this strategy has been applied to the development of covalent kinase inhibitors, a significant opportunity exists to apply this approach to discover novel antiviral targets as well as to develop and validate potent antiviral compounds that act via these targets. This approach complements on-going efforts to develop non-covalent inhibitors targeting essential viral proteins.

Although structure-guided drug discovery approaches have traditionally been biased against covalent inhibitors due to concerns about off-target effects and potential toxicity, this belies the historical success of drugs that act via covalent mechanisms, including thirty-nine FDA-approved drugs (Johnson et al., *Future Med. Chem.* (2010) 2:949-964; and Singh et al., *Nat. Rev. Drug Discov.* (2011) 10:307-317). These include compounds targeting enzyme and non-enzyme targets such as, rasagiline (Hubalek et al., *J. Med. Chem.* (2004) 47:1760-1766) (monoamine oxidase), clopidogrel (Herbert et al., *Seminars in Vascular Medicine* (2003) 3:113-122) (G protein coupled receptor), omeprazole (Im et al., *J. Biol. Chem.* (1985) 260:4591-4597) (proton pump inhibitor), amongst many others (Johnson et al., *Future Med. Chem.* (2010) 2:949-964; and Singh et al., *Nat. Rev. Drug Discov.* (2011) 10:307-317). Importantly, covalent inhibitors are not simply highly reactive electrophiles. Specific covalent inhibitors typically have warheads that are only weakly reactive compared to the quinones and acyl halides typically present in highly reactive compounds and electrophilic metabolites. In addition, covalent inhibitors usually must form specific, non-covalent interactions and bind in a particular orientation in order to undergo covalent reaction with a nucleophile whereas highly reactive compounds more commonly react non-specifically with the nucleophiles that are most accessible to solution on the protein surface.

Covalent inhibitors, when properly deployed, have several potential advantages over non-covalent inhibitors. First, the covalent attachment means that the inhibitor has a kinetic off-rate of essentially zero. This can boost potency by several orders of magnitude. For example, WZ4002 (see FIG. 1 for the chemical structure) inhibits T790M EGFR-dependent cellular proliferation with an $EC_{50}$ of 10 nM, while the corresponding non-covalent inhibitor has an $EC_{50}$ higher than 10 μM (Zhou et al., *Nature* (2009) 462:1070-1074). Second, transient exposure is often sufficient to achieve complete modification of the target. Third, if designed and screened appropriately, very potent target modulation can be achieved with covalent inhibitors. For example, WZ4002 was identified from an acrylamide-containing library and found to be efficacious in T790M EGFR-dependent lung tumor models (Zhou et al., *Nature* (2009) 462:1070-1074). Fourth, since the potency of the inhibitors of the present invention relies upon their covalent modification of a cysteine residue, the pharmacological selectivity of the inhibitors can be established by introducing a cysteine to serine mutation into the target enzyme and looking for reversal of the inhibitor-induced pharmacology. This approach has been used previously to prove that the functional target of WZ4002 is T790M EGFR and that the functional target of FIIN 1 is FGFR (Zhou et al., *Nature* (2009) 462:1070-1074; and Zhou et al., *Chem. Biol.* (2010) 17:285-295). Fifth, covalent attachment of the inhibitor can facilitate identification of the inhibitor's target by affinity purification. Identification of the target(s) of non-covalent inhibitors following phenotypic, cell-based screens can be more challenging in comparison. It is noted that while a cysteine-directed inhibitor of the HCV protease has recently been disclosed (Hagel et al., *Nature Chem. Biol.* (2011) 7:22-24).

Cysteines are functionally important as catalytic residues as well as sites for numerous types of post-translational modification including disulfide formation, oxidation, nitrosolyation, and alkylation. Although thiol groups are predominantly protonated at physiological pH ranges, the $pK_a$ of the thiol groups is greatly affected by the surrounding amino acids. Consequently, a thiolate can act as an extremely potent nucleophile even at physiological pH and can serve as a key catalytic residue in several large enzyme families, including cysteine proteases, phosphatases, acyl transferases, and E2 ubiquitin transferases. Small molecules that are capable of covalently modifying the thiol group of cysteine are quite frequently found in nature, and the nucleophilicity of active-site cysteines has been exploited to develop potent, irreversible inhibitors that covalently modify catalytic cysteines of proteases, phosphatases, and E2 ubiquitin transferases (Singh et al., *Nat. Rev. Drug Discov.* (2011) 10:307-317). In addition, cysteine residues located in or near small molecule binding clefts outside of the active site have been successfully targeted with small molecule inhibitors.

Cysteine-targeted covalent inhibitors take advantage of non-covalent interactions to selectively target a particular protein binding site and to position the electrophilic moiety in a conformation that permits bond formation with a specific cysteine residue. This strategy prevents non-selective reaction of an electrophile with the cysteine-containing proteome (the "cysteineome") and has successfully yielded inhibitors with a remarkable level of functional selectivity in cellular assays and in vivo. For example, several inhibitors that function by this mechanism are in clinical trials, including four different compounds targeting a unique cysteine located in the periphery of the ATP-binding site of EGFR kinases. This approach has been recently applied to develop selective covalent inhibitors of a number of different human kinases, including inhibitors of Rsk (CMK, FMK) (Cohen et al., *Science* (2005) 308:1318-1321 and Cohen et al., *Nature Chem. Biol.* (2007) 3:156-160), BTK (PCI-32765) (Honigberg et al., *Proc. Nat. Acad. Sci. USA* (2010) 107:13075-13080), c-kit (Leproult et al., *J. Med. Chem.* (2011) 54:1347-1355), Nek2 (Henise et al., *J. Med. Chem.* (2011) 54:4133-4146), and a subset of the MAPKs (resorcylic acid lactone polyketides (Schirmer et al., *Proc. Nat. Acad. Sci. USA* (2006) 103:4234-4239)). Studies suggest that this strategy might be applied more broadly to identify selective, irreversible inhibitors of not only additional kinases, but other protein classes as well. In a recent quantitative chemoproteomic study, Cravatt and colleagues utilized an alkynylated iodoacetamide probe and quantitative mass spectrometry to identify the reactive cysteinome (Weerapana et al., *Nature* (2010) 468:790-795). Out of a total of 8,910 cysteines present on the 890 human proteins detected in this analysis, 1,082 cysteines were found to be hyper-reactive. Importantly, hyper-reactivity was found to be a good predictor of a cysteine's function as a catalytic residue, as a non-catalytic residue present in an enzyme active site, or as a site of post-translational oxidative modification.

Compounds

In one aspect of the present invention, provided are compounds of Formula (I):

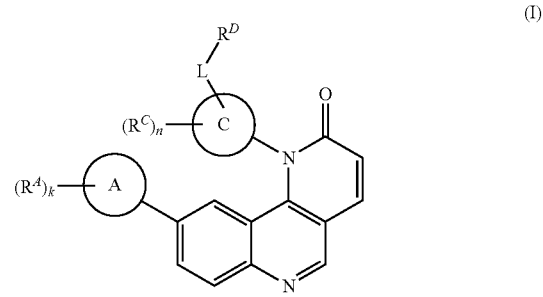

or a pharmaceutically acceptable salt thereof;
wherein:
Ring A is aryl, arylalkenyl, or heteroaryl;
each instance of $R^A$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{A1}$, $-N(R^{A1})_2$, $-SR^{A1}$, $-CN$, $-C(=NR^{A1})R^{A1}$, $-C(=NR^{A1})OR^{A1}$, $-C(=NR^{A1})SR^{A1}$, $-C(=NR^{A1})N(R^{A1})_2$, $-C(=O)NR^{A1}$, $-NR^{A1}C(=O)-$, $-C(=O)R^{A1}$, $-C(=S)R^{A1}$, $-C(=S)OR^{A1}$, $-C(=S)SR^{A1}$, $-C(=S)N(R^{A1})_2$, $-NO_2$, $-N_3$, $-N(R^{A1})_3^+F^-$, $-N(R^{A1})_3^+Cl^-$, $-N(R^{A1})_3^+Br^-$, $-N(R^{A1})_3^+I^-$, $-N(OR^{A1})R^{A1}$, $-NR^{A1}C(=O)R^{A1}$, $-NR^{A1}C(=O)OR^{A1}$, $-NR^{A1}C(=O)SR^{A1}$, $-NR^{A1}C(=O)N(R^{A1})_2$, $-NR^{A1}C(=S)R^{A1}$, $-NR^{A1}C(=S)OR^{A1}$, $-NR^{A1}C(=S)SR^{A1}$, $-NR^{A1}C(=S)N(R^{A1})_2$, $-NR^{A1}C(=NR^{A1})R^{A1}$, $-NR^{A1}C(=NR^{A1})OR^{A1}$, $-NR^{A1}C(=NR^{A1})SR^{A1}$, $-NR^{A1}C(=NR^{A1})N(R^{A1})_2$, $-NR^{A1}S(=O)_2R^{A1}$, $-NR^{A1}S(=O)_2OR^{A1}$, $-NR^{A1}S(=O)_2SR^{A1}$, $-NR^{A1}S(=O)_2N(R^{A1})_2$, $-NR^{A1}S(=O)R^{A1}$, $-NR^{A1}S(=O)OR^{A1}$, $-NR^{A1}S(=O)SR^{A1}$, $-NR^{A1}S(=O)N(R^{A1})_2$, $-NR^{A1}P(=O)$, $-NR^{A1}P(=O)_2$, $-NR^{A1}P(=O)(R^{A1})_2$, $-NR^{A1}P(=O)R^{A1}(OR^{A1})$, $-NR^{A1}P(=O)(OR^{A1})_2$, $-OC(=O)R^{A1}$, $-OC(=O)OR^{A1}$, $-OC(=O)SR^{A1}$, $-OC(=O)N(R^{A1})_2$, $-OC(=NR^{A1})R^{A1}$, $-OC(=NR^{A1})OR^{A1}$, $-OC(=NR^{A1})N(R^{A1})_2$, $-OC(=S)R^{A1}$, $-OC(=S)OR^{A1}$, $-OC(=S)SR^{A1}$, $-OC(=S)N(R^{A1})_2$, $-ON(R^{A1})_2$, $-OS(=O)R^{A1}$, $-OS(=O)OR^{A1}$, $-OS(=O)SR^{A1}$, $-OS(=O)N(R^{A1})_2$, $-OS(=O)_2R^{A1}$, $-OS(=O)_2OR^{A1}$, $-OS(=O)_2SR^{A1}$, $-OS(=O)_2N(R^{A1})_2$, $-OP(=O)_2$, $-OP(=O)(R^{A1})_2$, $-OP(=O)R^{A1}(OR^{A1})$, $-OP(=O)(OR^{A1})_2$, $-OP(=O)$, $-OP(R^{A1})_2$, $-OPR^{A1}(OR^{A1})$, $-OP(OR^{A1})_2$, $-OSi(R^{A1})_3$, $-OSi(R^{A1})_2OR^{A1}$, $-OSi(R^{A1})(OR^{A1})_2$, $-OSi(OR^{A1})_3$, $-SSR^{A1}$, $-S(=O)R^{A1}$, $-S(=O)OR^{A1}$, $-S(=O)N(R^{A1})_2$, $-S(=O)_2R^{A1}$, $-S(=O)_2OR^{A1}$, $-S(=O)_2N(R^{A1})_2$, $-SC(=O)R^{A1}$, $-SC(=O)OR^{A1}$, $-SC(=O)SR^{A1}$, $-SC(=O)N(R^{A1})_2$, $-SC(=S)R^{A1}$, $-SC(=S)OR^{A1}$, $-SC(=S)SR^{A1}$, $-SC(=S)N(R^{A1})_2$, $-P(R^{A1})_2$, $-PR^{A1}(OR^{A1})$, $-P(OR^{A1})_2$, $-P(=O)$, $-P(=O)(R^{A1})_2$, $-P(=O)(OR^{A1})_2$, $-P(=O)R^{A1}(OR^{A1})$, $-P(=O)_2$, $-B(R^{A1})_2$, $-B(OR^{A1})_2$, $-BR^{A1}(OR^{A1})$, $-Si(R^{A1})_3$, $-Si(R^{A1})_2OR^{A1}$, $-SiR^{A1}(OR^{A1})_2$, and $-Si(OR^{A1})_3$, wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{A1}$ groups are joined to form an optionally substituted heterocyclic ring;

k is 0, 1, 2, 3, 4, or 5;

Ring C is a carbocyclic, heterocyclic, aryl, or heteroaryl ring;

each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1})_2$, —$SR^{C1}$, —CN, —$C(=NR^{C1})R^{C1}$, —$C(=NR^{C1})OR^{C1}$, —$C(=NR^{C1})SR^{C1}$, —$C(=NR^{C1})N(R^{C1})_2$, —$C(=O)R$, —$C(=S)R^{C1}$, —$C(=S)OR^{C1}$, —$C(=S)SR^{C1}$, —$C(=S)N(R^{C1})_2$, —$NO_2$, —$N_3$, —$N(R^{C1})_3{}^+F^-$, —$N(R^{C1})_3{}^+Cl^-$, —$N(R^{C1})_3{}^+Br^-$, —$N(R^{C1})_3{}^+I^-$, —$N(OR^{C1})R^{C1}$, —$NR^{C1}C(=O)R^{C1}$, —$NR^{C1}C(=O)OR^{C1}$, —$NR^{C1}C(=O)SR^{C1}$, —$NR^{C1}C(=O)N(R^{C1})_2$, —$NR^{C1}C(=S)R^{C1}$, —$NR^{C1}C(=S)OR^{C1}$, —$NR^{C1}C(=S)SR^{C1}$, —$NR^{C1}C(=S)N(R^{C1})_2$, —$NR^{C1}C(=NR^{C1})R^{C1}$, —$NR^{C1}C(=NR^{C1})OR^{C1}$, —$NR^{C1}C(=NR^{C1})SR^{C1}$, —$NR^{C1}C(=NR^{C1})N(R^{C1})_2$, —$NR^{C1}S(=O)_2R^{C1}$, —$NR^{C1}S(=O)_2OR^{C1}$, —$NR^{C1}S(=O)_2SR^{C1}$, —$NR^{C1}S(=O)_2N(R^{C1})_2$, —$NR^{C1}S(=O)R^{C1}$, —$NR^{C1}S(=O)OR^{C1}$, —$NR^{C1}S(=O)SR^{C1}$, —$NR^{C1}S(=O)N(R^{C1})_2$, —$NR^{C1}P(=O)$, —$NR^{C1}P(=O)_2$, —$NR^{C1}P(=O)(R^{C1})_2$, —$NR^{C1}P(=O)R^{C1}(OR^{C1})$, —$NR^{C1}P(=O)(OR^{C1})_2$, —$OC(=O)R^{C1}$, —$OC(=O)OR^{C1}$, —$OC(=O)SR^{C1}$, —$OC(=O)N(R^{C1})_2$, —$OC(=NR^{C1})R^{C1}$, —$OC(=NR^{C1})OR^{C1}$, —$OC(=NR^{C1})N(R^{C1})_2$, —$OC(=S)R^{C1}$, —$OC(=S)OR^{C1}$, —$OC(=S)SR^{C1}$, —$OC(=S)N(R^{C1})_2$, —$ON(R^{C1})_2$, —$OS(=O)R^{C1}$, —$OS(=O)OR^{C1}$, —$OS(=O)SR^{C1}$, —$OS(=O)N(R^{C1})_2$, —$OS(=O)_2R^{C1}$, —$OS(=O)_2OR^{C1}$, —$OS(=O)_2SR^{C1}$, —$OS(=O)_2N(R^{C1})_2$, —$OP(=O)_2$, —$OP(=O)(R^{C1})_2$, —$OP(=O)R^{C1}(OR^{C1})$, —$OP(=O)(OR^{C1})_2$, —$OP(=O)$, —$OP(R^{C1})_2$, —$OPR^{C1}(OR^{C1})$, —$OP(OR^{C1})_2$, —$OSi(R^{C1})_3$, —$OSi(R^{C1})_2OR^{C1}$, —$OSi(R^{C1})(OR^{C1})_2$, —$OSi(OR^{C1})_3$, —$SSR^{C1}$, —$S(=O)R^{C1}$, —$S(=O)OR^{C1}$, —$S(=O)N(R^{C1})_2$, —$S(=O)_2R^{C1}$, —$S(=O)_2OR^{C1}$, —$S(=O)_2N(R^{C1})_2$, —$SC(=O)R^{C1}$, —$SC(=O)OR^{C1}$, —$SC(=O)SR^{C1}$, —$SC(=O)N(R^{C1})_2$, —$SC(=S)R^{C1}$, —$SC(=S)OR^{C1}$, —$SC(=S)SR^{C1}$, —$SC(=S)N(R^{C1})_2$, —$P(R^{C1})_2$, —$PR^{C1}(OR^{C1})$, —$P(OR^{C1})_2$, —$P(=O)$, —$P(=O)(R^{C1})_2$, —$P(=O)(OR^{C1})_2$, —$P(=O)R^{C1}(OR^{C1})$, —$P(=O)_2$, —$B(R^{C1})_2$, —$B(OR^{C1})_2$, —$BR^{C1}(OR^{C1})$, —$Si(R^{C1})_3$, —$Si(R^{C1})_2OR^{C1}$, —$SiR^{C1}(OR^{C1})_2$, and —$Si(OR^{C1})_3$, wherein each occurrence of $R^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{C1}$ groups are joined to form an optionally substituted heterocyclic ring or optionally substituted heteroaryl ring;

n is 0, 1, 2, 3, or 4;

L is a bond or an optionally substituted, branched or unbranched $C_{1-6}$ hydrocarbon chain;

$R^D$ is any one of Formulae (i-1)-(i-43):

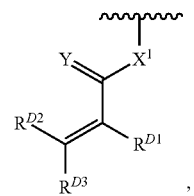

(i-1)

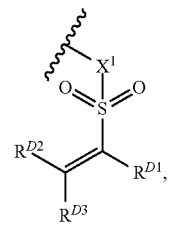

(i-2)

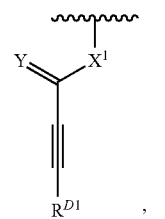

(i-3)

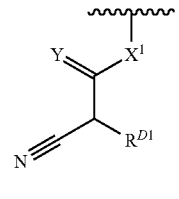

(i-4)

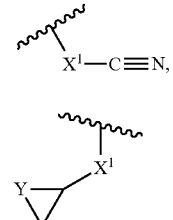

(i-5)

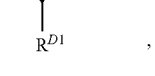

(i-6)

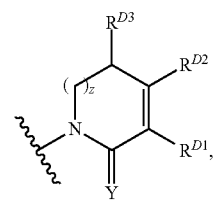

(i-7)

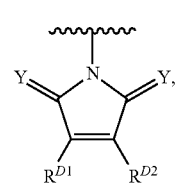

(i-8)

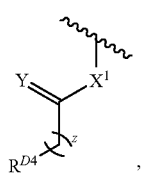 (i-9)
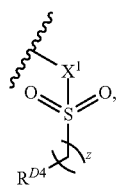 (i-10)
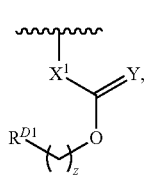 (i-11)
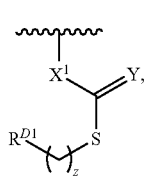 (i-12)
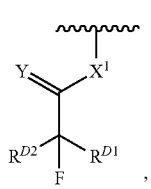 (i-13)
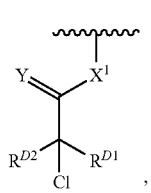 (i-14)
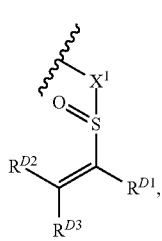 (i-15)
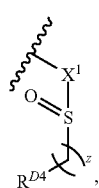 (i-16)
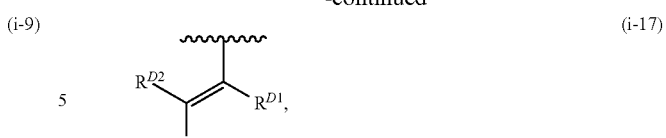 (i-17)
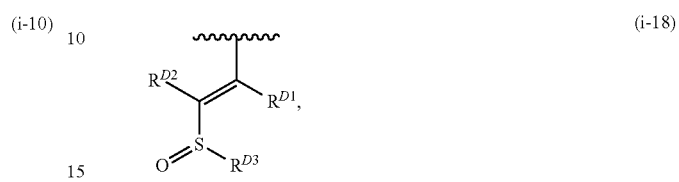 (i-18)
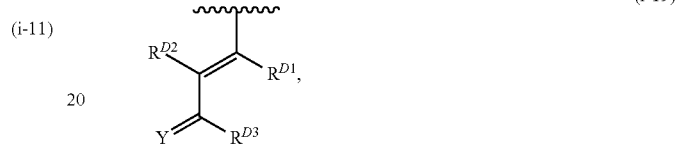 (i-19)
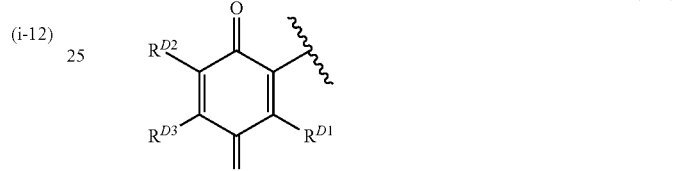 (i-20)
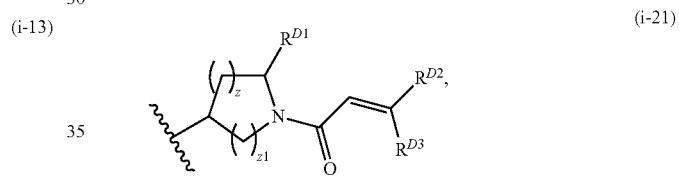 (i-21)
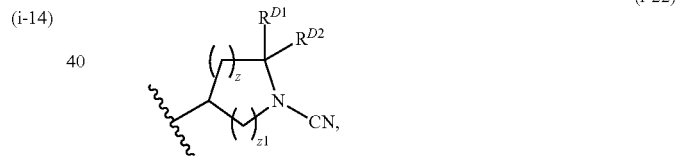 (i-22)
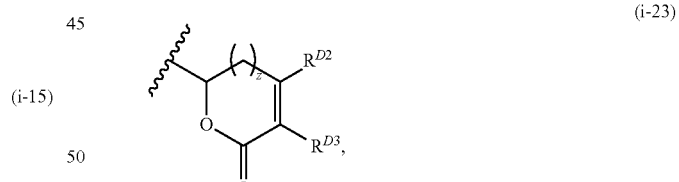 (i-23)
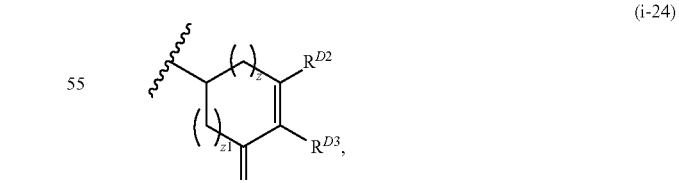 (i-24)
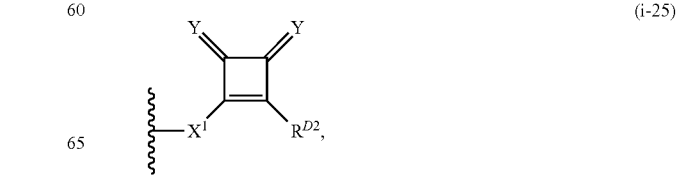 (i-25)

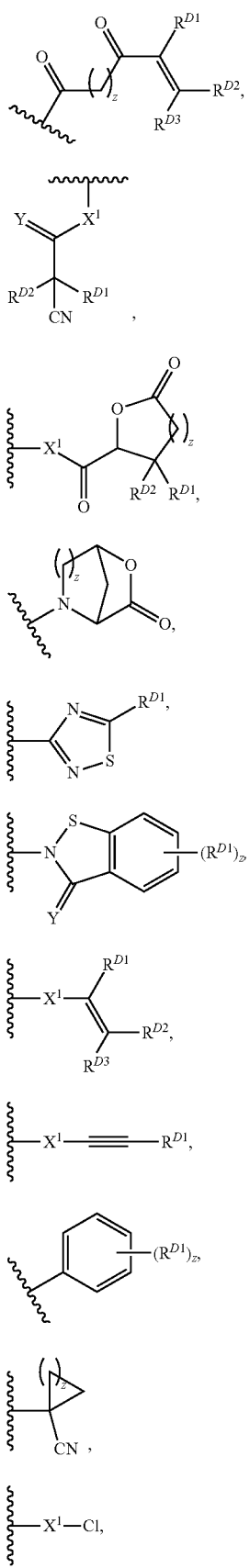
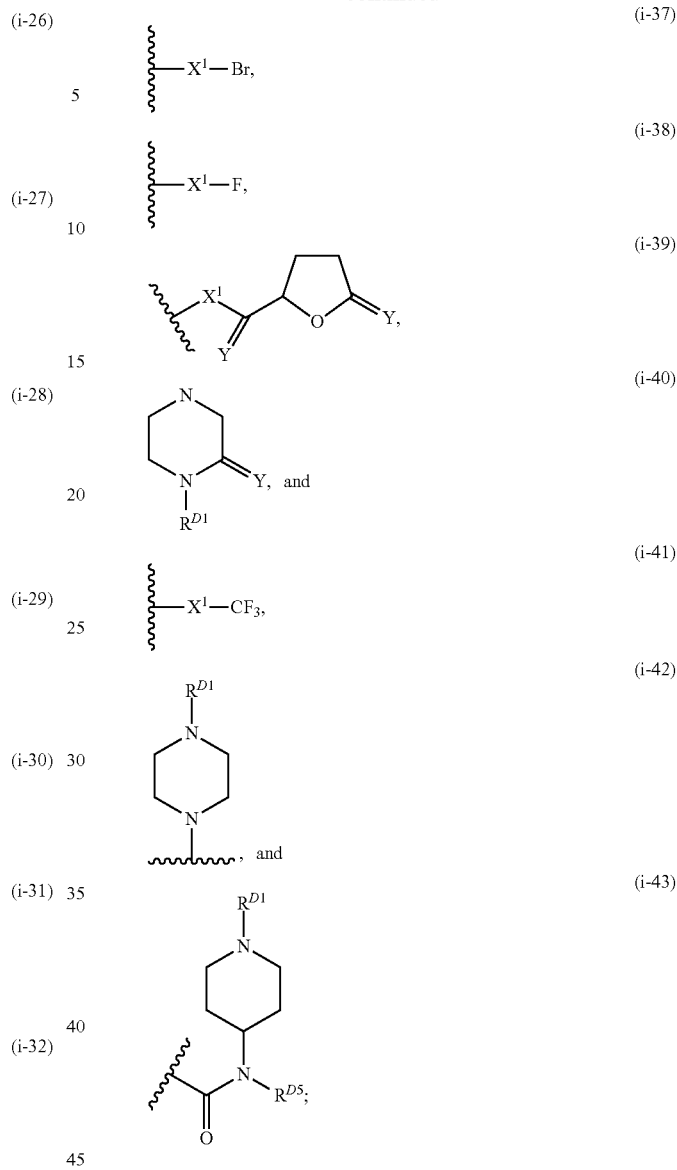

wherein:

each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;

each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —R$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)R$^{D2a}$, —C(=S)SR$^{D2a}$, —C(=S)N(R$^{D2a}$)$_2$, —C(=NR$^{D2a}$)R$^{D2a}$, —C(=NR$^{D2a}$)R$^{D2a}$, —C(=NR$^{D2a}$)SR$^{D2a}$, and C(=NR$^{D2a}$)N(R$^{D2a}$)$_2$, wherein each occurrence of R$^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{D2a}$ groups are joined to form an substituted or unsubstituted heterocyclic ring;

each instance of R$^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of R$^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D3a}$ groups are joined to form an substituted or unsubstituted heterocyclic ring;

optionally R$^{D1}$ and R$^{D3}$, or R$^{D2}$ and R$^{D3}$, or R$^{D1}$ and R$^{D2}$ are joined to form an substituted or unsubstituted carbocyclic or substituted or unsubstituted heterocyclic ring;

R$^{D4}$ is a leaving group selected from the group consisting of —Br, —Cl, —I, and —OS(=O)$_w$R$^{D4a}$, wherein w is 1 or 2, and R$^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of X$^1$ is independently a bond, —C(=O)—, —SO$_2$—, —NR$^{D5}$—, optionally substituted alkylene, or optionally substituted heteroarylene, wherein R$^{D5}$ is hydrogen, C$_{1-6}$ alkyl, or a nitrogen protecting group;

each instance of Y is independently O, S, or NR$^{D6}$, wherein R$^{D6}$ is hydrogen, C$_{1-6}$ alkyl, or a nitrogen protecting group; and each instance of z and z$_1$ is independently 0, 1, 2, 3, 4, 5, or 6, as valency permits.

In another aspect of the present invention, provided are compounds of Formula (II):

or a pharmaceutically acceptable salt thereof;

wherein:
Ring A is aryl, arylalkenyl, or heteroaryl;
each instance of R$^A$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{A1}$, —N(R$^{A1}$)$_2$, —SR$^{A1}$, —CN, —C(=NR$^{A1}$)R$^{A1}$, —C(=NR$^{A1}$)OR$^{A1}$, —C(=NR$^{A1}$)SR$^{A1}$, —C(=NR$^{A1}$)N(R$^{A1}$)$_2$, —C(=O)NR$^{A1}$, —NR$^{A1}$C(=O)—, —C(=O)R$^{A1}$, —C(=S)R$^{A1}$, —C(=S)OR$^{A1}$, —C(=S)SR$^{A1}$, —C(=S)N(R$^{A1}$)$_2$, —NO$_2$, —N$_3$, —N(R$^{A1}$)$_3$$^+$F$^-$, —N(R$^{A1}$)$_3$$^+$Cl$^-$, —N(R$^{A1}$)$_3$$^+$Br$^-$, —N(R$^{A1}$)$_3$$^+$I$^-$, —N(OR$^{A1}$)R$^{A1}$, —NR$^{A1}$C(=O)R$^{A1}$, —NR$^{A1}$C(=O)OR$^{A1}$, —NR$^{A1}$C(=O)SR$^{A1}$, —NR$^{A1}$C(=O)N(R$^{A1}$)$_2$, —NR$^{A1}$C(=S)R$^{A1}$, —NR$^{A1}$C(=S)OR$^{A1}$, —NR$^{A1}$C(=S)SR$^{A1}$, —NR$^{A1}$C(=S)N(R$^{A1}$)$_2$, —NR$^{A1}$C(=NR$^{A1}$)R$^{A1}$, —NR$^{A1}$C(=NR$^{A1}$)OR$^{A1}$, —NR$^{A1}$C(=NR$^{A1}$)SR$^{A1}$, —NR$^{A1}$C(=NR$^{A1}$)N(R$^{A1}$)$_2$, —NR$^{A1}$S(=O)$_2$R$^{A1}$, —NR$^{A1}$S(=O)$_2$OR$^{A1}$, —NR$^{A1}$S(=O)$_2$SR$^{A1}$, —NR$^{A1}$S(=O)$_2$N(R$^{A1}$)$_2$, —NR$^{A1}$S(=O)R$^{A1}$, —NR$^{A1}$S(=O)OR$^{A1}$, —NR$^{A1}$S(=O)SR$^{A1}$, —NR$^{A1}$S(=O)N(R$^{A1}$)$_2$, —NR$^{A1}$P(=O), —NR$^{A1}$P(=O)$_2$, —NR$^{A1}$P(=O)(R$^{A1}$)$_2$, —NR$^{A1}$P(=O)R$^{A1}$(OR$^{A1}$), —NR$^{A1}$P(=O)(OR$^{A1}$)$_2$, —OC(=O)R$^{A1}$, —OC(=O)OR$^{A1}$, —OC(=O)SR$^{A1}$, —OC(=O)N(R$^{A1}$)$_2$, —OC(=NR$^{A1}$)R$^{A1}$, —OC(=NR$^{A1}$)OR$^{A1}$, —OC(=NR$^{A1}$)N(R$^{A1}$)$_2$, —OC(=S)R$^{A1}$, —OC(=S)OR$^{A1}$, —OC(=S)SR$^{A1}$, —OC(=S)N(R$^{A1}$)$_2$, —ON(R$^{A1}$)$_2$, —OS(=O)R$^{A1}$, —OS(=O)OR$^{A1}$, —OS(=O)SR$^{A1}$, —OS(=O)N(R$^{A1}$)$_2$, —OS(=O)$_2$R$^{A1}$, —OS(=O)$_2$OR$^{A1}$, —OS(=O)$_2$SR$^{A1}$, —OS(=O)$_2$N(R$^{A1}$)$_2$, —OP(=O)$_2$, —OP(=O)(R$^{A1}$)$_2$, —OP(=O)R$^{A1}$(OR$^{A1}$), —OP(=O)(OR$^{A1}$)$_2$, —OP(=O), —OP(R$^{A1}$)$_2$, —OPR$^{A1}$(OR$^{A1}$), —OP(OR$^{A1}$)$_2$, —OSi(R$^{A1}$)$_3$, —OSi(R$^{A1}$)$_2$OR$^{A1}$, —OSi(R$^{A1}$)(OR$^{A1}$)$_2$, —OSi(OR$^{A1}$)$_3$, —SSR$^{A1}$, —S(=O)R$^{A1}$, —S(=O)OR$^{A1}$, —S(=O)N(R$^{A1}$)$_2$, —S(=O)$_2$R$^{A1}$, —S(=O)$_2$OR$^{A1}$, —S(=O)$_2$N(R$^{A1}$)$_2$, —SC(=O)R$^{A1}$, —SC(=O)OR$^{A1}$, —SC(=O)SR$^{A1}$, —SC(=O)N(R$^{A1}$)$_2$, —SC(=S)R$^{A1}$, —SC(=S)OR$^{A1}$, —SC(=S)SR$^{A1}$, —SC(=S)N(R$^{A1}$)$_2$, —P(R$^{A1}$)$_2$, —PR$^{A1}$(OR$^{A1}$), —P(OR$^{A1}$)$_2$, —P(=O), —P(=O)(R$^{A1}$)$_2$, —P(=O)(OR$^{A1}$)$_2$, —P(=O)R$^{A1}$(OR$^{A1}$), —P(=O)$_2$, —B(R$^{A1}$)$_2$, —B(OR$^{A1}$)$_2$, —BR$^{A1}$(OR$^{A1}$), —Si(R$^{A1}$)$_3$, —Si(R$^{A1}$)$_2$OR$^{A1}$, —SiR$^{A1}$(OR$^{A1}$)$_2$, and —Si(OR$^{A1}$)$_3$, wherein each occurrence of R$^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{A1}$ groups are joined to form an optionally substituted heterocyclic ring;

k is 0, 1, 2, 3, 4, or 5;
Ring C is a carbocyclic, heterocyclic, aryl, or heteroaryl ring;
each instance of R$^{j1}$, R$^{j2}$, R$^{j3}$, and R$^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{C1}$, —N(R$^{C1}$)$_2$, —SR$^{C1}$, —CN, —C(=NR$^{C1}$)R$^{C1}$, —C(=NR$^{C1}$)OR$^{C1}$, —C(=NR$^{C1}$)SR$^{C1}$, —C(=NR$^{C1}$)N(R$^{C1}$)$_2$, —C(=O)R$^{C1}$, —C(=S)R$^{C1}$, —C(=S)OR$^{C1}$, —C(=S)SR$^{C1}$, —C(=S)N(R$^{C1}$)$_2$, —NO$_2$, —N$_3$, —N(R$^{C1}$)$_3$$^+$F$^-$, —N(R$^{C1}$)$_3$$^+$Cl$^-$, —N(R$^{C1}$)$_3$$^+$Br$^-$, —N(R$^{C1}$)$_3$$^+$I$^-$, —N(OR$^{C1}$)R$^{C1}$, —NR$^{C1}$C(O)R$^{C1}$, —NR$^{C1}$C(=O)OR$^{C1}$, —NR$^{C1}$C(=O)SR$^{C1}$, —NR$^{C1}$C(O)N(R$^{C1}$)$_2$, —NR$^{C1}$C(=S)R$^{C1}$, —NR$^{C1}$C(=S)OR$^{C1}$, —NR$^{C1}$C(=S)SR$^{C1}$, —NR$^{C1}$C(=S)N(R$^{C1}$)$_2$, —NR$^{C1}$C(=NR$^{C1}$)R$^{C1}$, —NR$^{C1}$C(=NR$^{C1}$)OR$^{C1}$, —NR$^{C1}$C(=NR$^{C1}$)SR$^{C1}$, —NR$^{C1}$C(=NR$^{C1}$)N(R$^{C1}$)$_2$, —NR$^{C1}$S(=O)$_2$R$^{C1}$, —NR$^{C1}$S(=O)$_2$OR$^{C1}$, —NR$^{C1}$S(=O)$_2$SR$^{C1}$, —NR$^{C1}$S(=O)$_2$N(R$^{C1}$)$_2$, —NR$^{C1}$S(=O)R$^{C1}$, —NR$^{C1}$S(=O)OR$^{C1}$, —NR$^{C1}$S(=O)SR$^{C1}$, —NR$^{C1}$S(=O)N(R$^{C1}$)$_2$, —NR$^{C1}$P(=O), —NR$^{C1}$P(=O)$_2$, —NR$^{C1}$P(=O)(R$^{C1}$)$_2$, —NR$^{C1}$P(=O)R$^{C1}$(OR$^{C1}$), —NR$^{C1}$P(=O)(OR$^{C1}$)$_2$, —OC(=O)R$^{C1}$, —OC(=O)OR$^{C1}$, —OC(=O)SR$^{C1}$, —OC(=O)N(R$^{C1}$)$_2$, —OC(=NR$^{C1}$)R$^{C1}$, —OC(=NR$^{C1}$)OR$^{C1}$, —OC(=NR$^{C1}$)N(R$^{C1}$)$_2$, —OC(=S)R$^{C1}$, —OC(=S)OR$^{C1}$, —OC(=S)SR$^{C1}$, —OC(=S)N(R$^{C1}$)$_2$, —ON(R$^{C1}$)$_2$, —OS(=O)R$^{C1}$, —OS(=O)OR$^{C1}$, —OS(=O)SR$^{C1}$, —OS(=O)N(R$^{C1}$)$_2$, —OS(=O)$_2$R$^{C1}$, —OS(=O)$_2$OR$^{C1}$, —OS(=O)$_2$SR$^{C1}$, —OS(=O)$_2$N(R$^{C1}$)$_2$, —OP(=O)$_2$, —OP(=O)(R$^{C1}$)$_2$, —OP(=O)R$^{C1}$(OR$^{C1}$), —OP(=O)(OR$^{C1}$)$_2$, —OP(=O), —OP(R$^{C1}$)$_2$, —OPR$^{C1}$(OR$^{C1}$), —OP(OR$^{C1}$)$_2$, —OSi(R$^{C1}$)$_3$, —OSi(R$^{C1}$)$_2$OR$^{C1}$, —OSi(R$^{C1}$)(OR$^{C1}$)$_2$, —OSi(OR$^{C1}$)$_3$, —SSR$^{C1}$, —S(=O)R$^{C1}$, —S(=O)OR$^{C1}$, —S(=O)N(R$^{C1}$)$_2$, —S(=O)$_2$R$^{C1}$, —S(=O)$_2$OR$^{C1}$, —S(=O)$_2$N(R$^{C1}$)$_2$, —SC(=O)R$^{C1}$, —SC(=O)OR$^{C1}$, —SC(=O)SR$^{C1}$, —SC(=O)N(R$^{C1}$)$_2$, —SC(=S)R$^{C1}$, —SC(=S)OR$^{C1}$, —SC(=S)SR$^{C1}$, —SC(=S)N(R$^{C1}$)$_2$, —P(R$^{C1}$)$_2$, —PR$^{C1}$(OR$^{C1}$), —P(OR$^{C1}$)$_2$, —P(=O), —P(=O)(R$^{C1}$)$_2$, —P(=O)(OR$^{C1}$)$_2$, —P(=O)R$^{C1}$(OR$^{C1}$), —P(=O)$_2$, —B(R$^{C1}$)$_2$, —B(OR$^{C1}$)$_2$, —BR$^{C1}$(OR$^{C1}$), —Si(R$^{C1}$)$_3$, —Si(R$^{C1}$)$_2$OR$^{C1}$, —SiR$^{C1}$(OR$^{C1}$)$_2$, and —Si(OR$^{C1}$)$_3$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{C1}$ groups are joined to form an optionally substituted heterocyclic ring or optionally substituted heteroaryl ring;

n is 0, 1, 2, 3, or 4;

L is a bond or an optionally substituted, branched or unbranched C$_{1-6}$ hydrocarbon chain;

R$^D$ is any one of Formulae (i-1)-(i-43):

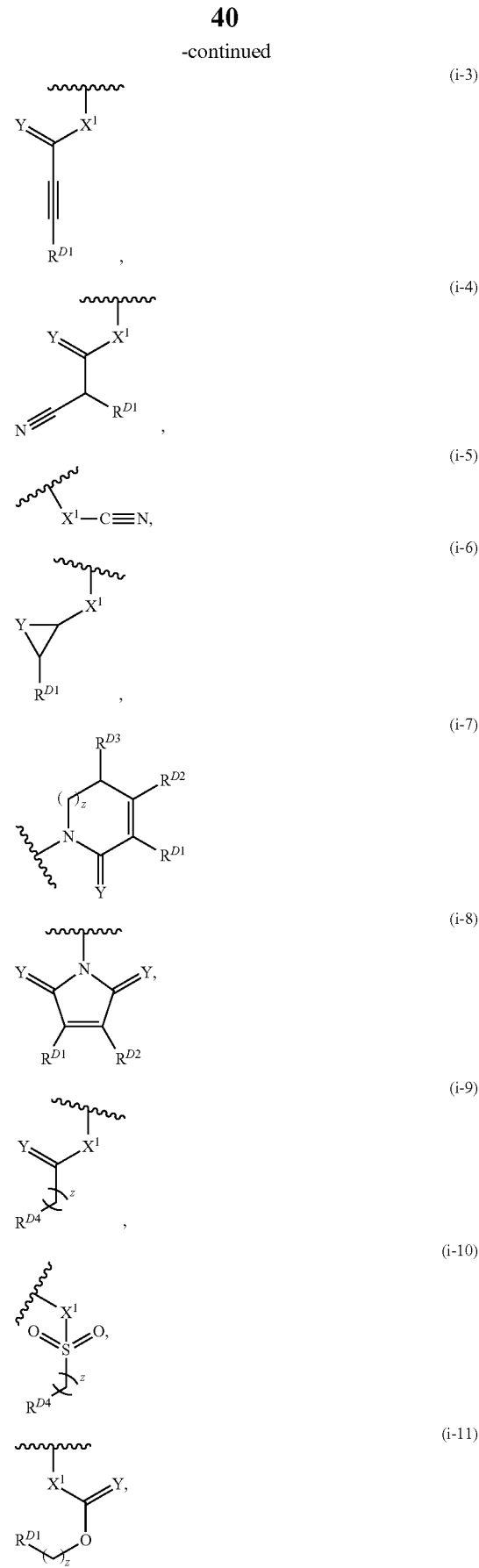

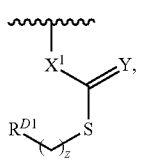 (i-12)
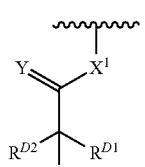 (i-13)
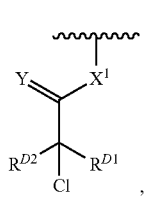 (i-14)
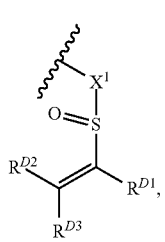 (i-15)
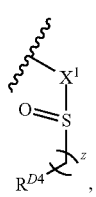 (i-16)
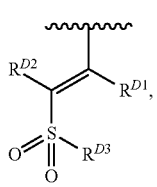 (i-17)
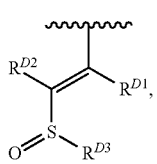 (i-18)
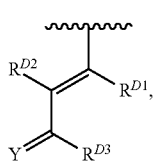 (i-19)
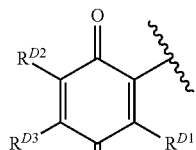 (i-20)
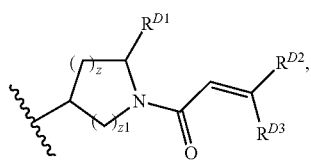 (i-21)
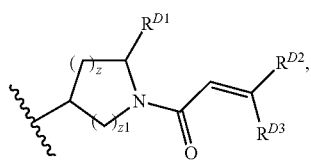 (i-22)
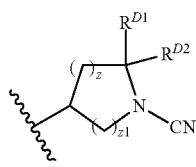 (i-23)
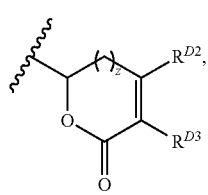 (i-24)
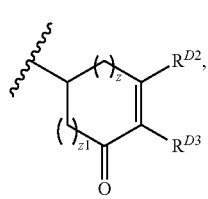 (i-25)
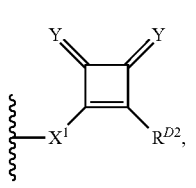 (i-26)
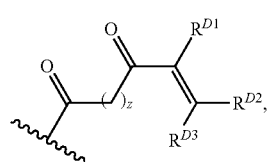 (i-27)
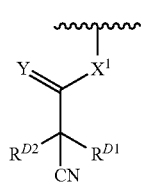

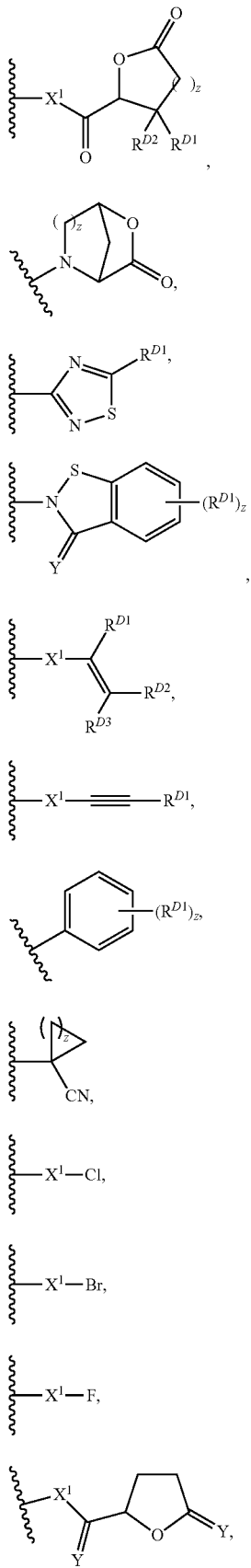

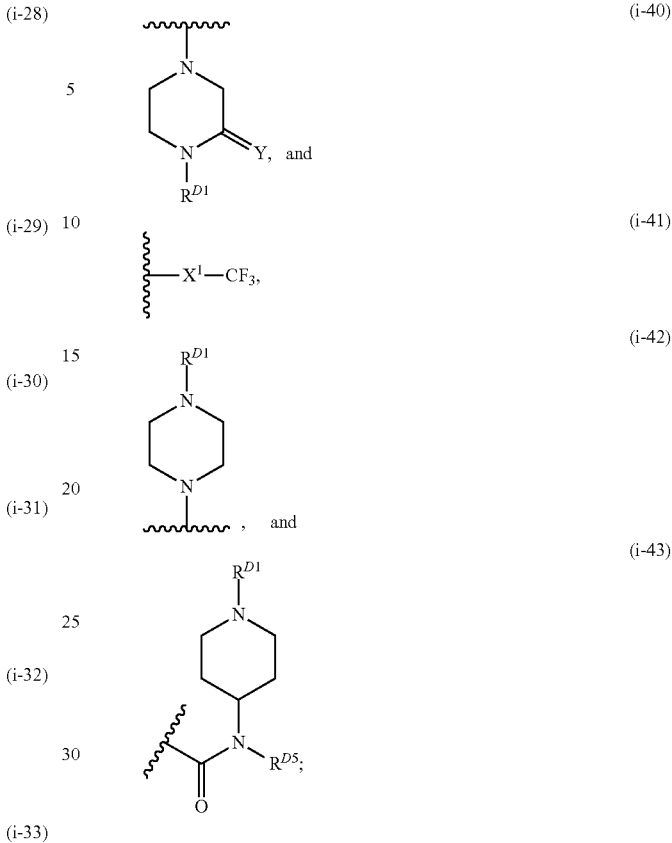

wherein:

each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of $R^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D1a}$ groups are joined to form an substituted or unsubstituted heterocyclic ring;

each instance of $R^{D2}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$R$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of $R^{D2a}$ is independently hydrogen, acyl, substituted or unsubstituted unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two $R^{D2a}$ groups are joined to form an substituted or unsubstituted heterocyclic ring;

each instance of $R^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{D3a}$, —$N(R^{D3a})_2$, —$SR^{D3a}$, —$CH_2OR^{D3a}$, —$CH_2N(R^{D3a})_2$, —$CH_2SR^{D3a}$, —$C(=O)R^{D3a}$, —$C(=O)OR^{D3a}$, —$C(=O)SR^{D3a}$, —$C(=O)N(R^{D3a})_2$, —$C(=S)R^{D3a}$, —$C(=S)OR^{D3a}$, —$C(=S)SR^{D3a}$, —$C(=S)N(R^{D3a})_2$, —$C(=NR^{D3a})R^{D3a}$, —$C(=NR^{D3a})OR^{D3a}$, —$C(=NR^{D3a})SR^{D3a}$, or —$C(=NR^{D3a})N(R^{D3a})_2$ wherein each occurrence of $R^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two $R^{D3a}$ groups are joined to form an substituted or unsubstituted heterocyclic ring;

optionally $R^{D1}$ and $R^{D3}$, or $R^{D2}$ and $R^{D3}$, or $R^{D1}$ and $R^{D2}$ are joined to form an substituted or unsubstituted carbocyclic or substituted or unsubstituted heterocyclic ring; $R^{D4}$ is a leaving group selected from the group consisting of —Br, —Cl, —I, and —$OS(=O)_wR^{D4a}$, wherein w is 1 or 2, and $R^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $X^1$ is independently a bond, —C(=O)—, —$SO_2$—, —$NR^{D5}$—, optionally substituted alkylene, or optionally substituted heteroarylene, wherein $R^{D5}$ is hydrogen, $C_{1-6}$ alkyl, or a nitrogen protecting group;

each instance of Y is independently O, S, or $NR^{D6}$, wherein $R^{D6}$ is hydrogen, $C_{1-6}$ alkyl, or a nitrogen protecting group; and each instance of z and $z_1$ is independently 0, 1, 2, 3, 4, 5, or 6, as valency permits.

In another aspect of the present invention, provided are compounds of Formula (III):

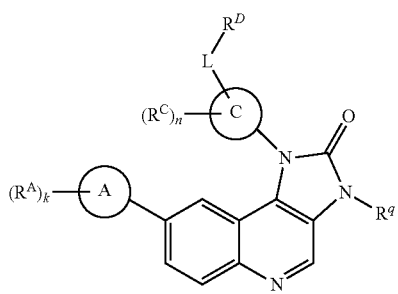

(III)

or a pharmaceutically acceptable salt thereof;
wherein:
Ring A is aryl, arylalkenyl, or heteroaryl;
each instance of $R^A$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{A1}$, —$N(R^{A1})_2$, —$SR^{A1}$, —CN, —$C(=NR^{A1})R^{A1}$, —$C(=NR^{A1})OR^{A1}$, —$C(=NR^{A1})SR^{A1}$, —$C(=NR^{A1})N(R^{A1})_2$, —$C(=O)NR^{A1}$—, —$NR^{A1}C(=O)$—, —$C(=O)R^{A1}$, —$C(=S)R^{A1}$, —$C(=S)OR^{A1}$, —$C(=S)SR^{A1}$, —$C(=S)N(R^{A1})_2$, —$NO_2$, —$N_3$, —$N(R^{A1})_3{}^+F^-$, —$N(R^{A1})_3{}^+Cl^-$, —$N(R^{A1})_3{}^+Br^-$, —$N(R^{A1})_3{}^+I^-$, —$N(OR^{A1})R^{A1}$, —$NR^{A1}C(=O)R^{A1}$, —$NR^{A1}C(=O)OR^{A1}$, —$NR^{A1}C(=O)SR^{A1}$, —$NR^{A1}C(=O)N(R^{A1})_2$, —$NR^{A1}C(=S)R^{A1}$, —$NR^{A1}C(=S)OR^{A1}$, —$NR^{A1}C(=S)SR^{A1}$, —$NR^{A1}C(=S)N(R^{A1})_2$, —$NR^{A1}C(=NR^{A1})R^{A1}$, —$NR^{A1}C(=NR^{A1})OR^{A1}$, —$NR^{A1}C(=NR^{A1})SR^{A1}$, —$NR^{A1}C(=NR^{A1})N(R^{A1})_2$, —$NR^{A1}S(=O)_2R^{A1}$, —$NR^{A1}S(=O)_2OR^{A1}$, —$NR^{A1}S(=O)_2SR^{A1}$, —$NR^{A1}S(=O)_2N(R^{A1})_2$, —$NR^{A1}S(=O)R^{A1}$, —$NR^{A1}S(=O)OR^{A1}$, —$NR^{A1}S(=O)SR^{A1}$, —$NR^{A1}S(=O)N(R^{A1})_2$, —$NR^{A1}P(=O)$, —$NR^{A1}P(=O)_2$, —$NR^{A1}P(=O)(R^{A1})_2$, —$NR^{A1}P(=O)R^{A1}(OR^{A1})$, —$NR^{A1}P(=O)(OR^{A1})_2$, —$OC(=O)R^{A1}$, —$OC(=O)OR^{A1}$, —$OC(=O)SR^{A1}$, —$OC(=O)N(R^{A1})_2$, —$OC(=NR^{A1})R^{A1}$, —$OC(=NR^{A1})OR^{A1}$, —$OC(=NR^{A1})N(R^{A1})_2$, —$OC(=S)R^{A1}$, —$OC(=S)OR^{A1}$, —$OC(=S)SR^{A1}$, —$OC(=S)N(R^{A1})_2$, —$ON(R^{A1})_2$, —$OS(=O)R^{A1}$, —$OS(=O)OR^{A1}$, —$OS(=O)SR^{A1}$, —$OS(=O)N(R^{A1})_2$, —$OS(=O)_2R^{A1}$, —$OS(=O)_2OR^{A1}$, —$OS(=O)_2SR^{A1}$, —$OS(=O)_2N(R^{A1})_2$, —$OP(=O)_2$, —$OP(=O)(R^{A1})_2$, —$OP(=O)R^{A1}(OR^{A1})$, —$OP(=O)(OR^{A1})_2$, —$OP(=O)$, —$OP(R^{A1})_2$, —$OPR^{A1}(OR^{A1})$, —$OP(OR^{A1})_2$, —$OSi(R^{A1})_3$, —$OSi(R^{A1})_2OR^{A1}$, —$OSi(R^{A1})(OR^{A1})_2$, —$OSi(OR^{A1})_3$, —$SSR^{A1}$, —$S(=O)R^{A1}$, —$S(=O)OR^{A1}$, —$S(=O)N(R^{A1})_2$, —$S(=O)_2R^{A1}$, —$S(=O)_2OR^{A1}$, —$S(=O)_2N(R^{A1})_2$, —$SC(=O)R^{A1}$, —$SC(=O)OR^{A1}$, —$SC(=O)SR^{A1}$, —$SC(=O)N(R^{A1})_2$, —$SC(=S)R^{A1}$, —$SC(=S)OR^{A1}$, —$SC(=S)SR^{A1}$, —$SC(=S)N(R^{A1})_2$, —$P(R^{A1})_2$, —$PR^{A1}(OR^{A1})$, —$P(OR^{A1})_2$, —$P(=O)$, —$P(=O)(R^{A1})_2$, —$P(=O)(OR^{A1})_2$, —$P(=O)R^{A1}(OR^{A1})$, —$P(=O)_2$, —$B(R^{A1})_2$, —$B(OR^{A1})_2$, —$BR^{A1}(OR^{A1})$, —$Si(R^{A1})_3$, —$Si(R^{A1})_2OR^{A1}$, —$SiR^{A1}(OR^{A1})_2$, and —$Si(OR^{A1})_3$, wherein each occurrence of $R^{A1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{A1}$ groups are joined to form an optionally substituted heterocyclic ring;

k is 0, 1, 2, 3, 4, or 5;

Ring C is a carbocyclic, heterocyclic, aryl, or heteroaryl ring;

each instance of $R^C$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{C1}$, —$N(R^{C1})_2$, —$SR^{C1}$, —CN, —$C(=NR^{C1})R^{C1}$, —$C(=NR^{C1})OR^{C1}$, —$C(=NR^{C1})SR^{C1}$, —$C(=NR^{C1})N(R^{C1})_2$, —$C(=O)R^{C1}$, —$C(=S)R^{C1}$, —$C(=S)OR^{C1}$, —$C(=S)SR^{C1}$, —$C(=S)N(R^{C1})_2$, —$NO_2$, —$N_3$, —$N(R^{C1})_3{}^+F^-$, —$N(R^{C1})_3{}^+Cl^-$, —$N(R^{C1})_3{}^+Br^-$, —$N(R^{C1})_3{}^+I^-$, —$N(OR^{C1})R^{C1}$, —$NR^{C1}C(=O)R^{C1}$, —$NR^{C1}C(=O)OR^{C1}$, —$NR^{C1}C(=O)SR^{C1}$, —$NR^{C1}C(=O)N(R^{C1})_2$, —$NR^{C1}C(=S)R^{C1}$, —$NR^{C1}C(=S)OR^{C1}$, —$NR^{C1}C(=S)SR^{C1}$, —$NR^{C1}C(=S)N(R^{C1})_2$, —$NR^{C1}C(=NR^{C1})R^{C1}$, —$NR^{C1}C(=NR^{C1})OR^{C1}$, —$NR^{C1}C(=NR^{C1})SR^{C1}$, —$NR^{C1}C(=NR^{C1})N(R^{C1})_2$, —NR$^{C1}$S(=O)$_2$R$^{C1}$, —NR$^{C1}$S(=O)$_2$OR$^{C1}$, —NR$^{C1}$S(=O)$_2$SR$^{C1}$, —NR$^{C1}$S(=O)$_2$N(R$^{C1}$)$_2$, —NR$^{C1}$S(=O)R$^{C1}$, —NR$^{C1}$S(=O)OR$^{C1}$, —NR$^{C1}$S(=O)SR$^{C1}$, —NR$^{C1}$S(=O)N(R$^{C1}$)$_2$, —NR$^{C1}$P(=O), —NR$^{C1}$P(=O)$_2$, —NR$^{C1}$P(=O)(R$^{C1}$)$_2$, —NR$^{C1}$P(=O)R$^{C1}$(OR$^{C1}$), —NR$^{C1}$P(=O)(OR$^{C1}$)$_2$, —OC(=O)R$^{C1}$, —OC(=O)OR$^{C1}$, —OC(=O)SR$^{C1}$, —OC(=O)N(R$^{C1}$)$_2$, —OC(=NR$^{C1}$)R$^{C1}$, —OC(=NR$^{C1}$)OR$^{C1}$, —OC(=NR$^{C1}$)N(R$^{C1}$)$_2$, —OC(=S)R$^{C1}$, —OC(=S)OR$^{C1}$, —OC(=S)SR$^{C1}$, —OC(=S)N(R$^{C1}$)$_2$, —ON(R$^{C1}$)$_2$, —OS(=O)R$^{C1}$, —OS(=O)OR$^{C1}$, —OS(=O)SR$^{C1}$, —OS(=O)N(R$^{C1}$)$_2$, —OS(=O)$_2$R$^{C1}$, —OS(=O)$_2$OR$^{C1}$, —OS(=O)$_2$SR$^{C1}$, —OS(=O)$_2$N(R$^{C1}$)$_2$, —OP(=O)$_2$, —OP(=O)(R$^{C1}$)$_2$, —OP(=O)R$^{C1}$(OR$^{C1}$), —OP(=O)(OR$^{C1}$)$_2$, —OP(=O), —OP(R$^{C1}$)$_2$, —OPR$^{C1}$(OR$^{C1}$), —OP(OR$^{C1}$)$_2$, —OSi(R$^{C1}$)$_3$, —OSi(R$^{C1}$)$_2$OR$^{C1}$, —OSi(R$^{C1}$)(OR$^{C1}$)$_2$, —OSi(OR$^{C1}$)$_3$, —SSR$^{C1}$, —S(=O)R$^{C1}$, —S(=O)OR$^{C1}$, —S(=O)N(R$^{C1}$)$_2$, —S(=O)$_2$R$^{C1}$, —S(=O)$_2$OR$^{C1}$, —S(=O)$_2$N(R$^{C1}$)$_2$, —SC(=O)R$^{C1}$, —SC(=O)OR$^{C1}$, —SC(=O)SR$^{C1}$, —SC(=O)N(R$^{C1}$)$_2$, —SC(=S)R$^{C1}$, —SC(=S)OR$^{C1}$, —SC(=S)SR$^{C1}$, —SC(=S)N(R$^{C1}$)$_2$, —P(R$^{C1}$)$_2$, —PR$^{C1}$(OR$^{C1}$), —P(OR$^{C1}$)$_2$, —P(=O), —P(=O)(R$^{C1}$)$_2$, —P(=O)(OR$^{C1}$)$_2$, —P(=O)R$^{C1}$(OR$^{C1}$), —P(=O)$_2$, —B(R$^{C1}$)$_2$, —B(OR$^{C1}$)$_2$, —BR$^{C1}$(OR$^{C1}$), —Si(R$^{C1}$)$_3$, —Si(R$^{C1}$)$_2$OR$^{C1}$, —SiR$^{C1}$(OR$^{C1}$)$_2$, and —Si(OR$^{C1}$)$_3$, wherein each occurrence of R$^{C1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two R$^{C1}$ groups are joined to form an optionally substituted heterocyclic ring or optionally substituted heteroaryl ring;

R$^q$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

n is 0, 1, 2, 3, or 4;

L is a bond or an optionally substituted, branched or unbranched C$_{1-6}$ hydrocarbon chain;

R$^D$ is any one of Formulae (i-1)-(i-43):

(i-1)

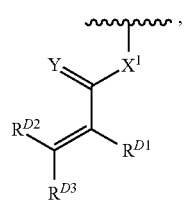

(i-2)

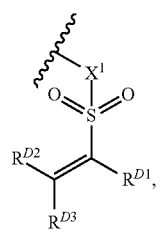

(i-3)

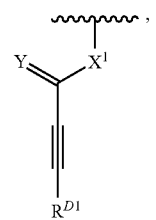

(i-4)

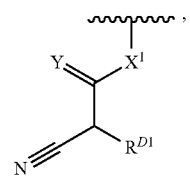

(i-5)

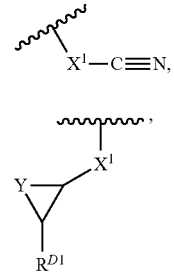

(i-6)

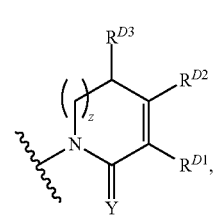

(i-7)

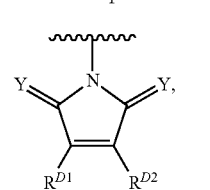

(i-8)

(i-9)

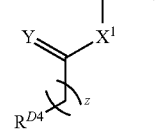

(i-10)

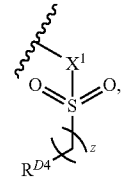

(i-11)

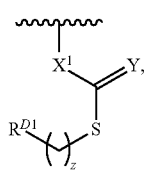 (i-12)
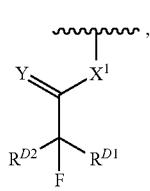 (i-13)
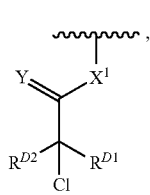 (i-14)
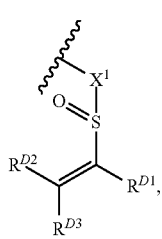 (i-15)
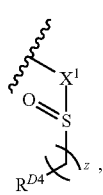 (i-16)
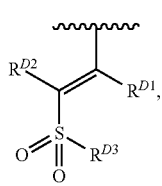 (i-17)
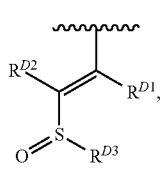 (i-18)
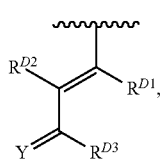 (i-19)
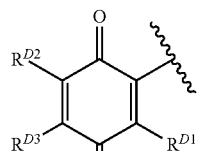 (i-20)
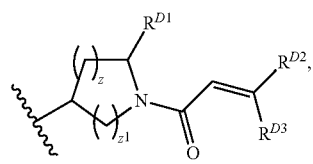 (i-21)
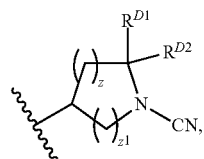 (i-22)
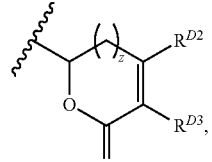 (i-23)
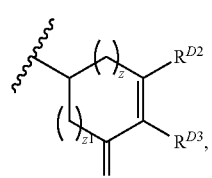 (i-24)
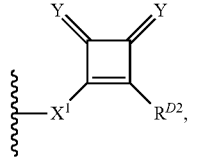 (i-25)
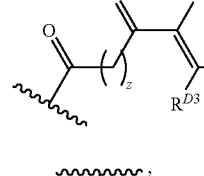 (i-26)
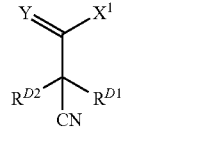 (i-27)
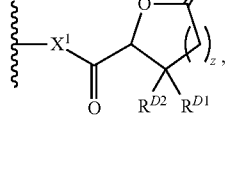 (i-28)

-continued (i-29) 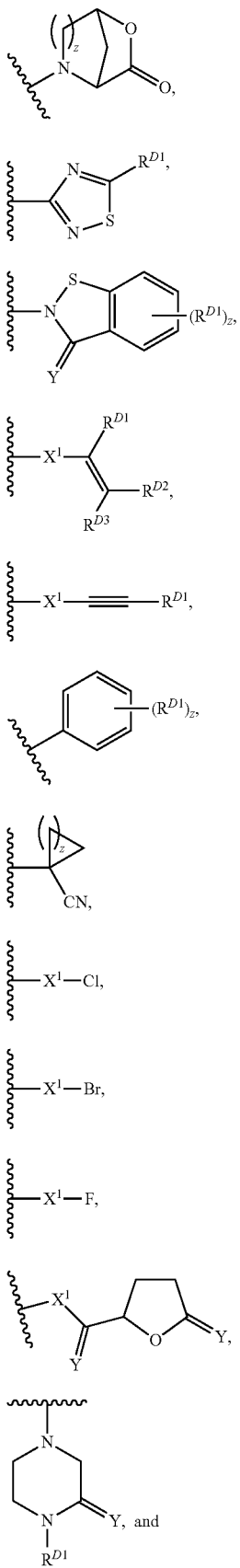

(i-30)

(i-31)

(i-32)

(i-33)

(i-34)

(i-35)

(i-36)

(i-37)

(i-38)

(i-39)

(i-40)

-continued

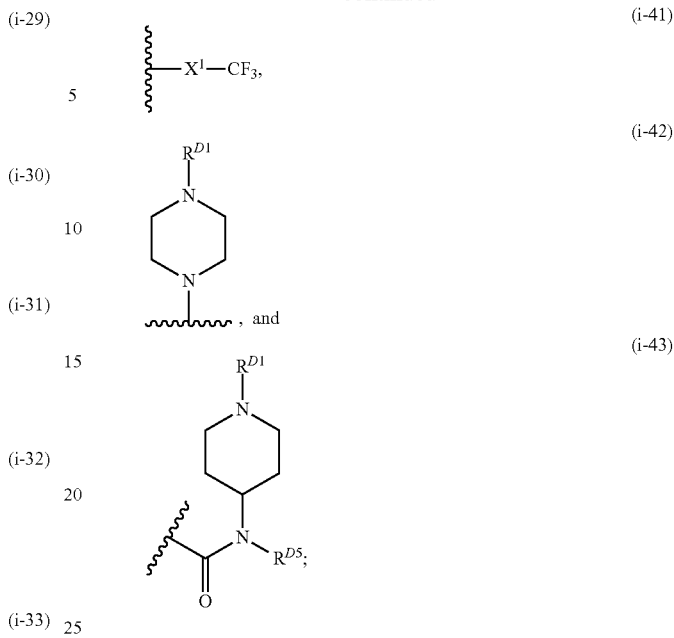

(i-41)

(i-42)

(i-43)

wherein:
each instance of $R^{D1}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(═O)R$^{D1a}$, —C(═O)OR$^{D1a}$, —C(═O)SR$^{D1a}$, —C(═O)N(R$^{D1a}$)$_2$, —C(═S)R$^{D1a}$, —C(═S)OR$^{D1a}$, —C(═S)SR$^{D1a}$, —C(═S)N(R$^{D1a}$)$_2$, —C(═NR$^{D1a}$)R$^{D1a}$, —C(═NR$^{D1a}$)OR$^{D1a}$, —C(═NR$^{D1a}$)SR$^{D1a}$, or —C(═NR$^{D1a}$)N(R$^{D1a}$)$_2$, wherein each occurrence of R$^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D1a}$ groups are joined to form an substituted or unsubstituted heterocyclic ring;
each instance of R$^{D2a}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(═O)R$^{D2a}$, —C(═O)OR$^{D2a}$, —C(═O)SR$^{D2a}$, —C(═O)N(R$^{D2a}$)$_2$, —C(═S)R$^{D2a}$, —C(═S)OR$^{D2a}$, —C(═S)SR$^{D2a}$, —C(═S)N(R$^{D2a}$)$_2$, —C(═NR$^{D2a}$)R$^{D2a}$, —C(═NR$^{D2a}$)OR$^{D2a}$, —C(═NR$^{D2a}$)SR$^{D2a}$, and C(═NR$^{D2a}$)N(R$^{D2a}$)$_2$, wherein each occurrence of R$^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{D2a}$ groups are joined to form an substituted or unsubstituted heterocyclic ring;
each instance of R$^{D3}$ is independently hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of R$^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D3a}$ groups are joined to form an substituted or unsubstituted heterocyclic ring;

optionally R$^{D1}$ and R$^{D3}$, or R$^{D2}$ and R$^{D3}$, or R$^{D1}$ and R$^{D2}$ are joined to form an substituted or unsubstituted carbocyclic or substituted or unsubstituted heterocyclic ring; R$^{D4a}$ is a leaving group selected from the group consisting of —Br, —Cl, —I, and —OS(=O)$_w$R$^{D4a}$, wherein w is 1 or 2, and R$^{D2a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of X$^1$ is independently a bond, —C(=O)—, —SO$_2$—, —NR$^{D5}$—, optionally substituted alkylene, or optionally substituted heteroarylene, wherein R$^{D5}$ is hydrogen, C$_{1-6}$ alkyl, or a nitrogen protecting group;

each instance of Y is independently O, S, or NR$^{D6}$, wherein R$^{D6}$ is hydrogen, C$_{1-6}$ alkyl, or a nitrogen protecting group; and each instance of z and z$_1$ is independently 0, 1, 2, 3, 4, 5, or 6, as valency permits.

As generally defined above, Ring A is aryl, arylalkenyl, or heteroaryl. In certain embodiments, Ring A is heteroaryl. In certain embodiments, Ring A is arylalkenyl. In certain embodiments, Ring A is aryl. Ring A may be substituted with one or more substituents R$^A$. The substituent R$^A$ may be attached to a carbon atom or heteroatom of Ring A. In certain embodiments, Ring A is a monocyclic heteroaryl ring. In certain embodiments, Ring A is a bicyclic heteroaryl ring. In certain embodiments, Ring A is a tricyclic heteroaryl ring. In certain embodiments, Ring A is a substituted heteroaryl ring. In certain embodiments, Ring A is an unsubstituted heteroaryl ring. In certain embodiments, Ring A is substituted pyridyl. In certain embodiments, Ring A is unsubstituted pyridyl. In certain embodiments, Ring A is a heteroaryl ring fused with one or more carbocyclic, heterocyclic, aryl, or heteroaryl groups wherein the point of attachment is on the heteroaryl ring.

In certain embodiments, Ring A is a 6-membered heteroaryl ring.

In certain embodiments,

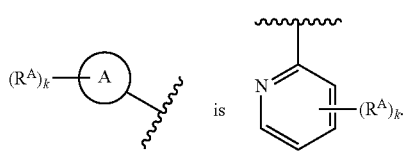

In certain embodiments,

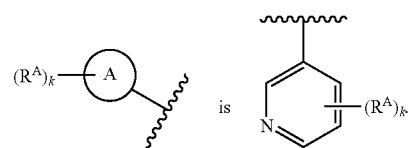

In certain embodiments,

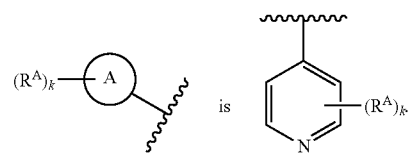

In certain embodiments,

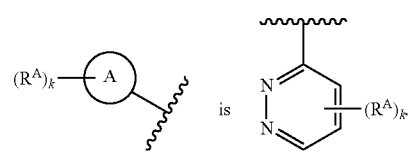

In certain embodiments,

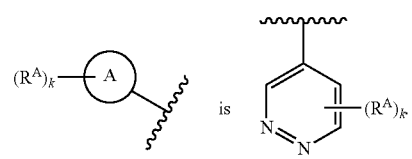

In certain embodiments,

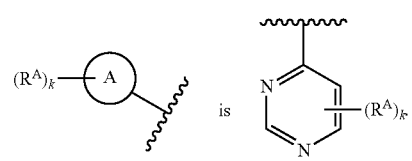

In certain embodiments,

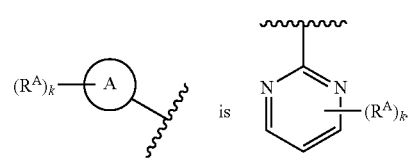

In certain embodiments,

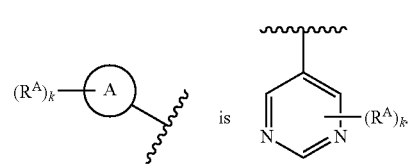

In certain embodiments,

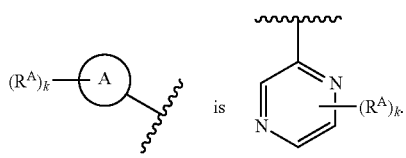 is 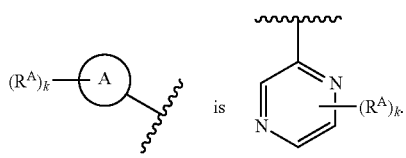.

In certain embodiments,

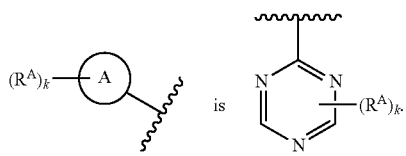 is 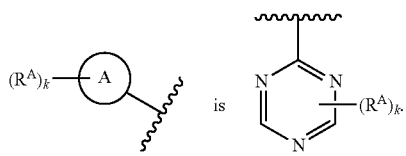.

Ring A of Formula (I) may also be a 5-membered heteroaryl ring. In certain embodiments, Ring A is a 5-membered heteroaryl ring wherein one of the five ring carbon atoms is replaced by nitrogen, oxygen, or sulfur.

In certain embodiments,

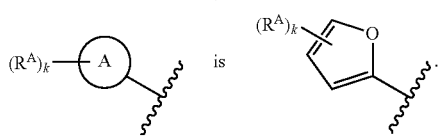 is 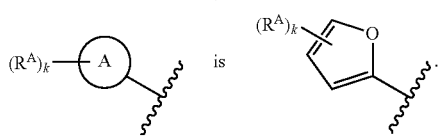.

In certain embodiments

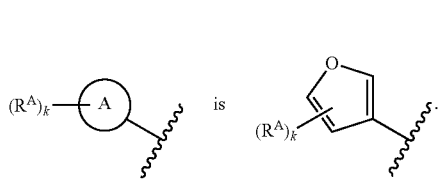 is 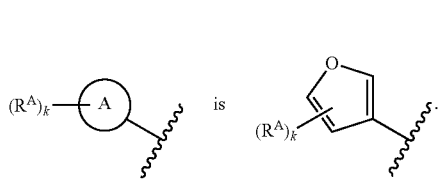.

In certain embodiments,

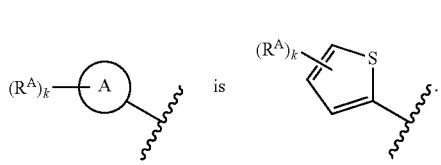 is 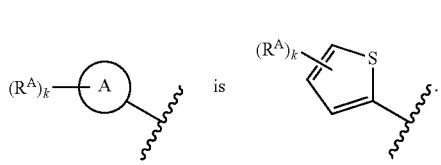.

In certain embodiments

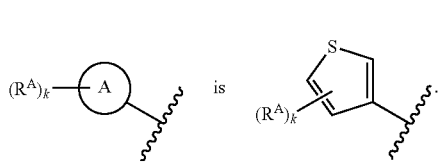 is 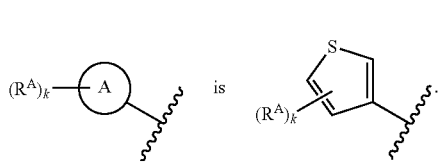.

In certain embodiments,

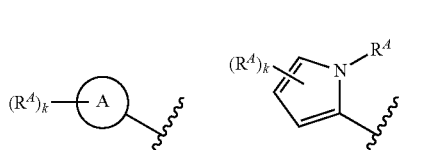 is 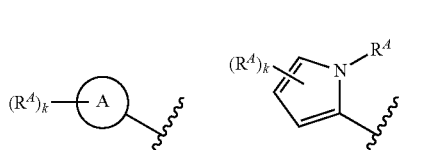.

In certain embodiments,

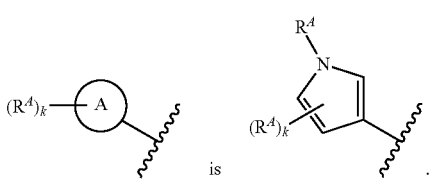 is 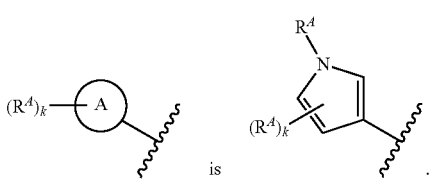.

In certain embodiments, Ring A is a 5-membered heteroaryl ring wherein two of the five ring carbon atoms are independently replaced by nitrogen, oxygen, or sulfur.

In certain embodiments,

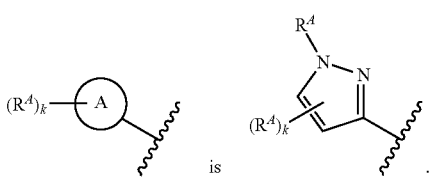 is 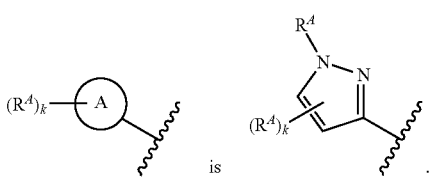.

In certain embodiments,

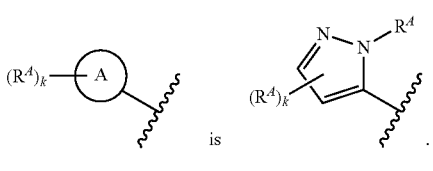 is 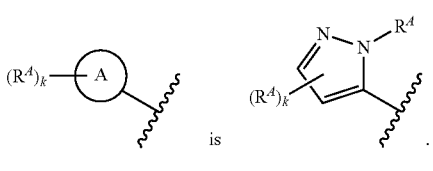.

In certain embodiments,

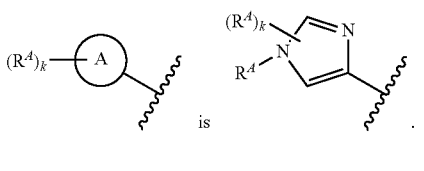 is 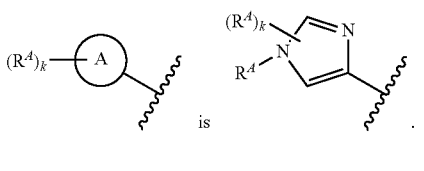.

In certain embodiments,

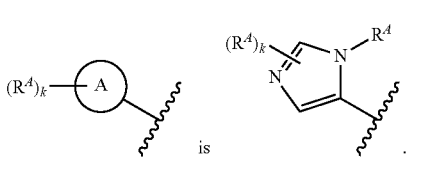 is 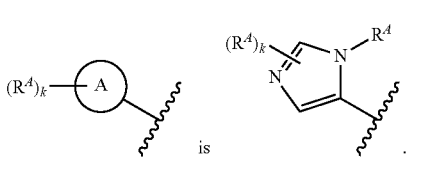.

In certain embodiments,

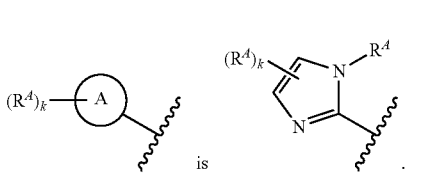 is 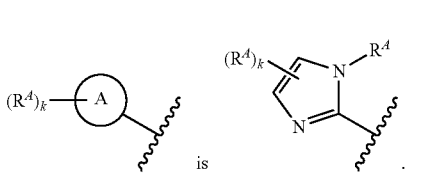.

In certain embodiments,

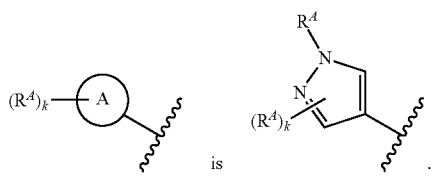

is

In certain embodiments,

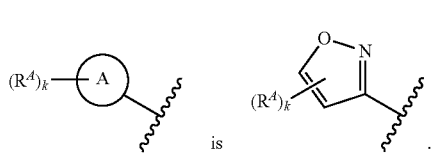

is

In certain embodiments,

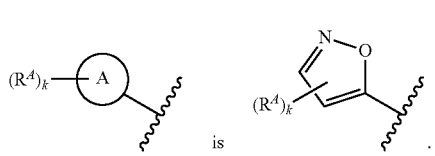

is

In certain embodiments,

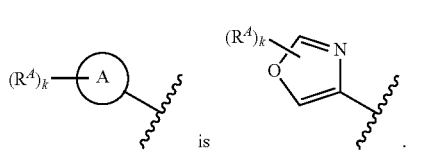

is

In certain embodiments,

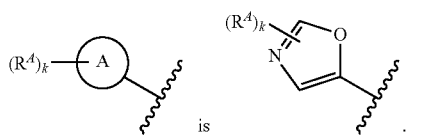

is

In certain embodiments,

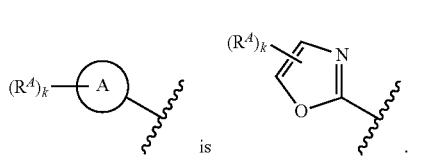

is

In certain embodiments,

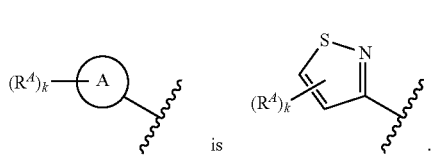

is

In certain embodiments,

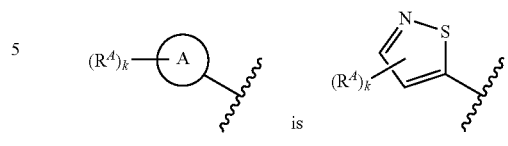

is

In certain embodiments,

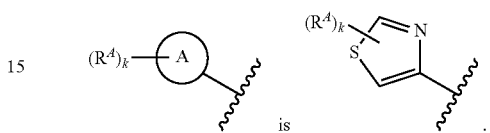

is

In certain embodiments,

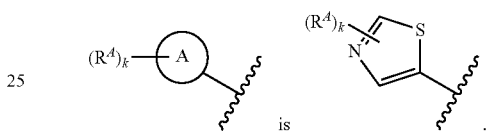

is

In certain embodiments,

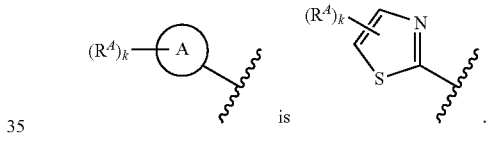

is

In certain embodiments, Ring A is a 5-membered heteroaryl ring wherein three of the five ring carbon atoms are independently replaced by nitrogen, oxygen, or sulfur.

In certain embodiments,

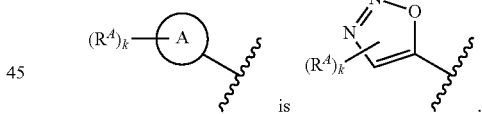

is

In certain embodiments,

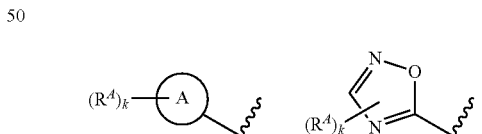

is

In certain embodiments,

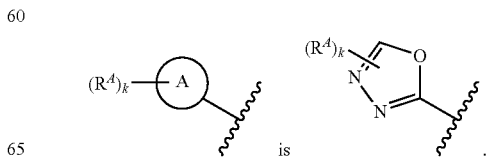

is

In certain embodiments, 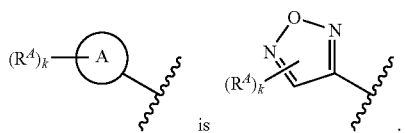 is 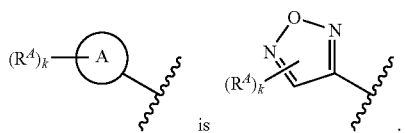.

In certain embodiments, 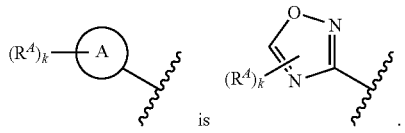 is 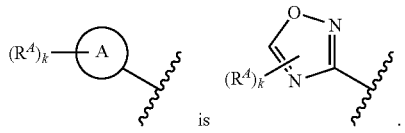.

In certain embodiments, 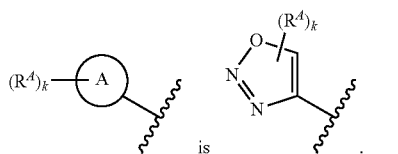 is 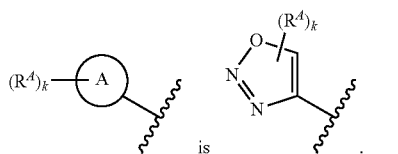.

In certain embodiments, 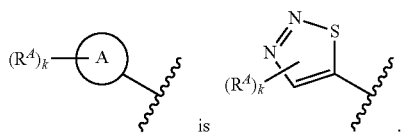 is 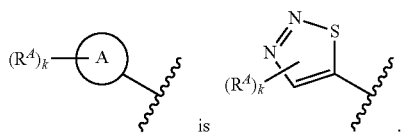.

In certain embodiments, 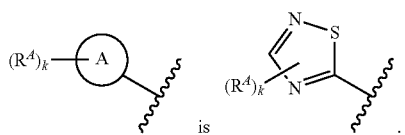 is 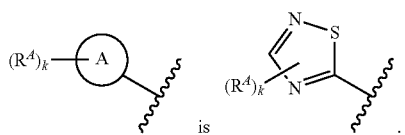.

In certain embodiments, 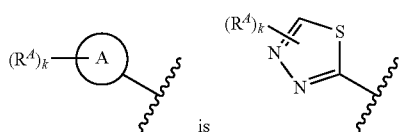 is 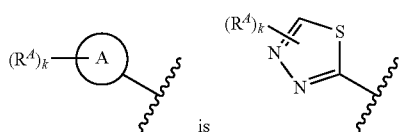.

In certain embodiments, 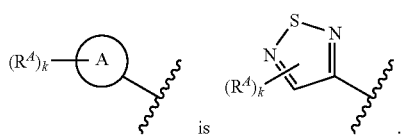 is 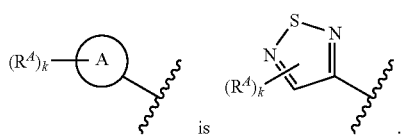.

In certain embodiments, 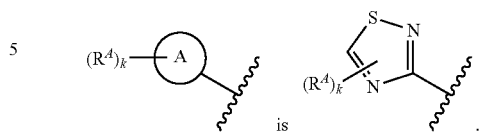 is 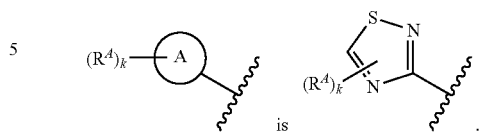.

In certain embodiments, 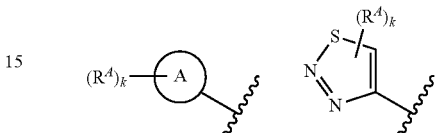 is 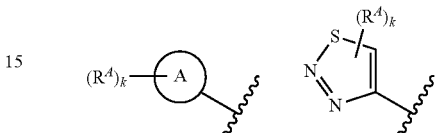.

In certain embodiments, 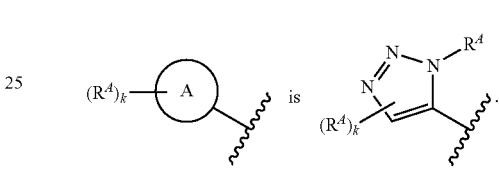 is 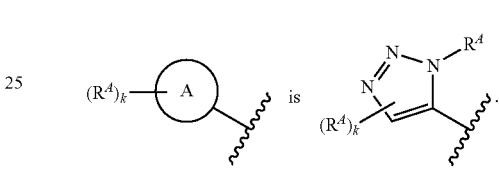.

In certain embodiments, 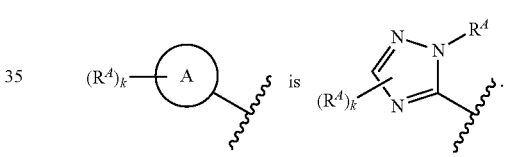 is 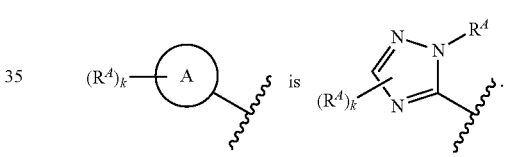.

In certain embodiments, 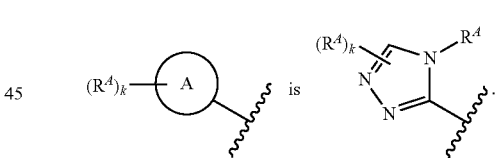 is 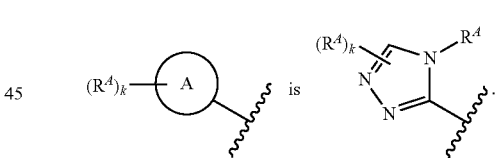.

In certain embodiments, 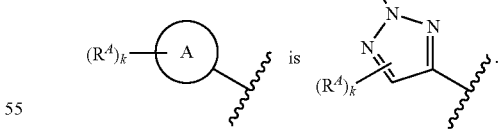 is 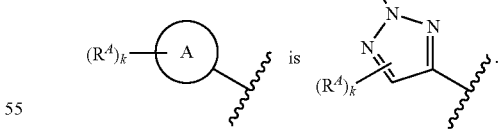.

In certain embodiments, 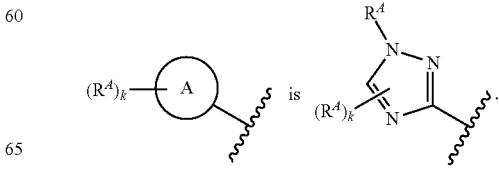 is 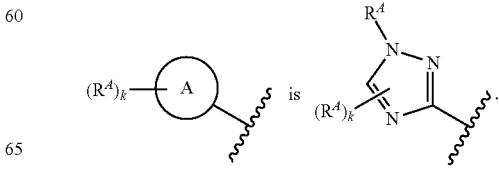.

In certain embodiments,

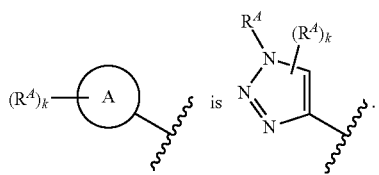

In certain embodiments,

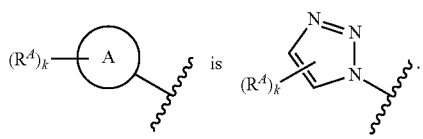

In certain embodiments,

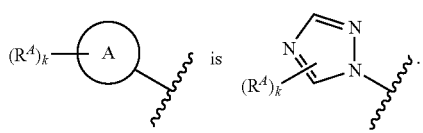

In certain embodiments,

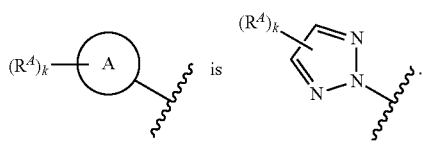

In certain embodiments,

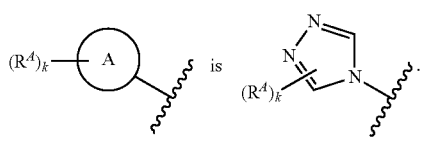

In certain embodiments, Ring A is a 5-membered heteroaryl ring wherein four of the five ring carbon atoms are independently replaced by nitrogen, oxygen, or sulfur.

In certain embodiments,

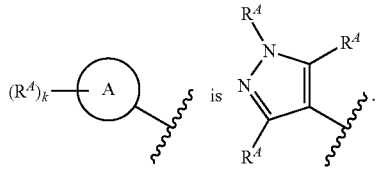

In certain embodiments,

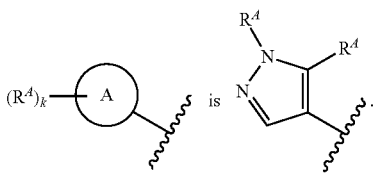

In certain embodiments,

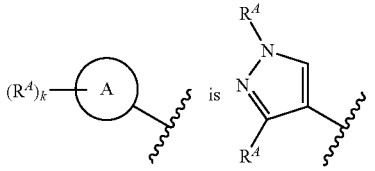

In certain embodiments,

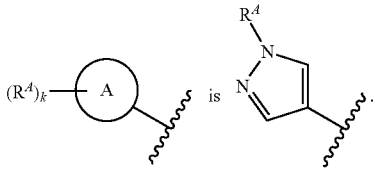

In certain embodiments,

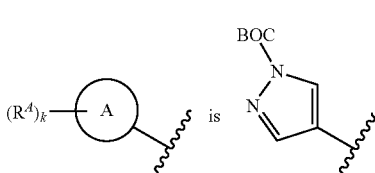

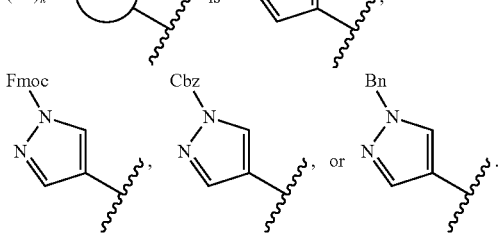

In certain embodiments,

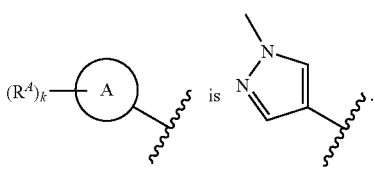

In certain embodiments,

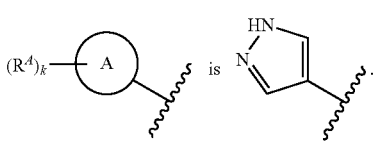

In certain embodiments, Ring A is bicyclic heteroaryl. In certain embodiments,

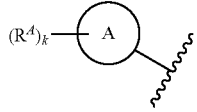

is one of the following formulae:

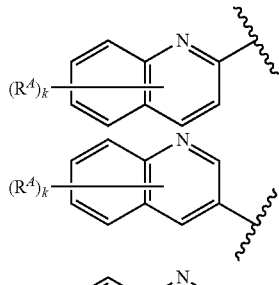
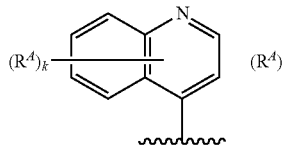
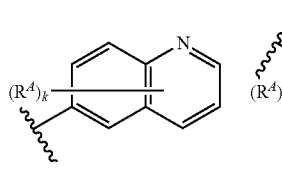
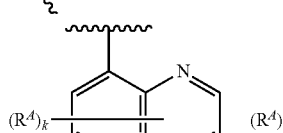
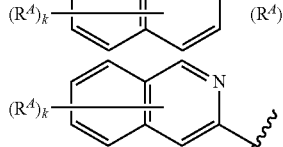
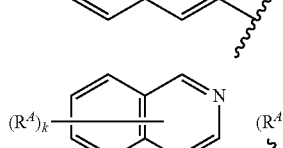
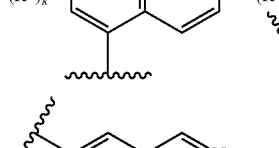
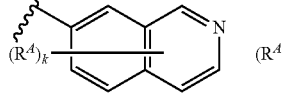
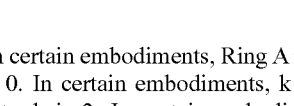

In certain embodiments, Ring A is unsubstituted, and thus k is 0. In certain embodiments, k is 1. In certain embodiments, k is 2. In certain embodiments, k is 3. In certain embodiments, k is 4. In certain embodiments, k is 5.

In certain embodiments, Ring A is aryl. In certain embodiments, Ring A is phenyl. In certain embodiments, Ring A is arylalkenyl. In certain embodiments, Ring A is phenylalkenyl. In certain embodiments,

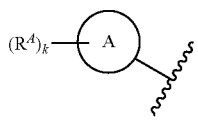

is one of the following formulae:

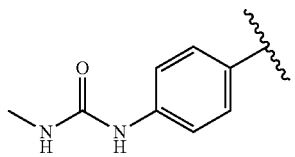
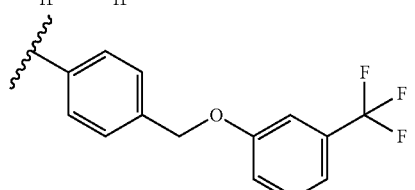
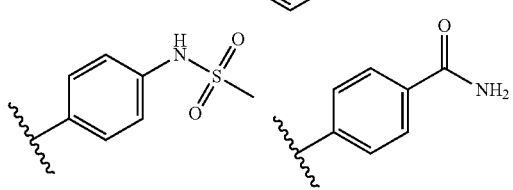
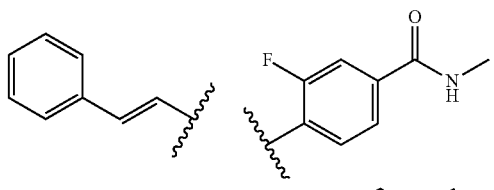
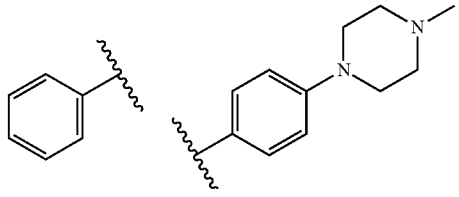
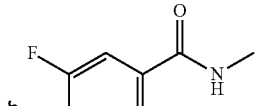
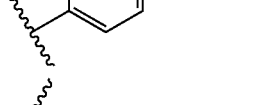
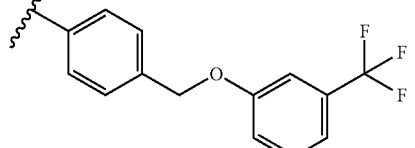
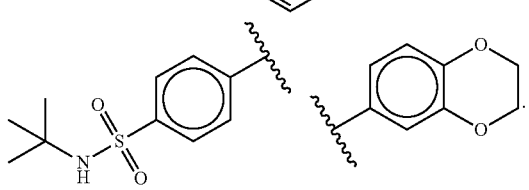

In certain embodiments, at least one $R^A$ is H. In certain embodiments, at least one $R^A$ is halogen. In certain embodiments, at least one $R^A$ is F. In certain embodiments, at least one $R^A$ is Cl. In certain embodiments, at least one $R^A$ is Br. In certain embodiments, at least one $R^A$ is I (iodine). In certain embodiments, at least one $R^A$ is substituted acyl. In certain embodiments, at least one $R^A$ is unsubstituted acyl. In certain embodiments, at least one $R^A$ is acetyl. In certain embodiments, at least one $R^A$ is substituted alkyl. In certain embodiments, at least one $R^A$ is unsubstituted alkyl. In certain embodiments, at least one $R^A$ is $C_{1-6}$ alkyl. In certain embodiments, at least one $R^A$ is methyl. In certain embodiments, at least one $R^A$ is ethyl. In certain embodiments, at least one $R^A$ is propyl. In certain embodiments, at least one $R^A$ is optionally substituted -alkyl-O-alkyl. In certain embodiments, at least one $R^A$ is optionally substituted alkylene-O-aryl. In certain embodiments, at least one $R^A$ is optionally substituted alkylene-O-phenyl. In certain embodiments, at least one $R^A$ is optionally substituted alkylene-O-(p-$CF_3$-phenyl). In certain embodiments, at least one $R^A$ is optionally substituted alkylene-O-(o-$CF_3$-phenyl). In certain embodiments, at least one $R^A$ is optionally substituted alkylene-O-(m-$CF_3$-phenyl). In certain embodiments, at least one $R^A$ is butyl. In certain embodiments, at least one $R^A$ is substituted alkenyl. In certain embodiments, at least one $R^A$ is unsubstituted alkenyl. In certain embodiments, at least one $R^A$ is substituted alkynyl. In certain embodiments, at least one $R^A$ is unsubstituted alkynyl. In certain embodiments, at least one $R^A$ is substituted carbocyclyl. In certain embodiments, at least one $R^A$ is unsubstituted carbocyclyl. In certain embodiments, at least one $R^A$ is substituted heterocyclyl. In certain embodiments, at least one $R^A$ is unsubstituted heterocyclyl. In certain embodiments, at least one $R^A$ is substituted aryl. In certain embodiments, at least one $R^A$ is unsubstituted aryl. In certain embodiments, at least one $R^A$ is substituted phenyl. In certain embodiments, at least one $R^A$ is unsubstituted phenyl. In certain embodiments, at least one $R^A$ is substituted heteroaryl. In certain embodiments, at least one $R^A$ is unsubstituted heteroaryl. In certain embodiments, at least one $R^A$ is substituted pyridyl. In certain embodiments, at least one $R^A$ is unsubstituted pyridyl. In certain embodiments, at least one $R^A$ is —$OR^{A1}$. In certain embodiments, at least one $R^A$ is —$N(R^{A1})_2$. In certain embodiments, at least one $R^A$ is —$SR^{A1}$. In certain embodiments, at least one $R^A$ is —OH. In certain embodiments, at least one $R^A$ is —$NH_2$. In certain embodiments, at least one $R^A$ is —SH.

In certain embodiments, when $R^A$ is —$OR^{A1}$, —$N(R^{A1})_2$, or —$SR^{A1}$, at least one $R^{A1}$ is H. In certain embodiments, at least one $R^{A1}$ is substituted acyl. In certain embodiments, at least one $R^{A1}$ is unsubstituted acyl. In certain embodiments, at least one $R^{A1}$ is acetyl. In certain embodiments, at least one $R^{A1}$ is substituted alkyl. In certain embodiments, at least one $R^{A1}$ is unsubstituted alkyl. In certain embodiments, at least one $R^{A1}$ is $C_{1-6}$ alkyl. In certain embodiments, at least one $R^{A1}$ is methyl. In certain embodiments, at least one $R^{A1}$ is ethyl. In certain embodiments, at least one $R^{A1}$ is propyl. In certain embodiments, at least one $R^{A1}$ is butyl. In certain embodiments, at least one $R^{A1}$ is substituted alkenyl. In certain embodiments, at least one $R^{A1}$ is unsubstituted alkenyl. In certain embodiments, at least one $R^{A1}$ is substituted alkynyl. In certain embodiments, at least one $R^{A1}$ is unsubstituted alkynyl. In certain embodiments, at least one $R^{A1}$ is substituted carbocyclyl. In certain embodiments, at least one $R^{A1}$ is unsubstituted carbocyclyl. In certain embodiments, at least one $R^{A1}$ is substituted heterocyclyl. In certain embodiments, at least one $R^{A1}$ is unsubstituted heterocyclyl. In certain embodiments, at least one $R^{A1}$ is substituted aryl. In certain embodiments, at least one $R^{A1}$ is unsubstituted aryl. In certain embodiments, at least one $R^{A1}$ is substituted phenyl. In certain embodiments, at least one $R^{A1}$ is unsubstituted phenyl. In certain embodiments, at least one $R^{A1}$ is substituted heteroaryl. In certain embodiments, at least one $R^{A1}$ is unsubstituted heteroaryl. In certain embodiments, at least one $R^{A1}$ is substituted pyridyl. In certain embodiments, at least one $R^{A1}$ is unsubstituted pyridyl. In certain embodiments, at least one $R^{A1}$ is a nitrogen protecting group when attached to a nitrogen atom. In certain embodiments, at least one $R^{A1}$ is an oxygen protecting group when attached to an oxygen atom. In certain embodiments, at least one $R^{A1}$ is a sulfur protecting group when attached to a sulfur atom. In certain embodiments, two $R^{A1}$ groups are joined to form a substituted heterocyclic ring. In certain embodiments, two $R^{A1}$ groups are joined to form an unsubstituted heterocyclic ring.

In certain embodiments, $R^A$ is —$N(R^{A1})C(\!=\!O)R^{A1}$. In certain embodiments, $R^A$ is —$N(R^{A1})C(\!=\!O)$-alkenyl. In certain embodiments, $R^A$ is —$N(R^{A1})C(\!=\!O)$—CH=$CH_2$. In certain embodiments, $R^A$ is —$C(\!=\!O)N(R^{A1})_2$. In certain embodiments, $R^A$ is —$C(\!=\!O)NH_2$. In certain embodiments, $R^A$ is —$C(\!=\!O)NHCH_3$. In certain embodiments, $R^A$ is $C(O)R^A$ In certain embodiments, $R^A$ is —$C(\!=\!O)$-alkenyl. In certain embodiments, $R^A$ is —$C(\!=\!O)$—CH=$CH_2$. In certain embodiments, $R^A$ is —$N(R^{A1})C(\!=\!O)N(R^{A1})_2$. In certain embodiments, $R^A$ is —$NHC(\!=\!O)N(R^{A1})_2$. In certain embodiments, $R^A$ is —$NHC(\!=\!O)NHCH_3$. In certain embodiments, $R^A$ is —$N(R^{A1})SO_2R^{A1}$. In certain embodiments, $R^A$ is —$NHSO_2R^{A1}$. In certain embodiments, $R^A$ is —$NHSO_2$-alkyl. In certain embodiments, $R^A$ is —$NHSO_2$—$CH_3$. In certain embodiments, $R^A$ is —$NHSO_2$—$C_2H_5$. In certain embodiments, $R^A$ is —$NHSO_2$-iPr. In certain embodiments, $R^A$ is —$NHSO_2$—Butyl. In certain embodiments, $R^A$ is —$NHSO_2$-tButyl.

In certain embodiments, $R^A$ is heterocyclic ring. In certain embodiments, $R^A$ is optionally substituted piperazine. In certain embodiments, $R^A$ is N-methyl-piperazine.

In certain embodiments, two $R^A$ on Ring A can optionally form another ring. In certain embodiments, $R^A$ is —$OR^{A1}$ and two $R^{A1}$ can optionally form a heterocyclic ring.

In certain embodiments, $R^A$ is substituted $C_{1-6}$ alkyl; and k is 1. In certain embodiments, $R^A$ is unsubstituted $C_{1-6}$ alkyl; and k is 1. In certain embodiments, $R^A$ is methyl; and k is 1. In certain embodiments, $R^A$ is ethyl; and k is 1. In certain embodiments, $R^A$ is propyl; and k is 1. In certain embodiments, $R^A$ is butyl; and k is 1.

In certain embodiments, $R^A$ is halogen; and k is 1. In certain embodiments, $R^A$ is F; and k is 1. In certain embodiments, $R^A$ is Cl; and k is 1. In certain embodiments, $R^A$ is Br; and k is 1. In certain embodiments, $R^A$ is I (iodine); and k is 1.

As generally defined above, Ring C is a carbocyclic, heterocyclic, aryl, or heteroaryl ring. Ring C may be substituted with one or more substituents $R^C$. $R^A$ may be a substituent on a carbon atom or heteroatom as valency permits. In certain embodiments, Ring C is a carbocyclic ring. In certain embodiments, Ring C is a monocyclic carbocyclic ring. In certain embodiments, Ring C is a bicyclic carbocyclic ring. In certain embodiments, Ring C is a substituted carbocyclic ring. In certain embodiments, Ring C is an unsubstituted carbocyclic ring. In certain embodiments, Ring C is a saturated carbocyclic ring. In certain embodiments, Ring C is an unsaturated carbocyclic ring. In certain embodiments, Ring C is a carbocyclic ring fused with one or more carbocyclic, heterocyclic, aryl, or heteroaryl groups wherein the point of attachment is on the carbocyclic ring.

In certain embodiments, Ring C is a heterocyclic ring. In certain embodiments, Ring C is a monocyclic heterocyclic ring. In certain embodiments, Ring C is a bicyclic heterocyclic ring. In certain embodiments, Ring C is a substituted heterocyclic ring. In certain embodiments, Ring C is an unsubstituted heterocyclic ring. In certain embodiments, Ring C is a saturated heterocyclic ring. In certain embodiments, Ring C is an unsaturated heterocyclic ring. In certain embodiments, Ring C is a heterocyclic ring fused with one or more carbocyclic, heterocyclic, aryl, or heteroaryl groups wherein the point of attachment is on the heterocyclic ring.

In certain embodiments, Ring C is an aryl ring. In certain embodiments, Ring C is a monocyclic aryl ring. In certain embodiments, Ring C is a bicyclic aryl ring. In certain embodiments, Ring C is a tricyclic aryl ring. In certain embodiments, Ring C is a substituted aryl ring. In certain embodiments, Ring C is an unsubstituted aryl ring. In certain embodiments, Ring C is substituted phenyl. In certain embodiments, Ring C is unsubstituted phenyl. In certain embodiments, Ring C is an aryl ring fused with one or more carbocyclic, heterocyclic, aryl, or heteroaryl groups wherein the point of attachment is on the aryl ring. In certain embodiments, Ring C is substituted naphthyl. In certain embodiments, Ring C is unsubstituted naphthyl.

In certain embodiments, the compound of Formula (I) is of formula:

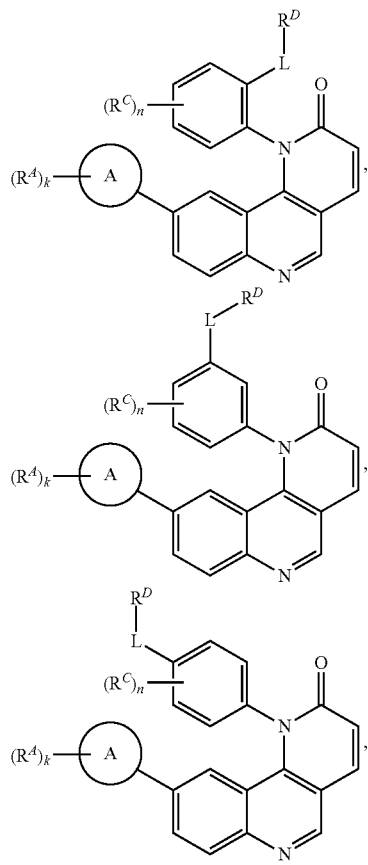

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

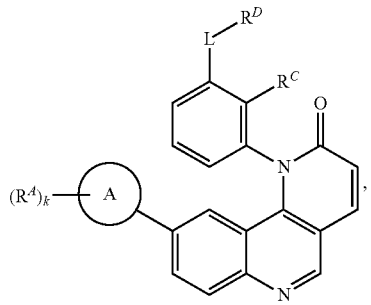

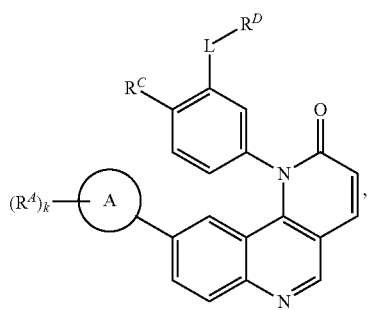

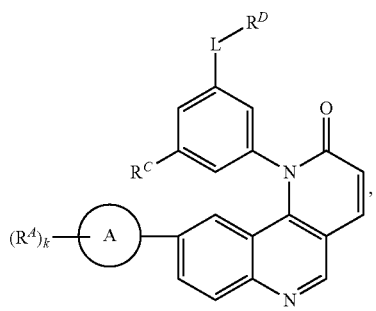

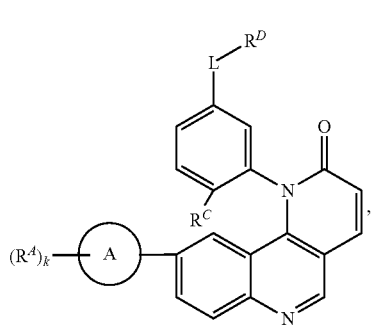

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

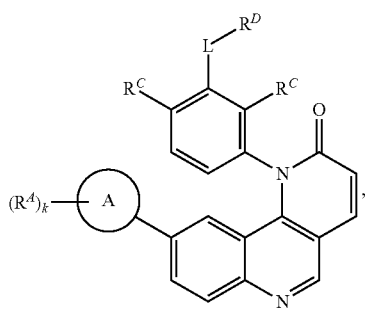

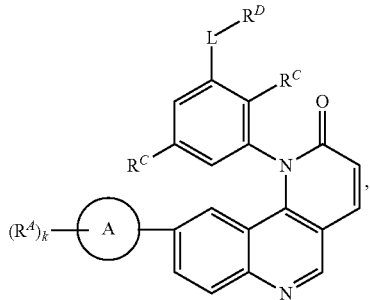

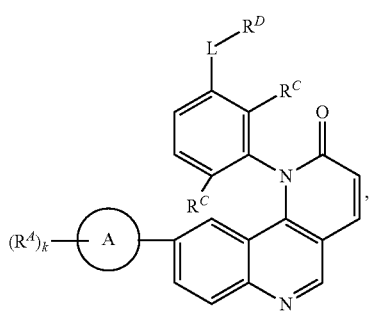

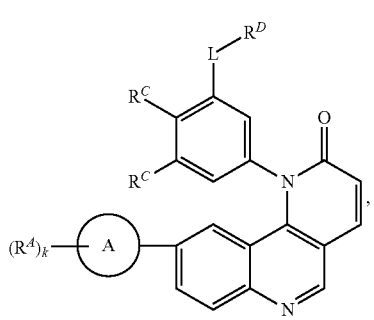

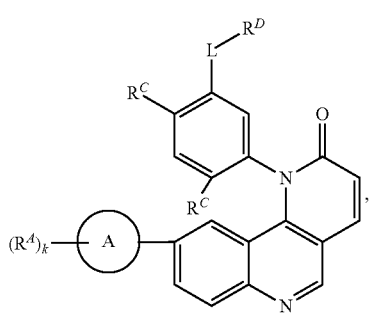

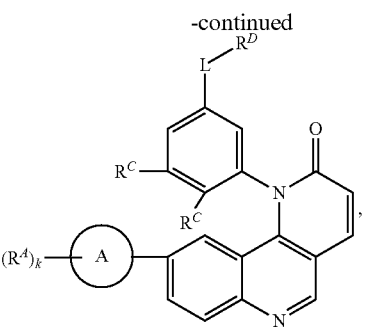

or a pharmaceutically acceptable salt, solvate, hydrate, polymorph, co-crystal, tautomer, stereoisomer, isotopically labeled derivative, or prodrug thereof.

In certain embodiments, Ring C is a heteroaryl ring. In certain embodiments, Ring C is a monocyclic heteroaryl ring. In certain embodiments, Ring C is a bicyclic heteroaryl ring. In certain embodiments, Ring C is a tricyclic heteroaryl ring. In certain embodiments, Ring C is a substituted heteroaryl ring. In certain embodiments, Ring C is an unsubstituted heteroaryl ring. In certain embodiments, Ring C is substituted pyridyl. In certain embodiments, Ring C is unsubstituted pyridyl. In certain embodiments, Ring C is a heteroaryl ring fused with one or more carbocyclic, heterocyclic, aryl, or heteroaryl groups wherein the point of attachment is on the heteroaryl ring. In certain embodiments, Ring C is a heteroaryl ring fused with a phenyl ring wherein the point of attachment is on the phenyl ring. In certain embodiments, Ring C is substituted indole. In certain embodiments, Ring C is unsubstituted indole. In certain embodiments, Ring C is substituted isoindole. In certain embodiments, Ring C is unsubstituted isoindole. In certain embodiments, Ring C is substituted indazole. In certain embodiments, Ring C is unsubstituted indazole. In certain embodiments, Ring C is substituted benzothiophene. In certain embodiments, Ring C is unsubstituted benzothiophene. In certain embodiments, Ring C is substituted isobenzothiophene. In certain embodiments, Ring C is unsubstituted isobenzothiophene. In certain embodiments, Ring C is substituted benzofuran. In certain embodiments, Ring C is unsubstituted benzofuran. In certain embodiments, Ring C is substituted benzoisofuran. In certain embodiments, Ring C is unsubstituted benzoisofuran. In certain embodiments, Ring C is substituted benzimidazole. In certain embodiments, Ring C is unsubstituted benzimidazole. In certain embodiments, Ring C is substituted benzoxazole. In certain embodiments, Ring C is unsubstituted benzoxazole. In certain embodiments, Ring C is substituted benzisoxazole. In certain embodiments, Ring C is unsubstituted benzisoxazole. In certain embodiments, Ring C is substituted benzothiazole. In certain embodiments, Ring C is unsubstituted benzothiazole. In certain embodiments, Ring C is substituted benzisothiazole. In certain embodiments, Ring C is unsubstituted benzisothiazole. In certain embodiments, Ring C is substituted benzotriazole. In certain embodiments, Ring C is unsubstituted benzotriazole. In certain embodiments, Ring C is substituted benzoxadiazole. In certain embodiments, Ring C is unsubstituted benzoxadiazole. In certain embodiments, Ring C is substituted quinoline. In certain embodiments, Ring C is unsubstituted quinoline. In certain embodiments, Ring C is substituted isoquinoline. In certain embodiments, Ring C is unsubstituted isoquinoline. In certain embodiments, Ring C is substituted cinnoline. In certain embodiments, Ring C is unsubstituted cinnoline. In certain embodiments, Ring C is substituted quinoxaline. In certain embodiments, Ring C is unsubstituted quinoxaline. In certain embodiments, Ring C is substituted phthalazine. In certain embodiments, Ring C is unsubstituted phthalazine. In certain embodiments, Ring C is substituted quinazoline. In certain embodiments, Ring C is unsubstituted quinazoline.

In certain embodiments, the compound of Formula (I) is of formula:

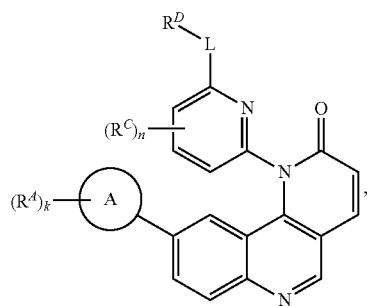

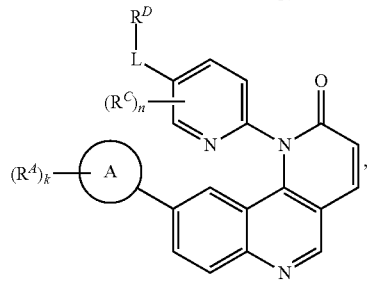

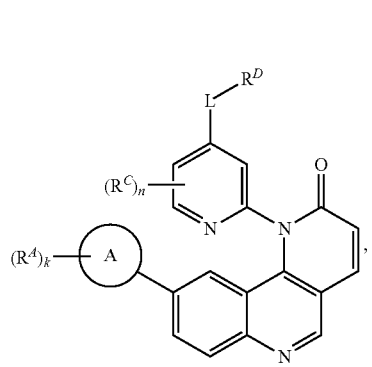

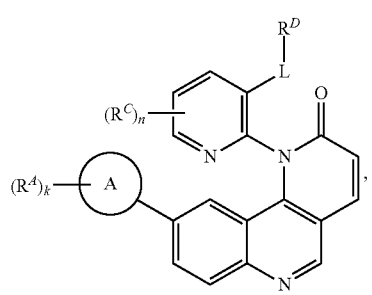

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

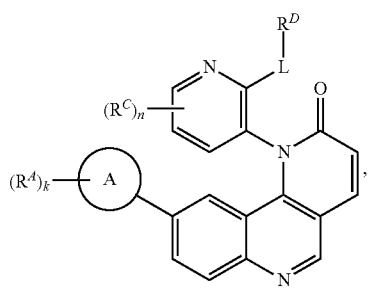

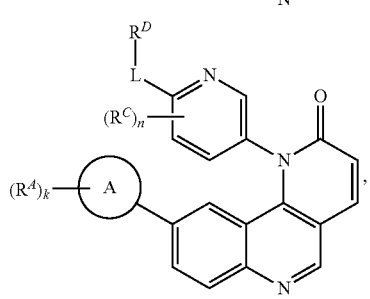

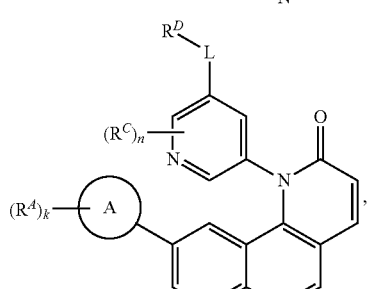

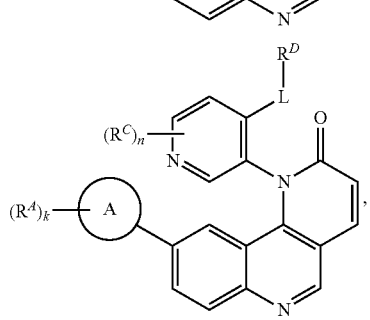

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

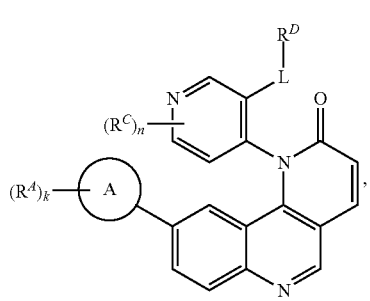

-continued

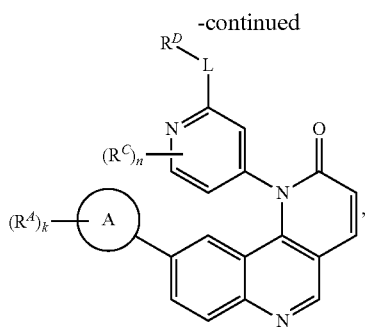

or a pharmaceutically acceptable salt, solvate, hydrate, polymorph, co-crystal, tautomer, stereoisomer, isotopically labeled derivative, or prodrug thereof.

In certain embodiments, Ring C is unsubstituted or substituted with one or more $R^C$. Substituent $R^C$ may be attached to a carbon atom or heteroatom as valency permits. In certain embodiments, Ring C is unsubstituted, and thus n is 0. In certain embodiments, n is 1. In certain embodiments, n is 2. In certain embodiments, n is 3. In certain embodiments, n is 4.

In certain embodiments, at least one $R^C$ is H. In certain embodiments, at least one $R^C$ is halogen. In certain embodiments, at least one $R^C$ is F. In certain embodiments, at least one $R^C$ is Cl. In certain embodiments, at least one $R^C$ is Br. In certain embodiments, at least one $R^C$ is I (iodine). In certain embodiments, at least one $R^C$ is substituted acyl. In certain embodiments, at least one $R^C$ is unsubstituted acyl. In certain embodiments, at least one $R^C$ is acetyl. In certain embodiments, at least one $R^C$ is substituted alkyl. In certain embodiments, at least one $R^C$ is unsubstituted alkyl. In certain embodiments, at least one $R^C$ is $C_{1-6}$ alkyl. In certain embodiments, at least one $R^C$ is methyl. In certain embodiments, at least one $R^C$ is ethyl. In certain embodiments, at least one $R^C$ is propyl. In certain embodiments, at least one $R^C$ is butyl. In certain embodiments, at least one $R^C$ is substituted alkenyl. In certain embodiments, at least one $R^C$ is unsubstituted alkenyl. In certain embodiments, at least one $R^C$ is substituted alkynyl. In certain embodiments, at least one $R^C$ is unsubstituted alkynyl. In certain embodiments, at least one $R^C$ is substituted carbocyclyl. In certain embodiments, at least one $R^C$ is unsubstituted carbocyclyl. In certain embodiments, at least one $R^C$ is substituted heterocyclyl. In certain embodiments, at least one $R^C$ is unsubstituted heterocyclyl. In certain embodiments, at least one $R^C$ is substituted aryl. In certain embodiments, at least one $R^C$ is unsubstituted aryl. In certain embodiments, at least one $R^C$ is substituted phenyl. In certain embodiments, at least one $R^C$ is unsubstituted phenyl. In certain embodiments, at least one $R^C$ is substituted heteroaryl. In certain embodiments, at least one $R^C$ is unsubstituted heteroaryl. In certain embodiments, at least one $R^C$ is substituted pyridyl. In certain embodiments, at least one $R^C$ is unsubstituted pyridyl. In certain embodiments, at least one $R^C$ is —$OR^{C1}$. In certain embodiments, at least one $R^C$ is —$N(R^{C1})_2$. In certain embodiments, at least one $R^C$ is —$SR^{C1}$. In certain embodiments, at least one $R^C$ is —OH. In certain embodiments, at least one $R^C$ is —$NH_2$. In certain embodiments, at least one $R^C$ is —SH.

In certain embodiments, when $R^C$ is —$OR^{C1}$, —$N(R^{C1})_2$, or —$SR^{C1}$, at least one $R^{C1}$ is H. In certain embodiments, at least one $R^{C1}$ is substituted acyl. In certain embodiments, at least one $R^{C1}$ is unsubstituted acyl. In certain embodiments, at least one $R^{C1}$ is acetyl. In certain embodiments, at least one $R^{C1}$ is substituted alkyl. In certain embodiments, at least one $R^{C1}$ is unsubstituted alkyl. In certain embodiments, at least one $R^{C1}$ is $C_{1-6}$ alkyl. In certain embodiments, at least one $R^{C1}$ is methyl. In certain embodiments, at least one $R^{C1}$ is ethyl. In certain embodiments, at least one $R^{C1}$ is propyl. In certain embodiments, at least one $R^{C1}$ is butyl. In certain embodiments, at least one $R^{C1}$ is substituted alkenyl. In certain embodiments, at least one $R^{C1}$ is unsubstituted alkenyl. In certain embodiments, at least one $R^{C1}$ is substituted alkynyl. In certain embodiments, at least one $R^{C1}$ is unsubstituted alkynyl. In certain embodiments, at least one $R^{C1}$ is substituted carbocyclyl. In certain embodiments, at least one $R^{C1}$ is unsubstituted carbocyclyl. In certain embodiments, at least one $R^{C1}$ is substituted heterocyclyl. In certain embodiments, at least one $R^{C1}$ is unsubstituted heterocyclyl. In certain embodiments, at least one $R^{C1}$ is substituted aryl. In certain embodiments, at least one $R^{C1}$ is unsubstituted aryl. In certain embodiments, at least one $R^{C1}$ is substituted phenyl. In certain embodiments, at least one $R^{C1}$ is unsubstituted phenyl. In certain embodiments, at least one $R^{C1}$ is substituted heteroaryl. In certain embodiments, at least one $R^{C1}$ is unsubstituted heteroaryl. In certain embodiments, at least one $R^{C1}$ is substituted pyridyl. In certain embodiments, at least one $R^{C1}$ is unsubstituted pyridyl. In certain embodiments, at least one $R^{C1}$ is a nitrogen protecting group when attached to a nitrogen atom. In certain embodiments, at least one $R^{C1}$ is an oxygen protecting group when attached to an oxygen atom. In certain embodiments, at least one $R^{C1}$ is a sulfur protecting group when attached to a sulfur atom. In certain embodiments, two $R^{C1}$ groups are joined to form a substituted heterocyclic ring. In certain embodiments, two $R^{C1}$ groups are joined to form an unsubstituted heterocyclic ring.

In certain embodiments, $R^C$ is substituted $C_{1-6}$ alkyl; and n is 1. In certain embodiments, $R^C$ is unsubstituted $C_{1-6}$ alkyl; and n is 1. In certain embodiments, $R^C$ is methyl; and n is 1. In certain embodiments, $R^C$ is ethyl; and n is 1. In certain embodiments, $R^C$ is propyl; and n is 1. In certain embodiments, $R^C$ is butyl; and n is 1.

In certain embodiments, $R^C$ is halogen; and n is 1. In certain embodiments, $R^C$ is F; and n is 1. In certain embodiments, $R^C$ is Cl; and n is 1. In certain embodiments, $R^C$ is Br; and n is 1. In certain embodiments, $R^C$ is I (iodine); and n is 1.

Linker L is a divalent linker moiety. L may contain 0-6 carbon atoms in the backbone of L. In certain embodiments, L contains 0-4 carbon atoms in the backbone of L. In certain embodiments, L contains 0-3 carbon atoms in the backbone of L. In certain embodiments, L contains 0-2 carbon atoms in the backbone of L. L may be saturated or unsaturated. L may be substituted or unsubstituted. L may be branched or unbranched. In certain embodiments, L is a bond directly connecting Ring C and $R^D$. In certain embodiments, L is a single bond. In certain embodiments, L is a $C_1$ hydrocarbon chain substituted with one or more $R^L$ groups. In certain embodiments, L is —$CH_2$—. In certain embodiments, L is a $C_2$ hydrocarbon chain substituted with one or more $R^L$ groups. In certain embodiments, L is —$(CH_2)_2$—. In certain embodiments, L is trans-CH═CH—. In certain embodiments, L is cis-CH═CH—. In certain embodiments, L is —C≡C—. In certain embodiments, L is a $C_3$ hydrocarbon chain substituted with one or more $R^L$ groups. In certain embodiments, L is —$(CH_2)_3$—. In certain embodiments, L is a $C_4$ hydrocarbon chain substituted with one or more $R^L$ groups. In certain embodiments, L is —$(CH_2)_4$—. In certain embodiments, L is a $C_5$ hydrocarbon chain substituted with one or more $R^L$ groups. In certain embodiments, L is —$(CH_2)_5$—. In certain embodiments, L is a $C_6$ hydrocarbon chain substituted with one or more $R^L$ groups. In certain embodiments, L is —$(CH_2)_6$—. Each occurrence of $R^L$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —C(=$NR^{L1}$)$R^{L1}$, —C(=$NR^{L1}$)$OR^{L1}$, —C(=$NR^{L1}$)$SR^{L1}$, —C(=$NR^{L1}$)N($R^{L1}$)$_2$, —C(=S)$R^{L1}$, —C(=S)$OR^{L1}$, —C(=S)$SR^{L1}$, —C(=S)N($R^{L1}$)$_2$, —$NO_2$, —$N_3$, —N($R^{L1}$)$_3^+$$F^-$, —N($R^{L1}$)$_3^+$$Cl^-$, —N($R^{L1}$)$_3^+$$Br^-$, —N($R^{L1}$)$_3^+$$I^-$, —N($OR^{L1}$)$R^{L1}$, —$NR^{L1}$C(=O)$R^{L1}$, —$NR^{L1}$C(=O)$OR^{L1}$, —$NR^{L1}$C(=O)$SR^{L1}$, —$NR^{L1}$C(=O)N($R^{L1}$)$_2$, —$NR^{L1}$C(=S)$R^{L1}$, —$NR^{L1}$C(=S)$OR^{L1}$, —$NR^{L1}$C(=S)$SR^{L1}$, —$NR^{L1}$C(=S)N($R^{L1}$)$_2$, —$NR^{L1}$C(=$NR^{L1}$)$R^{L1}$, —$NR^{L1}$C(=$NR^{L1}$)$OR^{L1}$, —$NR^{L1}$C(=$NR^{L1}$)$SR^{L1}$, —$NR^{L1}$C(=$NR^{L1}$)N($R^{L1}$)$_2$, —$NR^{L1}$S(=O)$_2$$R^{L1}$, —$NR^{L1}$S(=O)$_2$$OR^{L1}$, —$NR^{L1}$S(=O)$_2$$SR^{L1}$, —$NR^{L1}$S(=O)$_2$N($R^{L1}$)$_2$, —$NR^{L1}$S(=O)$R^{L1}$, —$NR^{L1}$S(=O)$OR^{L1}$, —$NR^{L1}$S(=O)$SR^{L1}$, —$NR^{L1}$S(=O)N($R^{L1}$)$_2$, —$NR^{L1}$P(=O), —$NR^{L1}$P(=O)$_2$, —$NR^{L1}$P(=O)($R^{L1}$)$_2$, —$NR^{L1}$P(=O)$R^{L1}$($OR^{L1}$), —$NR^{L1}$P(=O)($OR^{L1}$)$_2$, —OC(=O)$R^{L1}$, —OC(=O)$OR^{L1}$, —OC(=O)$SR^{L1}$, —OC(=O)N($R^{L1}$)$_2$, —OC(=$NR^{L1}$)$R^{L1}$, —OC(=$NR^{L1}$)$OR^{L1}$, —OC(=$NR^{L1}$)N($R^{L1}$)$_2$, —OC(=S)$R^{L1}$, —OC(=S)$OR^{L1}$, —OC(=S)$SR^{L1}$, —OC(=S)N($R^{L1}$)$_2$, —ON($R^{L1}$)$_2$, —OS(=O)$R^{L1}$, —OS(=O)$OR^{L1}$, —OS(=O)$SR^{L1}$, —OS(=O)N($R^{L1}$)$_2$, —OS(=O)$_2$$R^{L1}$, —OS(=O)$_2$$OR^{L1}$, —OS(=O)$_2$$SR^{L1}$, —OS(=O)$_2$N($R^{L1}$)$_2$, —OP(=O)$_2$, —OP(=O)($R^{L1}$)$_2$, —OP(=O)$R^{L1}$($OR^{L1}$), —OP(=O)($OR^{L1}$)$_2$, —OP(=O), —OP($R^{L1}$)$_2$, —$OPR^{L1}$($OR^{L1}$), —OP($OR^{L1}$)$_2$, —OSi($R^{L1}$)$_3$, —OSi($R^{L1}$)$_2$$OR^{L1}$, —OSi($R^{L1}$)($OR^{L1}$)$_2$, —OSi($OR^{L1}$)$_3$, —$SSR^{L1}$, —S(=O)$R^{L1}$, —S(=O)$OR^{L1}$, —S(=O)N($R^{L1}$)$_2$, —S(=O)$_2$$R^{L1}$, —S(=O)$_2$$OR^{L1}$, —S(=O)$_2$N($R^{L1}$)$_2$, —SC(=O)$R^{L1}$, —SC(=O)$OR^{L1}$, —SC(=O)$SR^{L1}$, —SC(=O)N($R^{L1}$)$_2$, —SC(=S)$R^{L1}$, —SC(=S)$OR^{L1}$, —SC(=S)$SR^{L1}$, —SC(=S)N($R^{L1}$)$_2$, —P($R^{L1}$)$_2$, —$PR^{L1}$($OR^{L1}$), —P($OR^{L1}$)$_2$, —P(=O), —P(=O)($R^{L1}$)$_2$, —P(=O)($OR^{L1}$)$_2$, —P(=O)$R^{L1}$($OR^{L1}$), —P(=O)$_2$, —B($R^{L1}$)$_2$, —B($OR^{L1}$)$_2$, —$BR^{L1}$($OR^{L1}$), —Si($R^{L1}$)$_3$, —Si($R^{L1}$)$_2$$OR^{L1}$, —$SiR^{L1}$($OR^{L1}$)$_2$, and —Si($OR^{L1}$)$_3$, wherein each occurrence of $R^{L1}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, a sulfur protecting group when attached to a sulfur atom, or two $R^{L1}$ groups are joined to form an optionally substituted heterocyclic ring.

Each of $R^{j1}$, $R^{j2}$, $R^{j3}$ is an independent substituent on the double bond in Formula (II). In certain embodiments, each of $R^{j1}$, $R^{j2}$, $R^{j3}$ is independently hydrogen or substituted $C_{1-6}$ alkyl. In certain embodiments, each of $R^{j1}$, $R^j$, $R^{j3}$ is independently hydrogen. In certain embodiments, each of $R^{j1}$, $R^{j2}$, $R^{j3}$ is independently unsubstituted $C_{1-6}$ alkyl. In certain embodiments, each of $R^{j1}$, $R^{j2}$, $R^{j4}$ is independently methyl, ethyl, propyl, butyl, pentyl, or hexyl. In certain embodiments, each of $R^{j1}$, $R^{j2}$, $R^{j3}$ is independently halogen. In certain embodiments, In certain embodiments, each of $R^{j1}$, $R^{j2}$, $R^{j3}$ is independently F. In certain embodiments, In certain embodiments, each of $R^{j1}$, $R^{j2}$, $R^{j3}$ is independently Cl. In certain embodiments, each of $R^{j1}$, $R^{j2}$, $R^{j3}$ is independently Br. In certain embodiments, each of $R^{j1}$, $R^{j2}$, $R^{j3}$ is independently I.

As generally defined herein, $R^q$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group. In certain embodiments, $R^q$ is hydrogen. In some embodiments, $R^q$ is optionally substituted alkyl, optionally substituted alkenyl, optionally substituted alkynyl, or optionally substituted carbocyclyl. In certain embodiments, $R^q$ is optionally substituted $C_{1-6}$ alkyl, optionally substituted $C_{2-6}$ alkenyl, optionally substituted $C_{2-6}$ alkynyl, or optionally substituted $C_{3-6}$ carbocyclyl. In certain embodiments, $R^q$ is optionally substituted $C_{1-6}$ alkyl. In certain embodiments, $R^q$ is substituted $C_{1-6}$ alkyl. In certain embodiments, $R^q$ is unsubstituted $C_{1-6}$ alkyl. In certain embodiments, $R^q$ is methyl, ethyl, propyl, butyl, pentyl, or hexyl. In certain embodiments, $R^q$ is isopropyl, isobutyl, or isoamyl. In certain embodiments, $R^q$ is isobutyl. In certain embodiments, $R^q$ is tert-butyl. In certain embodiments, $R^q$ is a nitrogen protecting group.

$R^D$ is a substituent on Ring C through linker L. In certain embodiments, $R^D$ includes a Michael acceptor moiety. This Michael acceptor moiety may react with a cysteine residue of a host factor to allow covalent attachment of the compound to the host factor. In certain embodiments, the covalent attachment is irreversible, and viral entry and/or infection is reduced. In certain embodiments, the covalent attachment is reversible, and viral entry and/or infection is reduced.

In certain embodiments, $R^D$ is a group selected from the group consisting of:

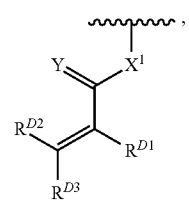
(i-1)

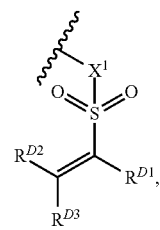
(i-2)

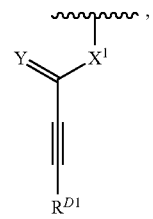
(i-3)

-continued
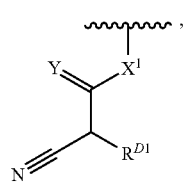 (i-4)
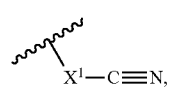 (i-5)
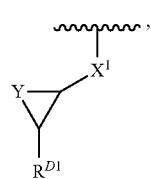 (i-6)
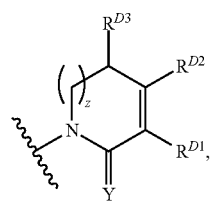 (i-7)
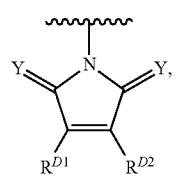 (i-8)
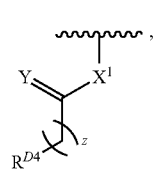 (i-9)
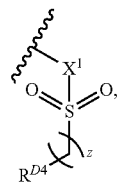 (i-10)
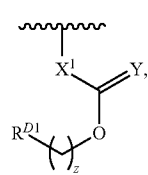 (i-11)
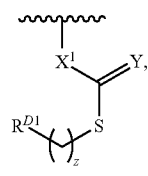 (i-12)
-continued
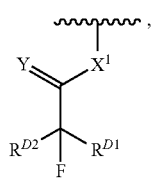 (i-13)
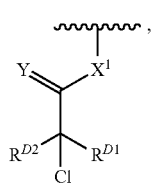 (i-14)
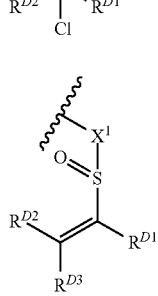 (i-15)
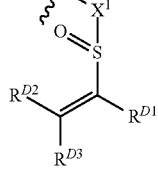 (i-16)
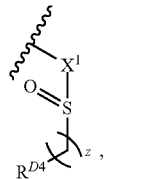 (i-17)
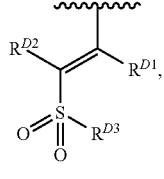 (i-18)
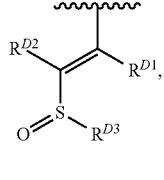 (i-19)
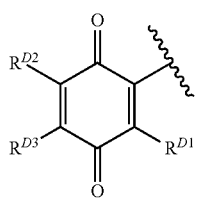 (i-20)

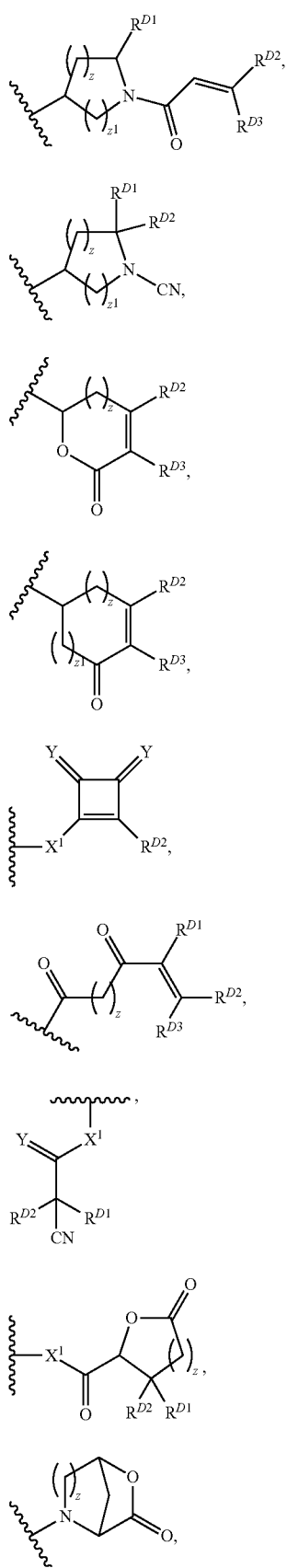
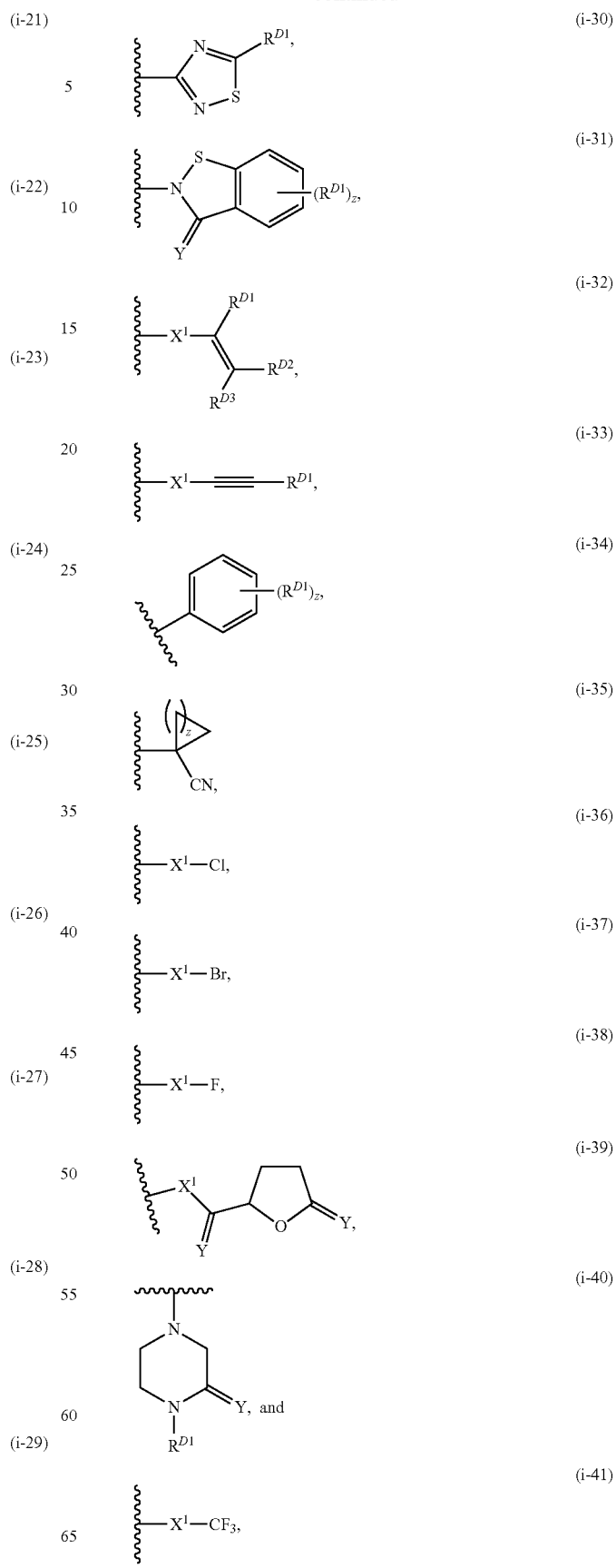

-continued

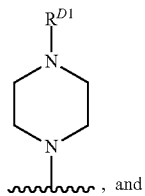

(i-42), and (i-43)

In certain embodiments, at least one $R^{D1}$ is H. In certain embodiments, at least one $R^{D1}$ is halogen. In certain embodiments, at least one $R^{D1}$ is F. In certain embodiments, at least one $R^{D1}$ is Cl. In certain embodiments, at least one $R^{D1}$ is Br. In certain embodiments, at least one $R^{D1}$ is I (iodine). In certain embodiments, at least one $R^{D1}$ is substituted acyl. In certain embodiments, at least one $R^{D1}$ is unsubstituted acyl. In certain embodiments, at least one $R^{D1}$ is acetyl. In certain embodiments, at least one $R^{D1}$ is substituted alkyl. In certain embodiments, at least one $R^{D1}$ is unsubstituted alkyl. In certain embodiments, at least one $R^{D1}$ is $C_{1-6}$ alkyl. In certain embodiments, at least one $R^{D1}$ is methyl. In certain embodiments, at least one $R^{D1}$ is ethyl. In certain embodiments, at least one $R^{D1}$ is propyl. In certain embodiments, at least one $R^{D1}$ is butyl. In certain embodiments, at least one $R^{D1}$ is substituted alkenyl. In certain embodiments, at least one $R^{D1}$ is unsubstituted alkenyl. In certain embodiments, at least one $R^{D1}$ is substituted alkynyl. In certain embodiments, at least one $R^{D1}$ is unsubstituted alkynyl. In certain embodiments, at least one $R^{D1}$ is substituted carbocyclyl. In certain embodiments, at least one $R^{D1}$ is unsubstituted carbocyclyl. In certain embodiments, at least one $R^{D1}$ is substituted heterocyclyl. In certain embodiments, at least one $R^{D1}$ is unsubstituted heterocyclyl. In certain embodiments, at least one $R^{D1}$ is substituted aryl. In certain embodiments, at least one $R^{D1}$ is unsubstituted aryl. In certain embodiments, at least one $R^{D1}$ is substituted phenyl. In certain embodiments, at least one $R^{D1}$ is unsubstituted phenyl. In certain embodiments, at least one $R^{D1}$ is substituted heteroaryl. In certain embodiments, at least one $R^{D1}$ is unsubstituted heteroaryl. In certain embodiments, at least one $R^{D1}$ is substituted pyridyl. In certain embodiments, at least one $R^{D1}$ is unsubstituted pyridyl. In certain embodiments, at least one $R^{D1}$ is $-OR^{D1a}$. In certain embodiments, at least one $R^{D1}$ is $-N(R^{D1a})_2$. In certain embodiments, at least one $R^{D1}$ is $-SR^{D1a}$. In certain embodiments, at least one $R^{D1}$ is $-OH$. In certain embodiments, at least one $R^{D1}$ is $-NH_2$. In certain embodiments, at least one $R^{D1}$ is $-SH$. In certain embodiments, at least one $R^{D1}$ is $-CH_2OR^{D1a}$. In certain embodiments, at least one $R^{D1}$ is $-CH_2N(R^{D1a})_2$. In certain embodiments, at least one $R^{D1}$ is $-CH_2SR^{D1a}$. In certain embodiments, at least one $R^{D1}$ is $-CH_2OH$. In certain embodiments, at least one $R^{D1}$ is $-CH_2NH_2$. In certain embodiments, at least one $R^{D1}$ is $-CH_2SH$.

In certain embodiments, at least one $R^{D1a}$ is H. In certain embodiments, at least one $R^{D1a}$ is substituted acyl. In certain embodiments, at least one $R^{D1a}$ is unsubstituted acyl. In certain embodiments, at least one $R^{D1a}$ is acetyl. In certain embodiments, at least one $R^{D1a}$ is substituted alkyl. In certain embodiments, at least one $R^{D1a}$ is unsubstituted alkyl. In certain embodiments, at least one $R^{D1a}$ is $C_{1-6}$ alkyl. In certain embodiments, at least one $R^{D1a}$ is methyl. In certain embodiments, at least one $R^{D1a}$ is ethyl. In certain embodiments, at least one $R^{D1a}$ is propyl. In certain embodiments, at least one $R^{D1a}$ is butyl. In certain embodiments, at least one $R^{D1a}$ is substituted alkenyl. In certain embodiments, at least one $R^{D1a}$ is unsubstituted alkenyl. In certain embodiments, at least one $R^{D1a}$ is substituted alkynyl. In certain embodiments, at least one $R^{D1a}$ is unsubstituted alkynyl. In certain embodiments, at least one $R^{D1a}$ is substituted carbocyclyl. In certain embodiments, at least one $R^{D1a}$ is unsubstituted carbocyclyl. In certain embodiments, at least one $R^{D1a}$ is substituted heterocyclyl. In certain embodiments, at least one $R^{D1a}$ is unsubstituted heterocyclyl. In certain embodiments, at least one $R^{D1a}$ is substituted aryl. In certain embodiments, at least one $R^{D1a}$ is unsubstituted aryl. In certain embodiments, at least one $R^{D1a}$ is substituted phenyl. In certain embodiments, at least one $R^{D1a}$ is unsubstituted phenyl. In certain embodiments, at least one $R^{D1a}$ is substituted heteroaryl. In certain embodiments, at least one $R^{D1a}$ is unsubstituted heteroaryl. In certain embodiments, at least one $R^{D1a}$ is substituted pyridyl. In certain embodiments, at least one $R^{D1a}$ is unsubstituted pyridyl. In certain embodiments, at least one $R^{D1a}$ is a nitrogen protecting group when attached to a nitrogen atom. In certain embodiments, at least one $R^{D1a}$ is an oxygen protecting group when attached to an oxygen atom. In certain embodiments, at least one $R^{D1a}$ is a sulfur protecting group when attached to a sulfur atom. In certain embodiments, two $R^{D1a}$ groups are joined to form a substituted heterocyclic ring. In certain embodiments, two $R^{D1a}$ groups are joined to form an unsubstituted heterocyclic ring.

In certain embodiments, at least one $R^{D2}$ is H. In certain embodiments, at least one $R^{D2}$ is halogen. In certain embodiments, at least one $R^{D2}$ is F. In certain embodiments, at least one $R^{D2}$ is Cl. In certain embodiments, at least one $R^{D2}$ is Br. In certain embodiments, at least one $R^{D2}$ is I (iodine). In certain embodiments, at least one $R^{D2}$ is substituted acyl. In certain embodiments, at least one $R^{D2}$ is unsubstituted acyl. In certain embodiments, at least one $R^{D2}$ is acetyl. In certain embodiments, at least one $R^{D2}$ is substituted alkyl. In certain embodiments, at least one $R^{D2}$ is unsubstituted alkyl. In certain embodiments, at least one $R^{D2}$ is $C_{1-6}$ alkyl. In certain embodiments, at least one $R^{D2}$ is methyl. In certain embodiments, at least one $R^{D2}$ is ethyl. In certain embodiments, at least one $R^{D2}$ is propyl. In certain embodiments, at least one $R^{D2}$ is butyl. In certain embodiments, at least one $R^{D2}$ is substituted alkenyl. In certain embodiments, at least one $R^{D2}$ is unsubstituted alkenyl. In certain embodiments, at least one $R^{D2}$ is substituted alkynyl. In certain embodiments, at least one $R^{D2}$ is unsubstituted alkynyl. In certain embodiments, at least one $R^{D2}$ is substituted carbocyclyl. In certain embodiments, at least one $R^{D2}$ is unsubstituted carbocyclyl. In certain embodiments, at least one $R^{D2}$ is substituted heterocyclyl. In certain embodiments, at least one $R^{D2}$ is unsubstituted heterocyclyl. In certain embodiments, at least one $R^{D2}$ is substituted aryl. In certain embodiments, at least one $R^{D2}$ is unsubstituted aryl. In certain embodiments, at least one $R^{D2}$ is substituted phenyl. In certain embodiments, at least one $R^{D2}$ is unsubstituted phenyl. In certain embodiments, at least one $R^{D2}$ is substituted heteroaryl. In certain embodiments, at least one $R^{D2}$ is unsubstituted heteroaryl. In certain embodiments, at least one $R^{D2}$ is substituted pyridyl. In certain embodiments, at least one $R^{D2}$ is unsubstituted pyridyl. In certain embodiments, at least one $R^{D2}$ is —$OR^{D2a}$. In certain embodiments, at least one $R^{D2}$ is —$N(R^{D2a})_2$. In certain embodiments, at least one $R^{D2}$ is —$SR^{D2a}$. In certain embodiments, at least one $R^{D2}$ is —OH. In certain embodiments, at least one $R^{D2}$ is —$NH_2$. In certain embodiments, at least one $R^{D2}$ is —SH. In certain embodiments, at least one $R^{D2}$ is —$CH_2OR^{D2a}$. In certain embodiments, at least one $R^{D2}$ is —$CH_2N(R^{D2a})_2$. In certain embodiments, at least one $R^{D2}$ is —$CH_2SR^{D2a}$. In certain embodiments, at least one $R^{D2}$ is —$CH_2OH$. In certain embodiments, at least one $R^{D2}$ is —$CH_2NH_2$. In certain embodiments, at least one $R^{D2}$ is —$CH_2SH$.

In certain embodiments, at least one $R^{D2a}$ is H. In certain embodiments, at least one $R^{D2a}$ is substituted acyl. In certain embodiments, at least one $R^{D2a}$ is unsubstituted acyl. In certain embodiments, at least one $R^{D2a}$ is acetyl. In certain embodiments, at least one $R^{D2a}$ is substituted alkyl. In certain embodiments, at least one $R^{D2a}$ is unsubstituted alkyl. In certain embodiments, at least one $R^{D2a}$ is $C_{1-6}$ alkyl. In certain embodiments, at least one $R^{D2a}$ is methyl. In certain embodiments, at least one $R^{D2a}$ is ethyl. In certain embodiments, at least one $R^{D2a}$ is propyl. In certain embodiments, at least one $R^{D2a}$ is butyl. In certain embodiments, at least one $R^{D2a}$ is substituted alkenyl. In certain embodiments, at least one $R^{D2a}$ is unsubstituted alkenyl. In certain embodiments, at least one $R^{D2a}$ is substituted alkynyl. In certain embodiments, at least one $R^{D2a}$ is unsubstituted alkynyl. In certain embodiments, at least one $R^{D2a}$ is substituted carbocyclyl. In certain embodiments, at least one $R^{D2a}$ is unsubstituted carbocyclyl. In certain embodiments, at least one $R^{D2a}$ is substituted heterocyclyl. In certain embodiments, at least one $R^{D2a}$ is unsubstituted heterocyclyl. In certain embodiments, at least one $R^{D2a}$ is substituted aryl. In certain embodiments, at least one $R^{D2a}$ is unsubstituted aryl. In certain embodiments, at least one $R^{D2a}$ is substituted phenyl. In certain embodiments, at least one $R^{D2a}$ is unsubstituted phenyl. In certain embodiments, at least one $R^{D2a}$ is substituted heteroaryl. In certain embodiments, at least one $R^{D2a}$ is unsubstituted heteroaryl. In certain embodiments, at least one $R^{D2a}$ is substituted pyridyl. In certain embodiments, at least one $R^{D2a}$ is unsubstituted pyridyl. In certain embodiments, at least one $R^{D2a}$ is a nitrogen protecting group when attached to a nitrogen atom. In certain embodiments, at least one $R^{D2a}$ is an oxygen protecting group when attached to an oxygen atom. In certain embodiments, at least one $R^{D2a}$ is a sulfur protecting group when attached to a sulfur atom. In certain embodiments, two $R^{D2a}$ groups are joined to form a substituted heterocyclic ring. In certain embodiments, two $R^{D2a}$ groups are joined to form an unsubstituted heterocyclic ring.

In certain embodiments, at least one $R^{D3}$ is H. In certain embodiments, at least one $R^{D3}$ is halogen. In certain embodiments, at least one $R^{D3}$ is F. In certain embodiments, at least one $R^{D3}$ is Cl. In certain embodiments, at least one $R^{D3}$ is Br. In certain embodiments, at least one $R^{D3}$ is I (iodine). In certain embodiments, at least one $R^{D3}$ is substituted acyl. In certain embodiments, at least one $R^{D3}$ is unsubstituted acyl. In certain embodiments, at least one $R^{D3}$ is acetyl. In certain embodiments, at least one $R^{D3}$ is substituted alkyl. In certain embodiments, at least one $R^{D3}$ is unsubstituted alkyl. In certain embodiments, at least one $R^{D3}$ is $C_{1-6}$ alkyl. In certain embodiments, at least one $R^{D3}$ is methyl. In certain embodiments, at least one $R^{D3}$ is ethyl. In certain embodiments, at least one $R^{D3}$ is propyl. In certain embodiments, at least one $R^{D3}$ is butyl. In certain embodiments, at least one $R^{D3}$ is substituted alkenyl. In certain embodiments, at least one $R^{D3}$ is unsubstituted alkenyl. In certain embodiments, at least one $R^{D3}$ is substituted alkynyl. In certain embodiments, at least one $R^{D3}$ is unsubstituted alkynyl. In certain embodiments, at least one $R^{D3}$ is substituted carbocyclyl. In certain embodiments, at least one $R^{D3}$ is unsubstituted carbocyclyl. In certain embodiments, at least one $R^{D3}$ is substituted heterocyclyl. In certain embodiments, at least one $R^{D3}$ is unsubstituted heterocyclyl. In certain embodiments, at least one $R^{D3}$ is substituted aryl. In certain embodiments, at least one $R^{D3}$ is unsubstituted aryl. In certain embodiments, at least one $R^{D3}$ is substituted phenyl. In certain embodiments, at least one $R^{D3}$ is unsubstituted phenyl. In certain embodiments, at least one $R^{D3}$ is substituted heteroaryl. In certain embodiments, at least one $R^{D3}$ is unsubstituted heteroaryl. In certain embodiments, at least one $R^{D3}$ is substituted pyridyl. In certain embodiments, at least one $R^{D3}$ is unsubstituted pyridyl. In certain embodiments, at least one $R^{D3}$ is —$OR^{D3a}$. In certain embodiments, at least one $R^{D3}$ is —$N(R^{D3a})_2$. In certain embodiments, at least one $R^{D3}$ is —$SR^{D3a}$. In certain embodiments, at least one $R^{D3}$ is —OH. In certain embodiments, at least one $R^{D3}$ is —$NH_2$. In certain embodiments, at least one $R^{D3}$ is —SH. In certain embodiments, at least one $R^{D3}$ is —$CH_2OR^{D3a}$. In certain embodiments, at least one $R^{D3}$ is —$CH_2N(R^{D3a})_2$. In certain embodiments, at least one $R^{D3}$ is —$CH_2SR^{D3a}$. In certain embodiments, at least one $R^{D3}$ is —$CH_2OH$. In certain embodiments, at least one $R^{D3}$ is —$CH_2NH_2$. In certain embodiments, at least one $R^{D3}$ is —$CH_2SH$.

In certain embodiments, at least one $R^{D3a}$ is H. In certain embodiments, at least one $R^{D3a}$ is substituted acyl. In certain embodiments, at least one $R^{D3a}$ is unsubstituted acyl. In certain embodiments, at least one $R^{D3a}$ is acetyl. In certain embodiments, at least one $R^{D3a}$ is substituted alkyl. In certain embodiments, at least one $R^{D3a}$ is unsubstituted alkyl. In certain embodiments, at least one $R^{D3a}$ is C-alkyl. In certain embodiments, at least one $R^{D3a}$ is methyl. In certain embodiments, at least one $R^{D3a}$ is ethyl. In certain embodiments, at least one $R^{D3a}$ is propyl. In certain embodiments, at least one $R^{D3a}$ is butyl. In certain embodiments, at least one $R^{D3a}$ is substituted alkenyl. In certain embodiments, at least one $R^{D3a}$ is unsubstituted alkenyl. In certain embodiments, at least one $R^{D3a}$ is substituted alkynyl. In certain embodiments, at least one $R^{D3a}$ is unsubstituted alkynyl. In certain embodiments, at least one $R^{D3a}$ is substituted carbocyclyl. In certain embodiments, at least one $R^{D3a}$ is unsubstituted carbocyclyl. In certain embodiments, at least one $R^{D3a}$ is substituted heterocyclyl. In certain embodiments, at least one $R^{D3a}$ is unsubstituted heterocyclyl. In certain embodiments, at least one $R^{D3a}$ is substituted aryl. In certain embodiments, at least one $R^{D3a}$ is unsubstituted aryl. In certain embodiments, at least one $R^{D3a}$ is substituted phenyl. In certain embodiments, at least one $R^{D3a}$ is unsubstituted phenyl. In certain embodiments, at least one $R^{D3a}$ is substituted heteroaryl. In certain embodiments, at least one $R^{D3a}$ is unsubstituted heteroaryl. In certain embodiments, at least one $R^{D3a}$ is substituted pyridyl. In certain embodiments, at least one $R^{D3a}$ is unsubstituted pyridyl. In certain embodiments, at least one $R^{D3a}$ is a nitrogen protecting group when attached to a nitrogen atom. In certain embodiments, at least one $R^{D3a}$ is an oxygen protecting group when attached to an oxygen atom. In certain embodiments, at least one $R^{D3a}$ is a sulfur protecting group when attached to a sulfur atom. In certain embodiments, two $R^{D3a}$ groups are joined to form a substituted heterocyclic ring. In certain embodiments, two $R^{D3a}$ groups are joined to form an unsubstituted heterocyclic ring.

In certain embodiments, $R^{D4}$ is a leaving group. In certain embodiments, $R^{D4}$ is Cl. In certain embodiments, $R^{D4}$ is Br. In certain embodiments, $R^{D4}$ is I (iodine). In certain embodiments, $R^{D4}$ is $-OS(=O)_w R^{D4a}$. In certain embodiments, $R^{D4}$ is $-OMs$. In certain embodiments, $R^{D4}$ is $-OTf$. In certain embodiments, $R^{D4}$ is $-OTs$.

In certain embodiments, w is 1. In certain embodiments, w is 2.

In certain embodiments, $R^{D4a}$ is substituted alkyl. In certain embodiments, $R^{D4a}$ is unsubstituted alkyl. In certain embodiments, $R^{D4a}$ is substituted alkenyl. In certain embodiments, $R^{D4a}$ is unsubstituted alkenyl. In certain embodiments, $R^{D4a}$ is substituted alkynyl. In certain embodiments, $R^{D4a}$ is unsubstituted alkynyl. In certain embodiments, $R^{D4a}$ is substituted carbocyclyl. In certain embodiments, $R^{D4a}$ is unsubstituted carbocyclyl. In certain embodiments, $R^{D4a}$ is substituted heterocyclyl. In certain embodiments, $R^{D4a}$ is unsubstituted heterocyclyl. In certain embodiments, $R^{D5}$ is substituted aryl. In certain embodiments, $R^{D4a}$ is unsubstituted aryl. In certain embodiments, $R^{D4a}$ is substituted heteroaryl. In certain embodiments, $R^{D4a}$ is unsubstituted heteroaryl.

In certain embodiments, $R^{D5}$ is H. In certain embodiments, $R^{D5}$ is substituted alkyl. In certain embodiments, $R^{D5}$ is unsubstituted alkyl. In certain embodiments, $R^{D5}$ is Cl-alkyl. In certain embodiments, $R^{D5}$ is methyl. In certain embodiments, $R^{D5}$ is ethyl. In certain embodiments, $R^{D5}$ is propyl. In certain embodiments, $R^{D5}$ is butyl. In certain embodiments, $R^{D5}$ is a nitrogen protecting group. In certain embodiments, $R^{D5}$ is BOC. In certain embodiments, $R^{D5}$ is Cbz. In certain embodiments, $R^{D5}$ is Fmoc. In certain embodiments, $R^{D5}$ is Bn.

In certain embodiments, a is 1. In certain embodiments, a is 2.

In certain embodiments, Y is $-O-$. In certain embodiments, Y is $=O$. In certain embodiments, Y is $-S-$. In certain embodiments, Y is $=S$. In certain embodiments, Y is $-NR^{D6}-$, wherein $R^{D6}$ is hydrogen, $C_{1-6}$ alkyl, or a nitrogen protecting group. In certain embodiments, Y is $-NH-$. In certain embodiments, Y is $-NCH_3-$. In certain embodiments, Y is $-N(BOC)-$. In certain embodiments, Y is $-N(Fmoc)-$. In certain embodiments, Y is $-N(Cbz)-$. In certain embodiments, Y is $-N(Bn)-$. In certain embodiments, Y is $=NR^{D6}$ wherein $R^{D6}$ is hydrogen, $C_{1-6}$ alkyl, or a nitrogen protecting group. In certain embodiments, Y is $=NH$. In certain embodiments, Y is $=NCH_3$. In certain embodiments, Y is $=NTs$. In certain embodiments, Y is $=NBn$. In certain embodiments, Y is $=NCH(Ph)_2$.

As used herein, each of z and z1 is independently 0, 1, 2, 3, 4, 5, or 6, as valency permits. In certain embodiments, z is 0. In certain embodiments, z is 1. In certain embodiments, z is 2. In certain embodiments, z is 3. In certain embodiments, z is 4. In certain embodiments, z is 5. In certain embodiments, z is 6. In certain embodiments, z1 is 0. In certain embodiments, z1 is 1. In certain embodiments, z1 is 2. In certain embodiments, z1 is 3. In certain embodiments, z1 is 4. In certain embodiments, z1 is 5. In certain embodiments, z1 is 6.

In certain embodiments, $R^D$ is

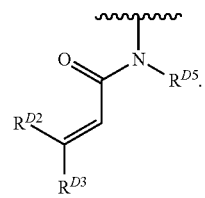

In certain embodiments, $R^D$ is

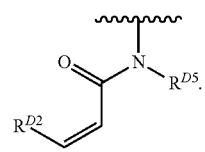

In certain embodiments, $R^D$ is

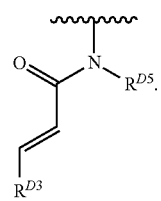

In certain embodiments, $R^D$ is

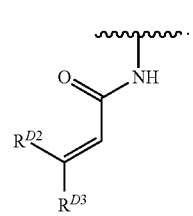

In certain embodiments, $R^D$ is

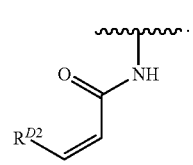

In certain embodiments, $R^D$ is

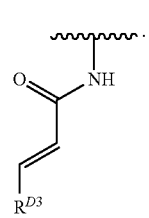

In certain embodiments, $R^D$

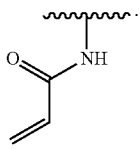

In certain embodiments, $R^D$

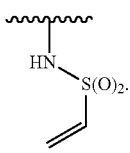

In certain embodiments, $R^D$ is

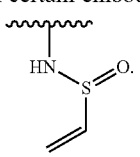

In certain embodiments, $R^D$ is

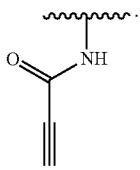

In certain embodiments, $R^D$ is

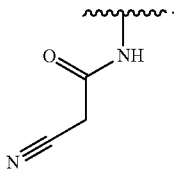

In certain embodiments, $R^D$ is

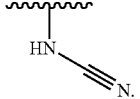 [SMILES: *NC#N]

In certain embodiments, $R^D$ is

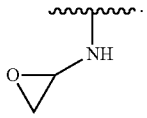

In certain embodiments, $R^D$ is

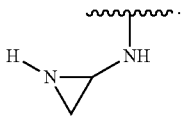 [SMILES: *NC1CN1]

In certain embodiments, $R^D$ is

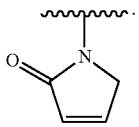

In certain embodiments, $R^D$ is

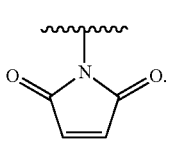 [SMILES: *N1C(=O)C=CC1=O]

In certain embodiments, $R^D$ is

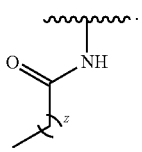

In certain embodiments, $R^D$ is

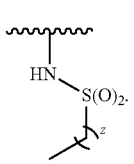

In certain embodiments, $R^D$ is

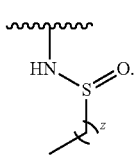

In certain embodiments, $R^D$ is

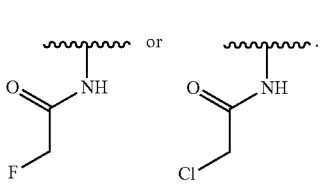 [SMILES: *NC(=O)CF ; *NC(=O)CCl]

In certain embodiments, $R^D$ is

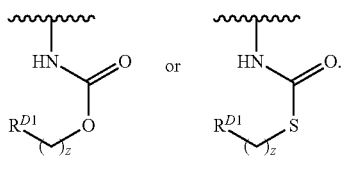 or 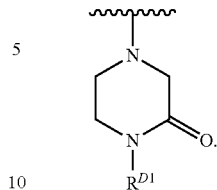

In certain embodiments, $R^D$ is

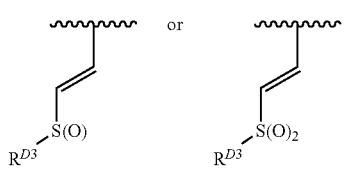

In certain embodiments, $R^D$ is

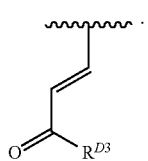

In certain embodiments, $R^D$ is

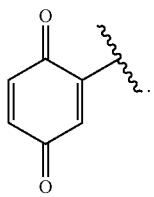 [SMILES: *C1=CC(=O)C=CC1=O]

In certain embodiments, $R^D$ is

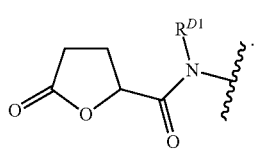

In certain embodiments, $R^D$ is

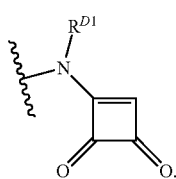

In certain embodiments, $R^D$ is

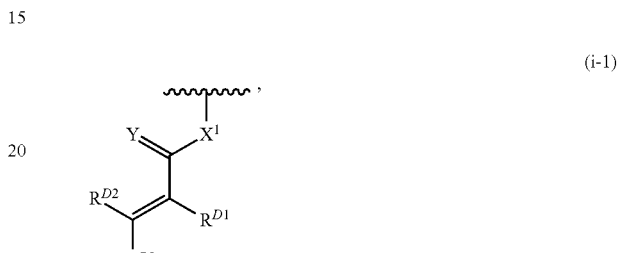

In certain embodiments, $R^D$ is a group of Formula (i-1), (i-3), or (i-20):

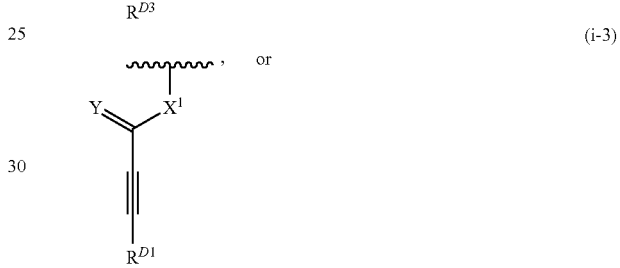

(i-1)

(i-3)

(i-20)

wherein each instance of $X^1$ is bond or $NR^{D5}$, Y is independently O, S, or $NR^{D6}$, and $R^{D1}$, $R^{D2}$, and $R^{D3}$ are as defined herein. In certain embodiments, $X^1$ is a bond. In certain embodiments, $X^1$ is $NR^{D5}$. In certain embodiments, Y is O. In certain embodiments, $R^{D1}$ is hydrogen. In certain embodiments, $R^{D1}$ is —CN. In certain embodiments, $R^{D2}$ is hydrogen. In certain embodiments, $R^{D3}$ is hydrogen. In certain embodiments, $R^{D2}$ is —CH$_2$N(R$^{D2a}$)$_2$, and $R^{D3}$ is hydrogen. In certain embodiments, $R^{D2}$ is —CH$_2$N(R$^{D3a}$)$_2$, and $R^{D3}$ is hydrogen. In certain embodiments, $R^{D2}$ and $R^{D3}$ are hydrogen. In certain embodiments, $R^{D1}$, $R^{D2}$ and $R^{D3}$ are hydrogen.

In certain embodiments, $R^D$ is a group of Formula (i-19), (i-17), or (i-18):

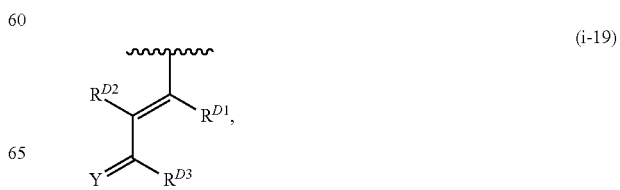

(i-19)

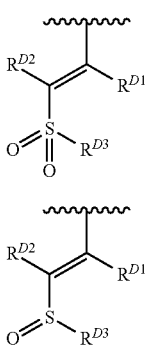

(i-17)

(i-18)

wherein Y is independently O, S, or $NR^{D6}$; and $R^{D1}$, $R^{D2}$, and $R^{D3}$ are as defined herein. In certain embodiments, Y is O. In certain embodiments, $R^{D1}$ is hydrogen. In certain embodiments, $R^{D2}$ is hydrogen. In certain embodiments, $R^{D2}$ is —CN. In certain embodiments, $R^{D3}$ is substituted or unsubstituted alkyl.

In certain embodiments, $R^D$ is a group of Formula (i-7) or (i-8):

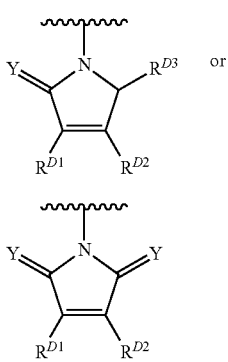

(i-7)

(i-8)

wherein Y is independently O, S, or $NR^{D6}$; and $R^{D1}$, $R^{D2}$, and $R^{D3}$ are as defined herein. In certain embodiments, Y is O. In certain embodiments, $R^{D1}$ is hydrogen. In certain embodiments, $R^{D2}$ is hydrogen. In certain embodiments, $R^{D3}$ is hydrogen.

In certain embodiments, $R^D$ is a group of Formula (i-13) or (i-14):

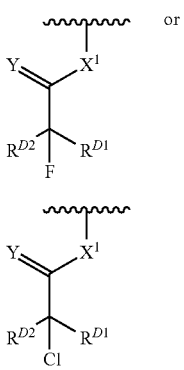

(i-13)

(i-14)

wherein each instance of $X^1$ is bond or $NR^{D5}$; Y is independently O, S, or $NR^{D6}$; and $R^{D1}$ and $R^{D2}$ are as defined herein. In certain embodiments, $X^1$ is a bond. In certain embodiments, $X^1$ is $NR^{D5}$. In certain embodiments, Y is O. In certain embodiments, $R^{D1}$ is hydrogen. In certain embodiments, $R^{D1}$ is halogen, e.g., —F or —Cl. In certain embodiments, $R^{D2}$ is hydrogen. In certain embodiments, $R^{D2}$ is halogen, e.g., —F or —Cl.

In certain embodiments, $R^D$ is a group of Formula (i-11) or (i-12):

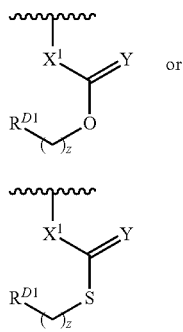

(i-11)

(i-12)

wherein each instance of $X^1$ is bond or $NR^{D5}$; Y is independently O, S, or $NR^{D6}$; z is 0, 1, 2, 3, 4, 5, or 6; and $R^{D1}$ is as defined herein. In certain embodiments, $X^1$ is a bond. In certain embodiments, $X^1$ is $NR^{D5}$. In certain embodiments, Y is O. In certain embodiments z is 0 or 1. In certain embodiments, $R^{D1}$ is substituted or unsubstituted alkyl.

In certain embodiments, $R^D$ is a group of Formula (i-10), (i-16), or (i-9):

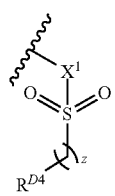

(i-10)

(i-16)

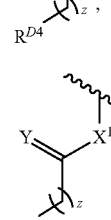

(i-9)

wherein each instance of $X^1$ is bond or $NR^{D5}$; Y is independently O, S, or $NR^{D6}$; z is 0, 1, 2, 3, 4, 5, or 6; and $R^{D4}$ is a leaving group selected from the group consisting of —Br, —Cl, —I, and —OS(=O)$_w$$R^{D4a}$, wherein w is 1 or 2. In certain embodiments, $X^1$ is a bond. In certain embodiments, $X^1$ is $NR^{D5}$. In certain embodiments, Y is O. In certain embodiments, z is 0. In certain embodiments, z is 1.

In certain embodiments, $R^D$ is a group of Formula (i-4) or (i-5):

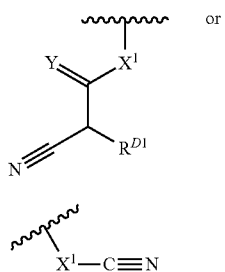

wherein each instance of $X^1$ is bond or $NR^{D5}$; and $R^{D1}$ is as defined herein. In certain embodiments, $X^1$ is a bond. In certain embodiments, $X^1$ is $NR^{D5}$. In certain embodiments, $R^{D1}$ is hydrogen.

In certain embodiments, $R^D$ is a group of Formula (i-6):

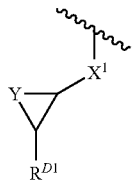

wherein each instance of $X^1$ is bond or $NR^{D5}$; Y is independently O, S, or $NR^{D6}$; and $R^{D1}$ is as defined herein. In certain embodiments, $X^1$ is a bond. In certain embodiments, $X^1$ is $NR^{D5}$. In certain embodiments, Y is O. In certain embodiments, $R^{D1}$ is hydrogen.

In certain embodiments, $R^D$ is a group of Formula (i-21)-(i-32), (1-39) and (1-40), wherein each instance of $X^1$ is independently a bond, —C(=O)—, —SO$_2$—, —$NR^{D5}$, optionally substituted alkylene, or optionally substituted heteroarylene, wherein $R^{D5}$ is hydrogen, $C_{1-6}$ alkyl, or a nitrogen protecting group; Y is independently O, S, or $NR^{D6}$; and $R^{D1}$, $R^{D5}$, and $R^{D3}$ are as defined herein. In certain embodiments, $X^1$ is a bond. In certain embodiments, $X^1$ is —C(=O)—. In certain embodiments, $X^1$ is —SO$_2$—. In certain embodiments, $X^1$ is —$NR^{D5}$. In certain embodiments, $X^1$ is optionally substituted alkylene. In certain embodiments, $X^1$ is substituted alkylene. In certain embodiments, $X^1$ is unsubstituted alkylene. In certain embodiments, Y is O. In certain embodiments, Y is S. In certain embodiments, Y is $NR^{D6}$. In certain embodiments, $R^{D1}$ is hydrogen. In certain embodiments, $R^{D2}$ is hydrogen. In certain embodiments, $R^{D2}$ is —CN. In certain embodiments, $R^{D3}$ is substituted or unsubstituted alkyl.

In certain embodiments, $R^D$ is a group of Formulae (i-33) and (i-36)-(i-38), wherein each instance of $X^1$ is independently a bond, —C(=O)—, —SO$_2$—, —$NR^{D5}$, optionally substituted alkylene, or optionally substituted heteroarylene, wherein $R^{D5}$ is hydrogen, $C_{1-6}$ alkyl, or a nitrogen protecting group; and $R^{D1}$ is as defined herein. In certain embodiments, $X^1$ is optionally substituted heteroarylene. In certain embodiments, $X^1$ is optionally substituted heteroarylene. In certain embodiments, $X^1$ is optionally substituted five-membered heteroarylene. In certain embodiments, $X^1$ is optionally substituted five-membered heteroarylene with at least one S, O, and N. In certain embodiments, $X^1$ is optionally substituted six-membered heteroarylene. In certain embodiments, $X^1$ is optionally substituted six-membered heteroarylene with at least one S, O, and N.

In certain embodiments, $R^D$ is a group of Formula (i-34), wherein each instance of z and $R^{D1}$ are as defined herein. In certain embodiments, $R^{D1}$ is halogen. In certain embodiments, $R^{D1}$ is F. In certain embodiments, $R^{D1}$ is Cl. In certain embodiments, $R^{D1}$ is Br. In certain embodiments, $R^{D1}$ is I In certain embodiments, $R^{D1}$ is CN. In certain embodiments, $R^{D1}$ is NO$_2$.

In certain embodiments, $R^D$ is

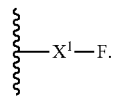

In certain embodiments, $R^D$ is

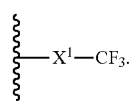

In certain embodiments, $R^D$ is

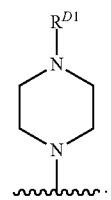

In certain embodiments, $R^D$ is

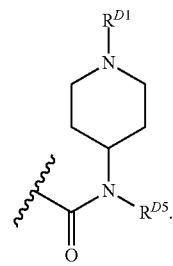

In certain embodiments, $R^D$ is selected from one of the following formulae:

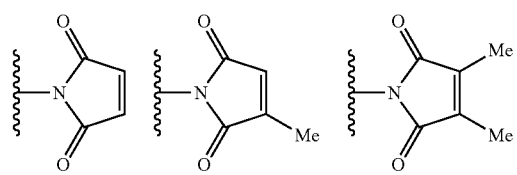

-continued
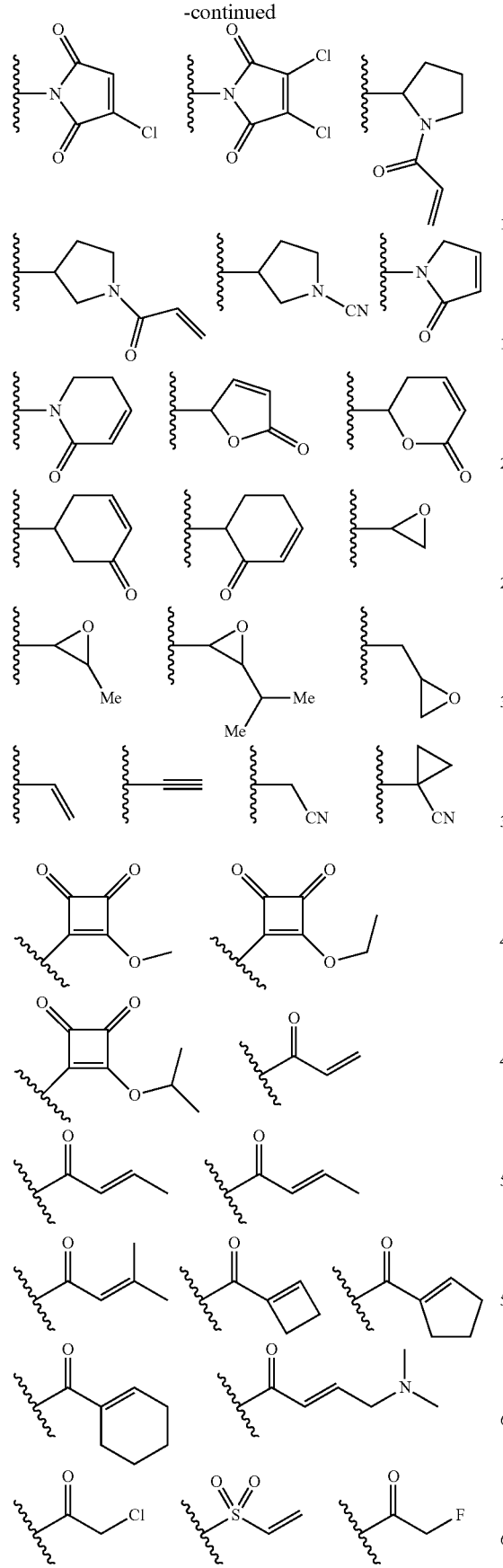
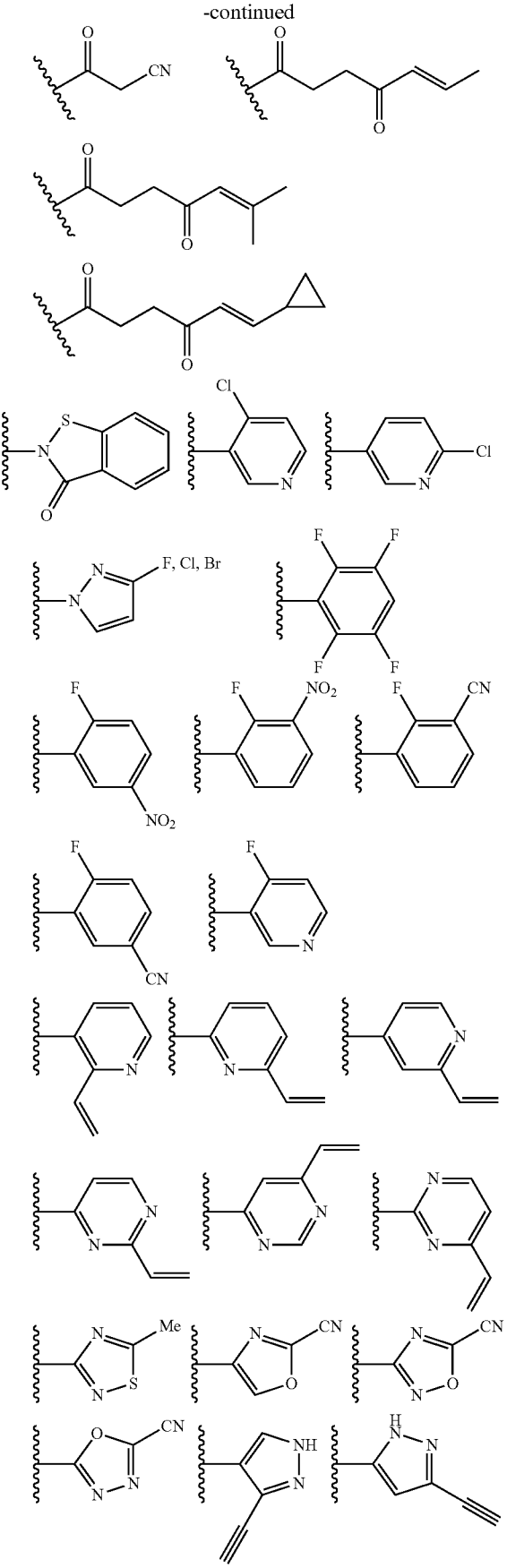

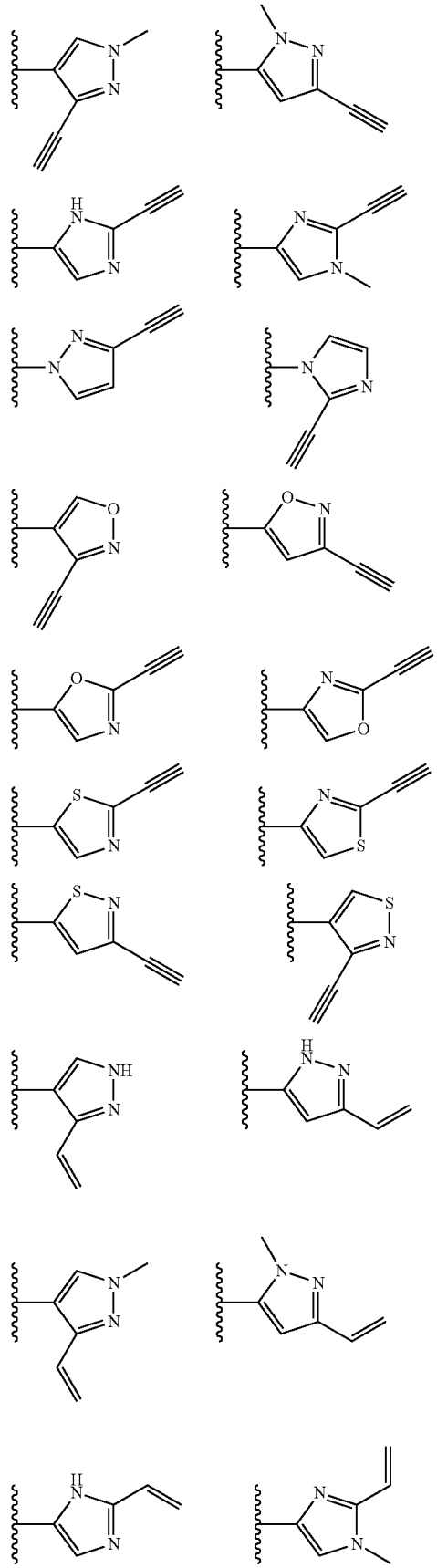
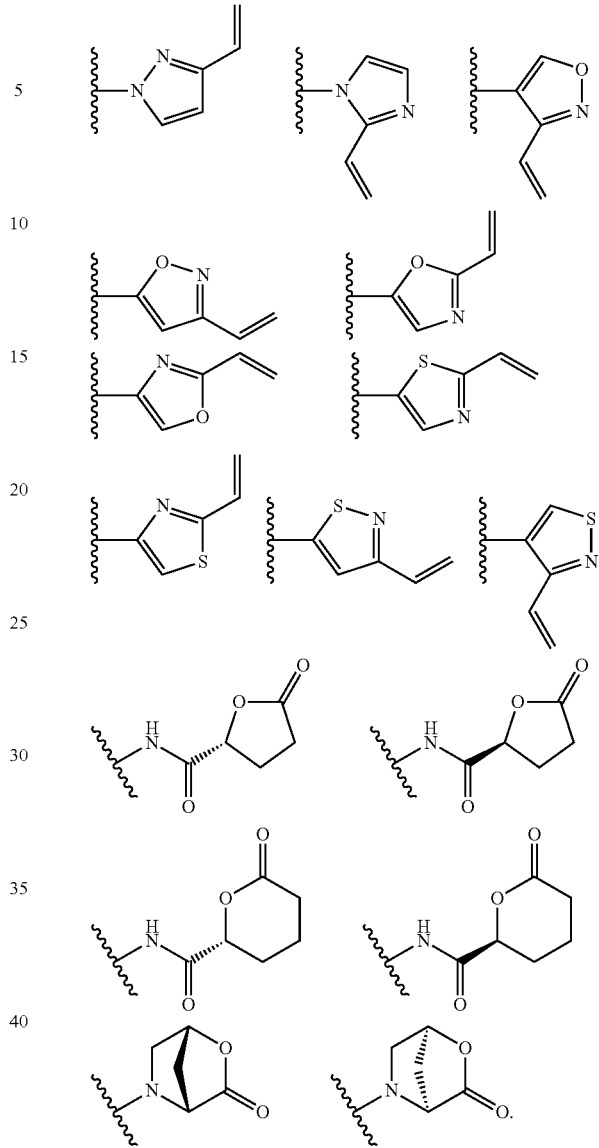
In certain embodiments, the invention provides intermediates of formulae (a)-(c) or salts thereof to prepare formulae (I)-(III), wherein $R^D$, L, Ring C, $R^C$, n, $R^{j1}$, $R^{j2}$, $R^{j3}$, $R^q$ are as defined above; and M is halogen. In certain embodiments, M is F. In certain embodiments, M is Cl. In certain embodiments, M is Br. In certain embodiments, M is I.
Formula (a)
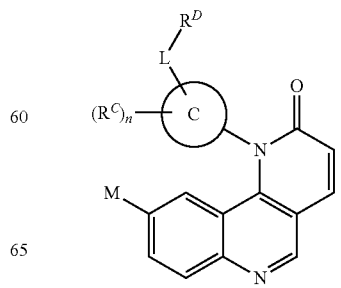

-continued

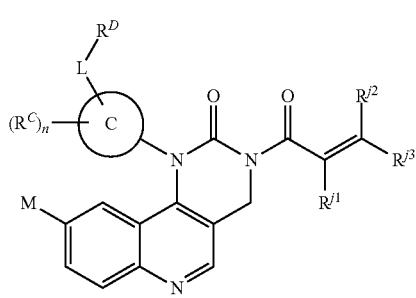
Formula (b)

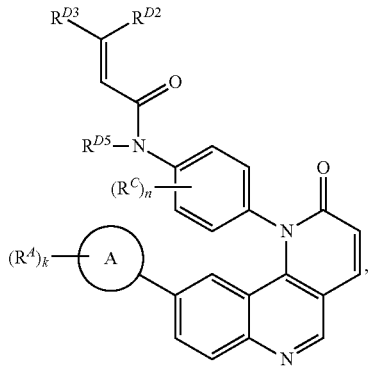

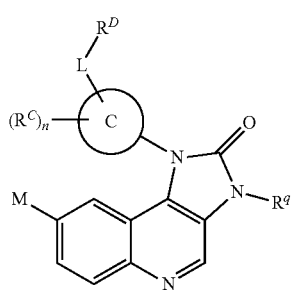
Formula (c)

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

In certain embodiments, the compound of Formula (I) is of formula:

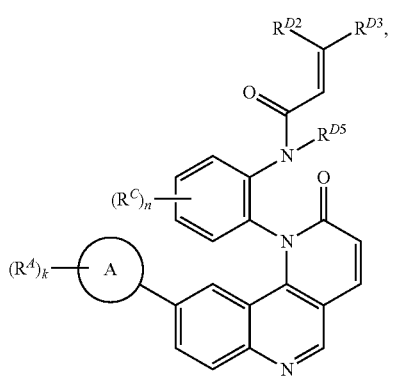

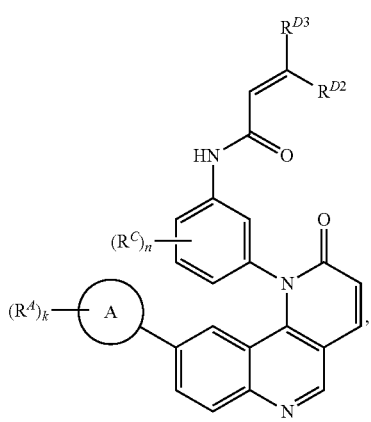

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

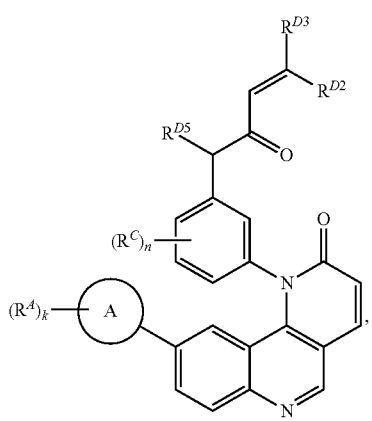

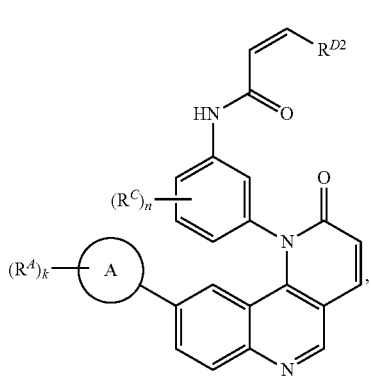

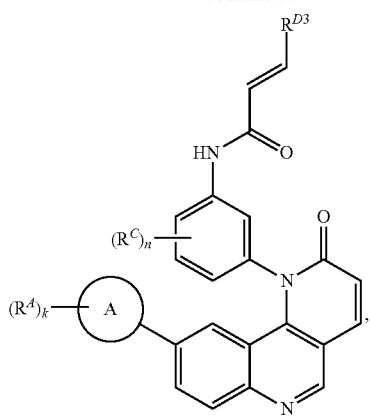

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

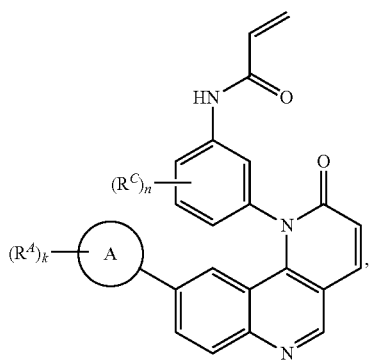

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

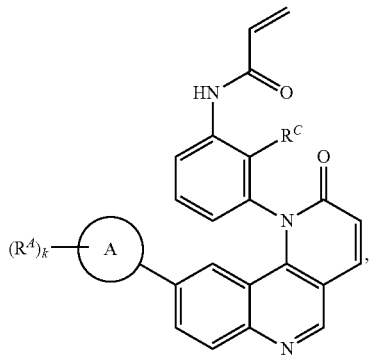

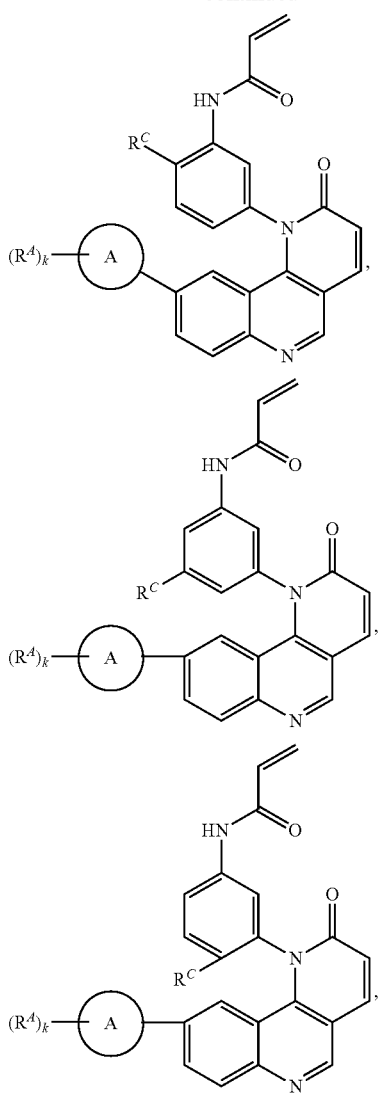

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

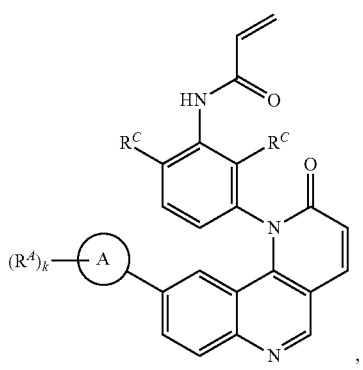

103
-continued
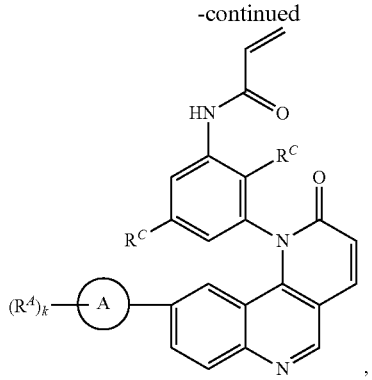
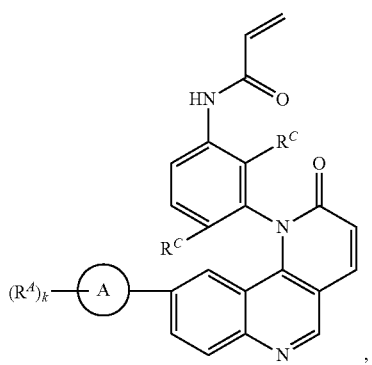
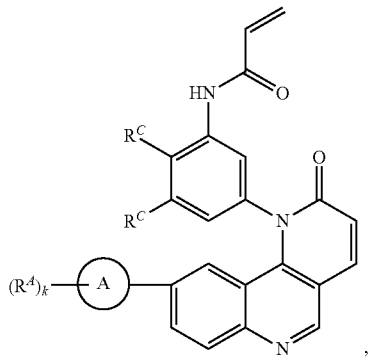
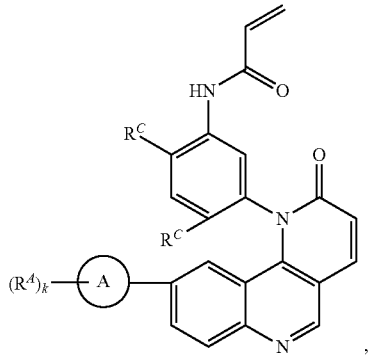
104
-continued
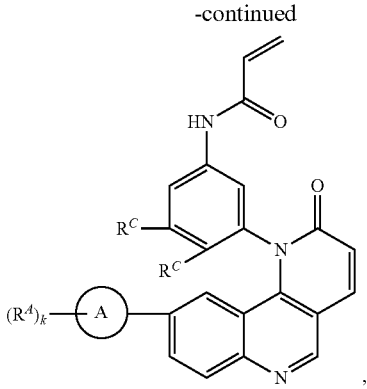
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of formula:
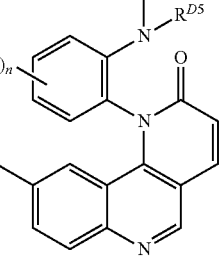
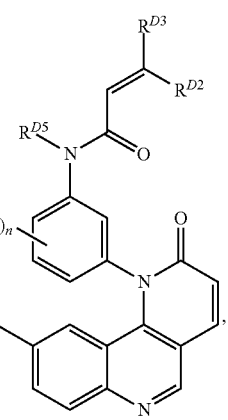

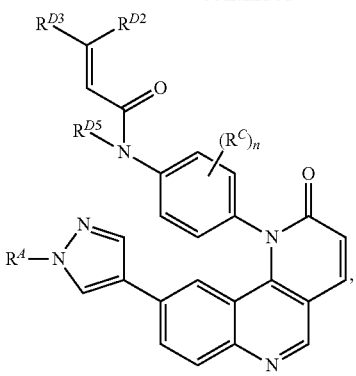

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

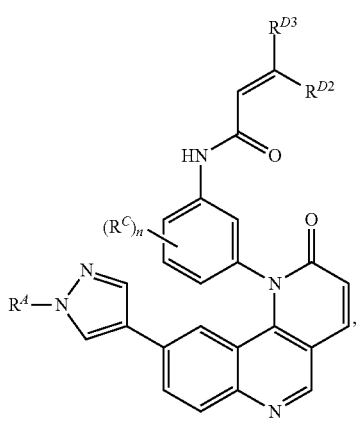

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

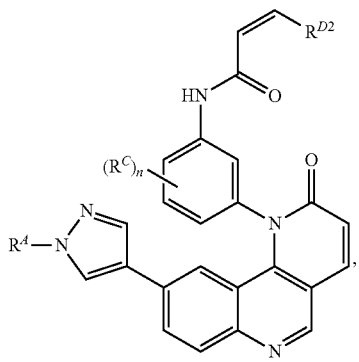

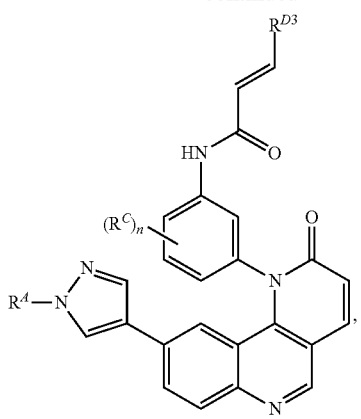

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

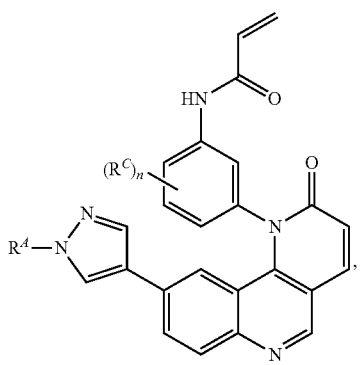

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

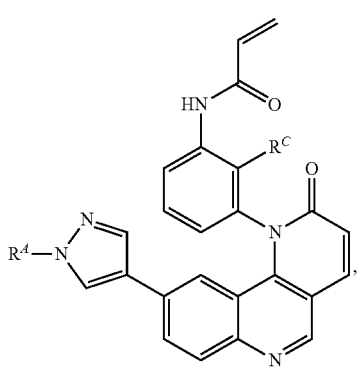

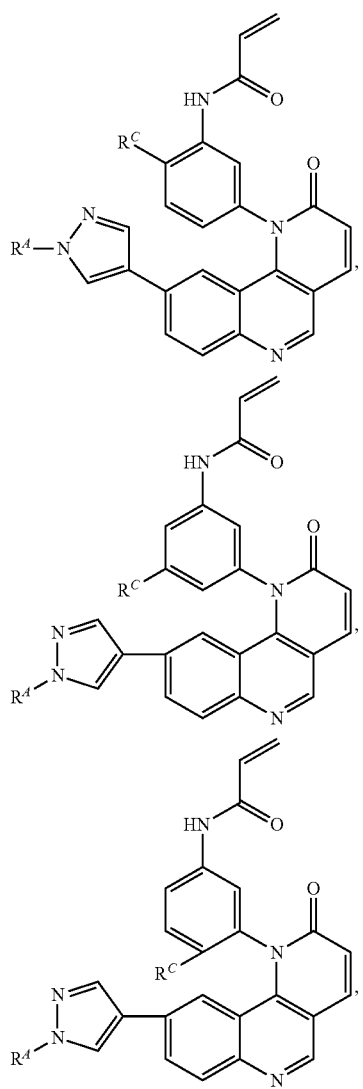
or a pharmaceutically acceptable salt, solvate, hydrate, polymorph, co-crystal, tautomer, stereoisomer, isotopically labeled derivative, or prodrug thereof.
In certain embodiments, the compound of Formula (I) is of formula:
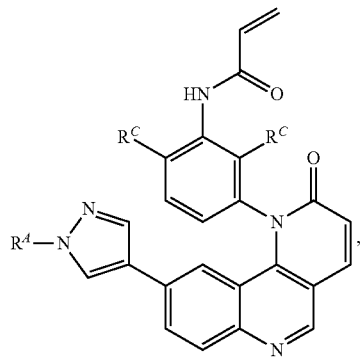
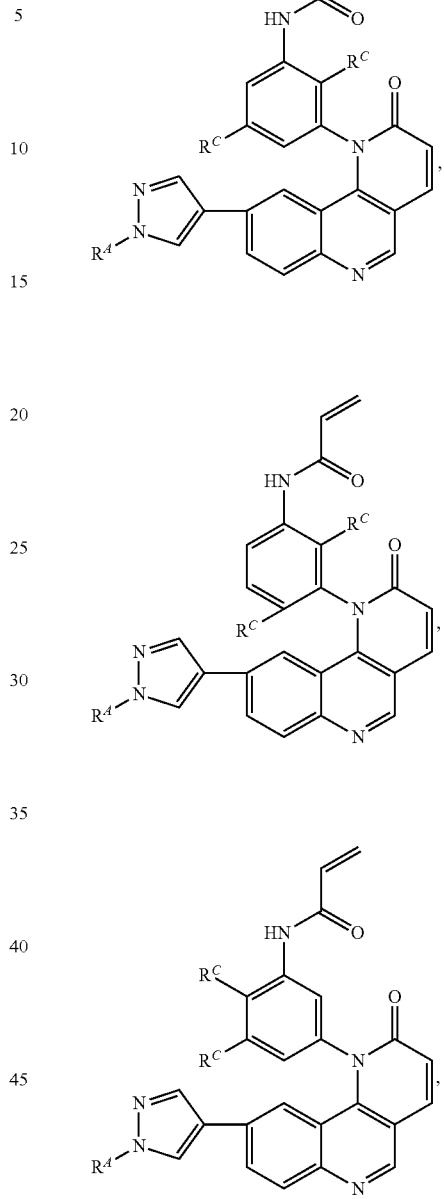

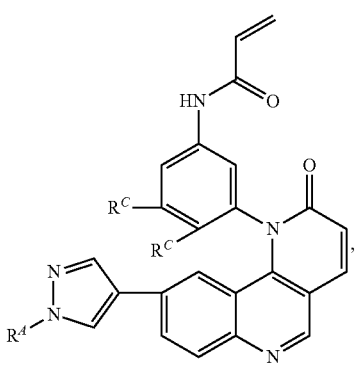

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

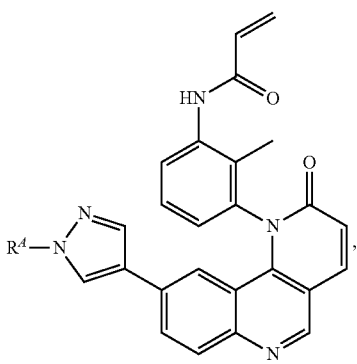

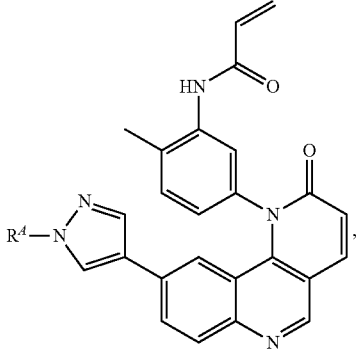

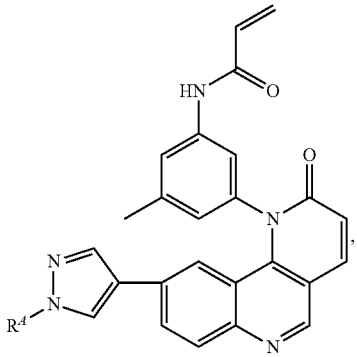

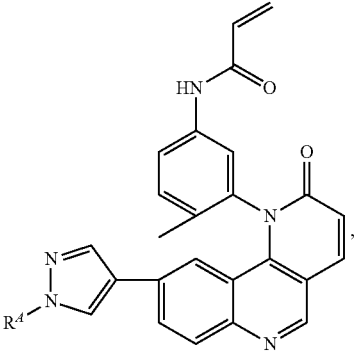

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

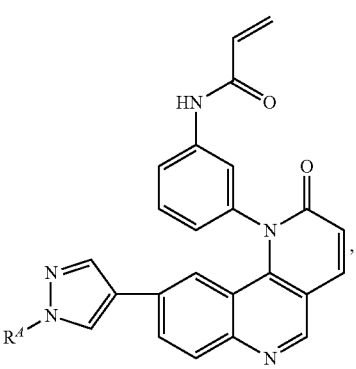

or a pharmaceutically acceptable salt, solvate, hydrate, polymorph, co-crystal, tautomer, stereoisomer, isotopically labeled derivative, or prodrug thereof.

$R^{D5}$ and one $R^C$ may be joined to form a substituted heteroaryl ring. $R^{D5}$ and one $R^C$ may also be joined to form an unsubstituted heteroaryl ring. In certain embodiments, $R^{D5}$ and one $R^C$ are joined to form a substituted 7-membered heteroaryl ring. In certain embodiments, $R^{D5}$ and one $R^C$ are joined to form an unsubstituted 7-membered heteroaryl ring. In certain embodiments, $R^{D5}$ and one $R^C$ are joined to form a substituted 5-membered heteroaryl ring. In certain embodiments, $R^D$ and one $R^C$ are joined to form an unsubstituted 5-membered heteroaryl ring.

In certain embodiments, the compound of Formula (I) is of formula:

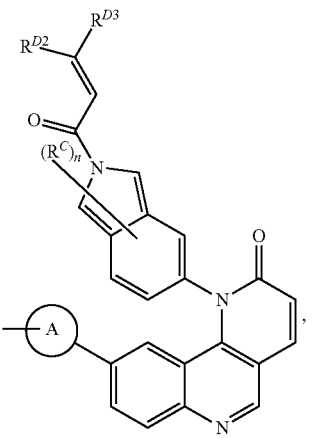

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

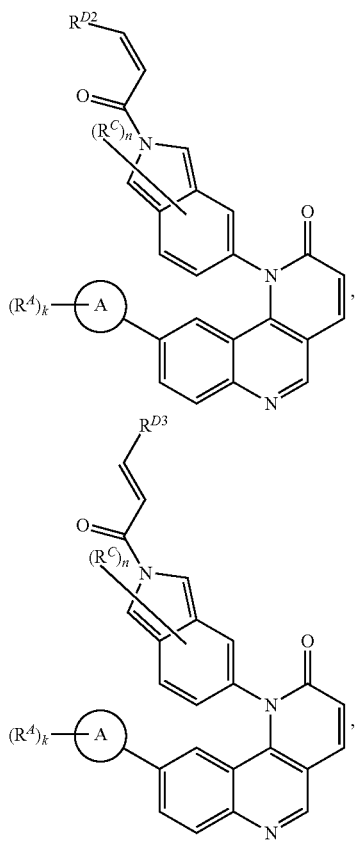

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

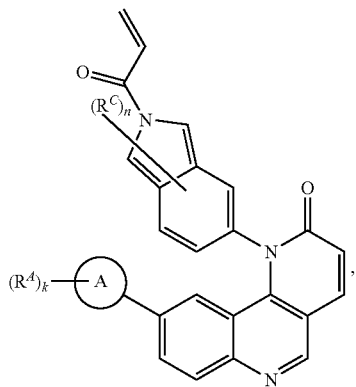

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

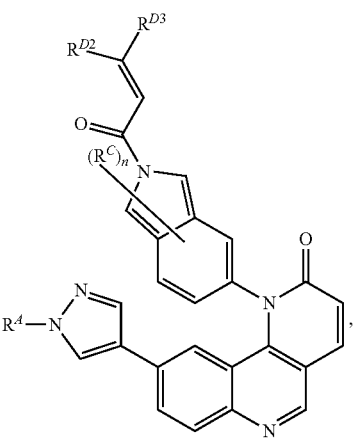

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

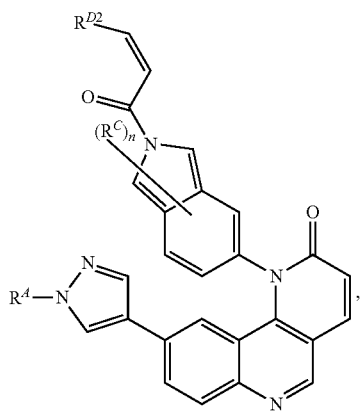

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

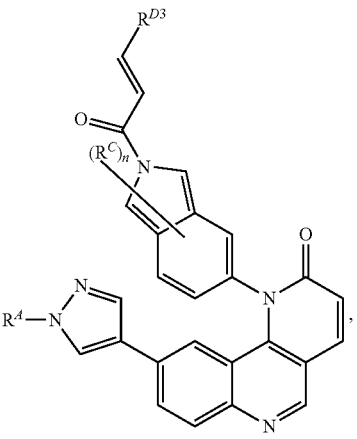

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

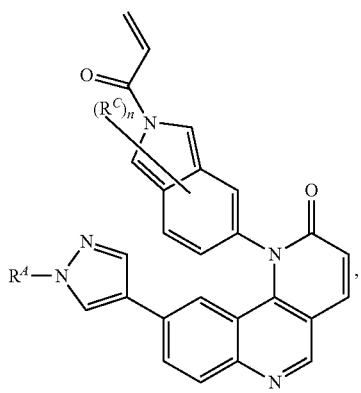

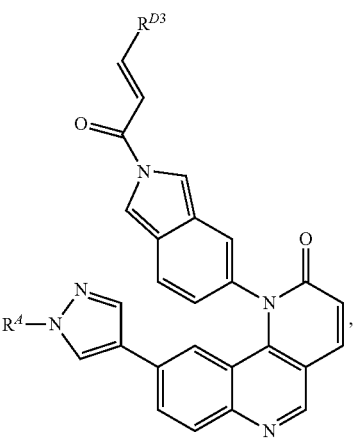

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

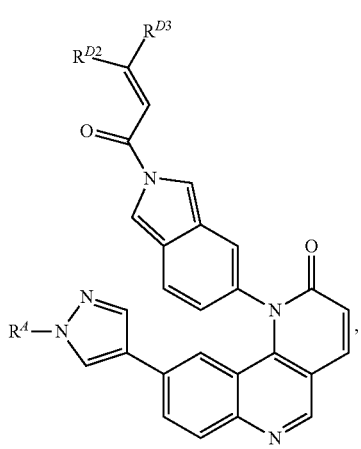

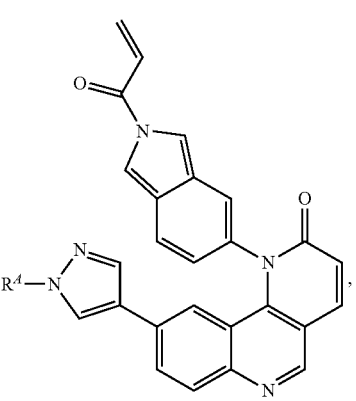

or a pharmaceutically acceptable salt, solvate, hydrate, polymorph, co-crystal, tautomer, stereoisomer, isotopically labeled derivative, and prodrug thereof.

In certain embodiments, the compound of Formula (I) is of formula:

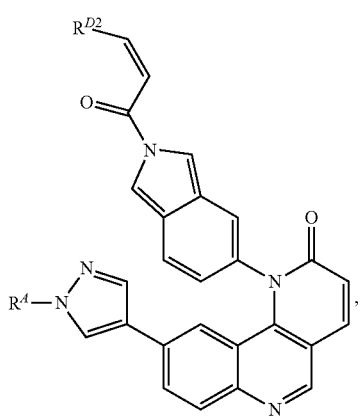

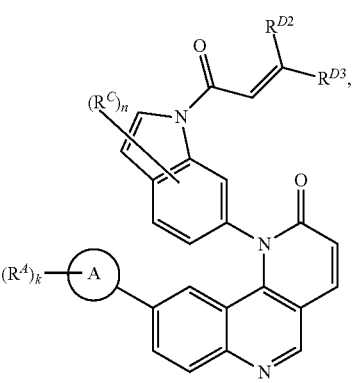

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

115

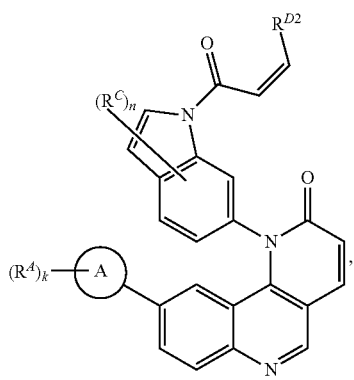

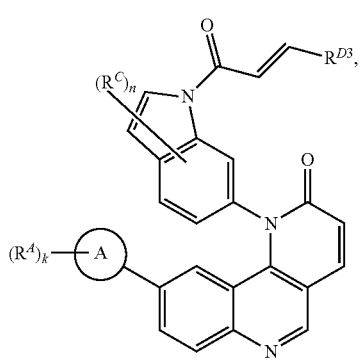

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

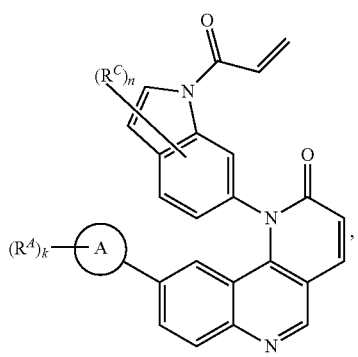

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

116

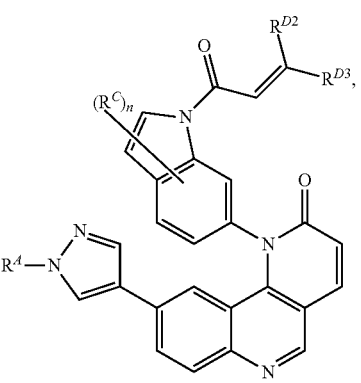

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

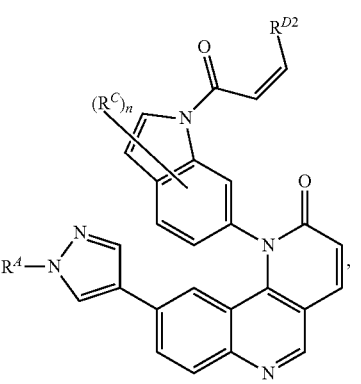

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

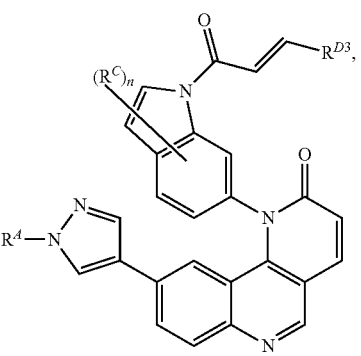

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

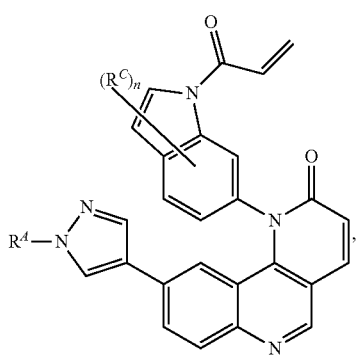

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

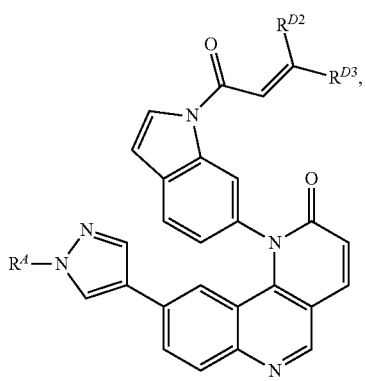

or a pharmaceutically acceptable salt, solvate, hydrate, polymorph, co-crystal, tautomer, stereoisomer, isotopically labeled derivative, or prodrug thereof.

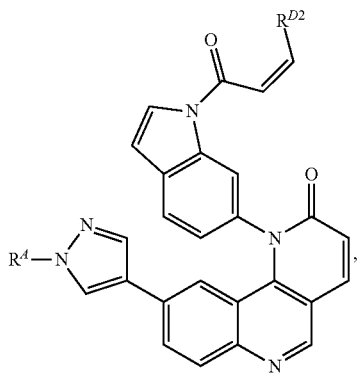

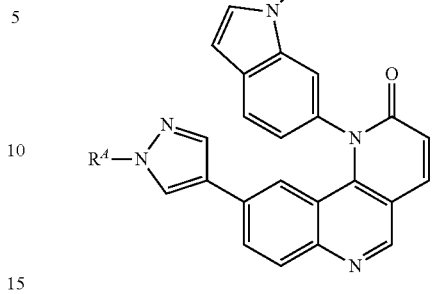

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

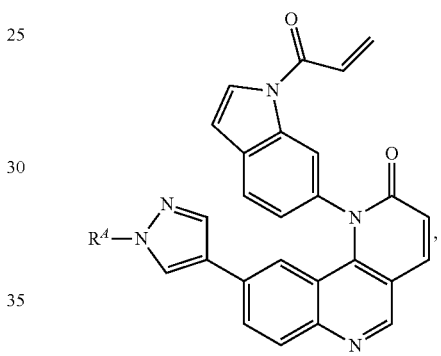

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

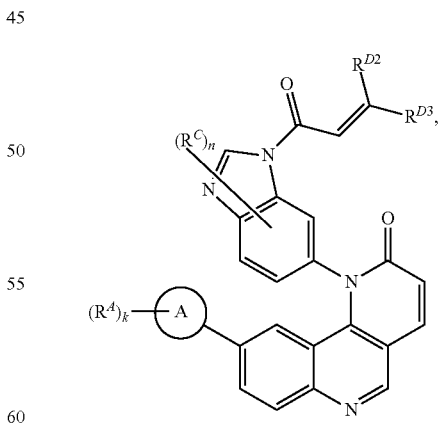

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

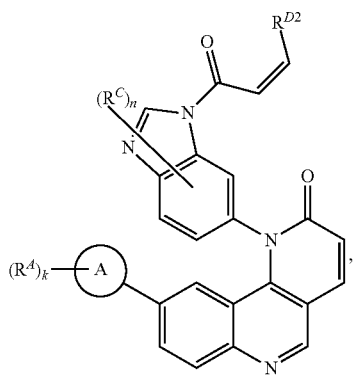

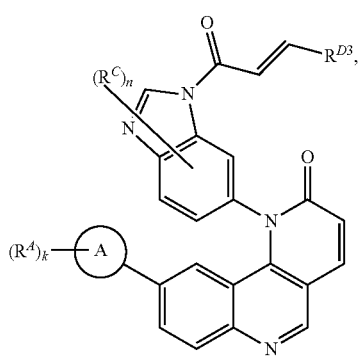

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

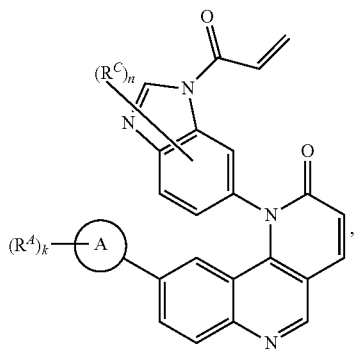

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

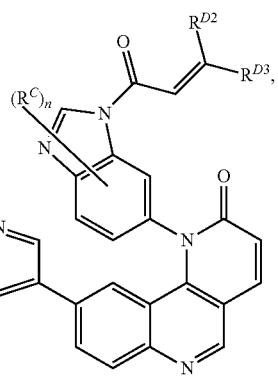

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

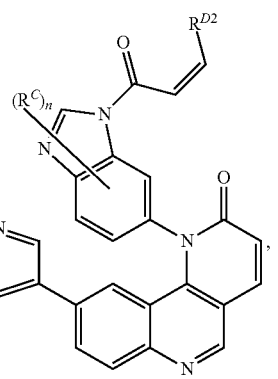

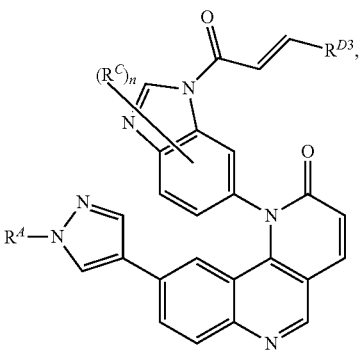

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

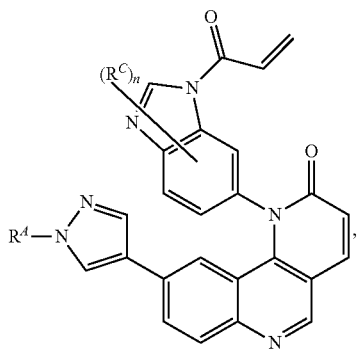

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

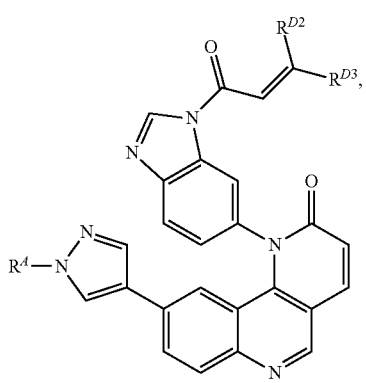

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

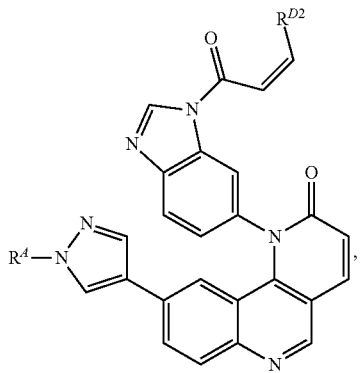

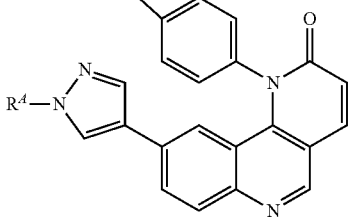

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

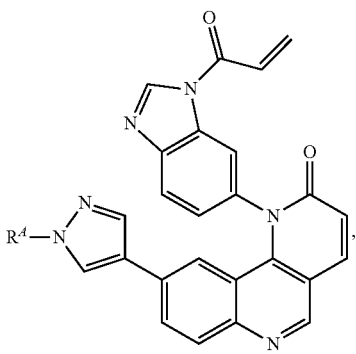

or a pharmaceutically acceptable salt, solvate, hydrate, polymorph, co-crystal, tautomer, stereoisomer, isotopically labeled derivative, or prodrug thereof.

$R^{D5}$ and one $R^C$ may be joined to form a substituted heterocyclic ring. $R^{D5}$ and one $R^C$ may also be joined to form an unsubstituted heterocyclic ring. In certain embodiments, $R^{D5}$ and one $R^C$ are joined to form a substituted 6-membered heterocyclic ring. In certain embodiments, $R^{D5}$ and one $R^C$ are joined to form an unsubstituted 6-membered heterocyclic ring.

In certain embodiments, the compound of Formula (I) is of formula:

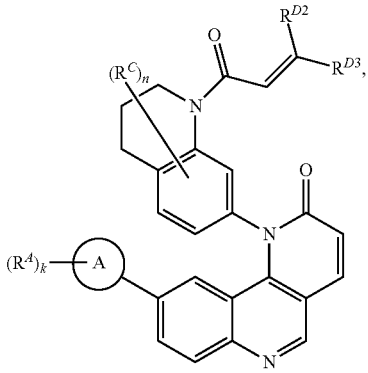

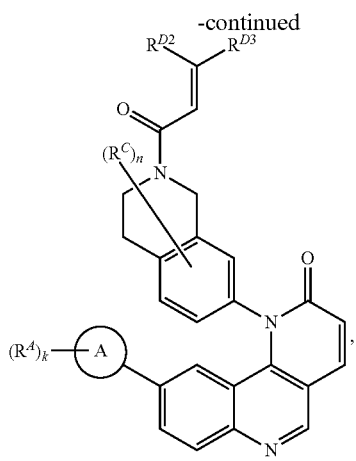

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

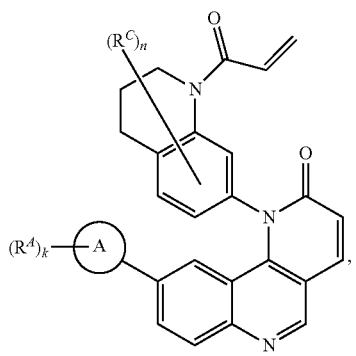

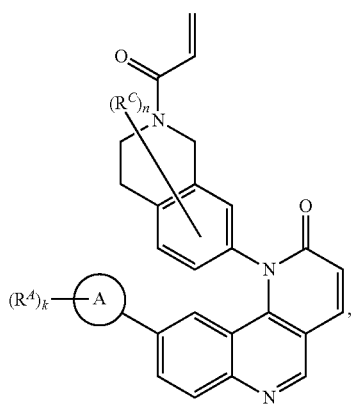

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

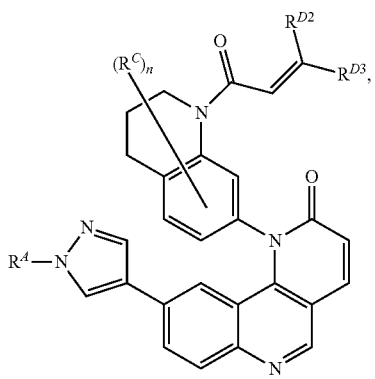

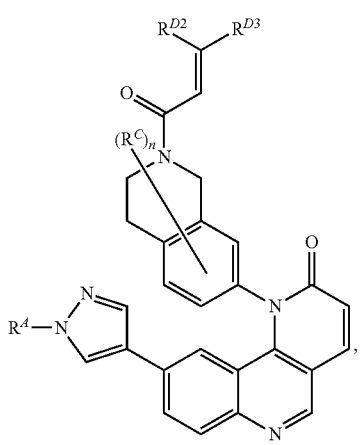

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

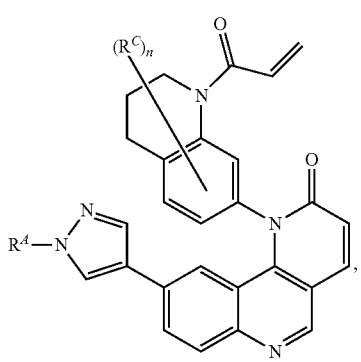

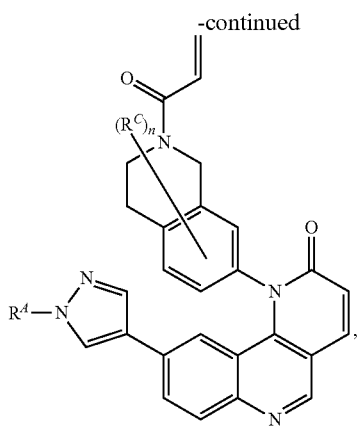

or a pharmaceutically acceptable salt, solvate, hydrate, polymorph, co-crystal, tautomer, stereoisomer, isotopically labeled derivative, or prodrug thereof.

$R^{D5}$ and one $R^C$ may be joined to form a substituted or unsubstituted 5-membered heterocyclic ring.

In certain embodiments, the compound of Formula (I) is of formula:

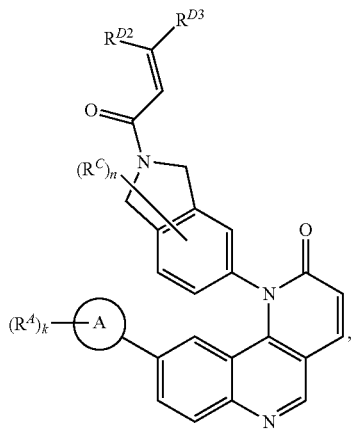

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

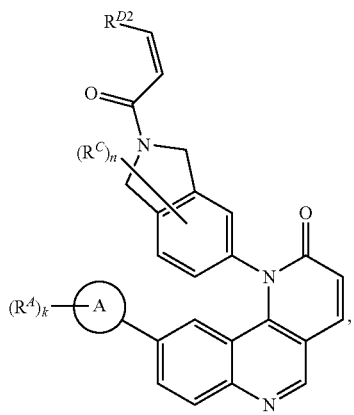

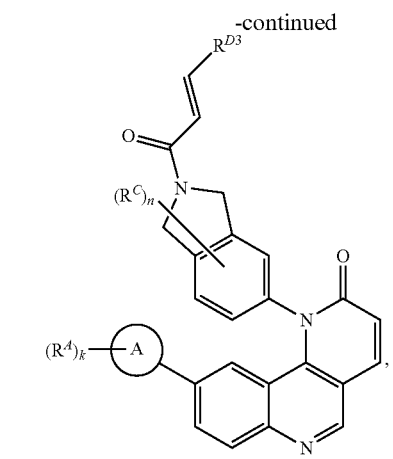

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

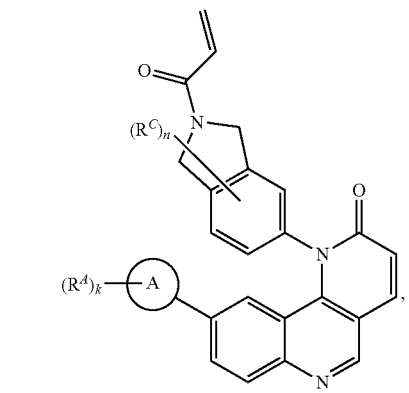

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

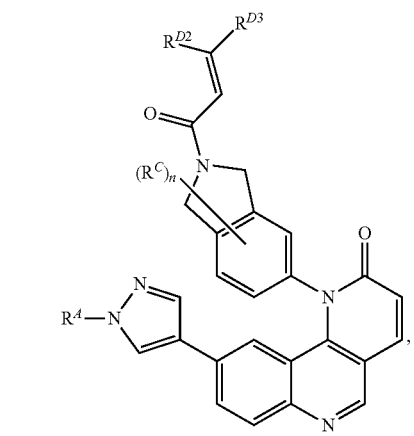

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

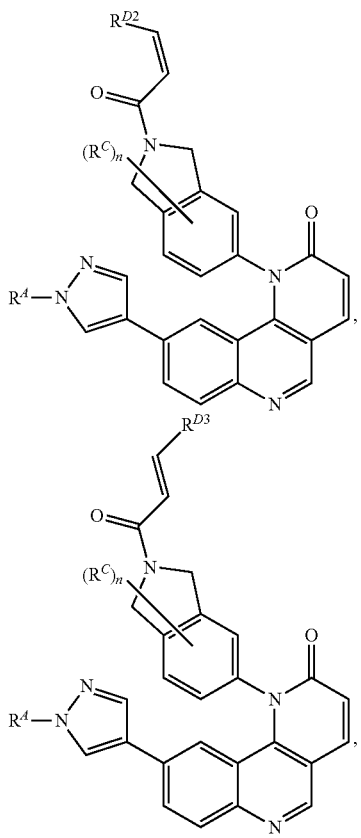

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

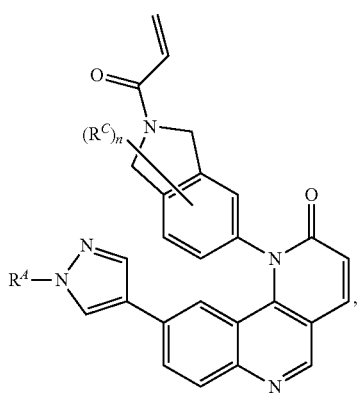

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

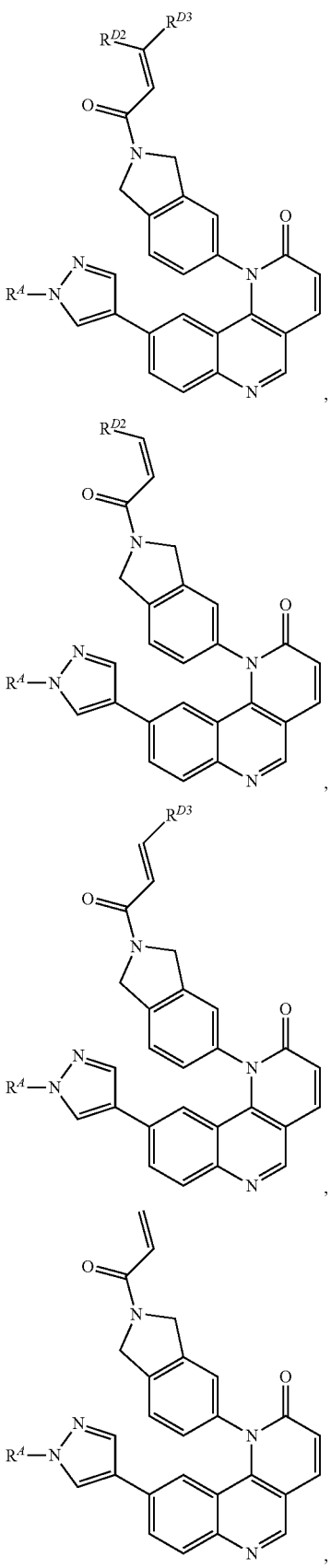

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

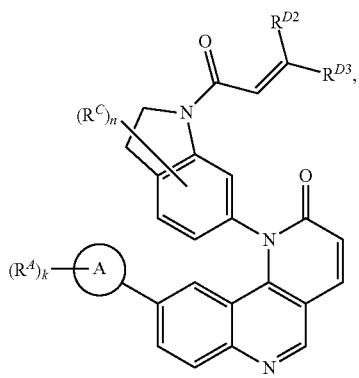

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

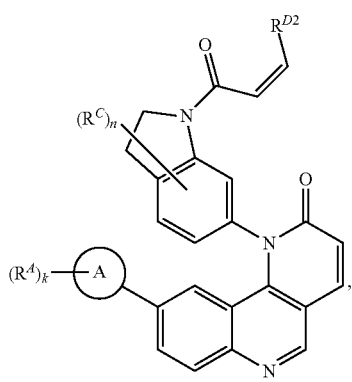

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

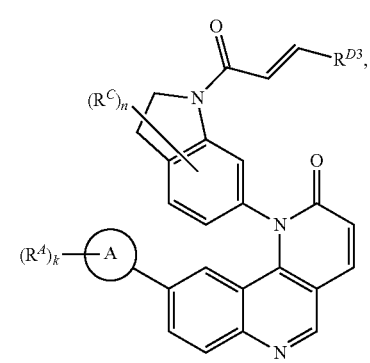

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

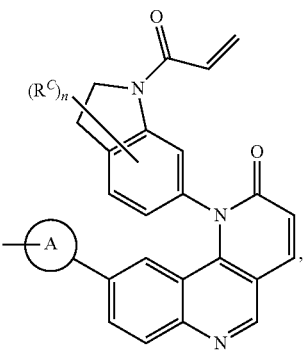

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

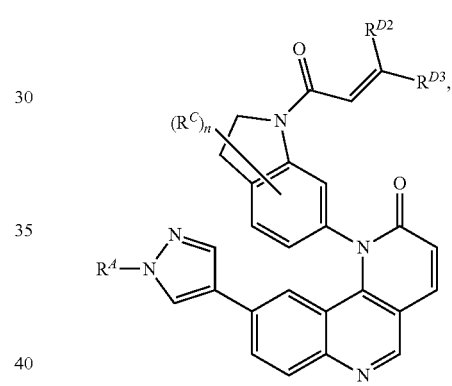

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

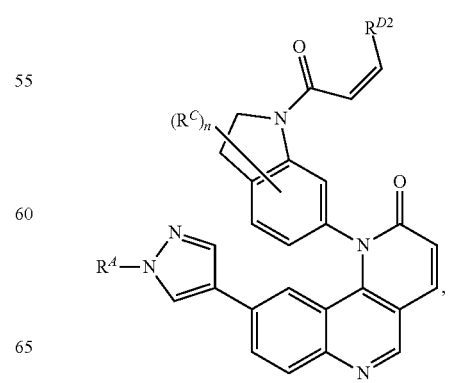

-continued

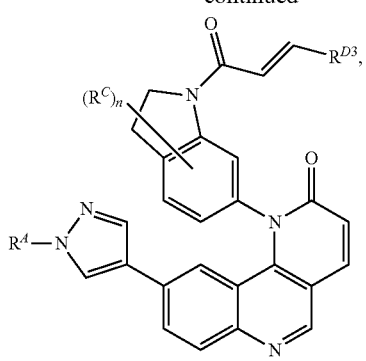

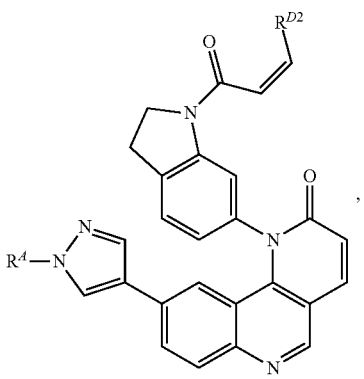

or a pharmaceutically acceptable salt, solvate, hydrate, polymorph, co-crystal, tautomer, stereoisomer, isotopically labeled derivative, or prodrug thereof.

In certain embodiments, the compound of Formula I) is of formula:

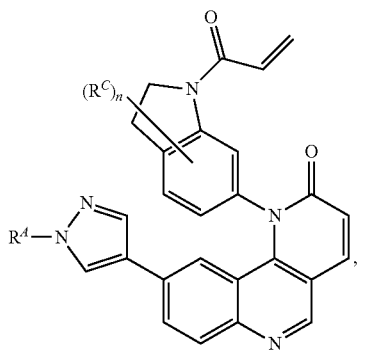

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

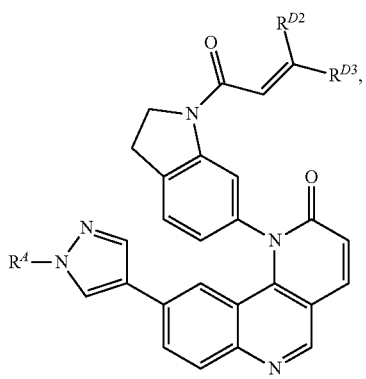

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of formula:

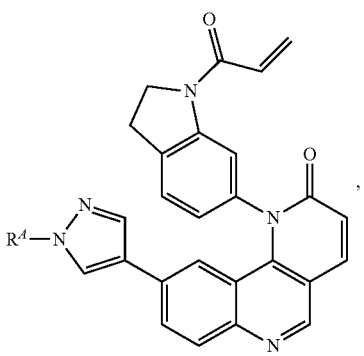

or a pharmaceutically acceptable salt, solvate, hydrate, polymorph, co-crystal, tautomer, stereoisomer, isotopically labeled derivative, or prodrug thereof.

In certain embodiments the compound of Formula (I) is of formula:

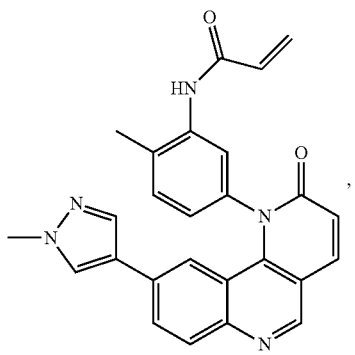

(QL-XII-56)

or a pharmaceutically acceptable salt, solvate, hydrate, polymorph, co-crystal, tautomer, stereoisomer, isotopically labeled derivative, or prodrug thereof.

In certain embodiments, the compound of Formula I) is of formula:

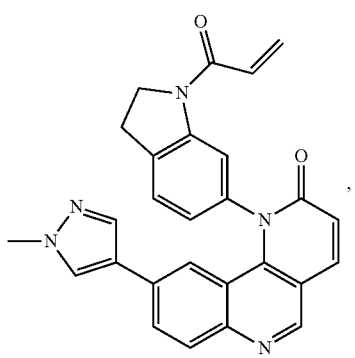

(QL-XII-47)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of formula:

(QL-XII-47), or a pharmaceutically acceptable salt, solvate, hydrate, polymorph, co-crystal, tautomer, stereoisomer, isotopically labeled derivative, or prodrug thereof.

Pharmaceutical Compositions, Kits, and Administration

The present invention provides pharmaceutical compositions comprising a compound of the present invention, e.g., a compound of Formula (I), and pharmaceutically acceptable salts, solvates, hydrates, polymorphs, co-crystals, tautomers, stereoisomers, isotopically labeled derivatives, and prodrugs thereof, as described herein, and optionally a pharmaceutically acceptable excipient. In certain embodiments, the compound of the present invention, or a pharmaceutically acceptable salt thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of the present invention (the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier or excipient and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi-liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, anti-cancer agents, anti-diabetic agents, anti-inflammatory agents, immunosuppressant agents, and a pain-relieving agent Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the first container and the second container are combined to form one unit dosage form.

Thus, in one aspect, provided are kits for preventing and/or treating an infectious disease (e.g., a viral disease or viral infection) of a subject. In certain embodiments, the kits include a first container comprising a compound, or a pharmaceutically acceptable salt, solvate, hydrate, polymorph, co-crystal, tautomer, stereoisomer, isotopically labeled derivative, prodrug, and composition thereof; and an instruction for administering the compound, or a pharmaceutically acceptable salt, solvate, hydrate, polymorph, co-crystal, tautomer, stereoisomer, isotopically labeled derivative, prodrug, and composition thereof, to a subject to prevent or treat the infectious disease. The first container of the provided kit may comprise a compound of the present invention. In certain embodiments, the first container comprises QL-XII-47, or a pharmaceutical salt thereof. In certain embodiments, the first container comprises QL-XII-56, or a pharmaceutical salt thereof. In certain embodiments, the first container comprises a therapeutically effective amount of an inventive compound. In certain embodiments, the first container comprises a prophylactically effective amount of an inventive compound.

The kits of the present invention may be used for treating or preventing Dengue fever, Dengue hemorrhagic fever (DHF), Dengue shock syndrome (DSS), hepatitis B, hepatitis C, fulminant viral hepatitis, severe acute respiratory syndrome (SARS), viral myocarditis, influenza A virus infection, influenza B virus infection, parainfluenza virus infection, RS virus (RSV) infections (e.g., RSV bronchiolitis, RSV pneumonia, especially infant and childhood RSV infections and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes simplex virus 1 infection, poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, encephalitis, Saint Louise encephalitis, Kyasanur Forest disease, Murray Valley encephalitis, tick-borne encephalitis, West Nile encephalitis, yellow fever, and/or viral infections in subjects with immune disorders. In certain embodiments, the provided kits are used for treating or preventing Dengue fever. In certain embodiments, the provided kits are used for treating or preventing Dengue hemorrhagic fever (DHF). In certain embodiments, the provided kits are used for treating or preventing Dengue shock syndrome (DSS). The kits of the present invention may also be used for treating or preventing a disease caused by Flaviviridae virus (e.g., Dengue virus (DENV), including Dengue virus 1 (DENV1), Dengue virus 2 (DENV2), Dengue virus 3 (DENV3), and Dengue virus 4 (DENV4); West Nile virus; tick-borne encephalitis virus; yellow fever virus; hepatitis C virus; hepatitis G virus; bovine viral diarrhea; classical swine fever virus; and hog cholera virus), Kunjin virus, Japanese encephalitis virus, vesicular stomatitis virus (VSV), vesicular stomatitis virus (VSV) pseudotyped with rabies glycoprotein, vesicular stomatitis virus (VSV) pseudotyped with Ebola glycoprotein, herpes simplex virus 1 (HSV-1), human cytomegalovirus (HCMV), poliovirus, Junin virus, Ebola virus, Marburg virus (MARV), Lassa fever virus (LASV), Venezuelan equine encephalitis virus (VEEV), Rift Valley Fever virus (RVFV), hepatitis B virus, cytomegalovirus, papillomavirus, coronavirus, Epstein-Barr virus (EBV), human immunodeficiency virus (HIV), orthomyxovirus, paramyxovirus, arenavirus, bunyavirus, adenovirus, poxvirus, retrovirus, rhabdovirus, picornavirus, or herpesvirus. In certain embodiments, the provided kits are used for treating or preventing a disease caused by Flaviviridae virus. In certain embodiments, the provided kits are used for treating or preventing a disease caused by Dengue virus (DENV). In certain embodiments, the provided kits are used for treating or preventing a disease caused by Dengue virus 1 (DENV1), Dengue virus 2 (DENV2), Dengue virus 3 (DENV3), or Dengue virus 4 (DENV4).

In certain embodiments, the subject administered the inventive compound or composition is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent or non-human primate. In certain embodiments, the subject is a non-human transgenic animal such as a transgenic mouse or transgenic pig. In certain embodiments, the subject is a fish.

Methods of Treatment and Uses

In one aspect, the present invention provides methods for the prevention and/or treatment of infectious diseases in a subject suffered therefrom. In certain embodiments, the methods of prevention and/or treatment include administering to a subject with an infectious disease an effective amount of a compound of the present invention (e.g., QL-XII-47 or QL-XII-56), or a pharmaceutically acceptable salt, solvate, hydrate, polymorph, co-crystal, tautomer, stereoisomer, isotopically labeled derivative, prodrug, or pharmaceutical composition thereof. In certain embodiments, the methods of prevention and/or treatment comprise administering to a subject with an infectious disease an effective amount of QL-XII-47, or a pharmaceutically acceptable salt thereof. In certain embodiments, the methods of prevention and/or treatment comprise administering to a subject with an infectious disease an effective amount of QL-XII-56, or a pharmaceutical salt thereof.

In certain embodiments, the effective amount is a therapeutically effective amount. In certain embodiments, the effective amount is a prophylactically effective amount.

The infectious disease prevented and/or treated by the compounds or pharmaceutical compositions of the present invention is typically caused by a virus. In certain embodiments, the infectious disease is prevented and/or treated by blocking entry of the virus into a host cell. Entry of a virus into a host cell involves an early entry step that occurs before the uptake of the virus by the host cell. Entry of a virus into a host cell also involves a late entry step that occurs after the uptake of the virus by the host cell but prior to the release of the genome of the virus from the virus's nucleocapsid. In certain embodiments, entry of the virus is blocked at an early entry step. In certain embodiments, entry of the virus is blocked at a late entry step. In certain embodiments, the infectious disease is prevented and/or treated by reducing the count of the virus in the subject. In certain embodiments, the infectious disease is prevented and/or treated by inhibiting the activity of the virus in the subject. In certain embodiments, the infectious disease is prevented and/or treated by reducing the susceptibility of a host factor in the subject to the virus. In certain embodiments, the infectious disease is prevented and/or treated by attaching a compound of the present invention to a cysteine residue of the host factor. In certain embodiments, the infectious disease is prevented and/or treated by irreversible binding of a compound of the present invention to a cysteine residue of the host factor. In certain embodiments, the infectious disease is prevented and/or treated by covalently attaching a compound of the present invention to a cysteine residue of the host factor.

In certain embodiments, the infectious disease prevented and/or treated by the inventive compounds is caused by Flaviviridae virus. In certain embodiments, the infectious disease prevented and/or treated by the inventive compounds is caused by Dengue virus (DENV). In certain embodiments, the infectious disease prevented and/or treated by the inventive compounds is caused by Dengue virus 1 (DENV1). In certain embodiments, the infectious disease prevented and/or treated by the inventive compounds is caused by Dengue virus 2 (DENV2). In certain embodiments, the infectious disease prevented and/or treated by the inventive compounds is caused by Dengue virus 3 (DENV3). In certain embodiments, the infectious disease prevented and/or treated by the inventive compounds is caused by Dengue virus 4 (DENV4). In certain embodiments, the infectious disease prevented and/or treated by the inventive compounds is caused by Kunjin virus. In certain embodiments, the infectious disease prevented and/or treated by the inventive compounds is caused by Japanese encephalitis virus. In certain embodiments, the infectious disease prevented and/or treated by the inventive compounds is caused by vesicular stomatitis virus (VSV). In certain embodiments, the infectious disease prevented and/ or treated by the inventive compounds is caused by vesicular stomatitis virus (VSV) pseudotyped with rabies glycoprotein. In certain embodiments, the infectious disease prevented and/or treated by the inventive compounds is caused by vesicular stomatitis virus (VSV) pseudotyped with Ebola glycoprotein. In certain embodiments, the infectious disease prevented and/or treated by the inventive compounds is caused by herpes simplex virus 1 (HSV-1). In certain embodiments, the infectious disease prevented and/or treated by the inventive compounds is caused by human cytomegalovirus (HCMV). In certain embodiments, the infectious disease prevented and/or treated by the inventive compounds is caused by poliovirus. In certain embodiments, the infectious disease prevented and/or treated by the inventive compounds is caused by Junin virus. In certain embodiments, the infectious disease prevented and/or treated by the inventive compounds is caused by Ebola virus. In certain embodiments, the infectious disease prevented and/or treated by the inventive compounds is caused by Marburg virus (MARV). In certain embodiments, the infectious disease prevented and/or treated by the inventive compounds is caused by Lassa fever virus (LASV). In certain embodiments, the infectious disease prevented and/or treated by the inventive compounds is caused by Venezuelan equine encephalitis virus (VEEV). In certain embodiments, the infectious disease prevented and/or treated by the inventive compounds is caused by Rift Valley Fever virus (RVFV). The infectious disease prevented and/or treated by the inventive compounds may also be caused by, without limitation, West Nile virus, tick-borne encephalitis virus, yellow fever virus, hepatitis C virus, hepatitis G virus, bovine viral diarrhea, classical swine fever virus, hog cholera virus, hepatitis B virus, cytomegaloviruses, papillomaviruses, coronaviruses, Epstein-Barr virus (EBV), human immunodeficiency virus (HIV), orthomyxoviruses, paramyxoviruses, arenaviruses, bunyaviruses, adenoviruses, poxviruses, retroviruses, rhabdoviruses, picornaviruses, or herpesviruses.

In certain embodiments, the infectious disease prevented and/or treated by the inventive compounds is Dengue fever. In certain embodiments, the infectious disease prevented and/or treated by the inventive compounds is Dengue hemorrhagic fever (DHF). In certain embodiments, the infectious disease prevented and/or treated by the inventive compounds is Dengue shock syndrome (DSS). Other infectious disease that may be prevented and/or treated by the inventive compounds include, but not limited to, hepatitis B, hepatitis C, fulminant viral hepatitis, severe acute respiratory syndrome (SARS), viral myocarditis, influenza A virus infection, influenza B virus infection, parainfluenza virus infection, RS virus (RSV) infections (e.g., RSV bronchiolitis, RSV pneumonia, especially infant and childhood RSV infections and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes simplex virus 1 infection, poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, encephalitis, Saint Louise encephalitis, Kyasanur Forest disease, Murray Valley encephalitis, tick-borne encephalitis, West Nile encephalitis, yellow fever, and viral infections in subjects with immune disorders.

The present invention also provides methods of reducing viral load in a subject. The methods of reducing viral load include administering to the subject an effective amount of a compound of the present invention (e.g., QL-XII-47 or QL-XII-56), or a pharmaceutically acceptable salt, solvate, hydrate, polymorph, co-crystal, tautomer, stereoisomer, isotopically labeled derivative, prodrug, or pharmaceutical composition thereof. The inventive compounds may be administered within 1 day, 2 days, 3 days, 4 days, 5 days, 6 days, 7 days, 2 weeks, 3 weeks, or 1 month of exposure to the virus. In certain embodiments, the time of viral clearance is reduced. In certain embodiments, morbidity or mortality of the subject, who may or may not have been infected with the virus or has been exposed to the virus, is reduced.

Viral load may be determined by measuring the titer or level of virus in a tissue or bodily fluid of the subject. Measuring the viral load can be accomplished by any conventional assay, such as ones described in the literature (see, e.g., *Medical Microbiology;* 3rd Ed.; Murray et al., eds.; Mosby, Inc.: Philadelphia, Pa., 1998). In certain embodiments, viral load is reduced to a undetectable level. In certain embodiments, viral load is reduced to a low level of, for example, less than about 20,000 cpm (genome copies per milliliter of serum of the subject), less than about 5000 cpm, less than about 2000 cpm, less than about 500 cpm, or less than about 200 cpm. In certain embodiments, viral load is reduced by at least about 5%, at least about 10%, at least about 25%, at least about 50%, at least about 75%, at least about 90%, at least about 95%, or at least about 99%. In certain embodiments, the inventive methods achieve a sustained viral response, e.g., the viral load is reduced to an undetectable or low level for a period of at least about one month, at least about two months, at least about three months, at least about four months, at least about five months, at least about six months, at least about one year, at least about two years, at least about three years, at least about four years, or at least about five years following cessation of administering a compound of the present invention to the subject.

The present invention also involves methods of preventing a viral infection in a subject who was or may be exposed to a virus. The methods of preventing a viral infection include administering to the subject who was or may be exposed to a virus an effective amount of a compound of the present invention (e.g., QL-XII-47 or QL-XII-56), or a pharmaceutically acceptable salt, solvate, hydrate, polymorph, co-crystal, tautomer, stereoisomer, isotopically labeled derivative, prodrug, or pharmaceutical composition thereof.

In certain embodiments, the subject was exposed to a virus. In certain embodiments, the subject may be exposed to a virus. In certain embodiments, the viral infection is prevented by blocking entry of the virus into the cells of the subject.

In certain embodiments, the virus to which a subject was or may be exposed is Flaviviridae virus. In certain embodiments, the virus to which a subject was or may be exposed is Dengue virus (DENV). In certain embodiments, the virus to which a subject was or may be exposed is Dengue virus 1 (DENV1). In certain embodiments, the virus to which a subject was or may be exposed is Dengue virus 2 (DENV2). In certain embodiments, the virus to which a subject was or may be exposed is Dengue virus 3 (DENV3). In certain embodiments, the virus to which a subject was or may be exposed is Dengue virus 4 (DENV4). In certain embodiments, the virus to which a subject was or may be exposed is Kunjin virus. In certain embodiments, the virus to which a subject was or may be exposed is Japanese encephalitis virus. In certain embodiments, the virus to which a subject was or may be exposed is vesicular stomatitis virus (VSV). In certain embodiments, the virus to which a subject was or may be exposed is vesicular stomatitis virus (VSV) pseudotyped with rabies glycoprotein. In certain embodiments, the virus to which a subject was or may be exposed is vesicular stomatitis virus (VSV) pseudotyped with Ebola glycoprotein. In certain embodiments, the virus to which a subject was or may be exposed is herpes simplex virus 1 (HSV-1). In certain embodiments, the virus to which a subject was or may be exposed is human cytomegalovirus (HCMV). In certain embodiments, the virus to which a subject was or may be exposed is poliovirus. In certain embodiments, the virus to which a subject was or may be exposed is Junin virus. In certain embodiments, the virus to which a subject was or may be exposed is Ebola virus. In certain embodiments, the virus to which a subject was or may be exposed is Marburg virus (MARV). In certain embodiments, the virus to which a subject was or may be exposed is Lassa fever virus (LASV). In certain embodiments, the virus to which a subject was or may be exposed is Venezuelan equine encephalitis virus (VEEV). In certain embodiments, the virus to which a subject was or may be exposed is Rift Valley Fever virus (RVFV). The virus to which a subject was or may be exposed may also include, but not limited to, West Nile virus, tick-borne encephalitis virus, yellow fever virus, hepatitis C virus, hepatitis G virus, bovine viral diarrhea, classical swine fever virus, hog cholera virus, hepatitis B virus, cytomegaloviruses, papillomaviruses, coronaviruses, Epstein-Barr virus (EBV), human immunodeficiency virus (HIV), orthomyxoviruses, paramyxoviruses, arenaviruses, bunyaviruses, adenoviruses, poxviruses, retroviruses, rhabdoviruses, picornaviruses, and herpesviruses.

Another aspect of the present invention relates to methods of inhibiting viral replication in vitro, in vivo, and/or ex vitro.

Another aspect of the present invention relates to methods of inhibiting viral production in vitro, in vivo, and/or ex vitro.

Another aspect of the present invention relates to methods of inhibiting viral activity in vitro, in vivo, and/or ex vitro.

Another aspect of the present invention relates to methods of killing a virus in vitro, in vivo, and/or ex vitro.

In certain embodiments, the methods of inhibiting viral replication, viral production, inhibiting viral activity, or killing a virus include contacting a virus in vitro, in vivo, and/or ex vitro with an effective amount of a compound of the present invention (e.g., QL-XII-47 or QL-XII-56), or a pharmaceutically acceptable salt, solvate, hydrate, polymorph, co-crystal, tautomer, stereoisomer, isotopically labeled derivative, prodrug, or pharmaceutical composition thereof.

Another aspect of the invention relates to methods of screening a library of compounds to identify one or more compounds that are useful in the treatment and/or prevention of a viral infection in a subject suffering therefrom, in inhibiting viral replication in vitro, in vivo, and/or ex vitro, in inhibiting viral production in vitro, in vivo, and/or ex vitro, in inhibiting viral activity in vitro, in vivo, and/or ex vitro, and/or in killing a virus in vitro, in vivo, and/or ex vitro. In certain embodiments, the library of compounds is a library of compounds of the present invention. The methods of screening a library include providing at least two different compounds of the present invention, or pharmaceutically acceptable salts, solvates, hydrates, polymorphs, co-crystals, tautomers, stereoisomers, isotopically labeled derivatives, or prodrugs thereof, or pharmaceutical compositions thereof; and performing at least one assay using the different compounds of the present invention, or pharmaceutically acceptable salts, solvates, hydrates, polymorphs, co-crystals, tautomers, stereoisomers, isotopically labeled derivatives, or prodrugs thereof, or pharmaceutical compositions thereof, to detect one or more characteristics. In certain embodiments, the methods of screening a library include providing at least two different compounds of the present invention, or pharmaceutically acceptable salts thereof, or pharmaceutical compositions thereof; and performing at least one assay using the different compounds of the present invention, or pharmaceutically acceptable salts thereof, or pharmaceutical compositions thereof, to detect one or more characteristics. In certain embodiments, the characteristic is a characteristic associated with the viral infection, the rival replication, and/or the viral activity. In certain embodiments, the characteristic is a desired characteristic. In certain embodiments, the desired characteristic is usefulness in treating and/or preventing the viral infection in the subject. In certain embodiments, the desired characteristic is usefulness in reducing the viral load in the subject. In certain embodiments, the desired characteristic is usefulness in inhibiting the viral replication. In certain embodiments, the desired characteristic is usefulness in inhibiting the viral production. In certain embodiments, the desired characteristic is usefulness in inhibiting the viral activity. In certain embodiments, the desired characteristic is usefulness in blocking entry of the virus into a host cell. In certain embodiments, the desired characteristic is usefulness in kill the virus. In certain embodiments, the desired characteristic is usefulness in preventing or inhibiting entry of a virus into a host cell. The characteristic to be detected may also be an undesired characteristic associated with the viral infection, the rival replication, and/or viral activity. In certain embodiments, the undesired characteristic is increased viral load in a host cell. In certain embodiments, the undesired characteristic is increased viral replication. In certain embodiments, the undesired characteristic is increased viral production. In certain embodiments, the undesired characteristic is increased viral activity. The present invention also provides methods of screening a library of compounds to identify one or more compounds that prevent or inhibit entry of a virus into a host cell. In certain embodiments, the methods of screening include providing at least two different compounds of the present invention, or pharmaceutically acceptable salts, solvates, hydrates, polymorphs, co-crystals, tautomers, stereoisomers, isotopically labeled derivatives, or prodrugs thereof, and performing at least one assay using the compounds of the present invention, or pharmaceutically acceptable salts, solvates, hydrates, polymorphs, co-crystals, tautomers, stereoisomers, isotopically labeled derivatives, or prodrugs thereof, to detect entry of a virus into a host cell.

The different compounds of the present invention may be provided from natural sources (see, e.g., Sternberg et al., *Proc. Nat. Acad. Sci. USA*, (1995) 92:1609-1613) or generated by synthetic methods such as combinatorial chemistry (see, e.g., Ecker et al., *Bio/Technology*, (1995) 13:351-360 and U.S. Pat. No. 5,571,902). In certain embodiments, the different compounds are provided by liquid-phase or solution synthesis. In certain embodiments, the different compounds are provided by solid-phase synthesis. In certain embodiments, the different compounds are provided by a high-throughput, parallel, or combinatorial synthesis. In certain embodiments, the different compounds are provided by a low-throughput synthesis. In certain embodiments, the different compounds are provided by a one-pot synthesis. The different compounds may be provided robotically or manually. In certain embodiments, the step of providing at least two different compounds of the present invention include arraying into at least two vessels at least two different compounds of the present invention wherein the compounds are bound to solid supports, cleaving the compounds from the solid supports, and dissolving the cleaved compounds in a solvent. The solid supports include, but do not limit to, beads (e.g., resin beads and magnetic beads), hollow fibers, solid fibers, plates, dishes, flasks, meshes, screens, and membranes. In certain embodiments, the solid supports are beads. In certain embodiments, one solid support is capable of supporting at least 50 nmol of a compound. In certain embodiments, one solid support is capable of supporting at least 100 nmol of a compound. In certain embodiments, one solid support is capable of supporting at least 200 nmol of a compound. Each vessel may contain one or more support-bound compounds of the present invention. In certain embodiments, each vessel contains one support-bound compounds of the present invention. The solid supports and/or the compounds may be labeled with one or more labeling agents for the identification or detection of the compounds. The vessels may be wells of a microtiter plate. The solvent may be an inorganic solvent, organic solvent, or a mixture thereof. The steps of arraying, cleaving, and dissolving may be performed robotically or manually.

Typically, the methods of screening a compound library involve at least one assay. In certain embodiments, the assay is performed to detect entry of a virus into a host cell of a subject. In certain embodiments, the assay is performed to determine the extent of the interaction between a compound of the present invention and a host factor of the subject using methods known in the art (see, e.g., Chu et al., *J. Am. Chem. Soc.* (1996) 118:7827-7835). In certain embodiments, the assay is an immunoassay, such as a sandwich-type assay, competitive binding assay, one-step direct test, two-step test, or blot assay. The step of performing at least one assay may be performed robotically or manually. In certain embodiments, an early viral entry step is prevented or inhibited. In certain embodiments, a late viral entry step is prevented or inhibited. The virus whose entry into the host cell may be prevented or inhibited include, but do not limit to, Flaviviridae viruses (e.g., Dengue virus (DENV), including Dengue virus 1 (DENV1), Dengue virus 2 (DENV2), Dengue virus 3 (DENV3), and Dengue virus 4 (DENV4); West Nile virus; tick-borne encephalitis virus; yellow fever virus; hepatitis C virus; hepatitis G virus; bovine viral diarrhea; classical swine fever virus; and hog cholera virus), Kunjin virus, Japanese encephalitis virus, vesicular stomatitis virus (VSV), vesicular stomatitis virus (VSV) pseudotyped with rabies glycoprotein, vesicular stomatitis virus (VSV) pseudotyped with Ebola glycoprotein, herpes simplex virus 1 (HSV-1), human cytomegalovirus (HCMV), poliovirus, Junin virus, Ebola virus, Marburg virus (MARV), Lassa fever virus (LASV), Venezuelan equine encephalitis virus (VEEV), Rift Valley Fever virus (RVFV), hepatitis B virus, cytomegaloviruses, papillomaviruses, coronaviruses, Epstein-Barr virus (EBV), human immunodeficiency virus (HIV), orthomyxoviruses, paramyxoviruses, arenaviruses, bunyaviruses, adenoviruses, poxviruses, retroviruses, rhabdoviruses, picomaviruses, and herpesviruses. In certain embodiments, the virus whose entry into the host cell may be prevented or inhibited is Flaviviridae virus. In certain embodiments, the virus whose entry into the host cell may be prevented or inhibited is Dengue virus (DENV). In certain embodiments, the virus whose entry into the host cell may be prevented or inhibited is Dengue virus 1 (DENV1), Dengue virus 2 (DENV2), Dengue virus 3 (DENV3), or Dengue virus 4 (DENV4).

EXAMPLES

In order that the invention described herein may be more fully understood, the following examples are set forth. The synthetic and biological examples described in this application are offered to illustrate the compounds, pharmaceutical compositions, and inventive compounds provided herein and are not to be construed in any way as limiting their scope.

Example 1. Synthesis of the Compounds

The compounds provided herein can be prepared from readily available starting materials using the following general methods and procedures. Various intermediates useful for preparation of the compounds of the invention can be prepared in accordance with methods described in the art (Upasani et al., *J. Med. Chem.* (1997) 40:73-84; and Hogenkamp et al., *J. Med. Chem.* (1997) 40:61-72) and using the appropriate reagents, starting materials, and purification methods known to those skilled in the art. Representative methods are demonstrated in Schemes 1-4. The compounds of the invention can be prepared using the intermediates described above. For example, a general method for preparing QL-XII-47 is illustrated in Scheme 1.

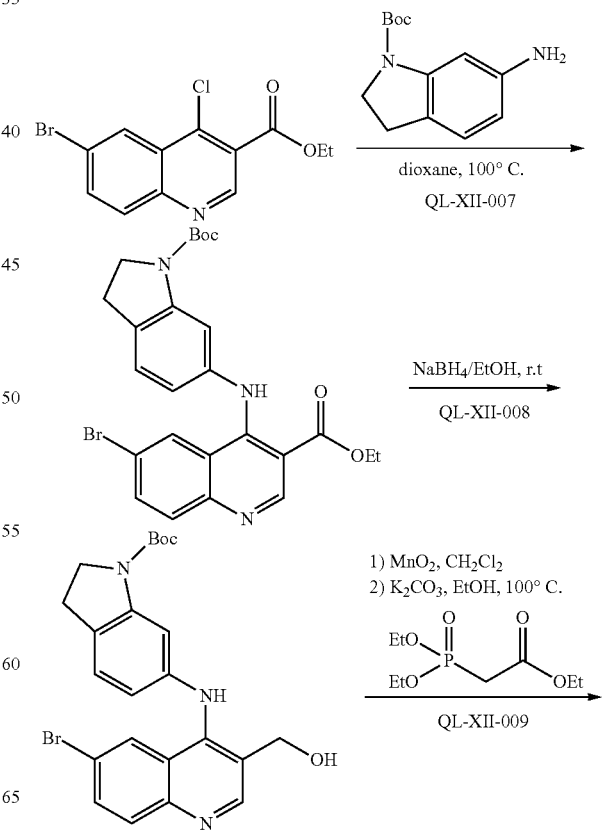

Scheme 1. Exempary synthesis of compound QL-XII-47

151
-continued
152
-continued
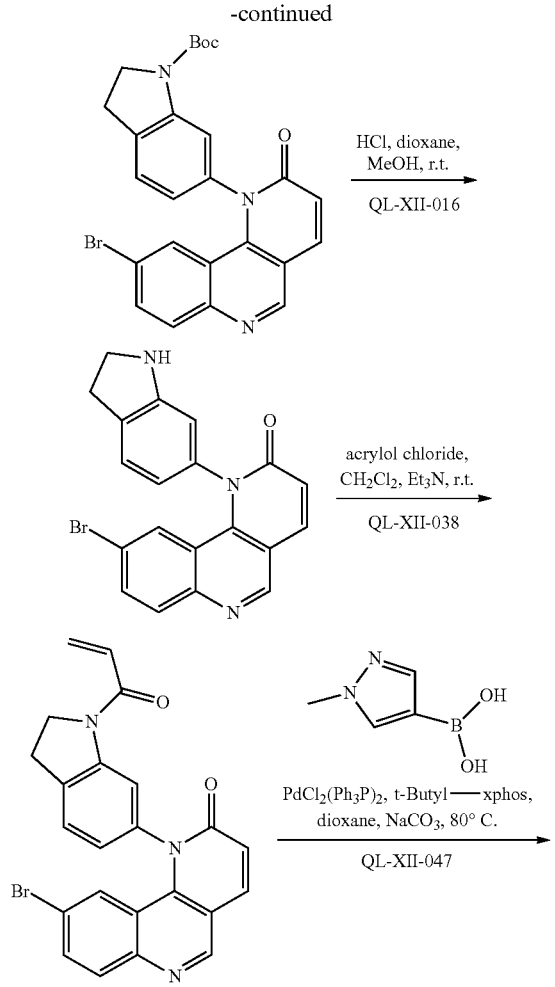
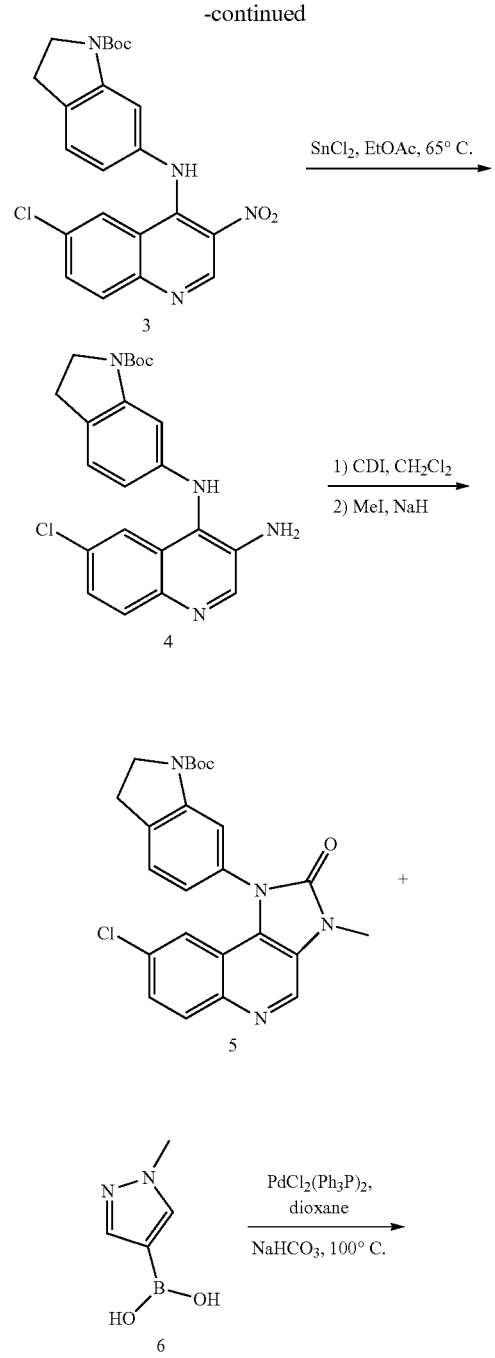
Scheme 2. Exemplary synthesis of compound 8
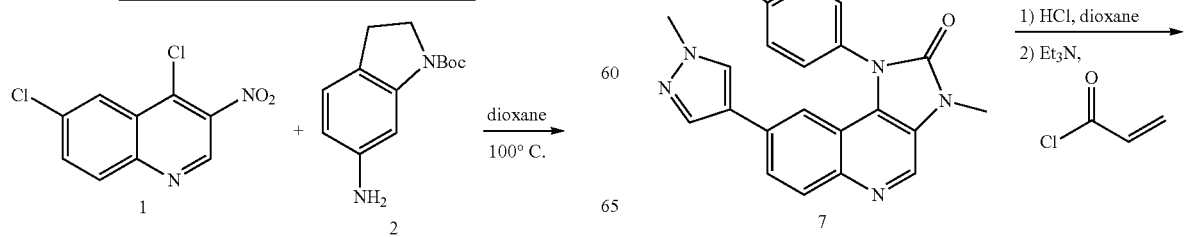

-continued

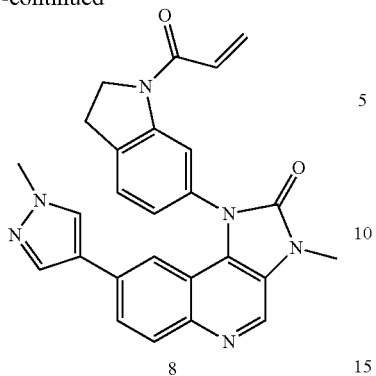

8

Compounds 1 (480 mg, 2 mmol, 1 equiv.) and 2 (470 mg, 2 mmol, 1 equiv.) were combined in 1,4-dioxane (13 mL) and heated at 100° C. for 4 h, cooled to room temperature, poured into brine, and extracted with ethyl acetate (3×). The organic phase was dried over sodium sulfate, filtered, and concentrated. The resulting residue was purified by flash chromatography on $SiO_2$ (methanol:dichloromethane; 1:15 to 1:9) to provide compound 3 (560 mg, 64% yield, LC-MS m/z (M+H)=441.15).

Compound 3 (440 mg, 1 mmol, 1 equiv.) was dissolved in ethyl acetate (7 mL) and treated with $SnCl_2$ (950 mg, 5 mmol, 5 equiv.). The resulting mixture was heated at 65° C. for 4 h and then filtered through Celite©. The filtrate was dried over sodium sulfate, filtered, and concentrated. The resulting residue was purified by flash chromatography on $SiO_2$ (methanol:dichloromethane; 1:10) to afford compound 4 (310 mg, 70% yield, LC-MS m/z (M+H)=411.23).

Compound 4 (300 mg, 0.73 mmol, 1 equiv.) was dissolved in dichloromethane (5 mL) and treated with carbonyl diimidazole (140 mg, 0.88 mmol, 1.2 equiv.) at room temperature. After 4 h, the reaction mixture was quenched with brine and extracted with dichloromethane (3×), and the combined organic layers were dried over sodium sulfate. Following filtration and concentration of the organic solution, the resulting crude residue was dissolved in THF (5 mL) and treated with NaH (53 mg, 2.2 mmol, 3 equiv.) and MeI (55 µL, 0.88 mmol, 1.2 equiv.). After stirring at room temperature for 12 h, the reaction was quenched with $NH_4Cl$ (saturated) and extracted with dichloromethane (3×). The organic solution was then dried over sodium sulfate, filtered, and concentrated. The resulting residue was purified by flash chromatography on $SiO_2$ (methanol:dichloromethane; 1:10) to afford compound 5 (147 mg, 45% yield, LC-MS m/z (M+H)=451.93).

Compounds 5 (135 mg, 0.3 mmol, 1 equiv.) and 6 (57 mg, 0.45 mmol, 1.5 equiv.) were dissolved in 1,4-dioxane (2 mL) and treated with $NaHCO_3$ (1.3 mL, 1 N, 3 equiv.) and $PdCl_2(Ph_3P)_2$ (21 mg, 0.03 mmol, 0.1 equiv.). The resulting solution was heated at 100° C. for 3 h, cooled to room temperature, and extracted with dichloromethane (3×). The organic solution was then dried over sodium sulfate, filtered, and concentrated. The resulting residue was purified by flash chromatography on $SiO_2$ (methanol:dichloromethane; 1:10) to afford compound 7 (67 mg, 45% yield. LC-MS m/z (M+H)=497.24).

Compound 7 (50 mg, 0.1 mmol, 1 equiv.) was dissolved in 1,4-dioxane (3 mL), treated with HCl in 1,4-dioxane (0.2 mL of a 4 N solution, 8 equiv.), stirred at room temperature for 1 h, and then treated with triethylamine (140 µL, 1 mmol, 10 equiv.) and acryloyl chloride (8 µL, 0.105 mmol, 1.05 equiv.). The resulting solution was stirred for 30 min, quenched with sodium bicarbonate (saturated), and extracted with dichloromethane (3×). The organic solution was then dried over sodium sulfate, filtered, and concentrated. The residue was purified by flash chromatography on $SiO_2$ (methanol:dichloromethane; 1:30 to 1:10) to provide compound 8 (13 mg, 30% yield, LC-MS m/z (M+H)=451.23).

Scheme 3. Exemplary synthesis of QL-XI-76 (compound 16).

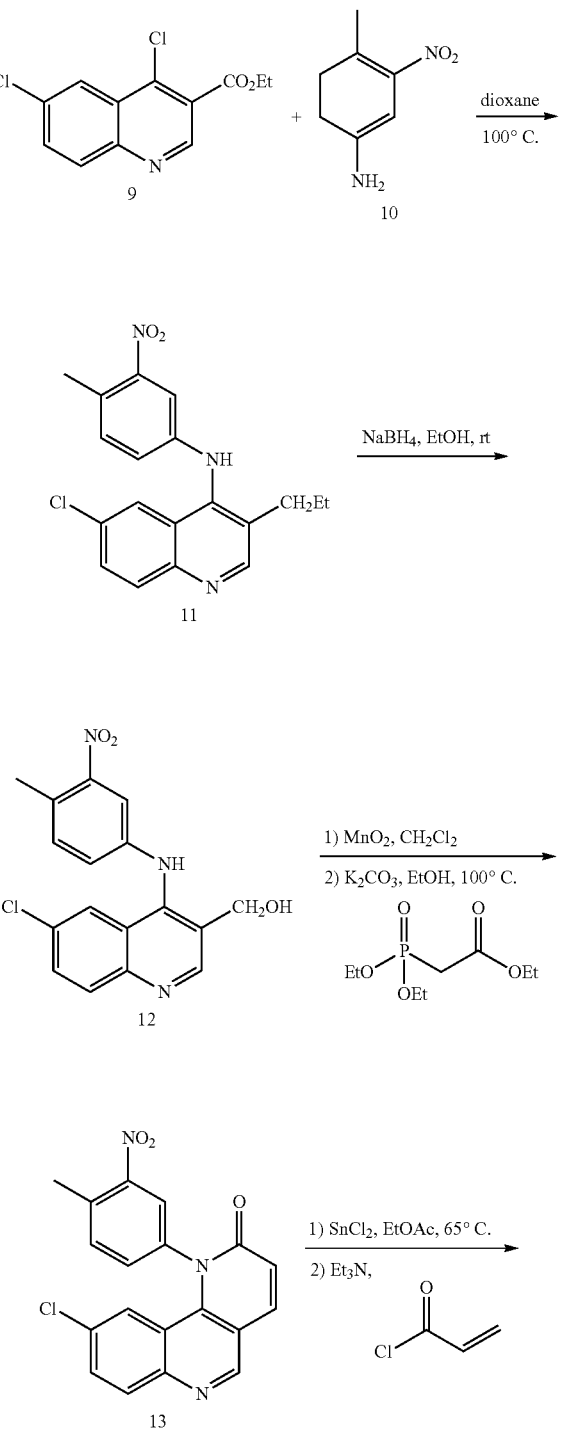

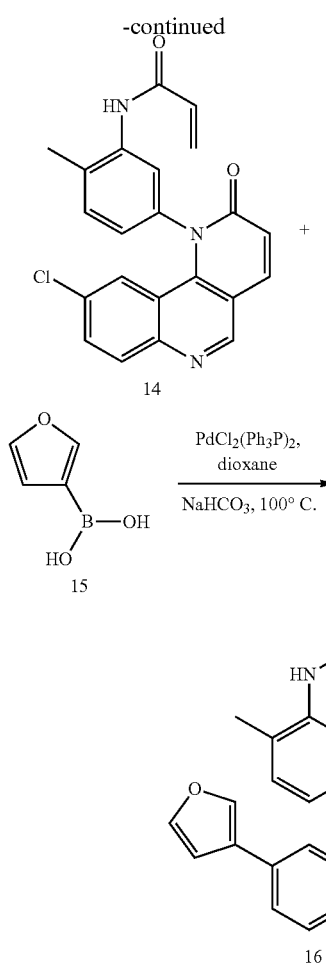

mixture was cooled to room temperature and filtered through Celite©, and the filtrate was extracted with ethyl acetate (3×). The organic phase was washed with water and brine, dried over sodium sulfate, filtered, and concentrated. The resulting residue was purified by flash chromatography on SiO$_2$ (methanol:dichloromethane; 1:20) to provide compound 13 (280 mg, 43% yield, LC-MS m/z (M+H)=366.13).

Compound 13 (250 mg, 0.68 mmol, 1 equiv.) was dissolved in ethyl acetate (10 mL) at room temperature, treated with SnCl$_2$.2H$_2$O (765 mg, 3.4 mmol, 5 equiv.) and heated at 65° C. for 4 h. The reaction mixture was cooled and filtered through Celite©. The filtrate was washed with NaHCO$_3$ and brine, dried over sodium sulfate, filtered, and concentrated. The resulting crude residue was dissolved in dichloromethane (10 mL) and treated with Et$_3$N (190 μL, 1.36 mmol, 2 equiv.) and acryloyl chloride (27 μL, 0.34 mmol, 0.5 equiv.). The reaction mixture was stirred at room temperature for 30 min, quenched with NaHCO$_3$ (saturated) and extracted with dichloromethane (3×). The organic phase was washed with water and brine, dried over sodium sulfate, filtered, and concentrated. The resulting residue was purified by flash chromatography on SiO$_2$ (methanol:dichloromethane; 1:30 to 1:10) to afford compound 14 (78 mg, 30% yield, LC-MS m/z (M+H)=390.11).

Compound 14 (78 mg, 0.2 mmol, 1 equiv.) was dissolved in 1,4-dioxane (5 mL) and treated with compound 15 (26 mg, 0.24 mmol, 1.2 equiv.), NaHCO$_3$ (0.6 mL, 1 N in water, 3 equiv.) and PdCl$_2$(Ph$_3$P)$_2$ (14 mg, 0.02 mmol, 0.1 equiv.). The reaction mixture was heated at 100° C. for 3 h, cooled to room temperature, filtered through Celite©, and the filtrate was extracted with ethyl acetate (3×). The organic phase was then washed with water and brine, dried over sodium sulfate, filtered, and concentrated. The resulting residue was purified by flash chromatography on SiO$_2$ (methanol:dichloromethane; 1:30 to 1:10) to afford compound 16 (40 mg, 48% yield, LC-MS m/z (M+H)=422.20).

Compounds 9 (1.35 g, 5 mmol, 1 equiv.) and 10 (760 mg, 5 mmol, 1 equiv.) were dissolved in 1,4-dioxane (10 mL) and heated at 100° C. for 4 h. The reaction mixture was then cooled to room temperature, washed with sodium bicarbonate (saturated) and extracted with ethyl acetate (3×). The organic solution was dried over sodium sulfate, filtered, and concentrated. The resulting residue was purified by flash chromatography on SiO$_2$ (methanol:dichloromethane; 1:10) to afford compound 11 (1.46 g, 76% yield, LC-MS m/z (M+H)=386.13).

Compound 11 (1.4 g, 3.6 mmol, 1 equiv.) was dissolved in ethanol (20 mL) at room temperature and treated with NaBH$_4$ (680 mg, 18 mmol, 5 equiv.) in 5 portions. The resulting solution was stirred for 4 h and filtered through celite. The filtrate was then washed with NaHCO$_3$ (saturated) and extracted with ethyl acetate (3×). The organic solution was dried over sodium sulfate, filtered, and concentrated. The resulting residue was purified by flash chromatography on SiO$_2$ (methanol:dichloromethane; 1:10) to afford compound 12 (620 mg, 50% yield, LC-MS m/z (M+H)=344.14).

Compound 12 (620 mg, 1.8 mmol, 1 equiv.) was dissolved in dichloromethane (20 mL) and treated with MnO$_2$ (3.1 g, 5 equiv. weights). After 4 hours, the reaction mixture was filtered through Celite©, and the filtrate was concentrated. The residue was then dissolved in EtOH (20 mL) in a sealed tube, treated with K$_2$CO$_3$ (745 mg, 5.4 mmol, 3 equiv.) followed by triethylphophonoacetate (1 mL, 5.4 mmol, 3 equiv.), and heated to 100° C. for 12 h. The reaction Scheme 4. Exemplary synthesis of compound 19.

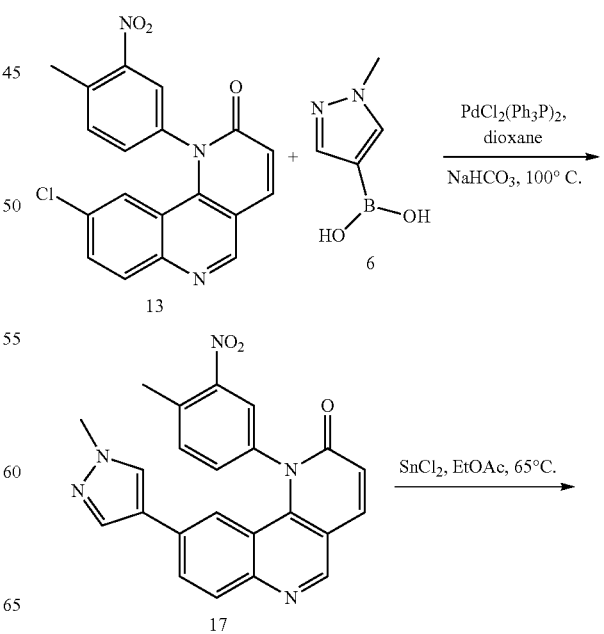

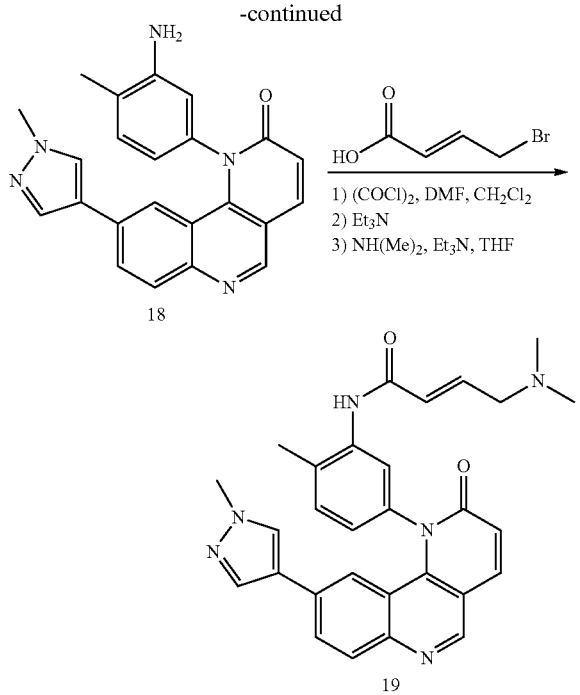

Compound 13 (360 mg, 1 mmol, 1 equiv.) was dissolved in 1,4-dioxane (5 mL) at room temperature and treated with compound 6 (190 mg, 1.5 mmol, 1.5 equiv.), PdCl$_2$(Ph$_3$P)$_2$ (70 mg, 0.1 mmol, 0.1 equiv.) and NaHCO$_3$ (3 mL, 1 N in water, 3 equiv.). The reaction mixture was heated at 100° C. for 3 h, cooled to room temperature, filtered through celite, and the filtrate was extracted with ethyl acetate (3×). The organic phase was then washed with water and brine, dried over sodium sulfate, filtered and concentrated. The resulting residue was purified by flash chromatography on SiO$_2$ (methanol:dichloromethane; 1:30 to 1:10) to afford compound 17 (210 mg, 52% yield, LC-MS m/z (M+H)=412.14).

Compound 17 (200 mg, 0.48 mmol, 1 equiv.) was dissolved in ethyl acetate (10 mL) at room temperature, treated with SnCl$_2$.2H$_2$O (540 mg, 2.4 mmol, 5 equiv.) and heated at 65° C. for 4 h. Following, the reaction mixture was cooled and filtered through celite. The resulting filtrate was washed with NaHCO$_3$ and brine, dried over sodium sulfate, filtered, and concentrated. The residue was then purified by flash chromatography on SiO$_2$ (methanol:dichloromethane; 1:30 to 1:10) to afford compound 18 (95 mg, 52% yield, LC-MS m/z (M+H)=382.24).

4-Bromo-but-2-enoic acid (21 mg, 0.13 mmol, 1.3 equiv.) was dissolved in dichloromethane (1 mL) and treated with (COCl)$_2$ (22 µL, 0.26 mmol, 2 equiv.) and DMF (1 drop, 0.1 equiv.). After 1 h at room temperature, the solvents were evaporated. The crude residue was then dissolved in dichloromethane (1 mL) and treated with Et$_3$N (36 µL, 0.26 mmol, 2 equiv.), and compound 18 (38 mg, 0.1 mmol, 1 equiv.). After 2 h, the solvent was removed and the crude residue was dissolved in THF (1 mL) and treated with dimethylamine (0.13 mL in THF of 2 M solution, 0.26 mmol, 2 equiv.). The reaction mixture was stirred for 2 h, quenched with NaHCO$_3$ (saturated), and extracted with dichloromethane (3×). The organic phase was washed with water and brine, dried over sodium sulfate, filtered, and concentrated. The resulting residue was purified by flash chromatography on SiO$_2$ (methanol:dichloromethane; 1:30 to 1:10) to afford compound 19 (12 mg, 25% yield, LC-MS m/z (M+H)=493.34).

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by those skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in Greene et al., *Protecting Groups in Organic Synthesis*, 2$^{nd}$ Ed.; Wiley: New York, 1991, and references cited therein.

The compounds provided herein may be isolated and purified by known standard procedures. Such procedures include, but are not limited to, trituration, recrystallization, column chromatography, or HPLC.

Example 2. X-Ray Crystal Structure of QL-X-138

Figure 7:
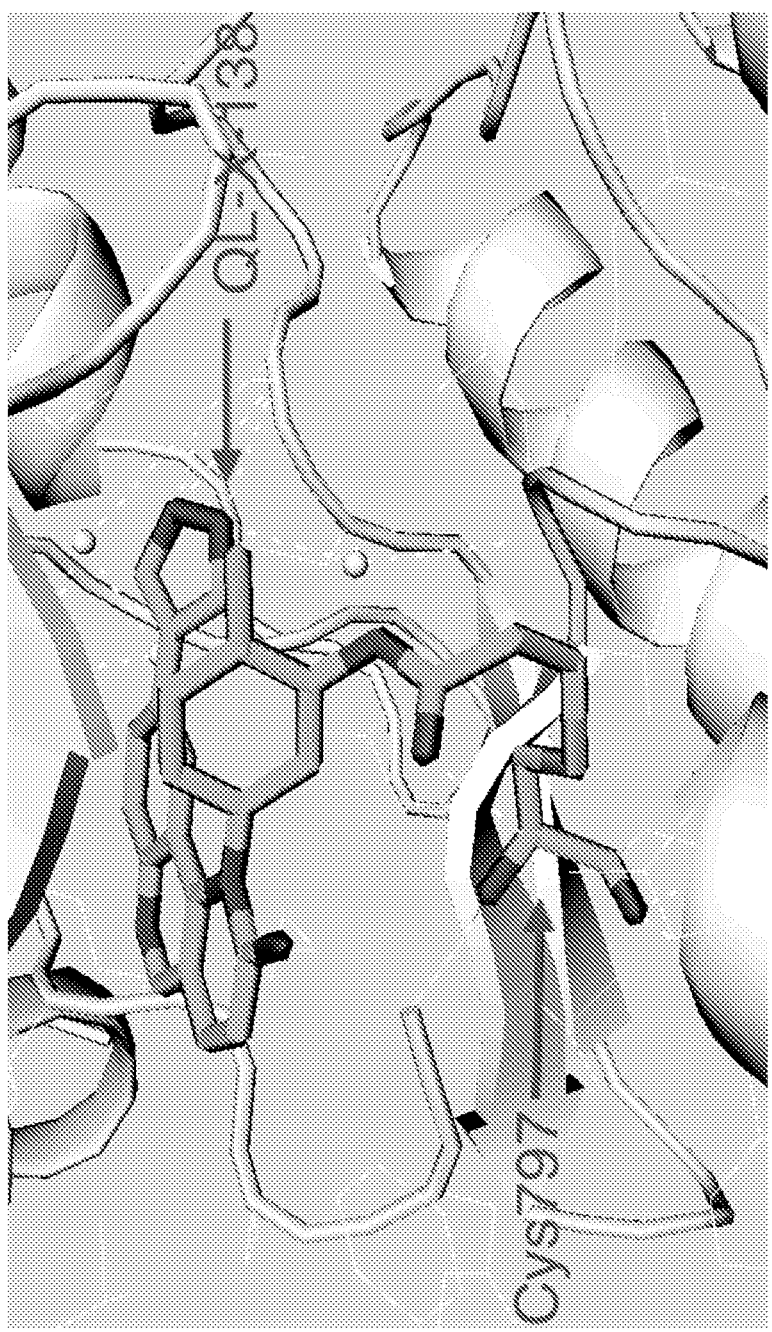
FIG. 7 depicts a crystal structure of QL-X-138 with T790M EGFR. A covalent bond formed between QL-X-138 and Cys797 is indicated.

QL-X-138 (see FIG. 7 for the chemical structure), a structural analog of QL-XII-47, has been successfully crystallized with EGFR kinase that contains a cysteine in the same position as the Tec-family kinases (FIG. 7). The structure shows the expected hydrogen bond between the quinoline nitrogen and the "hinge" region amino acid Met793. The pyrazole group is directed towards a hydrophobic pocket at the back of the ATP-pocket which the para-methyl aniline group is nestled beneath the P loop and a covalent bond with Cys797 is apparent.

Example 3. Cell-Based Mini-Screen of Acrylamide-Containing Compounds for the Identification of Novel Covalent Inhibitors of DENV Methods Small molecule screens (Chu et al., *Proc. Nat. Acad. Sci. USA* (2007) 104:3520-3525) and RNAi (Sessions et al., *Nature* (2009) 458:1047-1050) have been utilized to identify host factors that are required for Dengue virus (DENV) replication, with a particular interest in host kinases that modulate DENV replication. As an extension of this work, a cell-based mini-screen of a 30-compound subset of acrylamide-containing compounds was performed to identify novel covalent inhibitors of DENV. The compounds were designed to react covalently upon binding in the proper orientation near a reactive cysteine.

Huh7 cells were seeded in 24-well plates and infected at an MOI (multiplicity of infection) of 1 with 100 µl of DENV2 New Guinea C (DENV2-NGC). Plates were incubated for 1 hour at 37° C. and rocked every 15 min. Unadsorbed virus was removed by a PBS wash, after which 500 µl of Dulbecco's modified Eagle's medium (DMEM) supplemented with 2% FBS and the indicated concentrations of small molecule was added to each well. After incubation at 37° C. for 24 hours, the supernatants were collected for DENV2 titration using a focus forming assay, described as follows. BHK-21 cells were seeded in 24-well plates. Aliquots from infections were thawed at 37° C. in a water bath. Ten-fold dilutions in EBSS were prepared in duplicate, and 100 µl of each dilution were added to the cells. Plates were incubated for 1 hour at 37° C. and rocked every 15 min. Unadsorbed virus was removed by washes with PBS, after which 1 ml of MEM-α supplemented with carboxymethyl-cellulose (CMC), HEPES, and 2% FBS, was added to each well and incubated at 37° C. for 3 days. The CMC overlay was aspirated, and cells were washed with PBS and fixed with methanol for 15 min at −20° C. After fixation, the cells were washed with PBS and incubated for 1 hour at room temperature with anti-DENV2 C antibody (provided by John Aaskov), followed by incubation with HRP-conjugated anti-mouse IgG antibody. The plates were revealed with Vector VIP Peroxidase Substrate kit (Vector Laboratories SK-4600) following manufacturer's instructions. The results are shown in FIGS. 2B, 2C, and 2G.

Huh7 cells were seeded in 96-well plates and infected at an MOI of 1 with 100 µl of DENV2 supplemented with the indicated concentrations of small molecule. As a positive control for cytotoxicity, some wells were supplemented with 0.1% saponin. The plates were incubated for 24 hours at 37° C., and the cell cytotoxicity was measured following the instructions of the CellTiter-Glo Luminescent cell viability assay (Promega G7570). The results are shown in FIG. 2D.

Huh7 cells were infected at an MOI of 1 with DENV1-WP74, DENV2-NGC, DENV3-THD3, or DENV4-TVP360 as described in FIG. 2B. The supernatants collected at 24 hours post-infection were analyzed by focus forming assay in Vero cells. The experimental set up for focus forming assay in Vero cells was similar to what was described in FIG. 2B for BHK21 cells, except that the cells were incubated in DMEM for 4 days at 37° C. and revealed using anti-DENV E antibody (4G2). The results are shown in FIG. 2E.

Huh7 cells were infected at an MOI of 1 with Kunjin virus as described in FIG. 2B. The supernatants collected at 24 hours post-infection were analyzed by plaque assay in BHK21 cells. The experimental set up for plaque assay was similar to what was described in FIG. 2B for focus forming assay, except that after 3 days incubation at 37° C., the cells were stained with crystal violet to reveal the plaques. The results are shown in FIG. 2F.

Results

This screen allowed the identification of QL-XII-47, a tricyclic quinoline derivative, that causes >3-log$_{10}$ unit decrease in DENV2 New Guinea C (DENV2-NGC) yield at single-digit micromolar concentrations (EC$_{90}$ 400 nM) (FIGS. 2A and 2B). It was confirmed that QL-XII-47 is mostly likely functioning as a covalent inhibitor by demonstrating that QL-XII-47R, in which the reactive acrylamide has been replaced with an unreactive propyl amide, results in a complete loss of activity (FIGS. 2A and 2C). No cytotoxicity was observed for QL-XII-47 at 20 µM, the highest concentration tested (FIG. 2D). QL-XII-47 also inhibits additional DENV strains representative of the four DENV serotypes (DENV1 to DENV4) and Kunjin virus, another flavivirus, in yield reduction assays (FIGS. 2E and 2F). In addition, QL-XI-76 was identified, in which the pyrazole of QL-XII-47 is replaced with a furan, as a negative control compound that is devoid of anti-DENV activity at concentrations up to 10 µM (FIGS. 2A and 2G). QL-XI-76 demonstrates that non-covalent interactions are also key to QL-XII-47's activity and that the presence of an electrophilic acrylamide moiety is not sufficient to confer anti-DENV activity.

Example 4. Time-of-Addition Experiments for the Investigation of the Stage(s) of the Viral Life Cycle Affected by QL-XII-47

Methods

In order to investigate the stage(s) of the viral life cycle affected by QL-XII-47, time-of-addition experiments were performed.

The results shown in FIGS. 3A and 3B were obtained by using experiments performed essentially as described in Example 3. The small molecule was diluted in media and added to the cells at the indicated times pre- or post-DENV2 infection.

The plasmids used for recombinant viral particles (RVP) production were provided by Ted Pierson (Ansarah-Sobrinho et al., *Virology* (2008) 381:67-74). To produce RVPs, HEK293T cells were co-transfected with pCDNA6.2-D2.CprME (Ansarah-Sobrinho et al., *Virology* (2008) 381: 67-74) and pWIIrep-REN-IB (Pierson et al., *Virology* (2006) 346:53-65) using Lipofectamine 2000 (Life Technologies 11668-019) according to the manufacturer's instructions. The supernatants were collected at 2 days post-transfection and filtered through a 0.45 µm filter to remove contaminant cells in the supernatants. Huh7 cells seeded in 48-well plates were infected with 100 µl of RVPs. The plates were incubated for 1 hour at 37° C. and rocked every 15 min. Unadsorbed RVPs were removed by a PBS wash, after which 300 µl of DMEM supplemented with 2% FBS and the indicated concentrations of small molecule was added to each well. After incubation at 37° C. for 24 hours, the cells were collected and the samples were processed following the instructions in the *Renilla* luciferase assay system (Promega E2810). The *Renilla* luciferase signal was read using Perkin Elmer EnVision plate reader. The results are shown in FIG. 3C.

The plasmid containing a DENV2 replicon that expresses a reporter firefly luciferase in place of DENV2 structural proteins was provided by Eva Harris (Holden et al., *Virology* (2006) 344:439-452). In vitro transcripts were synthesized from PstI linearized pDENrep-FH using T7-Scribe Standard RNA IVT kit (CellScript C-AS3107) and m7G(5')ppp(5')A RNA cap structure analog (New England Biolabs S1405L) following the manufacturers instructions. Huh7 cells were washed twice in PBS and 1.10$^6$ cells were electroporated with DENV2 replicon in vitro transcripts using ECM 830 electroporator (BTX Harvard Apparatus) at the following settings: 5 pulses at 820 V, 100 µs per pulse with 1.1 s intervals. After electroporation, the cells were seeded in 24-well plates and at 24 hours post-electroporation, and the media was changed and supplemented with DMSO or 2 µM of the indicated small molecules. At 72 hours post-electroporation, the cells were collected, and the samples were processed following the instructions in the luciferase assay system (Promega E1483). The firefly luciferase signal was read using Perkin Elmer EnVision plate reader. The results are shown in FIG. 3D.

The plasmid used for virus-like particles (VLP) production was provided by Stephen Harrison. Briefly, the codon optimized sequence of DENV2-FGA/02 prM-E (Wang et al., *PLoS ONE* (2009) 4:e8325) was introduced in the pCDNA3.1 vector. To produce VLPs, Huh7 cells were transfected with pCDNA3.1-D2.VLP using Lipofectamine 2000 (Life Technologies 11668-019) according to the manufacturer's instructions. At 4 hours post transfection, the cells were treated with DMSO, 3 µM of QL-XII-47, or 10 µM of Ki20227 or GNF2. The supernatants were collected at 24 hours post-treatment and precipitated for 3 hours at 4° C. by the addition of 0.075% of PEG 8000. The VLPs were pelleted by centrifugation at 10,000 g for 15 min at 4° C. The pellet was suspended in 200 µl of 1×TNE (10 mM Tris-HCl pH 7.5, 2.5 mM EDTA, 50 mM NaCl), loaded over a sucrose cushion (800 µl of 12.5% sucrose in 1×TNE), and centrifuged at 100,000 g for 2 h at 4° C. The supernatants were discarded, and the purified VLPs were suspended in 50 µl of 1×TNE. 25 µl of purified VLPs were analyzed for DENV2 E protein expression by Western blotting using 4G2 antibody. An equal amount of purified VLPs was loaded on a SDS-PAGE and submitted to Coomassie staining to control for equal loading of the VLPs-enriched supernatants. Steady state expression of DENV2 E protein in the cell lysates was analyzed by Western blotting using 4G2 antibody. The results are shown in FIG. 3E.

Results

It was discovered that potent inhibition of DENV is still observed when cells are pretreated with QL-XII-47 for 6 hours and then washed prior to infection with DENV (FIG. 3A). This strongly suggests that QL-XII-47 acts via a host target and interferes with a step early in the DENV life cycle. The time-of-addition experiments show that the maximal anti-DENV effect was observed when QL-XII-47 is present at 0-3 hours post-infection (FIG. 3B); QL-XII-47's inhibitory activity is lost over time when QL-XII-47 is added at later times post-infection. Consistent with the idea that QL-XII-47 inhibits steps early in the DENV life cycle (e.g., entry), it was found that QL-XII-47 has potent inhibitory activity in a single cycle reporter Dengue virus assay (RVP) (Ansarah-Sobrinho et al., *Virology* (2008) 381:67-74) that expresses a luciferase reporter upon successful entry and translation of a subgenomic replicon RNA (FIG. 3C) but does not have activity in an assay in which a subgenomic reporter replicon RNA is electroporated into cells to bypass viral entry (FIG. 3D). Likewise, QL-XII-47 did not inhibit the yield of virus-like particles (VLPs) produced when a plasmid encoding the prM-E proteins was transfected into cells (FIG. 3E), suggesting that QL-XII-47 does not inhibit viral particle assembly or egress.

Example 5. Time-Course Experiments for the Determination of QL-XII-47's Effect on the Different Stages of DENV Entry Methods To better understand QL-XII-47's effect on DENV entry, a time course experiment was performed, and qRT-PCR and fluorescence in situ hybridization were used to monitor the fate of the genomic RNA of the DENV inoculum in the presence and absence of QL-XII-47 (FIG. 4).

Huh7 cells were seeded in 6-well plates and infected at an MOI of 1 with 300 µl of DENV2-NGC. As a positive control for inhibition of viral fusion, DENV2-NGC was pre-incubated at 37° C. for 15 min with 5 µM of DENV2 stem-peptide DENV2$^{419\text{-}447}$, which was provided by Aaron Schmidt and Stephen Harrison (Schmidt et al., *PLoS Pathogens* (2010) 6:e1000851). The plates were incubated with the virus for 1 hour at 37° C. and rocked every 15 min. Unadsorbed virus was removed by a PBS wash, after which 2 ml of media supplemented with DMSO or 2 µM of QL-XII-47 was added to each well. After incubation at 37° C. for the indicated time, total RNA was extracted from infected cells using TRIzol reagent following manufacturer's instructions (Life Technologies 15596-018). cDNA was generated on 500 ng of total RNA using random hexamers to prime reverse transcription reactions using iScript cDNA Synthesis kit (Bio-Rad 178-8890) following manufacturer's instructions. cDNAs were then diluted 1:10 with nuclease-free water, and qPCR was performed with the cDNA using the iQ SYBR Green Supermix kit (Bio-Rad 170-8880) according to the manufacturer's instructions. Reactions were run on a MyiQ iCycler (Bio-Rad) and analyzed with the MyiQ Optical System Software (Bio-Rad, Hercules, Calif.). qPCR conditions were an initial 95° C. for 5 min, followed by 40 cycles of 95° C. for 15 s and 60° C. for 30 s. Primers used were: DENV2 FW: 5'-AATATGCTGAAACGCGA-GAGA-3'(SEQ ID NO: 1); DENV2 RV: 5'-GGGATTGT-TAGGAAACGAAGG-3' (SEQ ID NO: 2); GAPDH FW: 5'-GAGTCAACGGATTTGGTCGT-3' (SEQ ID NO: 3); GAPDH RV: 5'-TTGATTTTGGAGGGATCTCG-3' (SEQ ID NO: 4). For each sample the DENV2 RNA copy number was normalized to the GAPDH RNA copy number. The results are shown in FIG. 4A.

Huh7 cells were seeded in 24-well plates on cover slips and infected at an MOI of 10 with 100 µl of DENV2-NGC. Plates were incubated with the virus for 1 hour at 37° C. and rocked every 15 min. Unadsorbed virus was removed by a PBS wash, and mock- or DENV2-infected cover slips were collected to serve as a reference before addition of the small molecule. 1 ml of media supplemented with DMSO or 2 µM of QL-XII-47 was added to the remaining wells, and the cells were incubated at 37° C. The remaining cover slips were collected at 3 h, 6 h, 9 h, 12 h, 15 h, and 18 h post small molecule treatment. For each collection the cover slips were fixed using 4% of paraformaldehyde. After incubation for 15 min at room temperature, the cover slips were washed with PBS and kept at 4° C. until processing. Detection of DENV2 viral RNA in the cells was done using QuantiGene ViewRNA ISH Cell Assay kit (Panomics QVC0001) following manufacturer's instructions using a DENV2 specific probe set (Panomics VF1-10744). The cover slips were mounted with ProLong Gold antifade reagent (Life Technologies P36930) prior to wide field imaging (nearest neighbors analysis) using a Marianas Spinning Disk confocal microscope. The results are shown in FIG. 4B.

Results

DENV genomic RNA persists at a relatively unchanged copy number in the presence of QL-XII-47 and exhibits a punctate, cytoplasmic localization. In untreated cells, this signal decays and disappears by 12 hours followed by abundant perinuclear genomic RNA at 18-24 hours due to synthesis of new viral RNA genomes. In cells treated with a DENV-derived peptide that has been previously demonstrated to block viral fusion (Schmidt et al., *PLoS Pathogens* (2010) 6:e1000851), DENV RNA is decreasing by 24 hours post-infection, presumably due to degradation of the virion in the lysosome (FIG. 4A). These data suggest that DENV entry is blocked at a "late entry step" that occurs after uptake of the virion but prior to release of the genome from the nucleocapsid since the DENV appears to be protected from cytoplasmic nucleases.

Example 6. Antiviral Activities of QL-XII-47 Against Additional Viruses

To examine QL-XII-47 and QL-XII-56's spectrum of activity as antiviral agents, QL-XII-47 and QL-XII-56 were tested against a panel of additional viral pathogens using methods similar to what are described in other Examples herein.

Figure 5E:
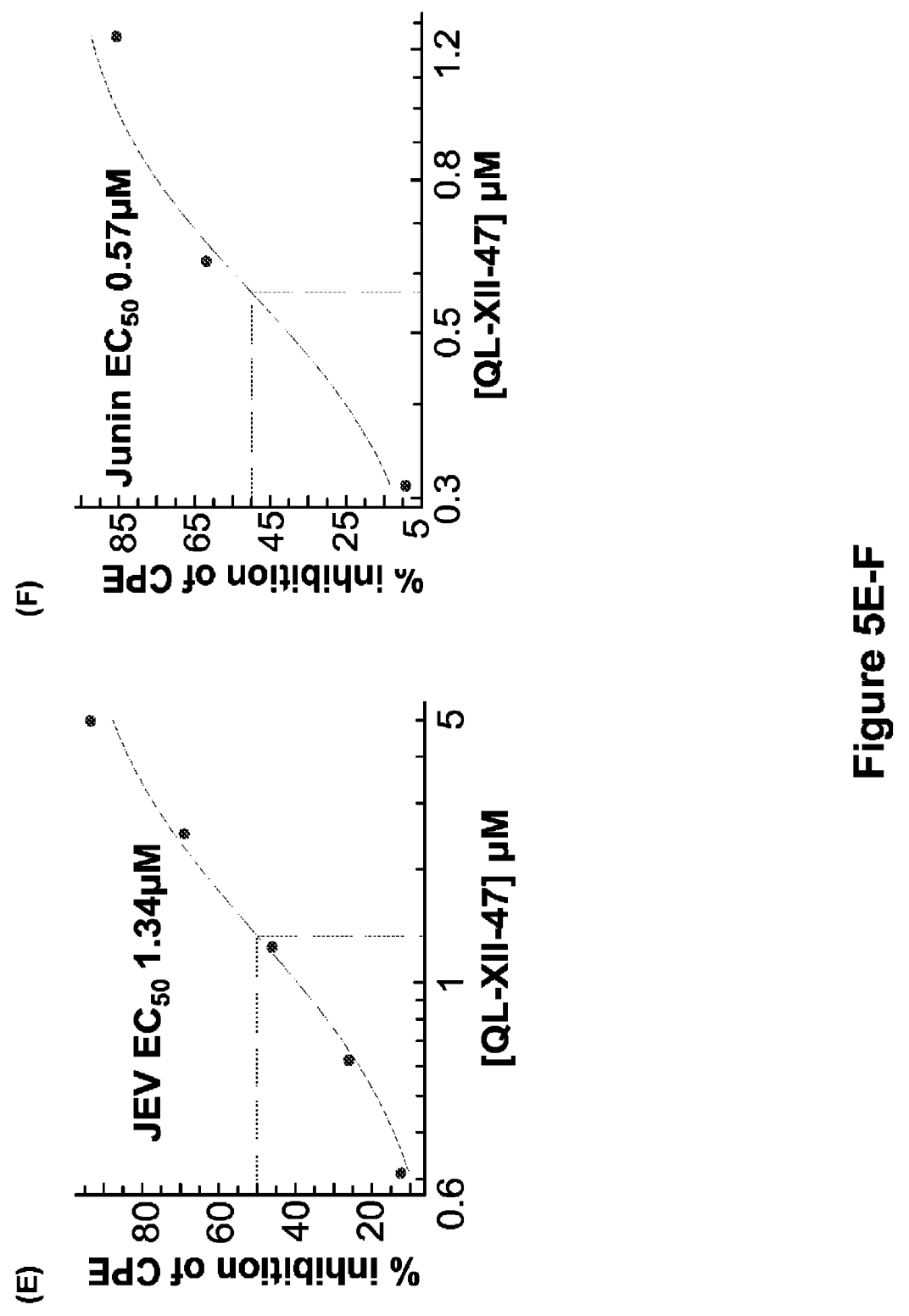
Figure 5G1:
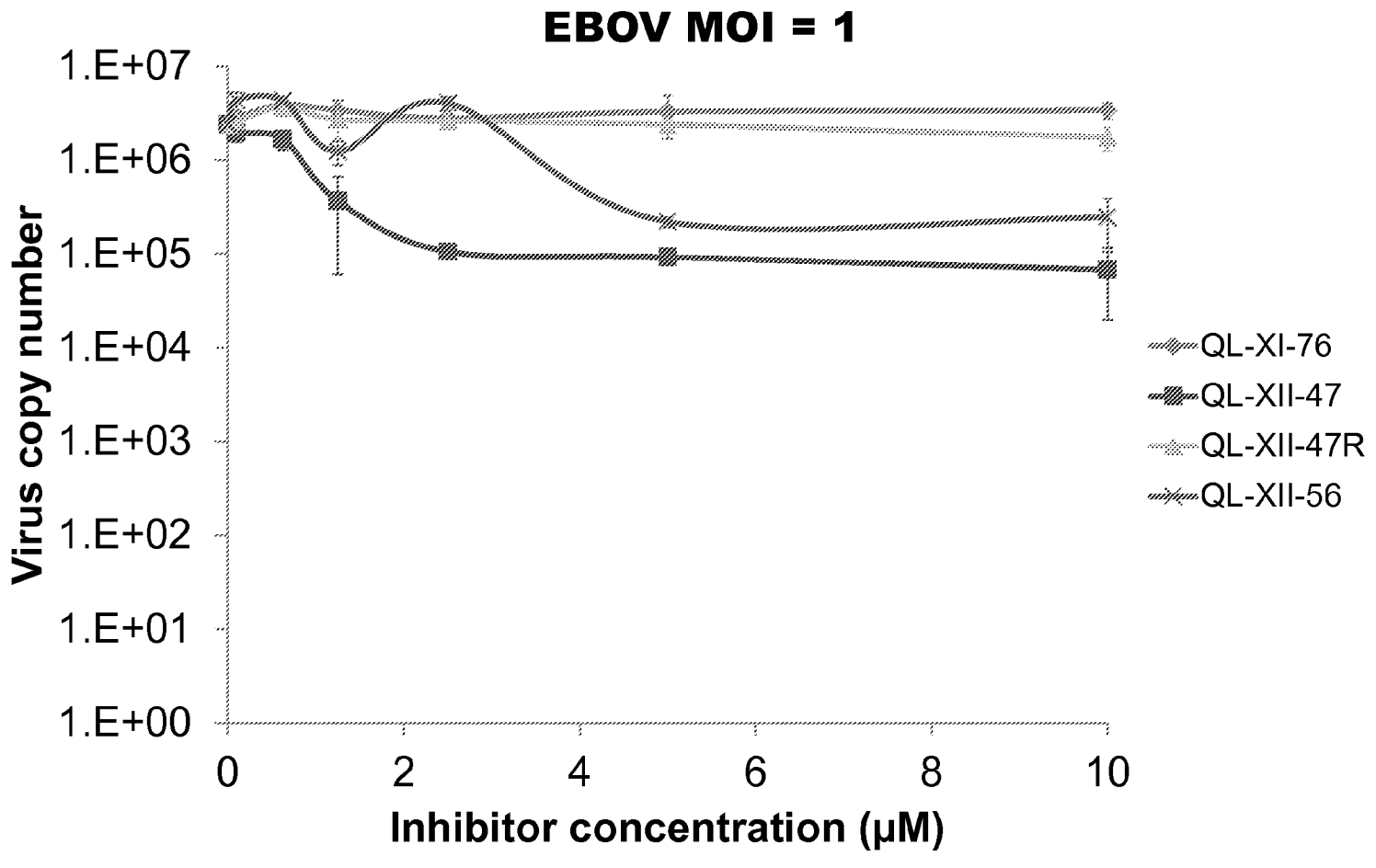
Figure 5J1:
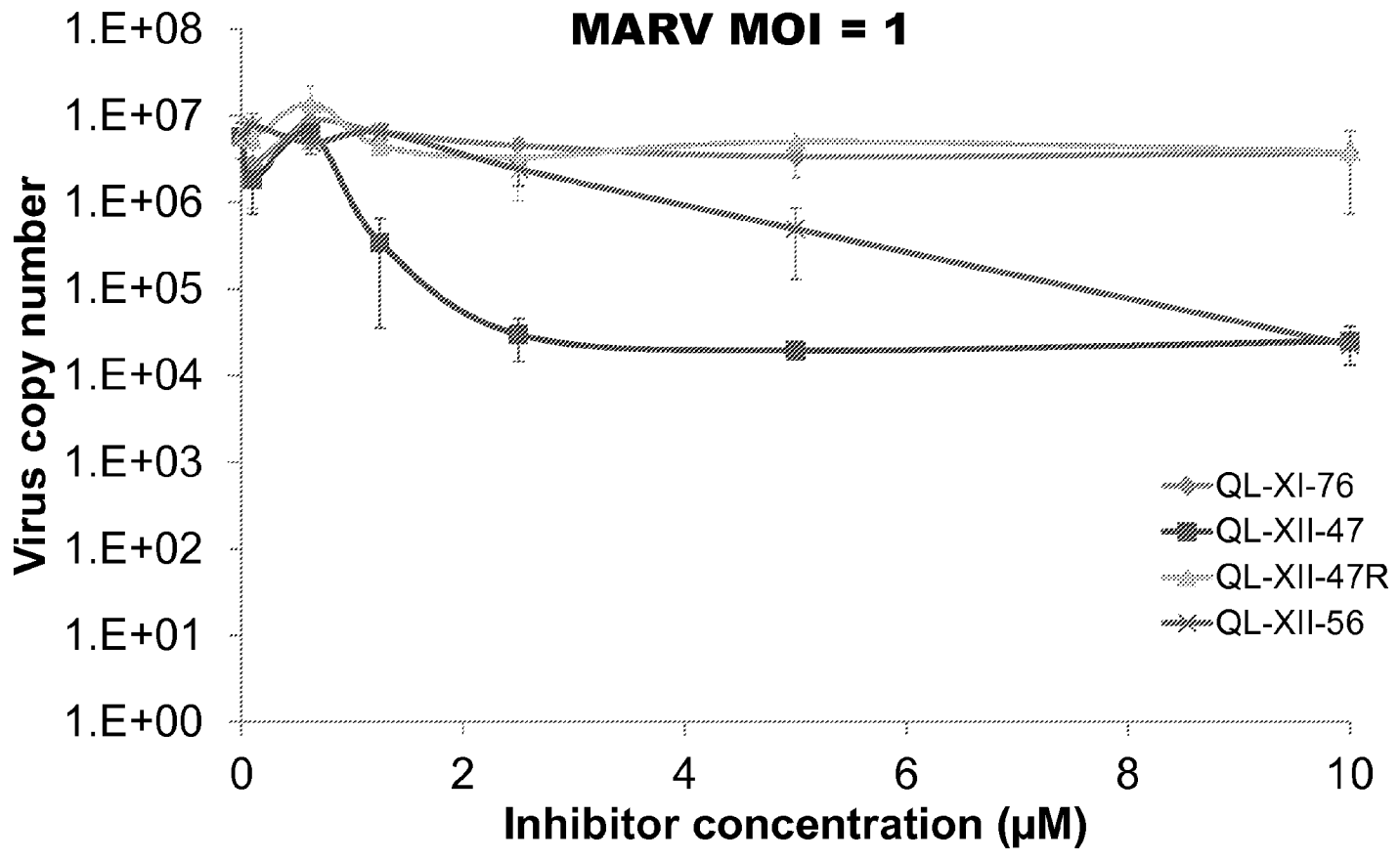
Figure 5J2:
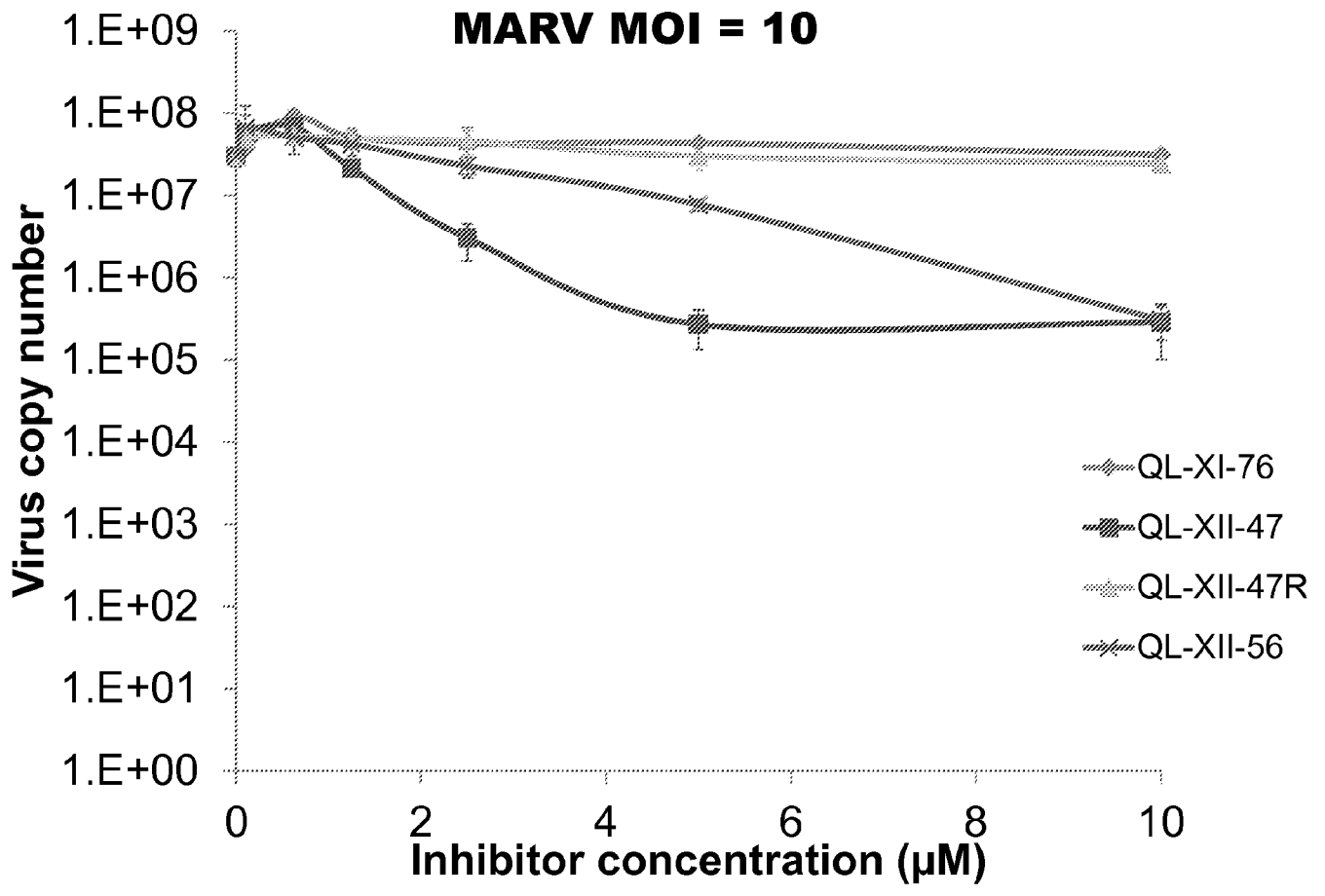
Figure 5T:
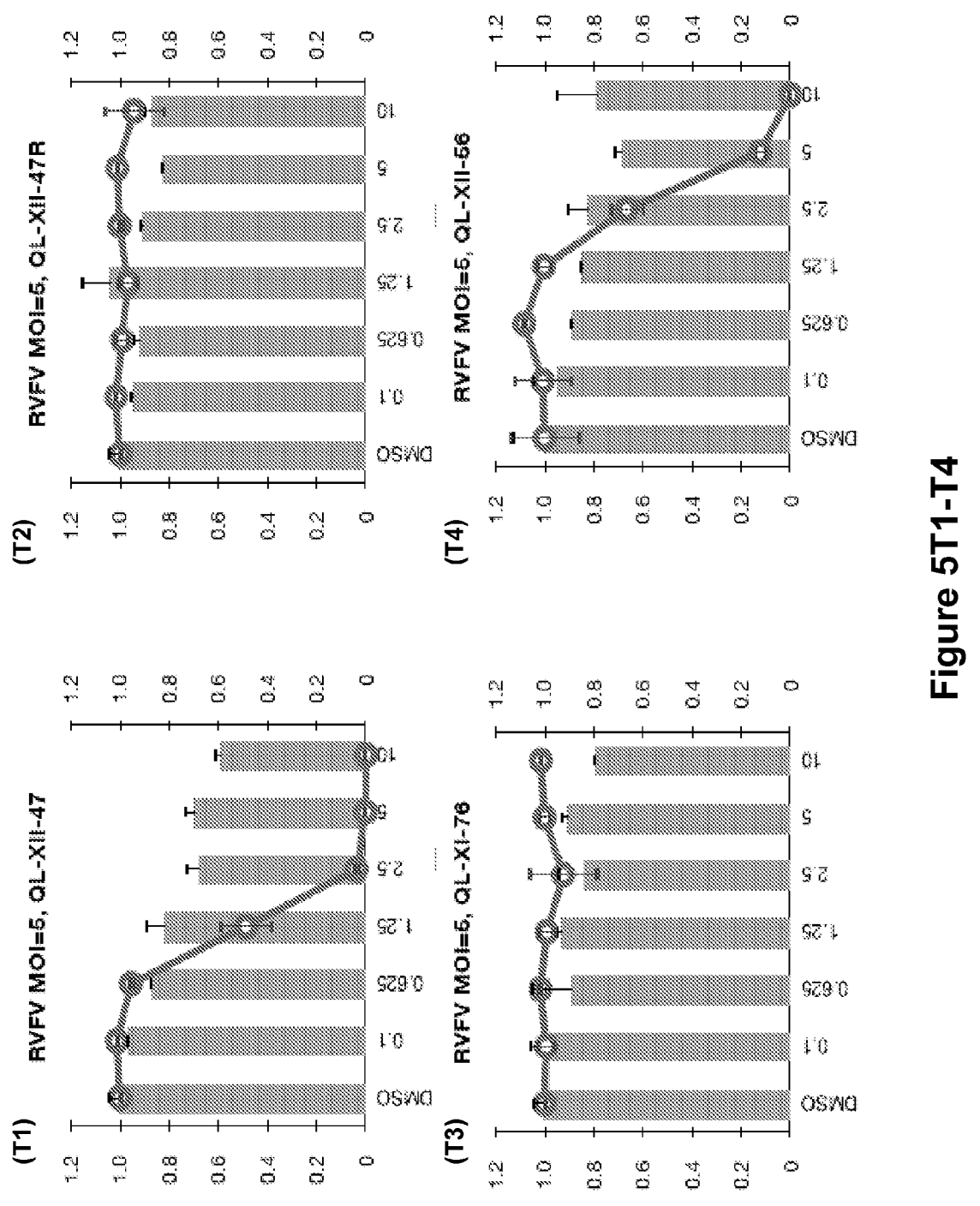

Potent inhibition of vesicular stomatitis virus (VSV), a negative-strand RNA virus unrelated to DENV, was observed; moreover, time-of-addition experiments indicate that QL-XII-47 inhibits VSV at a step early in the VSV life cycle (FIG. 5A). Furthermore, imaging experiments using fluorescently labeled VSV suggest that QL-XII-47 may interfere with a step late in VSV's entry process since it does not affect VSV attachment or uptake. QL-XII-47 also potently inhibits VSV pseudotyped with Ebola and rabies virus glycoproteins (EboV and RABV, respectively) (FIG. 5A). In general, the attachment, uptake, and fusion steps of pseudotyped virus entry are expected to be directed by the Ebola and rabies virus glycoproteins, while the steps of endosomal escape, genome release, and initiation of viral gene expression are believed to follow the mechanisms utilized by wildtype VSV. Therefore, current data may suggest that QL-XII-47 inhibits entry of Ebola and rabies viruses but may also suggest that QL-XII-47 acts at a post-fusion step of viral entry that is shared between wild-type VSV and its pseudotypes.

QL-XII-47 exhibits inhibitory activity against herpes simplex virus 1 (HSV-1), human cytomegalovirus (HCMV), and poliovirus (FIGS. 5B-5D) in assays that quantify viral entry and gene expression (HCMV and poliovirus) or plaque formation (HSV-1). In less sensitive assays measuring virus-induced cytopathic effects (CPE), QL-XII-47 was a modest inhibitor of Japanese Encephalitis virus (JEV) and Junin virus (FIGS. 5E and 5F) but had no activity against influenza virus or vaccinia virus. It was noted that since QL-XII-47 is believed to act via a host target, the cell line and species type used for testing is likely to affect the observed antiviral activity. On a similar note, although cytotoxicity with QL-XII-47 at concentrations up to 20 µM in experiments using Huh7, Vero, BHK21, and 3T3 cell lines was not observed, single-digit micromolar cytotoxicity was observed in Hela and 293 cell lines. Therefore, while it is known that QL-XII-47's activity against DENV and other viruses is not due to host cell death, on-going studies have been designed to clarify and to better understand QL-XII-47's range of antiviral activity and cytotoxicity profile in additional cell lines.

Both QL-XII-47 and QL-XII-56 show inhibitory activity against Ebola glycoprotein (EBOV) (FIGS. 5G1-5G2, 5H1-5H4, and 5I1-5I4), Marburg virus (MARV) (FIGS. 5J1-5J2, 5K1-5K4, and 5L1-5L4), Junin virus (JUNV) (FIGS. 5M1-5M4 and 5N1-5N4), Lassa fever virus (LASV) (FIGS. 5O1-5O4 and 5P1-5P4), Venezuelan equine encephalitis virus (VEEV) (FIGS. 5Q1-5Q4 and 5R1-5R4), and Rift Valley fever virus (RVFV) (FIGS. 5S1-5S4 and 5T1-5T).

Example 7. RNAi-Mediated Depletion Experiments and Cell-Based Assays Showing Bmx is not the Target Mediating QL-XII-47's Anti-DENV Activity Methods Huh7 cells were seeded in 24-well plates and concomitantly transfected with 100 nM of non-targeting (Sigma SIC001) or Bmx MISSION siRNAs (Sigma pool of SASI_Hs01_00019552, SASI_Hs01_00019553 and SASI_Hs01_00185298) using Lipofectamine RNAiMAX (Life Technologies 13778-075) and following the manufacturer's instructions. At 48 hours post-siRNA transfection, the cells were infected at an MOI of 1 with 100 µl of DENV2-NGC. The plates were incubated with the virus for 1 hour at 37° C. and rocked every 15 min. Unadsorbed virus was removed by a PBS wash, after which 500 µl of DMEM supplemented with 2% FBS was added to each well. After incubation at 37° C. for 24 hours, the supernatants were collected for DENV2 titration using a focus forming assay, as described in Example 3. The results are shown in FIG. 6A.

The results shown in FIG. 6B were obtained by using the methods described in Example 3.

Results

Extensive kinase profiling of QL-XII-47 using biochemical and chemical proteomic approaches such as KiNativ50 identified two Tec-family kinases, Bmx and Btk, as potent ($IC_{50}$ 7 nM) biochemical and cellular targets of QL-XII-47. However, data indicate that neither of these kinases is likely responsible for the potent anti-DENV activity of the compound. Btk is a B lymphocyte-specific kinase and not expressed in the Huh7 cells used in the DENV experiments. While Bmx is known to be more widely expressed, it was not detected in Huh7 by microarray expression profiling (see, e.g., biogps.org/#goto=genereport&id=660) or by Western blot. Moreover, RNAi-mediated depletion of any low level Bmx expression had no effect on DENV replication (FIG. 6A). In addition, DENV is not inhibited by PCI-32765, another covalent inhibitor of Bmx and Btk ($IC_{50}$ 0.5 nM) (Honigberg et al., Proc. Nat. Acad. Sci. USA (2010) 107:13075-13080) (FIG. 6B).

Example 8. Identification of Candidate Targets by "Click" Chemistry

To identify cellular proteins that are covalently targeted by QL-XII-47, a chemical proteomics approach using "click-chemistry" was performed.

QL-XII-47AL, an analog of QL-XII-47 modified with an alkyne group, was designed which can undergo a copper-catalyzed cyclo-addition reaction with an azide group (the so-called "click" reaction) and which retains the antiviral activity of QL-XII-47 (FIG. 8). The advantage of "click-chemistry" relative to conventional affinity chromatography is that the QL-XII-47AL can be introduced to living cells infected with DENV thereby allowing bond formation under more physiological conditions. Subsequent cell lysis and reaction with desthiobiotin-PEG-azide, followed by capture with streptavidin beads, trypsin digestion, and mass-spectrometry allows identification of potential target proteins. This approach is powerful because both host and viral targets can be identified. Several potential targets have been identified using this approach (FIG. 8). Analysis of the sites labeled demonstrates that many of these targets were modified on a cysteine residue located in the catalytic site, suggesting that QL-XII-47 is likely to disable enzymatic activity as predicted. This approach may be used to identify candidate targets of QL-XII-47 and other inhibitors and to generate "clickable" derivatives of compounds that are structurally similar to QL-XII-47 but that do not inhibit DENV (e.g., QL-XI-76, see FIGS. 2A and 2G). Parallel proteomic analysis using the negative controls should help to eliminate candidates that covalently react with the inhibitor but that are not relevant to antiviral activity.

Molecular modeling may also be performed of the inventive compounds bound to the targets identified by the click-chemistry pull-down experiments in order to rationalize target-based SAR and to guide potential chemical modifications. For example, QL-XII-47AL covalently modifies Cys302 of aldehyde dehydrodenase 1 (ALH1), and molecular docking suggests that QL-XII-47 fits well into the nicotinamide binding site of ALDH1 with the acrylamide perfectly poised to react with Cys302 (FIG. 9). Furthermore, the methyl pyrazole side-chain of QL-XII-47 is predicted to form a key hydrogen bond with the backbone NH of Cys302 and Cys303, an interaction that is lost in negative control compound QL-XI-76, which contains a non-hydrogen bond competent furan at this position. Based on these models, compounds may be designed that will disrupt key interactions, and this will allow for establishing whether a correlation exists between inhibition of a potential target (such as ALDH1) and the anti-DENV activity of the compound. This is a classical approach to establishing the relevance of a particular target that is complementary to the RNAi.

In sum, a class of substituted quinolones, exemplified by QL-XII-47, has been discovered to show potent anti-DENV activity in vitro. QL-XII-47 causes a >3-$\log_{10}$ unit drop in viral titer at single-digit micromolar concentrations with no observed cytotoxicity. QL-XII-47 has activity against strains representative of all four DENV serotypes (DENV1-DENV4) as well as against Kunjin virus (KUNV) and Japanese Encephalitis Virus (JEV), related members of the Flaviviridae family. In addition, it has been found that QL-XII-47 exhibits activity against vesicular stomatitis virus (VSV) and VSV expressing rabies or Ebola glycoproteins, and other viruses, suggesting that QL-XII-47 may have broad spectrum activity against additional Category A, B, or C viral pathogens. Preliminary experiments suggest strongly that QL-XII-47 inhibits a step early in the DENV life cycle by covalently modifying a reactive cysteine residue in a yet-to-be-identified host factor. QL-XII-47 ($EC_{90}$ 400 nM) is more than ten-fold more potent than 7-DMA, and thus it is believed that inhibitors similar to QL-XII-47 will have commensurately greater decreases in viral burden and the inflammatory cytokine response.

Example 9. QL-XII-47 Inhibited DENV2 Viral Production

Huh7 cells were infected with DENV2 virus at MOI of about 1 during one hour at 37° C. Then, at time (t)=0, the cells were rinsed once with PBS and then medium (DMEM supplemented with 2% FBS and either 4 μM QL-XII-47 or DMSO) was added. At each indicated time, supernatants were harvested for titration in FFU/ml, cell lysed for RNA extraction and reverse transcription quantitative polymerase chain reaction (RTqPCR). Additional duplicates were done in parallel for Western blotting.

Figure 10C:
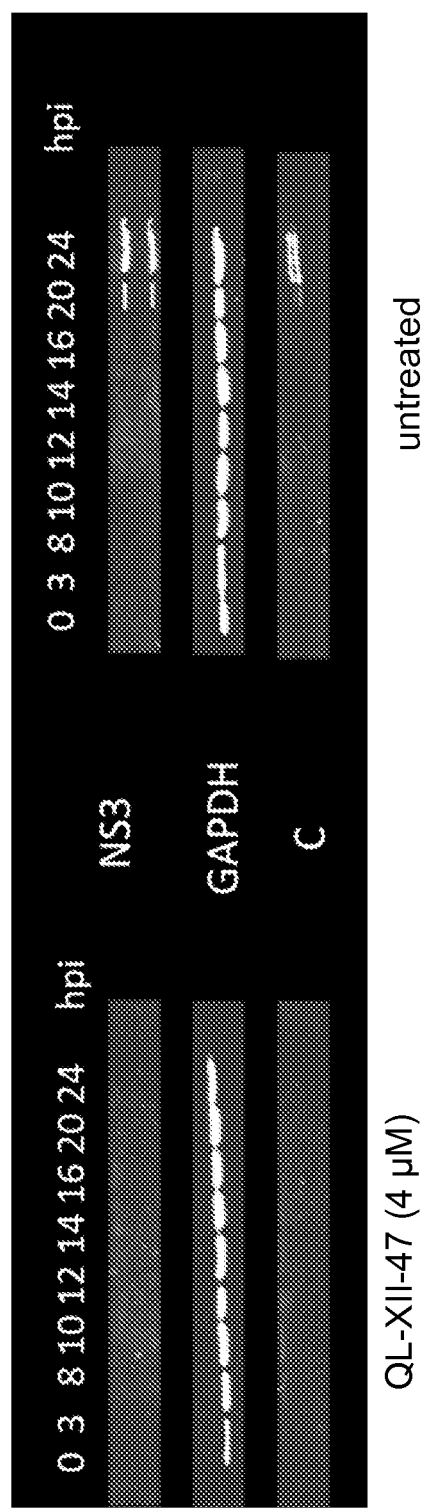
FIG. 10C shows Western blot analysis of DENV proteins NS3 and core, demonstrating reduced steady-state expression of both viral proteins in the presence of QL-XII-47 and suggesting that QL-XII-47 may prevent their expression and/or promote their degradation.

The results, shown in FIGS. 10A to 10C, indicate that QL-XII-47 inhibited DENV2 viral production. Values of FFU (focus forming units)/ml were decreased for the infected cells treated with QL-XII-47 after about 12 hours of infection compared to the infected cells not treated with a compound of the invention (FIG. 10A). Viral count was also decreased for the infected cells treated with QL-XII-47 after about 12 hours of infection compared to the infected cells not treated with a compound of the invention (FIG. 10B).

Example 10. QL-XII-47 and QL-XII-56 Inhibited DENV2 Translation

Plasmid pDV2-Fluc(WT) or pDV2-FlucGDV encode dengue virus serotype 2 RNAs in which a luciferase reporter gene replaces most of the genes encoding core, prM, and E. In vitro transcripts of the wildtype replicon (WT) and a mutant that cannot replicate RNA due to mutations in the active site of the viral polymerase (GDV mutant) were produced. Huh7 cells were electroporated with the respective DV2-replicon RNAs. Directly after electroporation cells are incubated with the indicated drug (QL-XII-47 2 μM, cycloheximide 30 μg/ml, MPA 5 μM). At the indicated time post-electroporation, luminescence was measured as a marker of translation. For the WT construct, luc activity at an early time point (12 hours or less) reflect translation of the input RNA delivered by electroporation; luc activity at later time points reflects luc translated from both input and newly synthesized replicon RNA. Since the GDV mutant cannot synthesize new viral RNA, luciferase activity observed at all time points is the product of the input RNA delivered by elecctroporation.

Figure 11:
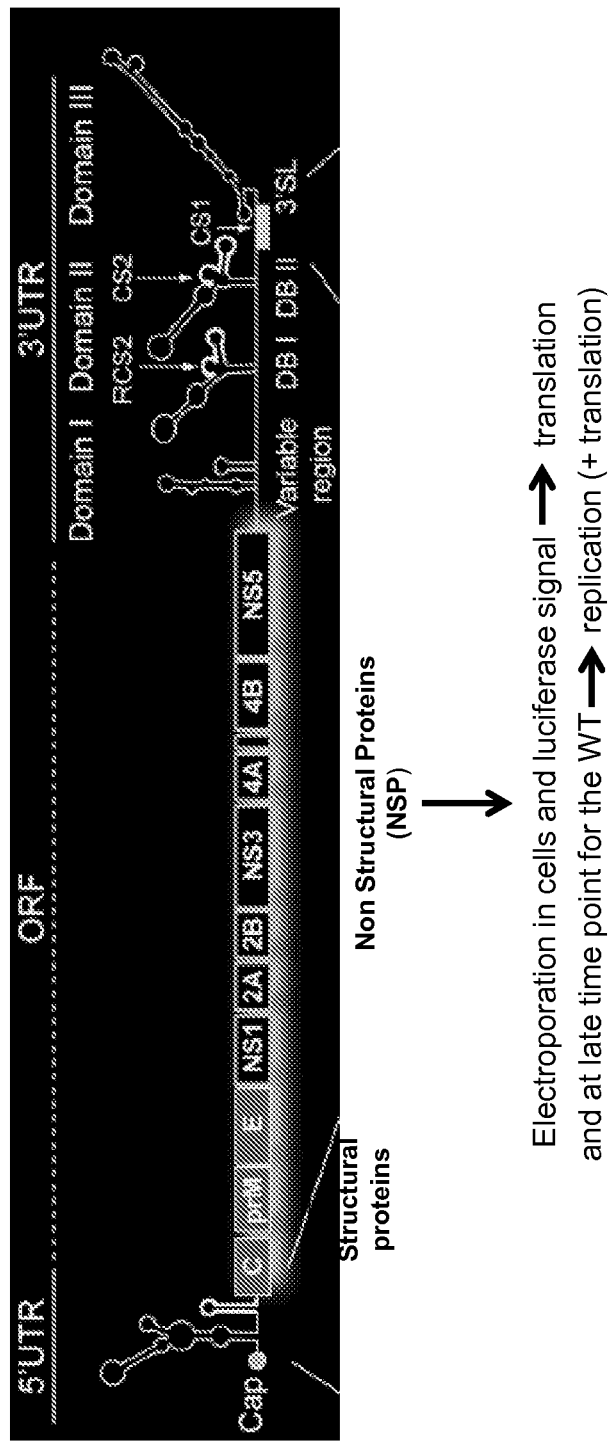
FIG. 11 shows a schematic of the replicon experiment used to examine the effects of QL-XII-47 on translation of the dengue RNA. Plasmid pDV2-Fluc(WT) or pDV2-FlucGDV encode dengue virus serotype 2 RNAs in which a luciferase reporter gene replaces most of the genes encoding core, prM, and E. In vitro transcripts of the wildtype replicon (WT) and a mutant that cannot replicate RNA due to mutations in the active site of the viral polymerase (GDV mutant) were produced. Huh7 cells were electroporated with the respective DV2-replicon RNAs. Directly after electroporation cells are incubated with the indicated drug (QL-XII-47 2 µM, cycloheximide 30 µg/ml, MPA 5 µM). At the indicated time post-electroporation, luminescence was measured as a marker of translation. For the WT construct, luc activity at an early time point (12 hours or less) reflect translation of the input RNA delivered by electroporation; luc activity at later time points reflects luc translated from both input and newly synthesized replicon RNA. Since the GDV mutant cannot synthesize new viral RNA, luciferase activity observed at all time points is the product of the input RNA delivered by electroporation.

Linearized plasmid was used for in vitro Transcription (IVT) and capped (no capping for IRES-EMC-Fluc). Those RNAs are then electroporated in Huh7 cells. Directly after electroporation cells are incubated with the indicated compound (QL-XII-47 (2 μM), cycloheximide (30 μg/ml), or mycophenolic acid (MPA, 5 μM)). At the indicated time post electroporation, cells were washed with PBS and lysed using the adapted lysis buffer (Firefly, *Renilla* or Dual lysis buffer from Promega). Luminescence is measured using Firefly, *Renilla* or Dual kit following recommendations, and read on Envision instrument. The results are shown in FIG. 11.

Figure 12A:
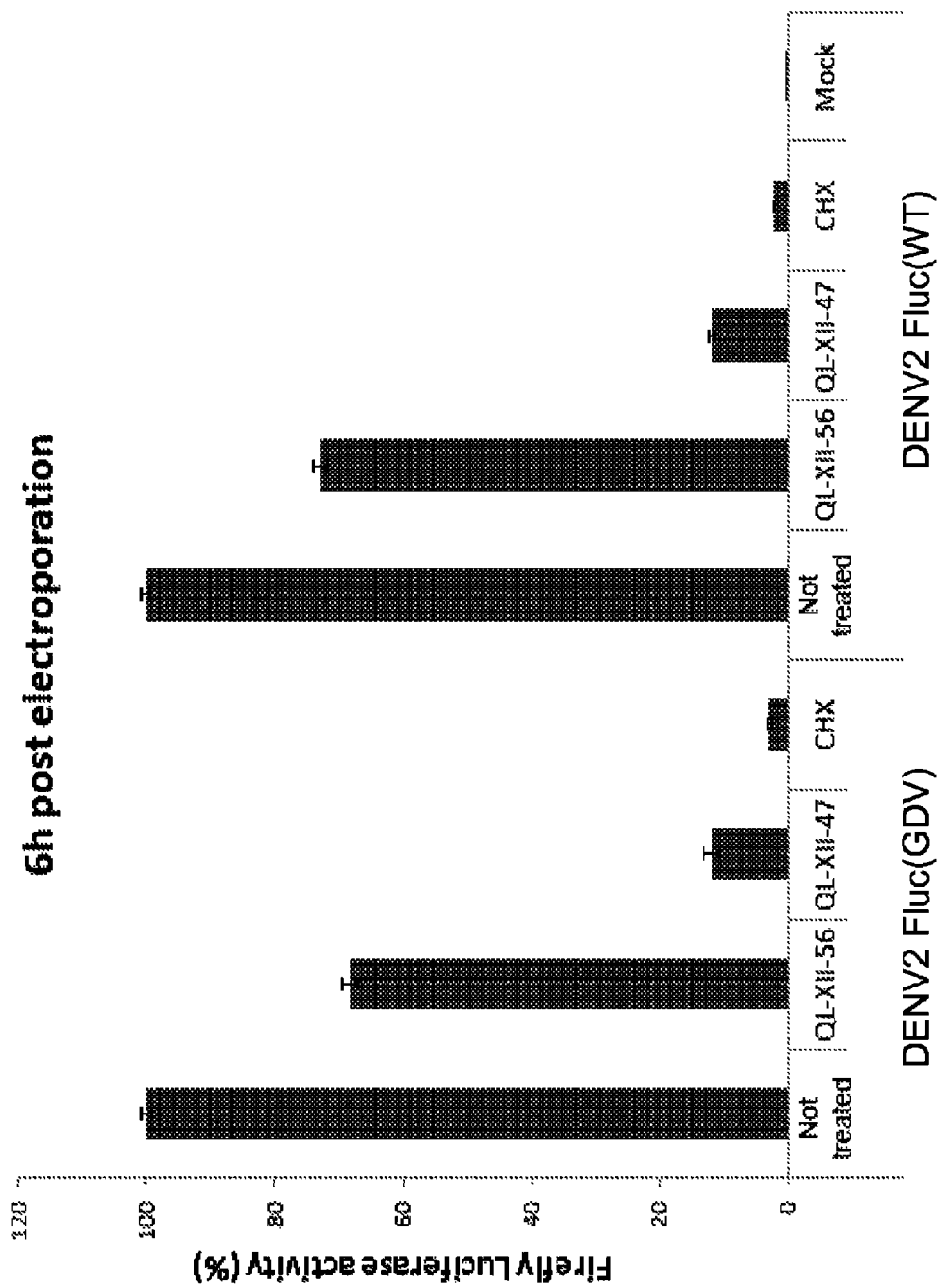
FIG. 12a shows the luciferase activity measured at 6 hours post-electroporation for Huh7 cells electroporated with the wildtype (WT) or mutant (MUT) replicon RNAs and then treated with 2 µM QL-XII-47, 2 µM QL-XII-56, 30 µg/mL cycloheximide (CHX) as general inhibitor of translation, or DMSO as a negative control.
Figure 12B:
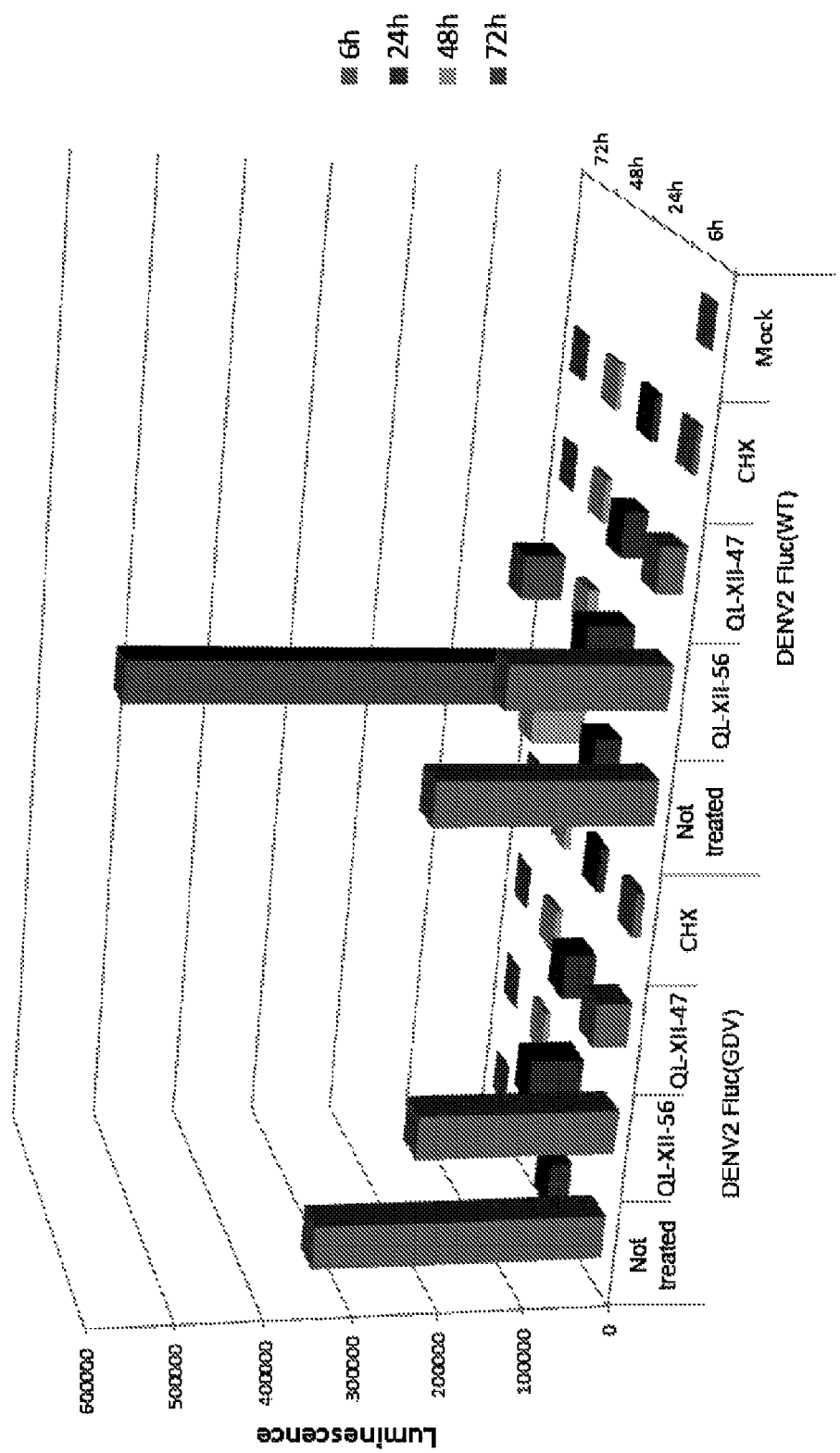
FIG. 12b shows luciferase activity measured at the indicated time point for cells electroporated with the WT or GVD replicon RNA and then treated with DMSO, QL-XII-47, QL-XII-56, or cycloheximide as indicated.
Figure 14:
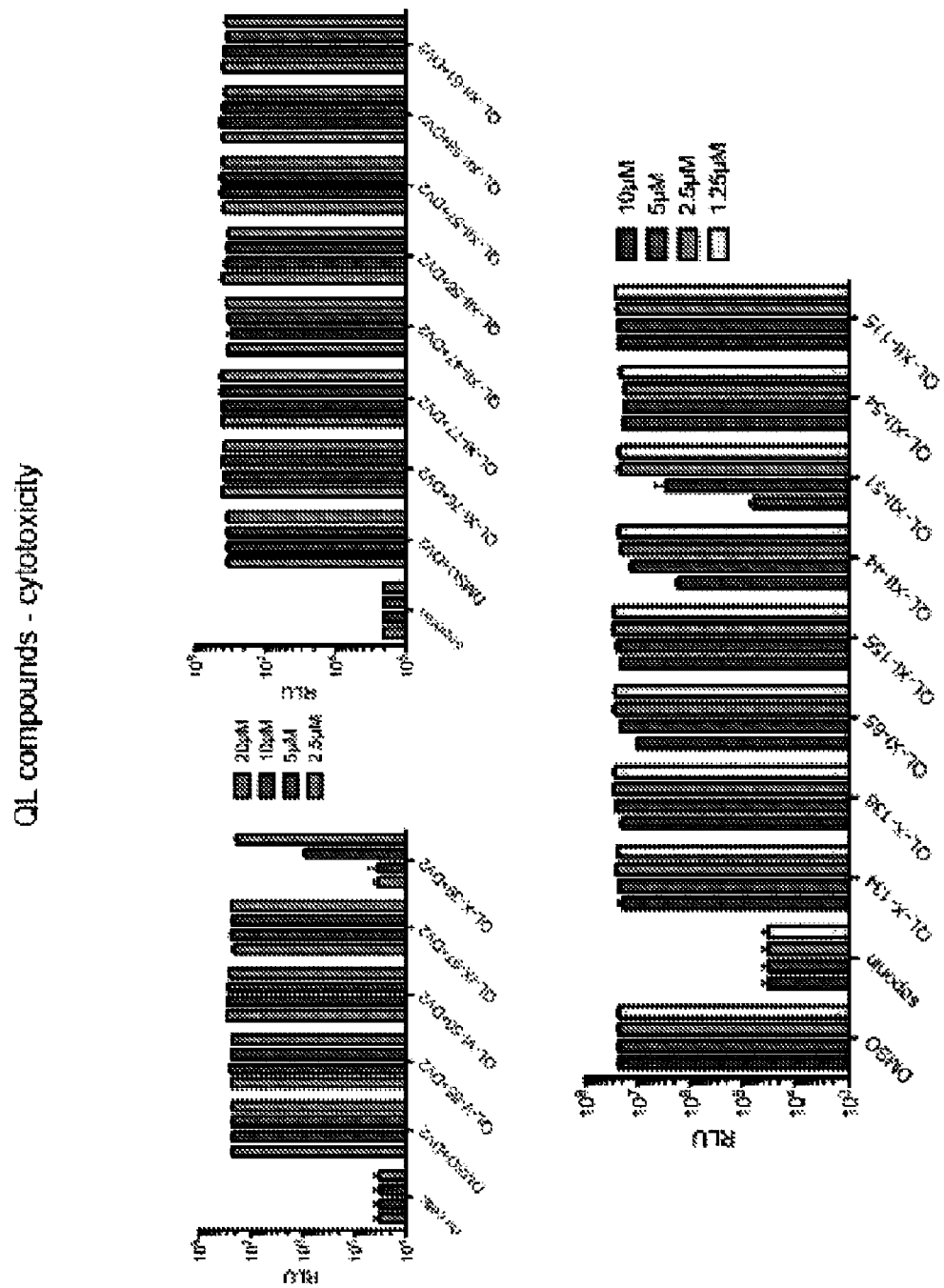
FIG. 14 shows cytotoxicity evaluation of the exemplary compounds.

Huh7 cells were electoporated with IVTs of DENV2-Fluc (WT) or DENV2-Fluc (GDV). Some cells were treated with the indicated compound (QL-XII-47 (2 μM), QL-XII-56 (2 μM), or cycloheximide (CHX, 30 μg/ml)), and other cells were not treated with the indicated compound. Firefly Luciferase luminescence was measured at indicated times. The results are shown in FIGS. 12A to 12B and Table 1. FIG. 12a shows the luciferase activity measured at 6 hours post-electroporation for Huh7 cells electroporated with the wildtype (WT) or mutant (MUT) replicon RNAs and then treated with 2 μM QL-XII-47, 2 μM QL-XII-56, 30 μg/mL cycloheximide (CHX) as general inhibitor of translation, or DMSO as a negative control. Luciferase at this time point is due to translation template by the input RNA electroporated into cells. Reduced luciferase activity for the cells treated with QL-XII-47, QL-XII-56, and cycloheximide indicates reduced translation of both WT and GVD replicons. FIG. 12b shows luciferase activity measured at the indicated time point for cells electroporated with the WT or GVD replicon RNA and then treated with DMSO, QL-XII-47, QL-XII-56, or cycloheximide as indicated. For the WT replicon, luciferase at early time points (6 h) reflects translation of the input RNA; luciferase activity at later time points (24, 48, 72 h) reflects translation template by newly synthesized RNA. For the GVD mutant, which cannot replicate viral RNA due to mutation of the viral polymerase active site, luciferase at all time points reflects the input RNA alone. The data in column 3 indicate the p-value calculated by the student's t-test for comparison of the compound-treated samples with the DMSO-treated negative control, demonstrating the statistical significance of the inhibition of viral RNA translation by QL-XII-56, QL-XII-47, and CHX.

TABLE 1

P-values of compound-treated samples

|  |  | P-value for student's t test comparison of compound-treated to untreated negative control (Cap-driven) |
|---|---|---|
| GDV | QL-XII-56 | 0.000441 |
|  | QL-XII-47 | 0.000121 |
|  | CHX | 0.000186 |
| WT | QL-XII-56 | 0.000181 |
|  | QL-XII-47 | 0.000039 |
|  | CHX | 0.000111 |

These results indicate that QL-XII-47 and QL-XII-56 inhibited DENV2 RNA translation.

Example 11. QL-XII-47 and QL-XII-56 Inhibited Encephalomyocarditis Virus (EMCV) IRES-Dependent Translation Huh7 cells were electroporated with in vitro transcripts of the DV2 WT and GVD replicon RNAs or an RNA encoding a luciferase reporter under the control of the encephalomyocarditis virus (EMCV) IRES element. Cells were treated QL-XII-47 or a combination of cycloheximide (CHX) as a general inhibitor of translation and mycophenolic acid (MPA) as an inhibitor of viral RNA replication or with DMSO as a negative control immediately post-electroporation. Luciferase activity was measured at 6 hours post-electroporation as a measure of the translation of the different RNAs. Reduced luciferase activity indicates reduction in translation of the RNA in that sample. The data indicate that QL-XII-47 reduces translation of WT and GVD DV replicon RNAs as well as translation of the EMCV IRES; moreover, the reduction in translation is comparable in magnitude to that caused by the CHX/MPA positive control.

Figure 15:
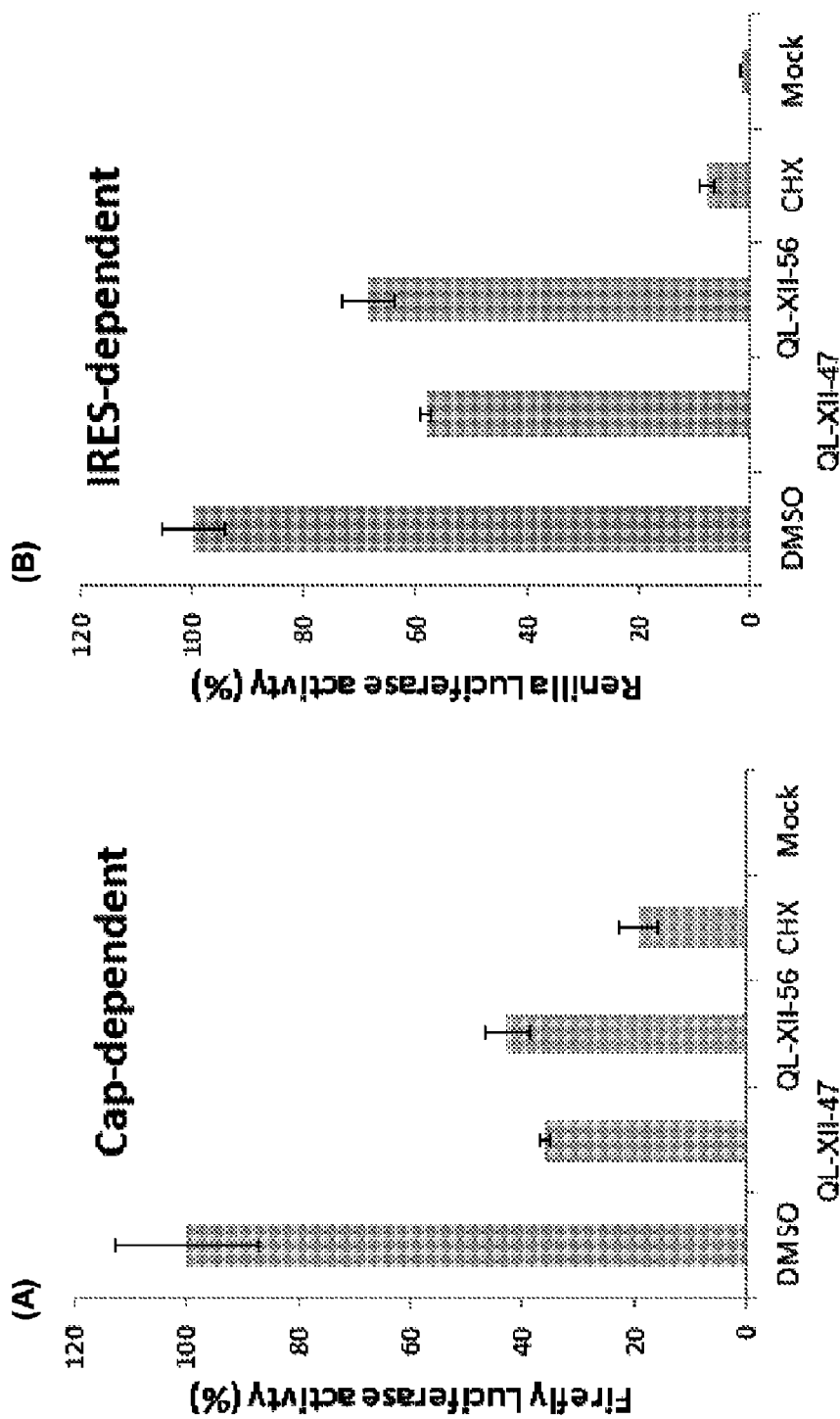
FIG. 15 shows that QL-XII-47 and QL-XII-56 inhibited encephalomyocarditis virus (EMCV) IRES-dependant translation.

In order investigate Cap-dependent or IRES-dependent translation of EMCV without DENV2 backbone, plasmid pFR-CrPV was used. pFR-CrPV, a plasmid encoding the bi-cistronic expression construct used to test cap-driven and IRES-driven translation from the same RNA template. Firefly luciferase translation is cap-driven while *renilla* luciferase expression is driven by the IRES element of the Cricket paralysis virus (CrPV). When transfected into cells, RNA pol II drives transcription to produce the bicistronic RNA. Dual luciferase assay can be performed to measure translation of both cap-dependent and IRES-driven translation. The plasmid was previously published, see www.pnas.org/content/early/2012/11/14/1216454109.abstract. Huh7 cells were retrotransfected with pFR-CrPV. 28 h post transfection, the cells were treated with the indicated compound (QL-XII-47 (2 µM), QL-XII-56 (2 µM), CHX (30 µg/ml)) for an additional 24 h. The cells were washed once with PBS and lysed with dual luciferase assay buffer. The results are shown in FIG. 15 and Table 2. The data in column 3 of Table 2 indicate the value calculated by the student's t-test for comparison of the compound-treated samples with the DMSO-treated negative control, demonstrating the statistical significance of the inhibition of translation by QL-XII-56, QL-XII-47, and CHX.

TABLE 2

Statistical analysis of the reduction in cap-dependent and IRES-dependent translation

|  | p-value for student's t-test comparison of compound-treated to DMSO negative control (Cap-driven translation) | p-value for student's t-test comparison of compound-treated to DMSO negative control (IRES-driven translation |
|---|---|---|
| QL-XII-47 | 0.019667 | 0.009291 |
| QL-XII-56 | 0.026517 | 0.026662 |
| CHX | 0.013357 | 0.001974 |
| Mock | 0.00817 | 0.001656 |

These results indicate that QL-XII-47 and QL-XII-56 inhibited EMCV-IRES dependant translation in Huh7 cells.

Example 12. QL-XII-47 Biotin Test

Huh7 cells were infected with DENV2 virus at an MOI of about 1 during one hour at 37° C. Then, at time (t)=0, the cells were rinsed once with PBS. The cells were treated with the indicated compound (QL-XII-47 or QL-XII-47 biotin) for 24 or 48 h. Supernatants were harvested for titration in FFU/ml, cell lysed for RNA extraction and RTqPCR. The structure of QL-XII-47 biotin is of the following formula:

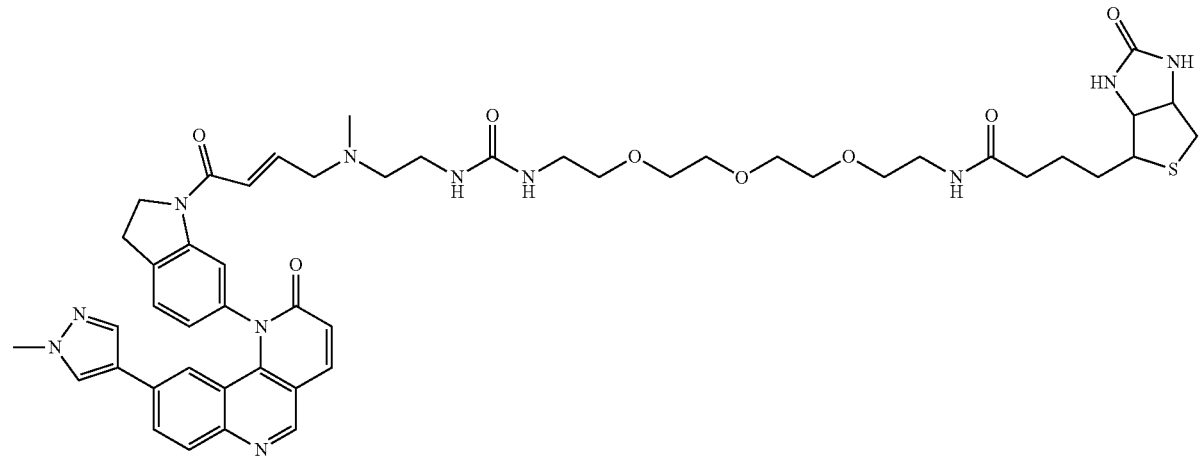 [SMILES: CN(C/C=C/C(=O)N1CCc2ccc(-n3c(=O)ccc4cnc5ccc(-c6cnn(C)c6)cc5c43)cc21)CCNC(=O)NCCOCCOCCOCCNC(=O)CCCC1SCC2NC(=O)NC21]

Figure 16:
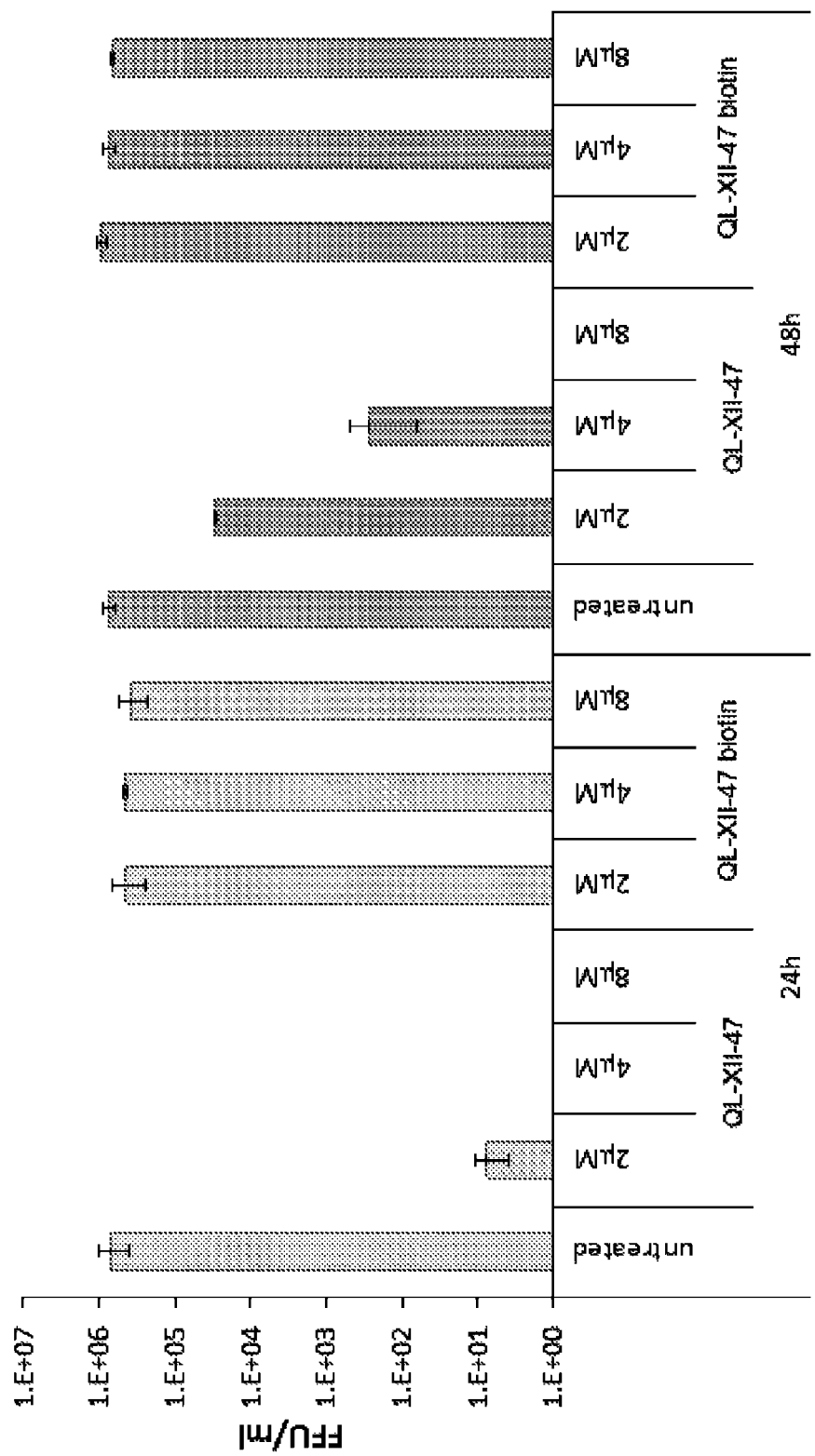
FIG. 16 shows that conjugation of QL-XII-47 to biotin significantly reduces the antiviral activity.

The results, shown in FIG. 16, indicate that QL-XII-47-biotin has significantly reduced inhibitory activity against dengue virus.

Example 13. Test of the Effects of RNAi-Mediated Depletion of Prdx1

Huh 7 cells were retrotransfected with siRNA Prdx1 and plated in 12 well plates. At 48 h, the cells were infected with DENV2 virus at an MOI of about 1 during one hour at 37° C. Some cells were treated for 24 h with 4 µM of QL-XII-47 or QL-XII-56, and other cells were not so treated. Supernatant were harvested for titration and cells lysed for Western blotting.

Figure 17A:
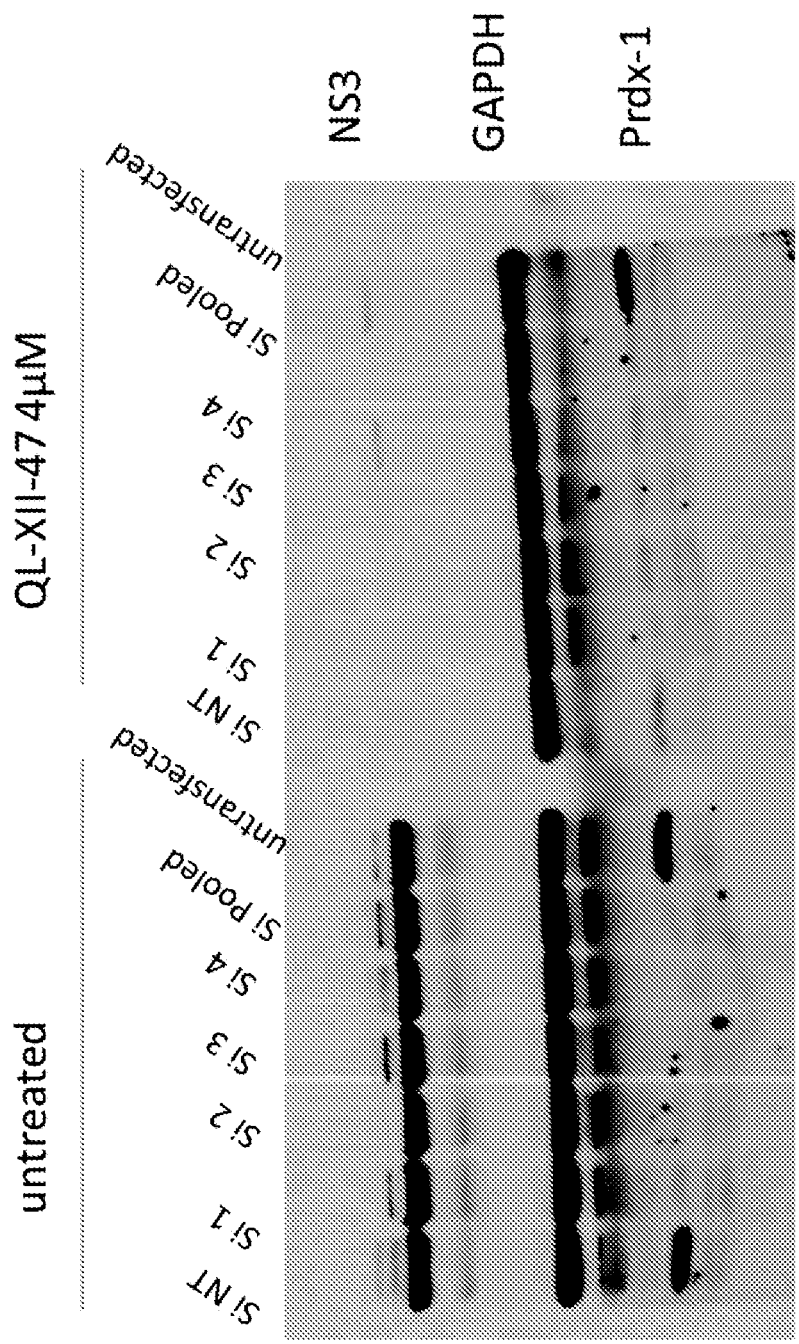
FIG. 17a shows that RNAi-mediated depletion of Prdx-1 does not reduce steady-state expression of dengue NS3 protein (left); moreover, combination treatment of cells with siRNAs against Prdx-1 and QL-XII-47 does not reduce steady-state expression of NS3 beyond what is observed with QL-XII-47 alone.
Figure 17B:
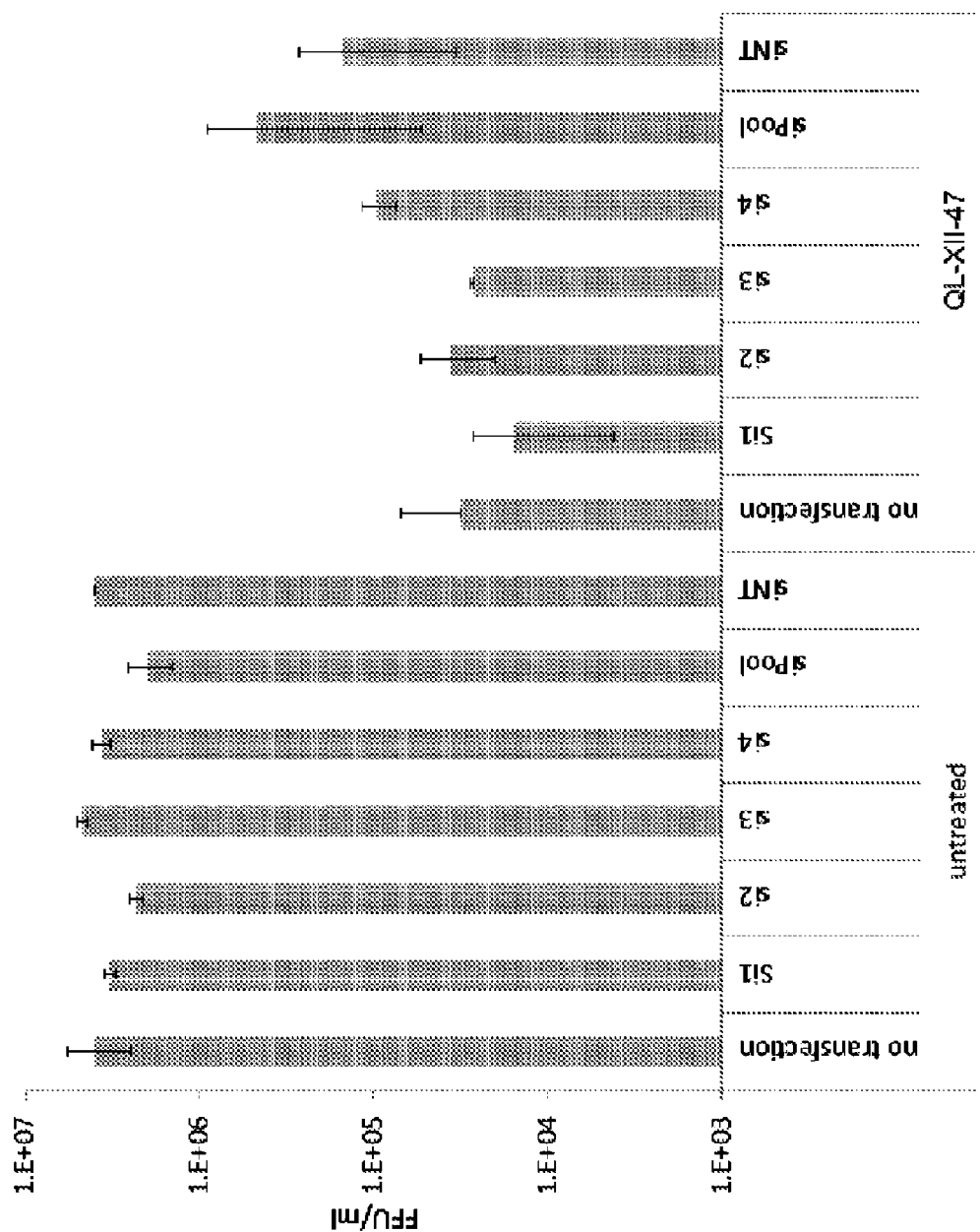
FIG. 17b shows the quantitation of infectious viral particles released to the culture supernatants at 24 hours post-infection showing that RNAi-mediated depletion of Prdx-1 does not appear to inhibit dengue virus.
Figure 20A:
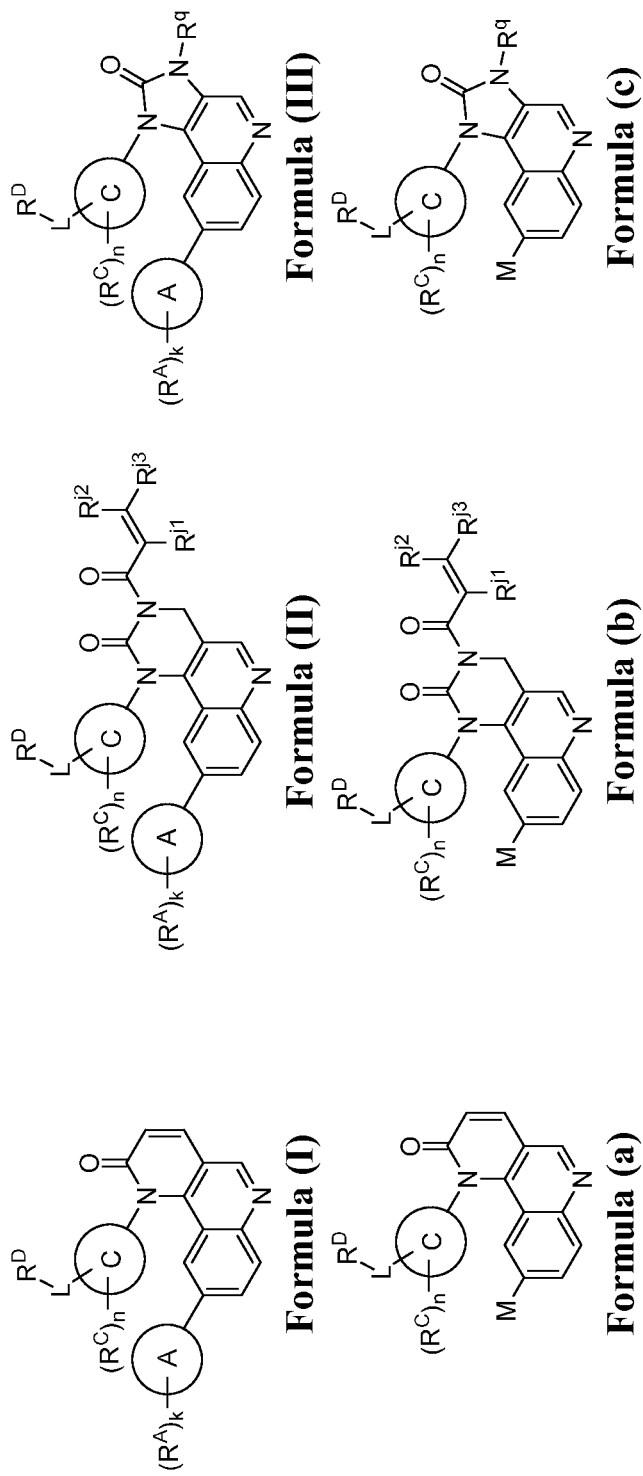
Figure 21A:
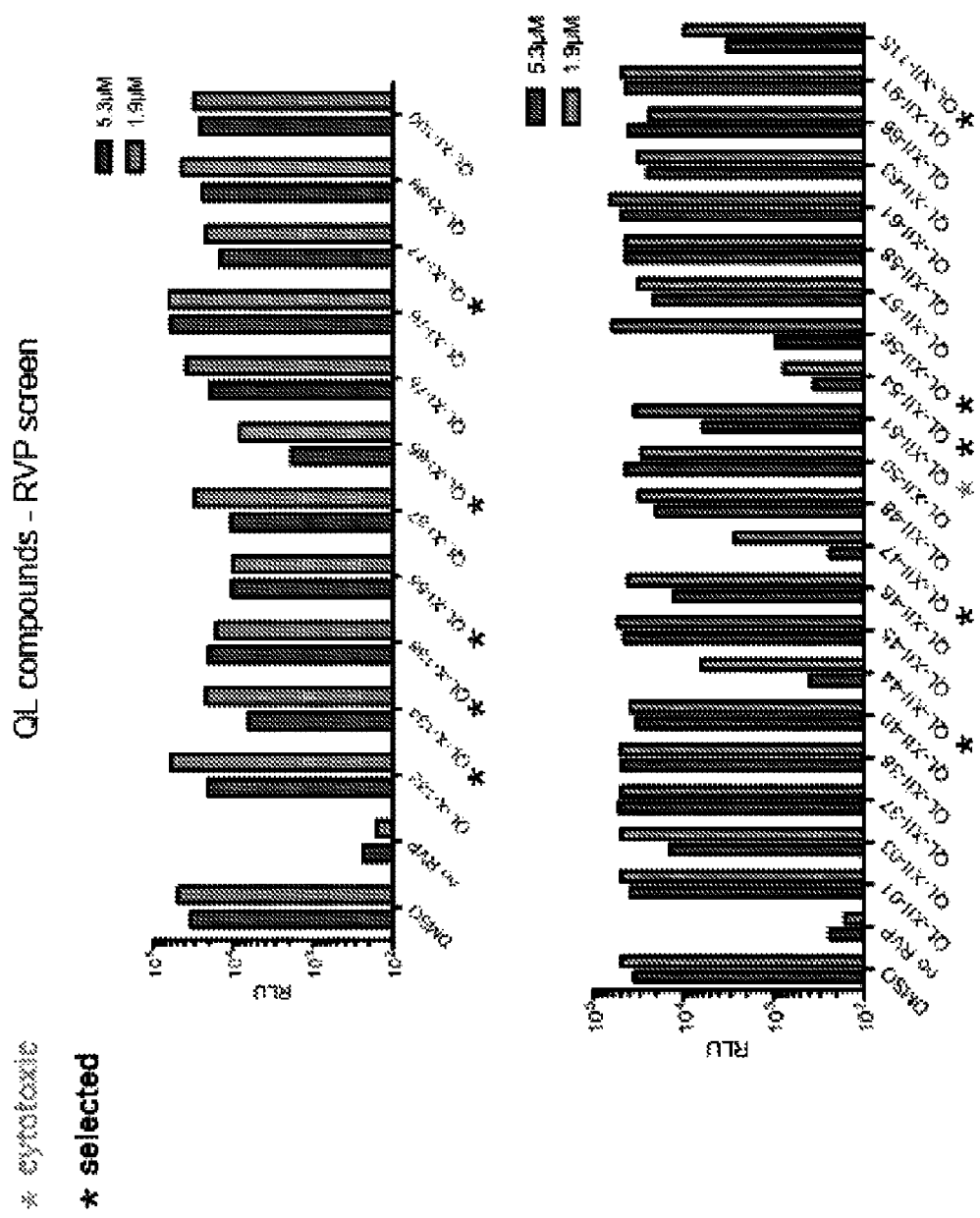
FIG. 21A-B shows recombinant viral particle or reporter viral particle (RVP) screening of the exemplary compounds. Used in the system are the particles with dengue structural proteins (E, prM/M, and core) and then an RNA derived from West Nile virus that encodes the nonstructural proteins as well as a luciferase reporter (Ansarah-Sobrinho et al., Virology, 2008, 381, 67-74). The resulting particle can infect new cells. Upon viral entry and release and translation of the WNV RNA, luc expression is obtained. The luc activity is a marker of steady-state viral RNA. Decreased luc activity can reflect inhibition of the initial entry step OR inhibition of translation of the viral RNA OR inhibition of steady-state RNA replication (increased synthesis and/or decreased turnover).
Figure 21B:
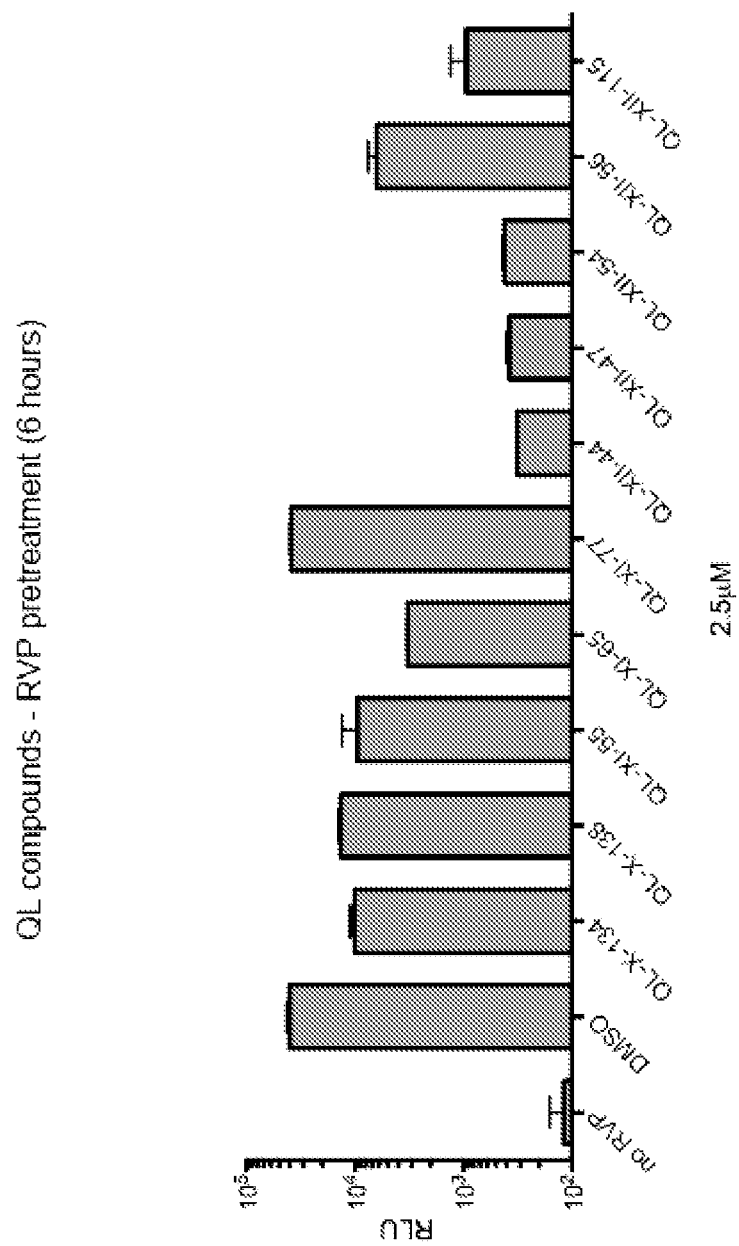
Figure 22:
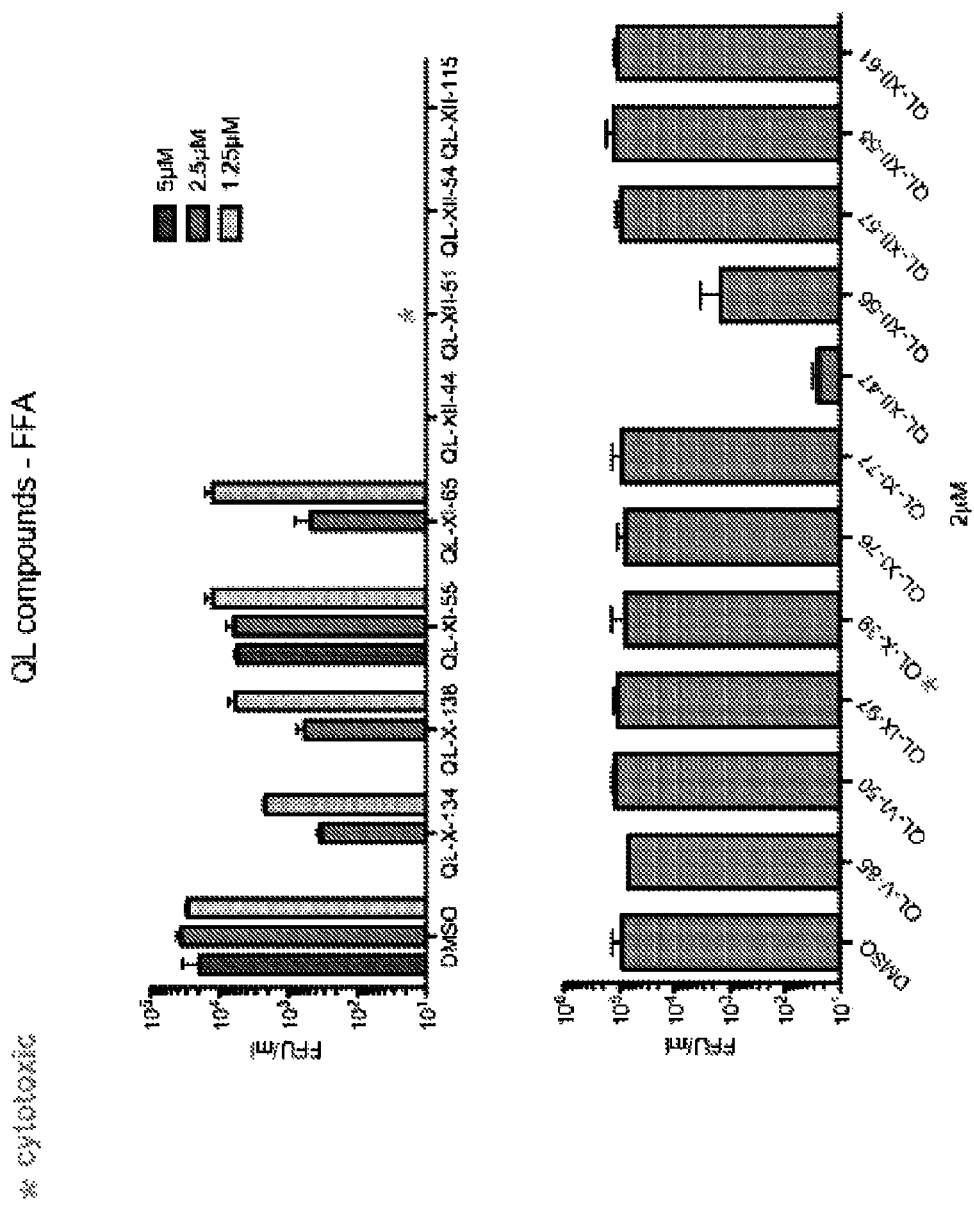
FIG. 22 shows FFA evaluation of the exemplary compounds.

The results are shown in FIGS. 17A to 17B. FIG. 17*a* shows that RNAi-mediated depletion of Prdx-1 does not reduce steady-state expression of dengue NS3 protein (left); moreover, combination treatment of cells with siRNAs against Prdx-1 and QL-XII-47 does not reduce steady-state expression of NS3 beyond what is observed with QL-XII-47 alone. FIG. 17b shows the quantitation of infectious viral particles released to the culture supernatants at 24 hours post-infection showing that RNAi-mediated depletion of Prdx-1 does not appear to inhibit dengue virus.

Example 14. QL-XII-47 and QL-XII-56 Inhibited Vesicular Stomatitis Virus (VSV)

Vero cells were infected at an MOI of about 1 with VSV for 1 h at 37° C. in Earle's balanced salt solution (EBSS). At t=0, the cells were washed once with PBS and then medium (DMEM with 10% fetal bovine serum) containing the indicated compounds (N-(4 hydroxyphenyl)retinamide (4HPR, 5 μM), QL-XII-47 (4 μM), or QL-XII-56 (4 μM)) was added. At 6 h post infection (6 hpi), supernatant were harvested for titration, and the cells were lysed for RNA extraction and RTqPCR.

The results, shown in FIGS. 18A and 18B, demonstrate that QL-XII-47 and QL-XII-56 inhibited VSV.

Example 15. QL-XII-47 and QL-XII-56 Inhibited Poliovirus Type 1 (PV1)

Vero cells were infected at an MOI of about 1 with PV1 for 1 h at 37° C. in Earle's balanced salt solution (EBSS). At t=0, the cells were washed once with PBS and then medium (DMEM with 10% fetal bovine serum) containing the indicated compound (N-(4 hydroxyphenyl)retinamide (4HPR, 5 μM), QL-XII-47 (4 μM), or QL-XII-56 (4 μM)) was added. At 6 h post infection (6 hpi), supernatant were harvested for titration, and the cells were lysed for RNA extraction and RTqPCR.

The results, shown in FIGS. 19A and 19B, demonstrate that QL-XII-47 and QL-XII-56 inhibited PV1.

Example 16. Summary of FFA, RVP, Cytotoxicity Evaluation of the Exemplary Compounds Table 3 lists the results of FFA and RVP evaluation of the exemplary compounds.

TABLE 3

FFA and RVP Evaluatin of Exemplary Compounds

| Compound No. | Cytotoxicity | FFA (2 or 2.5 uM) | RVP (2 uM screen) | RVP (2.5 uM pretreat) |
|---|---|---|---|---|
| QL-XI-57 | — | — | 2 | — |
| QL-XI-55 | NO | 6 | 5 | 4 |
| QL-VI-50 | — | 1 | — | — |
| QL-XI-65 | at 10 uM | 77 | 6 | 12 |
| QL-V-85 | — | 1 | — | — |
| QL-IX-97 | — | 1 | — | — |
| QL-X-39 | — | 1 | — | — |
| QL-X-132 | — | — | 1 | — |
| QL-XI-99 | — | — | 1 | — |
| QL-XI-100 | — | — | 2 | — |
| QL-XI-75 | — | — | 1 | — |
| QL-XII-01 | — | — | 1 | — |
| QL-XII-03 | — | — | 1 | — |
| QL-XII-37 | — | — | 1 | — |
| QL-XII-40 | — | — | 1 | — |
| QL-XII-58 | — | 1 | 1 | — |
| QL-XII-61 | — | 1 | 1 | — |
| QL-XI-76 | — | 1 | 1 | — |
| QL-XII-63 | — | — | 2 | — |
| QL-XII-66 | — | — | 2 | — |
| QL-XII-57 | — | 1 | 2 | — |
| QL-XI-77 | NO | 1 | 2 | 1 |
| QL-X-138 | NO | 61 | 3 | 3 |
| QL-X-134 | NO | 107 | 2 | 4 |
| QL-XII-56 | NO | 62 | 1 | 6 |
| QL-XII-115 | NO | 36000 | 5 | 43 |
| QL-XII-54 | NO | 36000 | 70 | 95 |
| QL-XII-38 | — | — | 1 | — |
| QL-XII-45 | — | — | 1 | — |
| QL-XII-46 | — | — | 1 | — |
| QL-XII-91 | — | — | 1 | — |
| QL-XII-48 | — | — | 2 | — |
| QL-XII-50 | — | — | 2 | — |
| QL-XII-51 | at 5 uM | 36000 | 2 | — |
| QL-XII-47 | NO | 3600 | 19 | 106 |
| QL-XII-44 | at 10 uM | 36000 | 8 | 125 |

Other Embodiments

The foregoing has been a description of certain non-limiting embodiments of the invention. Those of ordinary skill in the art will appreciate that various changes and modifications to this description may be made without departing from the spirit or scope of the present invention, as defined in the following claims.

All publications, including but not limited to journal articles, books, patents, and patent applications, cited in this specification are herein incorporated by reference as if each individual publication were specifically and individually indicated to be incorporated by reference herein as though fully set forth.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of the formula:

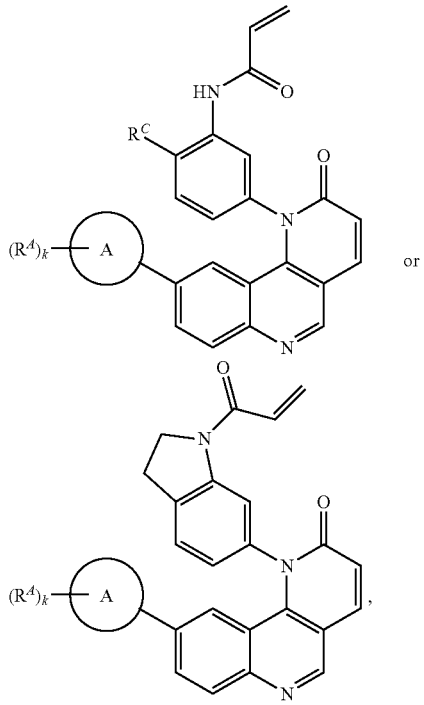

or a pharmaceutically acceptable salt thereof;
wherein:

is Ring A, wherein Ring A is 5 or 6-membered, monocyclic heteroaryl comprising 1 to 4 ring heteroatoms independently selected from the group consisting of nitrogen, oxygen, and sulfur; or 5,6- or 6,6-membered bicyclic heteroaryl comprising 1 to 4 ring heteroatoms independently selected from the group consisting of nitrogen, oxygen, and sulfur; and Ring A is optionally substituted with k instances of $R^A$;

each instance of $R^A$ is independently selected from the group consisting of halogen, optionally substituted $C_{1-6}$ alkyl, optionally substituted $C_{2-6}$ alkenyl, optionally substituted $C_{2-6}$ alkynyl, optionally substituted heterocyclyl, —$OR^{A1}$, —$N(R^{A1})_2$, —$SR^{A1}$, —CN, —C(=$NR^{A1}$)$R^{A1}$, —C($NR^{A1}$)$OR^{A1}$, —C($NR^{A1}$)N($R^{A1}$)$_2$, —$NO_2$, —$N_3$, —$NR^{A1}$C(=O)$R^{A1}$, —$NR^{A1}$C(=O)$OR^{A1}$, —$NR^{A1}$C(=O)N($R^{A1}$)$_2$, —$NR^{A1}$C(=$NR^{A1}$)$R^{A1}$, —$NR^{A1}$C(=$NR^{A1}$)$OR^{A1}$, —$NR^{A1}$C(=$NR^{A1}$)N($R^{A1}$)$_2$, —OC(=O)$R^{A1}$, —OC(=O)$OR^{A1}$, —OC(=O)N($R^{A1}$)$_2$, —OC(=$NR^{A1}$)$R^{A1}$, —OC(=$NR^{A1}$)$OR^{A1}$, —OC(=$NR^{A1}$)N($R^{A1}$)$_2$, —$NR^{A1}$S(=O)$_2$$R^{A1}$, —$NR^{A1}$S(=O)$_2$$OR^{A1}$, —$NR^{A1}$S(=O)$_2$N($R^{A1}$)$_2$, —OS(=O)$_2$$R^{A1}$, —OS(=O)$_2$$OR^{A1}$, —OS(=O)$_2$N($R^{A1}$)$_2$, —S(=O)$_2$$R^{A1}$, —S(=O)$_2$$OR^{A1}$, and —S(=O)$_2$N($R^{A1}$)$_2$, wherein each occurrence of $R^{A1}$ is independently selected from the group consisting of hydrogen, optionally substituted acyl, optionally substituted $C_{1-6}$ alkyl, optionally substituted $C_{2-6}$ alkenyl, optionally substituted $C_{2-6}$ alkynyl, a nitrogen protecting group when attached to a nitrogen atom, an oxygen protecting group when attached to an oxygen atom, and a sulfur protecting group when attached to a sulfur atom;

k is 0, 1, 2, or 3; and $R^C$ is selected from the group consisting of hydrogen, halogen, optionally substituted $C_{1-6}$ alkyl, optionally substituted $C_{2-6}$ alkenyl, optionally substituted $C_{2-6}$ alkynyl, —$OR^{C1}$, —$N(R^{C1})_2$, —$SR^{C1}$, —CN, —C(=$NR^{C1}$)$R^{C1}$, —C(=$NR^{C1}$)$OR^{C1}$, —C(=$NR^{C1}$)N($R^{C1}$)$_2$, —$NO_2$, —$N_3$, —$NR^{C1}$C(=O)$R^{C1}$, —$NR^{C1}$C(=O)$OR^{C1}$, —$NR^{C1}$C(=O)N($R^{C1}$)$_2$, —$NR^{C1}$C(=$NR^{C1}$)$R^{C1}$, —$NR^{C1}$C(=$NR^{C1}$)$OR^{C1}$, —$NR^{C1}$C(=$NR^{C1}$)N($R^{C1}$)$_2$, —OC(=O)$R^{C1}$, —OC(=O)$OR^{C1}$, —OC(=O)N($R^{C1}$)$_2$, —OC(=$NR^{C1}$)$R^{C1}$, —OC(=$NR^{C1}$)$OR^{C1}$, —OC(=$NR^{C1}$)N($R^{C1}$)$_2$, —$NR^{C1}$S(=O)$_2$$R^{C1}$, —$NR^{C1}$S(=O)$_2$$OR^{C1}$, —$NR^{C1}$S(=O)$_2$N($R^{C1}$)$_2$, —OS(=O)$_2$$R^{C1}$, —OS(=O)$_2$$OR^{C1}$, —OS(=O)$_2$N($R^{C1}$)$_2$, —S(=O)$_2$$R^{C1}$, —S(=O)$_2$$OR^{C1}$, and —S(=O)$_2$N($R^{C1}$)$_2$, wherein each occurrence of $R^{C1}$ is independently selected from the group consisting of hydrogen, optionally substituted acyl, optionally substituted $C_{1-6}$ alkyl, optionally substituted $C_{2-6}$ alkenyl, optionally substituted $C_{2-6}$ alkynyl, a nitrogen protecting group when attached to a nitrogen atom, an oxygen protecting group when attached to an oxygen atom, and a sulfur protecting group when attached to a sulfur atom;

when an optionally substituted moiety referred to above is substituted with one or more substituents at a carbon atom, the one or more substituents at the carbon atom are independently halogen, —CN, —$NO_2$, —$N_3$, —$SO_2H$, —$SO_3H$, —OH, —$OR^{aa}$, —ON($R^{bb}$)$_2$, —N($R^{bb}$)$_2$, —N($R^{bb}$)$_3^+X^-$, —N($OR^{cc}$)$R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, —$NR^{bb}$C(=$NR^{bb}$)N($R^{bb}$)$_2$, —C(=O)$NR^{bb}SO_2R^{aa}$, —$NR^{bb}SO_2R^{aa}$, —$SO_2$N($R^{bb}$)$_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)($R^{aa}$)$_2$, —OP(=O)($R^{aa}$)$_2$, —OP(=O)($OR^{cc}$)$_2$, —P(=O)(N$R^{bb}$)$_2$, —OP(=O)(N$R^{bb}$)$_2$, —$NR^{bb}$P(=O)($OR^{cc}$)$_2$, —$NR^{bb}$P(=O)(N$R^{bb}$)$_2$, —P($R^{cc}$)$_2$, —OP($R^{cc}$)$_2$, —B($R^{aa}$)$_2$, —B($OR^{cc}$)$_2$, —$BR^{aa}$($OR^{cc}$), $C_{1-10}$ alkyl, $C_{1-10}$ perhaloalkyl, $C_{2-10}$ alkenyl, or $C_{2-10}$ alkynyl, wherein each of the alkyl, alkenyl, and alkynyl is independently substituted with 0, 1, 2, 3, 4, or 5 $R^{dd}$ groups; or two geminal hydrogen atoms on the carbon atom are replaced with =O, =S, =NN($R^{bb}$)$_2$, =NN$R^{bb}$C(=O)$R^{aa}$, =NN$R^{bb}$C(=O)$OR^{aa}$, =NN$R^{bb}$S(=O)$_2R^{aa}$, =N$R^{bb}$, or =N$OR^{cc}$;

when an optionally substituted moiety referred to above is substituted with one or more substituents at a nitrogen atom, the one or more substituents at the nitrogen atom are independently a nitrogen protecting group, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(=S)N ($R^{cc}$)$_2$, —C(=O)S$R^{cc}$, —C(=S)S$R^{cc}$, —P(=O)($R^{aa}$)$_2$, —P(=O)(N$R^{cc}$)$_2$, $C_{1-10}$ alkyl, $C_{1-10}$ perhaloalkyl, $C_{2-10}$ alkenyl, or $C_{2-10}$ alkynyl, wherein each of the alkyl, alkenyl, and alkynyl is independently substituted with 0, 1, 2, 3, 4, or 5 $R^{dd}$ groups;

wherein:
each instance of $R^{aa}$ is, independently, $C_{1-10}$ alkyl, $C_{1-10}$ perhaloalkyl, $C_{2-10}$ alkenyl, $C_{2-10}$ alkynyl, or phenyl, wherein each of the alkyl, alkenyl, alkynyl, and phenyl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(N$R^{cc}$)$_2$, $C_{1-10}$ alkyl, $C_{1-10}$ perhaloalkyl, $C_{2-10}$ alkenyl, and $C_{2-10}$ alkynyl, wherein each of the alkyl, alkenyl, and alkynyl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, and $C_{2-10}$ alkynyl, wherein each of the alkyl, alkenyl, and alkynyl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, and $C_{2-6}$ alkynyl, wherein each of the alkyl, alkenyl, and alkynyl is independently substituted with 0, 1, 2, 3, 4, or 5 $R^{gg}$ groups;

each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, or $C_{2-6}$ alkynyl; or two geminal $R^{gg}$ substituents can be joined to form =O or =S;

X$^-$ is a counterion; and when an optionally substituted moiety referred to above is substituted with one or more substituents at a sulfur atom, the one or more substituents at the sulfur atom are independently an sulfur protecting group; and wherein the heterocyclyl is 3 to 10-membered and monocyclic, and comprises independently 1 to 4 ring heteroatoms independently selected from the group consisting of nitrogen, oxygen, and sulfur.

2. The compound of claim 1, or a pharmaceutically acceptable salt thereof, wherein Ring A is a 5-membered or 6-membered, monocyclic heteroaryl ring comprising 1 to 4 ring heteroatoms independently selected from the group consisting of nitrogen, oxygen, and sulfur, and is optionally substituted with k instances of $R^A$.

3. The compound of claim 2, or a pharmaceutically acceptable salt thereof, wherein

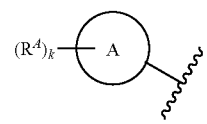

is of formula:

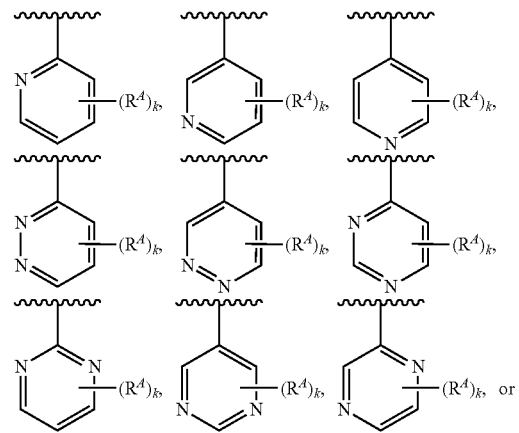

-continued
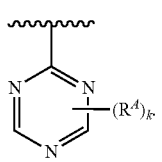
4. The compound of claim 2, or a pharmaceutically acceptable salt thereof, wherein
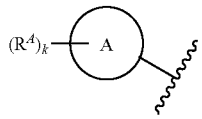
is of formula:
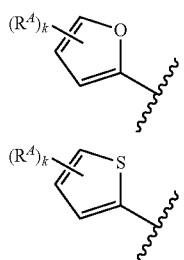 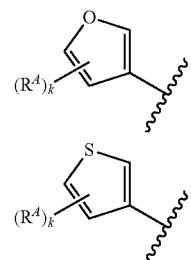
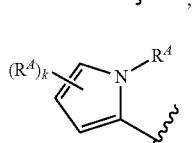 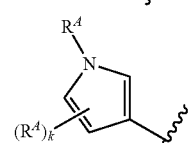
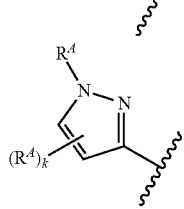 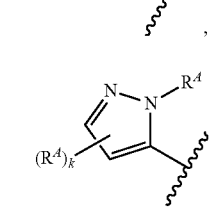
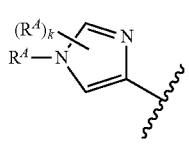 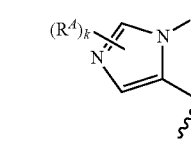
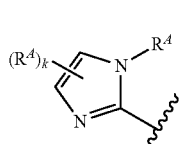 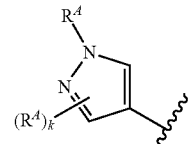
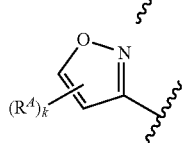 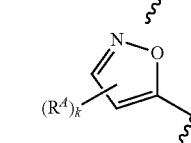
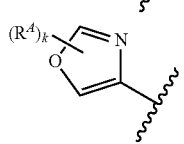 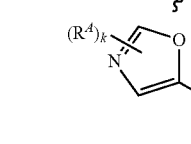
-continued
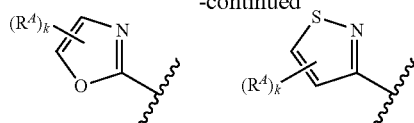
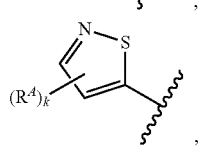 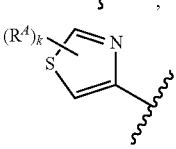
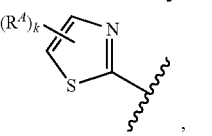
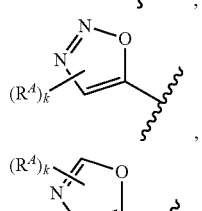
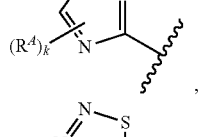 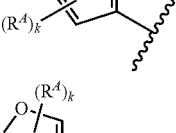
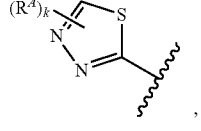 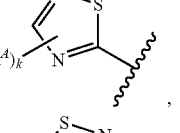
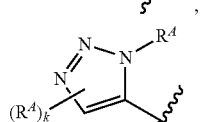 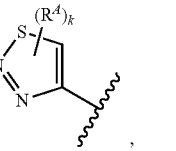
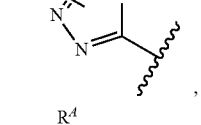 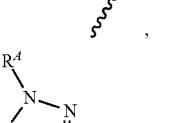
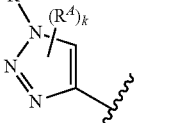

-continued

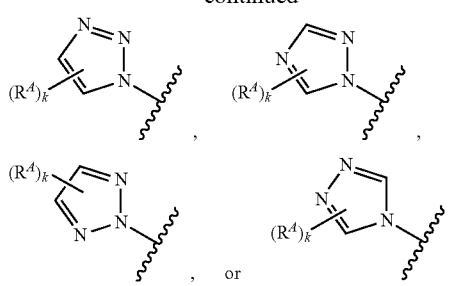

, or .

5. The compound of claim 1, wherein the compound is of formula:

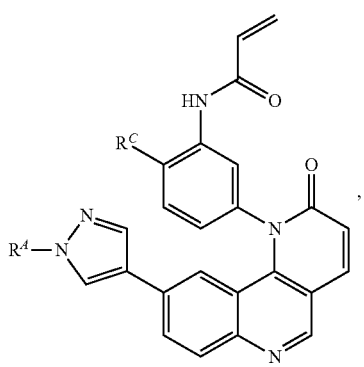

or a pharmaceutically acceptable salt thereof.

6. The compound of claim 1, wherein the compound is of formula:

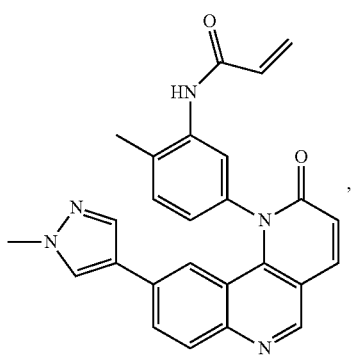

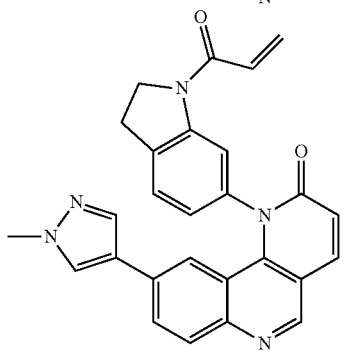

or a pharmaceutically acceptable salt thereof.

7. A pharmaceutical composition comprising a compound of claim 1, or a pharmaceutically acceptable salt thereof, and optionally a pharmaceutically acceptable excipient.

8. The compound of claim 1, wherein the compound is of the formula:

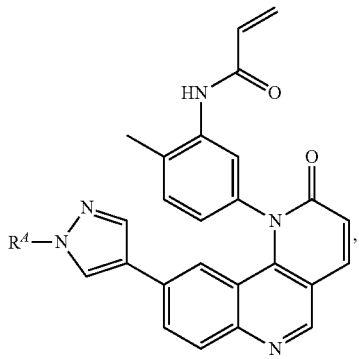

or a pharmaceutically acceptable salt thereof.

9. The compound of claim 1, wherein the compound is of the formula:

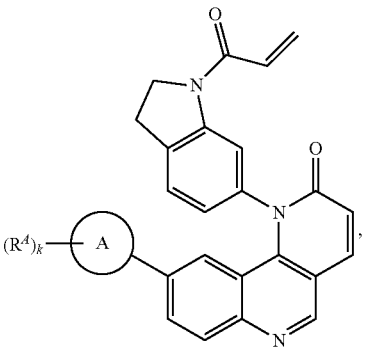

or a pharmaceutically acceptable salt thereof.

10. The compound of claim 1, or a pharmaceutically acceptable salt thereof, wherein Ring A is 5,6- or 6,6-membered bicyclic heteroaryl comprising 1 to 4 ring heteroatoms independently selected from the group consisting of nitrogen, oxygen, and sulfur, and is optionally substituted with k instances of $R^A$.

11. The compound of claim 1, or a pharmaceutically acceptable salt thereof, wherein Ring A is quinolinyl or isoquinolinyl and is optionally substituted with k instances of $R^A$.

12. The compound of claim 1, wherein the compound is of the formula:

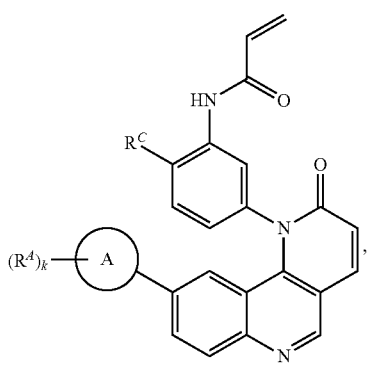

or a pharmaceutically acceptable salt thereof.

13. The compound of claim 1, or a pharmaceutically acceptable salt thereof, wherein

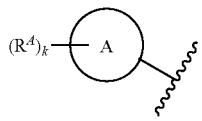

is of formula:

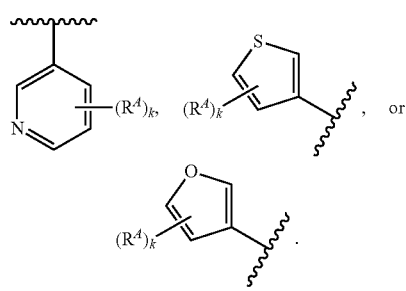

14. The compound of claim 1, or a pharmaceutically acceptable salt thereof, wherein

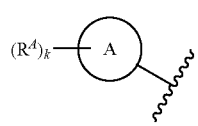

is of formula:

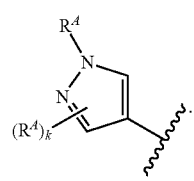

15. The compound of claim 1, or a pharmaceutically acceptable salt thereof, wherein

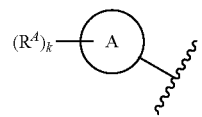

is of formula:

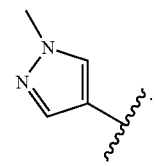

16. The compound of claim 1, or a pharmaceutically acceptable salt thereof, wherein at least one instance of $R^A$ is optionally substituted $C_{1-6}$ alkyl or halogen.

17. The compound of claim 1, or a pharmaceutically acceptable salt thereof, wherein at least one instance of $R^A$ is —N($R^{A1}$)$_2$, —N$R^{A1}$C(=O)N($R^{A1}$)$_2$, —N$R^{A1}$S(=O)$_2$$R^{A1}$, or —S(=O)$_2$N($R^{A1}$)$_2$.

18. The compound of claim 1, or a pharmaceutically acceptable salt thereof, wherein at least one instance of $R^A$ is optionally substituted heterocyclyl.

19. The compound of claim 1, or a pharmaceutically acceptable salt thereof, wherein k is 0.

20. The compound of claim 1, or a pharmaceutically acceptable salt thereof, wherein k is 1 or 2.

21. The compound of claim 1, or a pharmaceutically acceptable salt thereof, wherein $R^C$ is optionally substituted $C_{1-6}$ alkyl.

22. The compound of claim 1, or a pharmaceutically acceptable salt thereof, wherein $R^C$ is —CH$_3$.

23. The compound of claim 1, or a pharmaceutically acceptable salt thereof, wherein $R^C$ is hydrogen, halogen, or —OR$^{C1}$.

24. The compound of claim 1, wherein the compound is of the formula:

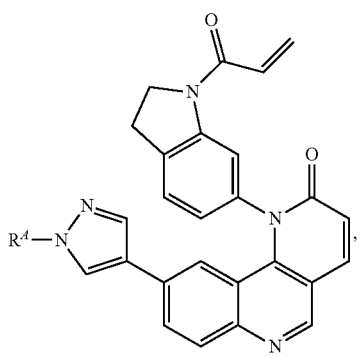

or a pharmaceutically acceptable salt thereof.

25. The compound of claim 1, wherein the compound is of formula:
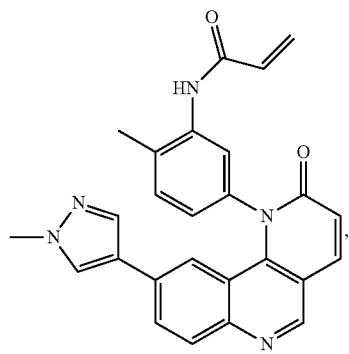 [SMILES: C=CC(=O)Nc1cc(-n2c(=O)ccc3cnc4ccc(-c5cnn(C)c5)cc4c32)ccc1C]
or a pharmaceutically acceptable salt thereof.
* * * * *